US006656961B2

(12) United States Patent
Danishefsky et al.

(10) Patent No.: US 6,656,961 B2
(45) Date of Patent: *Dec. 2, 2003

(54) SYNTHESIS OF EPOTHILONES, INTERMEDIATES THERETO, ANALOGUES AND USES THEREOF

(75) Inventors: Samuel J. Danishefsky, Englewood, NJ (US); Peter Bertinato, Old Lyme, CT (US); Dai-Shi Su, New York, NY (US); Dang Fang Meng, New York, NY (US); Ting-Chao Chou, Paramus, NJ (US); Ted Kamenecka, New York, NY (US); Erik J. Sorensen, San Diego, CA (US); Aaron Balog, New York, NY (US); Kenneth A. Savin, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 274 days.

This patent is subject to a terminal disclaimer.

(21) Appl. No.: 09/808,451

(22) Filed: Mar. 14, 2001

(65) Prior Publication Data

US 2003/0125362 A1 Jul. 3, 2003

Related U.S. Application Data

(63) Continuation of application No. 08/986,025, filed on Dec. 3, 1997, now Pat. No. 6,242,469.
(60) Provisional application No. 60/032,282, filed on Dec. 3, 1996, provisional application No. 60/033,767, filed on Jan. 14, 1997, provisional application No. 60/047,566, filed on May 22, 1997, provisional application No. 60/047,941, filed on May 29, 1997, and provisional application No. 60/055,533, filed on Aug. 13, 1997.

(51) Int. Cl.[7] .................... A61K 31/365; A61K 31/427; C07D 277/22; C07D 313/00
(52) U.S. Cl. ....................... 514/365; 548/204; 548/510; 549/271
(58) Field of Search .................. 549/271; 514/365; 548/204, 510

(56) References Cited

U.S. PATENT DOCUMENTS

| 5,021,430 A | 6/1991 | Ksander et al. | 514/332 |
| 5,917,084 A | 6/1999 | Jiang et al. | 560/174 |
| 5,969,145 A | 10/1999 | Schinzer et al. | 548/110 |
| 6,043,372 A | 3/2000 | Schinzer et al. | 548/110 |
| 6,156,905 A | 12/2000 | Schinzer et al. | 548/204 |

FOREIGN PATENT DOCUMENTS

| DE | 19542986.9 | 11/1995 |
| DE | 19639456.2 | 9/1996 |
| DE | 19542986 A1 | 5/1997 |
| DE | 19636343 C1 | 10/1997 |
| DE | 19639456 A1 | 3/1998 |
| DE | 19645361 A1 | 4/1998 |
| DE | 19645362 A1 | 4/1998 |
| WO | WO97/19086 | 5/1997 |
| WO | WO98/08849 | 5/1998 |
| WO | WO98/25929 | 6/1998 |
| WO | WO99/02514 | 1/1999 |

OTHER PUBLICATIONS

Bijoy, P. et al., "Synthetic Studies Directed Towards Epothilone A: . . . ", *Tetrahedron Letters* 39:209–212 (1998).

U.S. patent application Ser. No. 08/856,533, filed May 14, 1997.

U.S. patent application Ser. No. 08/923,869, filed Sep. 4, 1997.

U.S. provisional application Ser. No. 60/032,864, filed Dec. 13, 1996.

Bollag, Daniel M., "Epothilones, a New Class of MT–stabilizing Agents . . . ", *Cancer Research* 55:2325–2333 (1995).

Chakraborty, T.K. et al., "Radical–induced Opening of Trisubstituted Epothilones", *Tetrahedron Letters* 39:101–104 (1998).

Clause, E, et al., "Synthesis of the C1–C9 Segment of Epothilones", *Tetrahedron Letters* 38:8:1359–1362 (1997).

Gabriel, T., "The Chromium–Reformatsky Reaction: . . .", *Tetrahedron Letters* 38:8 1363–1366 (1997).

Gerth, K. et al., "Epothilone A and B: Antifungal and Cytotoxic Compounds . . . ", *Liebigs Ann. Chem.* 74 & 75, 49–53 (1996).

Giannakakou, P. et al., "Paclitaxel–resistant Human Ovarian Cancer Cells Have Mutant β–Tubulins . . . ", *J. Bio. Chem.* 272:27 17118–17125 (1997).

Höfle, G. et al. "Epothilone A and B–Novel 16–Membered Microlides with Cytotoxic . . . ",, *Chem Int. Ed. Engl.* 35:13 14, 1567–1569 (1996).

Kowalski, R.J. et al., "Activities of the Microtubule–stabilizing Agents Epothilones A and B . . . ", *J. of Bio. Chem.* 272:4 2534–2541 (1997).

Liu, Z.Y. et al., "Chiral Synthesis of the $C_{3-13}$ Segment of Epothilone A" *Synlett Letters* 1383–84 (1997).

March, Advanced Organic Chemistry, 2nd Ed., McGraw–Hill (1977); p. 940, section 7–21.

(List continued on next page.)

*Primary Examiner*—Taofiq Solola
(74) *Attorney, Agent, or Firm*—Choate, Hall & Stewart; Brenda H. Jarrell; C. Hunter Baker

(57) ABSTRACT

The present invention provides convergent processes for preparing epothilone A and B, desoxyepothilones A and B, and analogues thereof. Also provided are analogues related to epothilone A and B and intermediates useful for preparing same. The present invention further provides novel compositions based on analogues of the epothilones and methods for the treatment of cancer and cancer which has developed a multidrug-resistant phenotype.

93 Claims, 76 Drawing Sheets

OTHER PUBLICATIONS

Meng et al. "Studies toward a Synthesis of Epothilone A: Use of Hydropyran Templates for the Management of Acyclic Stereochemical Relationships" *J. Org. Chem.* 61:23 7998–8001 (1996).

Moasser et al., "Farnesyl transferase inhibitors cause enhanced mitotic sensitivity to taxol . . ." *Proc. Natl. Acad. Sci. USA*, 95:1369–1374 (1998).

Muhlradt et al., "Epothilone B Stabilizes Microtubuli of Macrophages Like Taxol. . . ", *Cancer Res.* 57, 3344–46 (1997).

Mulzer, J. et al., "Synthesis of the C(1)–C(9) Segment of the Cytotoxic Macrolides Epothilon A and B", *Terahedron Letters* 37:51, 9179–9182 (1996).

Nicolaou, K.C. et al., "Total Synthesis of 26–hydroxyepothilone B and related analogues", Chem. Commun. 2343–2344 (1997).

Nicolaou, K.C. et al., "Total Synthesis of Epothilone A: The Macrolactonization Approach",*Agnew Chem. Int. Ed. Engl.*, (1997).

Nicolaou, K.C. et al. "Total Synthesis of Epothilone A and B via a Macrolactonization–Based Strategy", *J. Am. Chem. Soc.* 119, 7974–7991 (1997).

Nicolaou, K.C. et al., "Total Synthesis of Oxazole–and Cyclopropane–Containing Epothilone A Analogues. . . ", *Chem. Eur. J.* 3:12 1957–1970 (1997).

Nicolaou, K.C. et al., "Total Synthesis of Oxazole–and Cyclopropane–Containing Epothilone B Analogues. . . ", *Chem. Eur. J.* 3:12 1971–1986 (1997).

Nicolaou, K.C. et al., "The Olefin Metathesis Approach to Epothilone A and Its Analogues", J. *Am. Chem. Soc.* 119, 7960–7973 (1997).

Nicolaou, K.C. et al., "Designed Epothilones: Combinatorial Synthesis, Tubulin Assembly . . . " *Agnew Chem. Inst. Ed. Engl.* 36:19 2097–2103 (1997).

Nicolaou, K.C. et al., "Synthesis of Epothilones A and B in solid and solution phase", *Nature* 387:15 268–272, 238–239 (1997).

Nicolaou, K.C. et al., "Probing the Rign Size of Epothilone: Total Synthesis of [14]–, [15]–,[17]–, . . . " *Agnew. Chem. Inst. Ed.* 37:1/2, 81–87 (1998).

Nicolaou, K.C. et al., "Variation der Ringgrösse von Epothilonen–Totalsynthese von [14]–, [15]–,[17]–, . . ." *Agnew. Chem.* 110:1/2 85–92 (1998).

Nicolaou, K.C. et al., "An Approach to Epothilones Based on Olefin Metathesis" *Angnew. Chem. Int. Ed. Engl.* 35:20 2399–2401 (1996).

Schinzer, D. et al., "Studies Toward the Total Synthesis of Epothilones: . . .". *Chem. Eur. J.* 2:11 1477–1488 (1996).

Schinzer, D. et al., "Total Synthesis of ()–Epothilone A", *Agnew. Chem. Int. Ed. Engl.* 36:5 523–524 (1997).

Taylor, R.E., et al., "Towards the Synthesis of Epothilone A: Enantioselctive Preparation . . . " *Tetrahedron Letters* 38:12 2061 2064 (1997).

Wessjohann, L., "Epothilones: Promising Natural products with Taxol–Like Activity", *Agnew. Chem. Int. Ed. Engl.* 36–7 715–718 (1997).

Victroy et al., "Relative Stereochemistry and Solution Conformation of the Novel Paclitaxel–Like Antimitotic Agent Epothilone A" *Bioorganic & Medicinal Chemistry Letters* 6:7 893–898 (1996).

1: R=H: epothilone A
2: R=CH₃: epothilone B

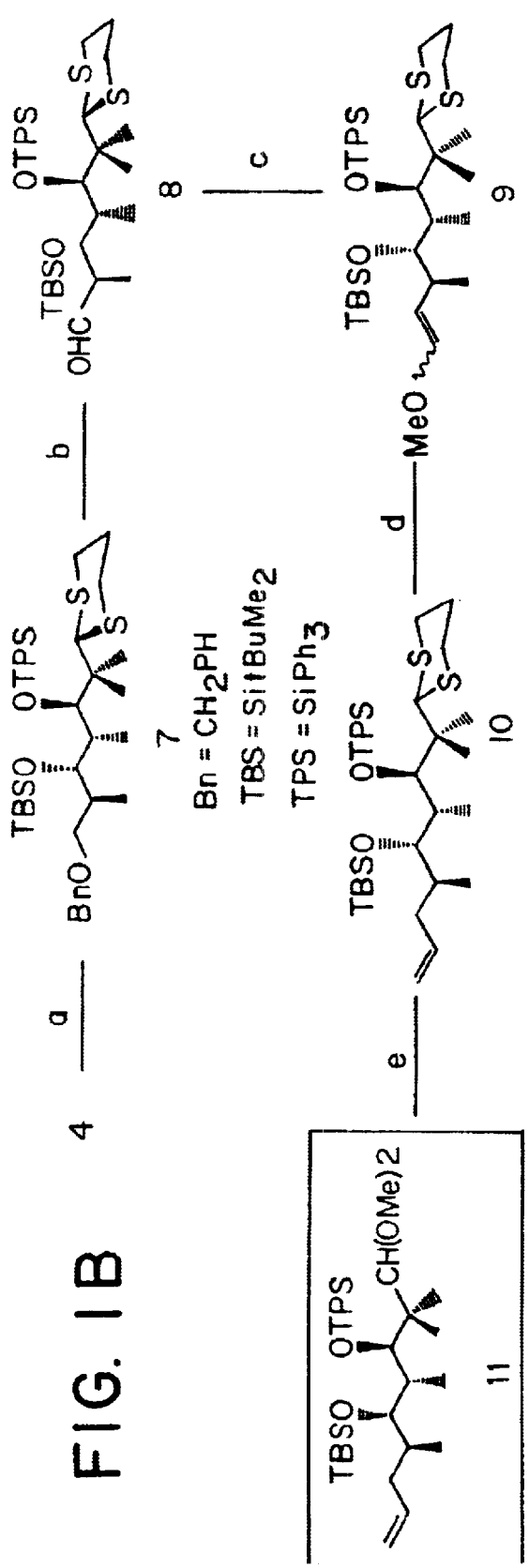
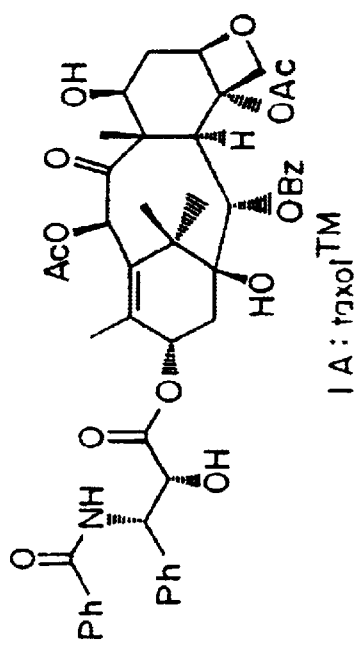
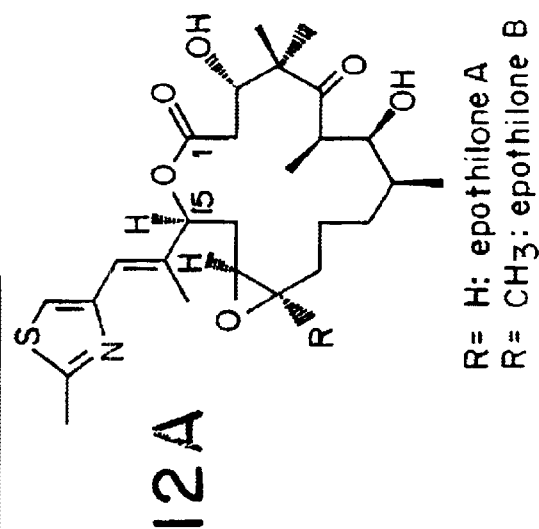
FIG. 1B
FIG. 12B
FIG. 12A

-12: R = H: (R)-glycidol
-13: R = THP

Convergent strategy for a total synthesis of epothilone A (1).

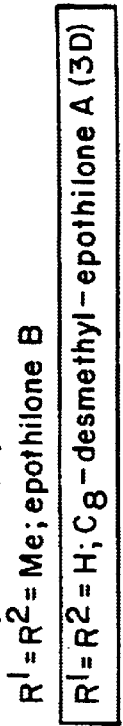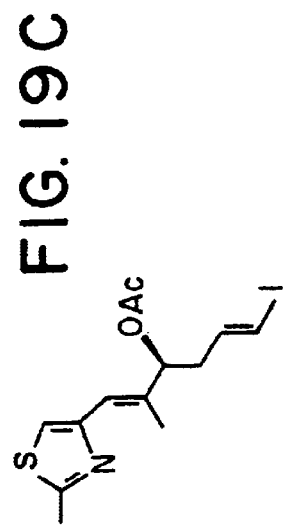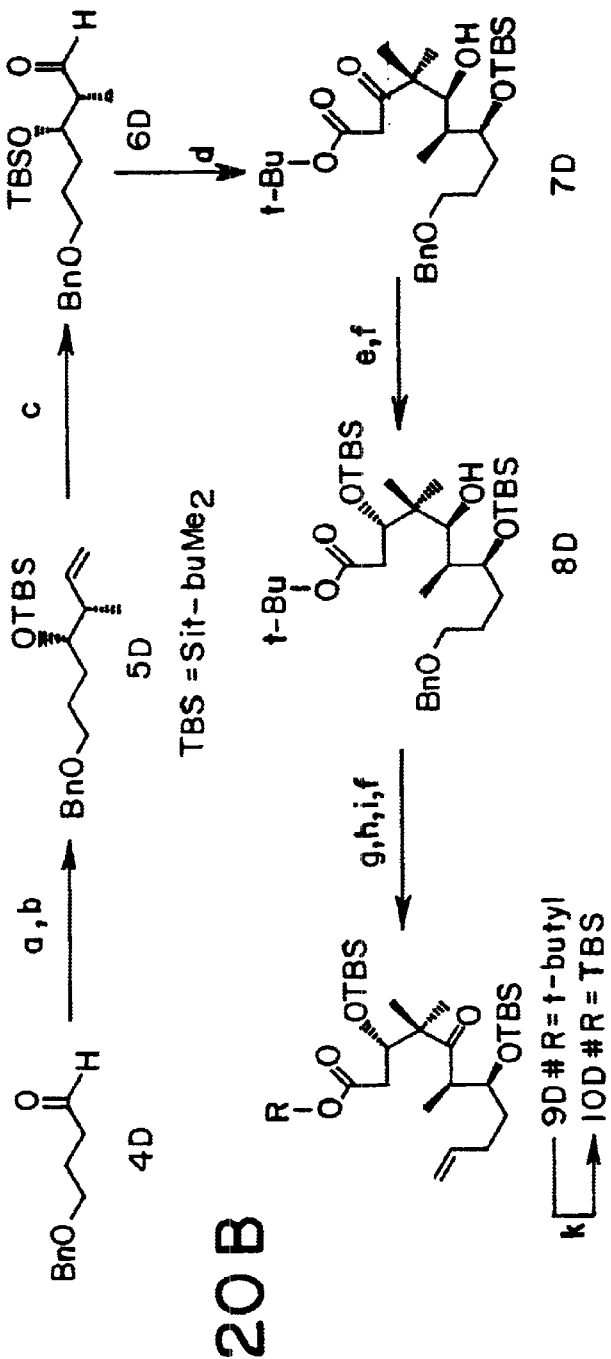
FIG. 20A
FIG. 19C
FIG. 20B

FIG. 22A
FIG. 22B
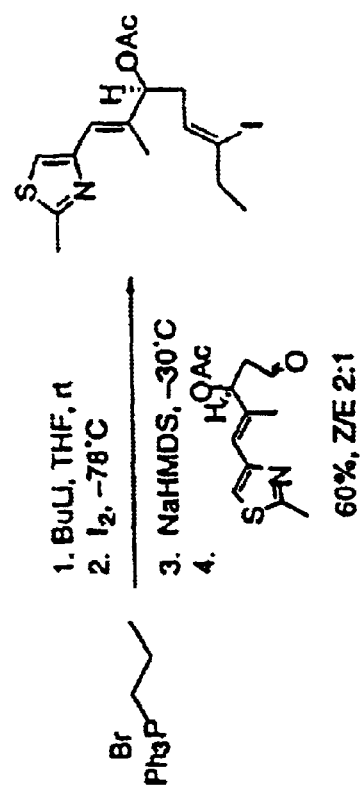
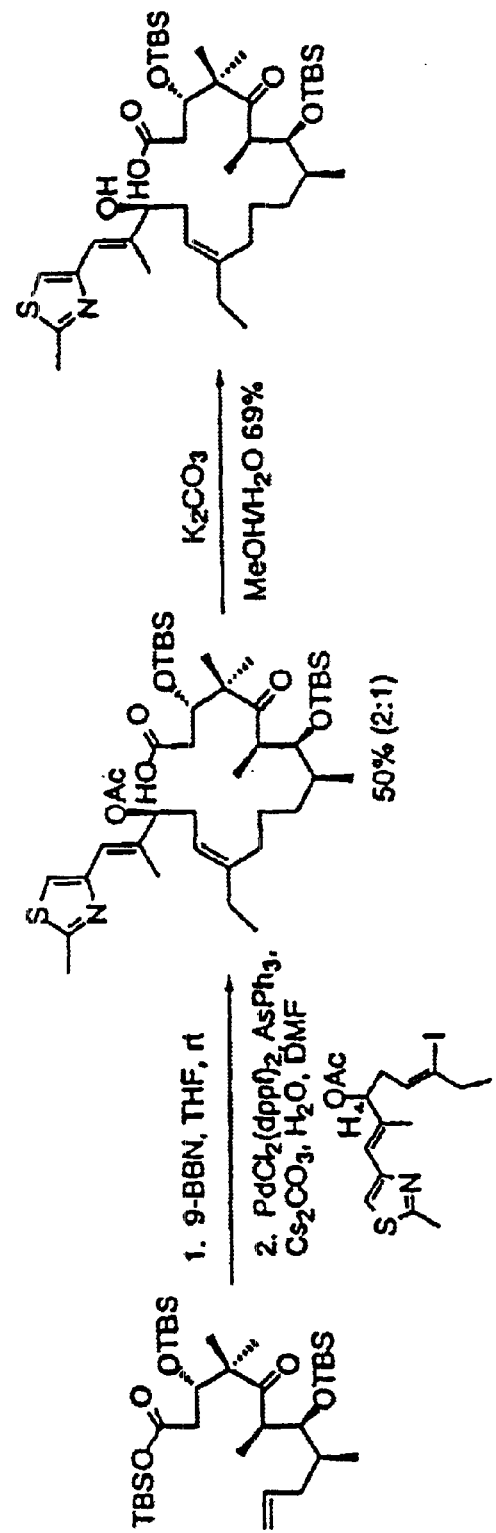

R = H, F, CF₃
R=H is the only compound completed, F and CF₃ are nearly completed

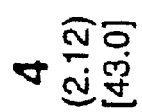
FIG. 39A
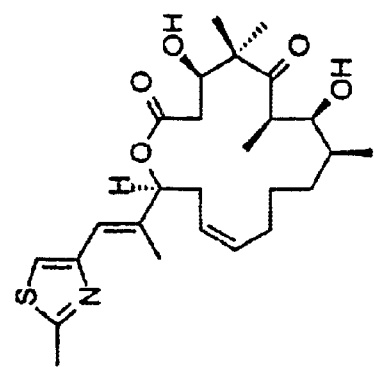
4
(2.12)
[43.0]
desoxyepothilone A
1
(0.022)
[0.012]
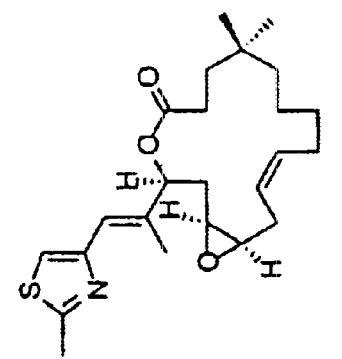
3
(271.1)
[22.4]
epothilone A
(0.0027)
[0.020]
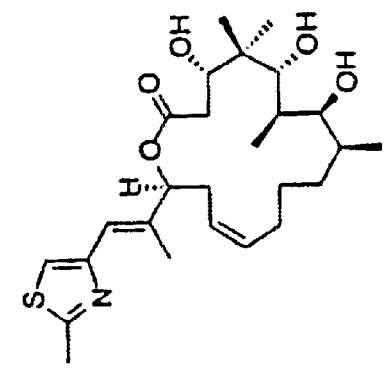
2
(14.23)
[6.28]

7
(7.36)
[9.82]

6
(0.052)
[0.035]

5
(>20)
[35.2]

16
(7.47)
[16.48]

15
(0.96)
[5.95]

14
(5.42)
[5.75]

22
(0.098)
[0.146]

19
(0.96)
[>1.0]

18
(1158)
[>720]

21

17
(0.090)
[0.254]

20
(0.030)
[0.049]

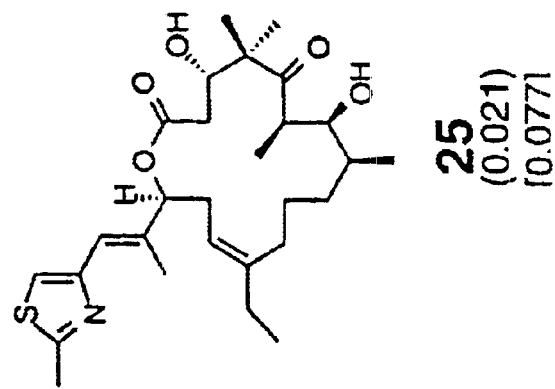
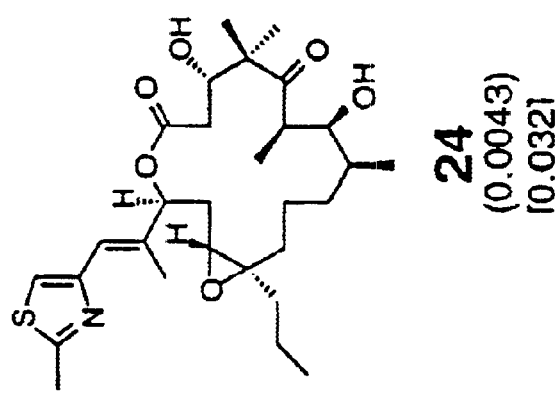
FIG. 41B
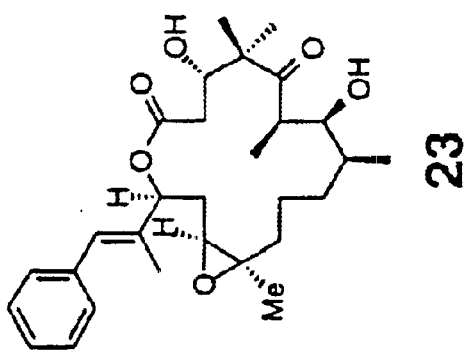

34
(0.143)
[0.276]

33
(0.0031)
[0.0093]

32
(0.063)
[0.380]

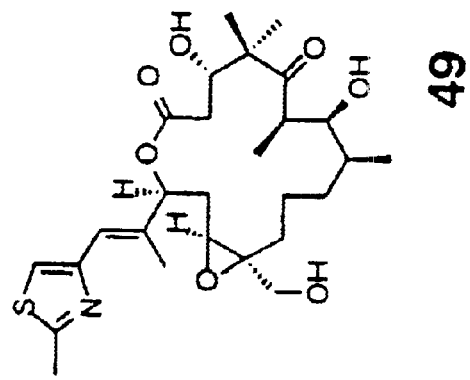
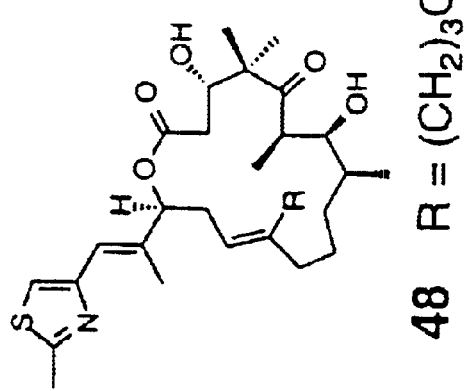
FIG. 42E
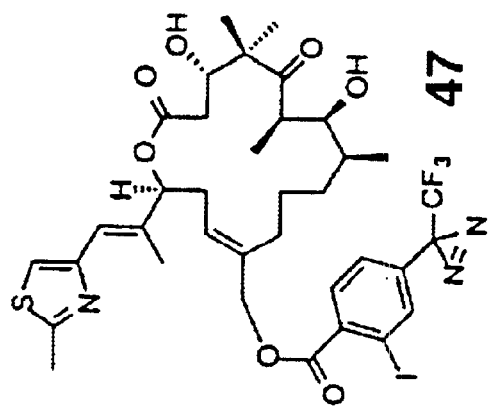

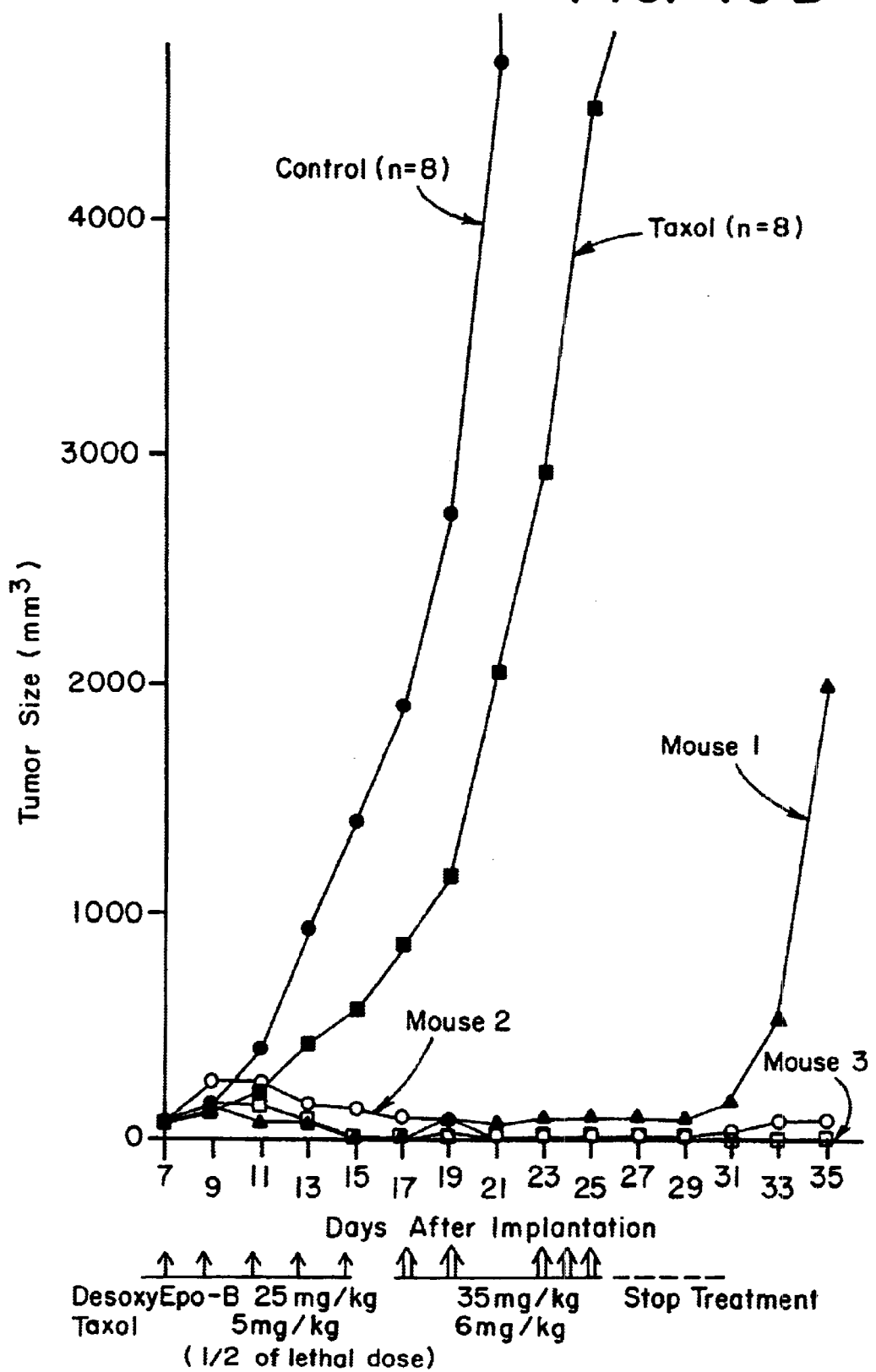

SYNTHESIS OF EPOTHILONES, INTERMEDIATES THERETO, ANALOGUES AND USES THEREOF

This application is a continuation application filed under 37 C.F.R. §1.53(b) of application Ser. No. 08/986,025, filed Dec. 3, 1997 now U.S. Pat. No. 6,242,469, the entire contents of which are hereby incorporated by reference, which is based on U.S. Provisional Application Serial Nos. 60/032,282, 60/033,767, 60/047,566, 60/047,941, and 60/055,533, filed Dec. 3, 1996, Jan. 14, 1997, May 22, 1997, May 29, 1997, and Aug. 13, 1997, respectively, the contents of which are hereby incorporated by reference into this application. This invention was made with government support under grants CA-28824, CA-39821, CA-GM 72231, CA-62948, and AI0-9355 from the National Institutes of Health, and grant CHE-9504805 from the National Science Foundation. Additionally, the present invention was supported in part by a fellowship from the United States Army to Dongfang Meng (DAMD 17-97-1-7146), and thus the government has certain rights in the invention.

FIELD OF THE INVENTION

The present invention is in the field of epothilone macrolides. In particular, the present invention relates to processes for the preparation of epothilones A and B, desoxyepothilones A and B, and analogues thereof which are useful as highly specific, non-toxic anticancer therapeutics. In addition, the invention provides methods of inhibiting multidrug resistant cells. The present invention also provides novel compositions of matter which serve as intermediates for preparing the epothilones.

Throughout this application, various publications are referred to, each of which is hereby incorporated by reference in its entirety into this application to more fully describe the state of the art to which the invention pertains.

BACKGROUND OF THE INVENTION

Epothilones A and B are highly active anticancer compounds isolated from the Myxobacteria of the genus Sorangium. The full structures of these compounds, arising from an x-ray crystallographic analysis were determined by Höfle. G. Höfle et al., *Angew. Chem. Int. Ed. Engl.*, 1996, 35, 1567. The total synthesis of the epothilones is an important goal for several reasons. Taxol is already a useful resource in chemotherapy against ovarian and breast cancer and its range of clinical applicability is expanding. G. I. Georg et al., *Taxane Anticancer Agents*; American Cancer Society: San Diego, 1995. The mechanism of the cytotoxic action of taxol, at least at the in vitro level, involves stabilization of microtubule assemblies. P. B. Schiff et al., *Nature* (London), 1979, 277, 665. A series of complementary in vitro investigations with the epothilones indicated that they share the mechanistic theme of the taxoids, possibly down to the binding sites to their protein target. D. M. Bollag et al., *Cancer Res.*, 1995, 55, 2325. Moreover, the epothilones surpass taxol in terms of cytotoxicity and far surpass it in terms of in vitro efficacy against drug resistant cells. Since multiple drug resistance (MDR) is one of the serious limitations of taxol (L. M. Landino and T. L. MacDonald in *The Chemistry and Pharmacology of Taxol and its Derivatives*, V. Farin, Ed., Elsevier: New York, 1995, ch. 7, p. 301), any agent which promises relief from this problem merits serious attention. Furthermore, formulating the epothilones for clinical use is more straightforward than taxol.

Accordingly, the present inventors undertook the total synthesis of the epothilones, and as a result, have developed efficient processes for synthesizing epothilones A and B, the corresponding desoxyepothilones, as well as analogues thereof. The present invention also provides novel intermediates useful in the synthesis of epothilones A and B and analogues thereof, compositions derived from such epothilones and analogues, purified compounds of epothilones A and B, and desoxyepothilones A and B, in addition to methods of use of the epothilone analogues in the treatment of cancer. Unexpectedly, certain epothilones have been found to be effective not only in reversing multi-drug resistance in cancer cells, both in vitro and in vivo, but have been determined to be active as collateral sensitive agents, which are more cytotoxic towards MDR cells than normal cells, and as synergistic agents, which are more active in combination with other cytotoxic agents, such as vinblastin, than the individual drugs would be alone at the same concentrations.

Remarkably, the desoxyepothilones of the invention have exceptionally high specificity as tumor cytotoxic agents in vivo, more effective and less toxic to normal cells than the principal chemotherapeutics currently in use, including taxol, vinblastin, adriamycin and camptothecin.

SUMMARY OF THE INVENTION

One object of the present invention is to provide processes for the preparation of epothilones A and B, and desoxyepothilones A and B, and related compounds useful as anticancer therapeutics. Another object of the present invention is to provide various compounds useful as intermediates in the preparation of epothilones A and B as well as analogues thereof.

A further object of the present invention is to provide synthetic methods for preparing such intermediates. An additional object of the invention is to provide compositions useful in the treatment of subjects suffering from cancer comprising any of the analogues of the epothilones available through the preparative methods of the invention optionally in combination with pharmaceutical carriers.

A further object of the invention is to provide methods of treating subjects suffering from cancer using any of the analogues of the epothilones available through the preparative methods of the invention optionally in combination with pharmaceutical carriers.

BRIEF DESCRIPTION OF THE DRAWINGS

FIG. 1(B) provides synthesis of compound 11. (a) t-BuMe$_2$OTf, 2,6-lutidine, CH$_2$Cl$_2$, 98%; (b) (1) DDQ, CH$_2$Cl$_2$/H$_2$O, 89%; (2) (COCl)$_2$, DMSO, CH$_2$Cl$_2$, −78° C.; then Et$_3$N, −78° C.→rt, 90%; (c) MeOCH$_2$PPh$_3$Cl, t-BuOK, THF, 0° C.→rt, 86%; (d) (1) p-TsOH, dioxane/H$_2$O, 50° C., 99%; (2) CH$_3$PPh$_3$Br, NaHMDS, PhCH$_3$, 0° C.→rt, 76%; (e) PhI(OCOCF$_3$)$_2$, MeOH/THF, rt, 0.25 h, 92%.

FIG. 12 illustrates (A) structures of epothilones A (1) and B (2) and (B) of Taxol™ (1A).

FIGS. 19(A), 19(B), and 19(C) provide a synthetic pathway to 8-desmethyl deoxyepothilone A and a trans-iodoolefin intermediate thereto.

FIG. 20(A) shows structures of epothilones A and B and 8-desmethylepothilone and FIG. 20(B) shows a synthetic pathway to intermediate TBS ester 10 used in the preparation of desmethylepothilone A. (a) (Z)-Crotyl-B[(-)-1pc]$_2$, $-78°$ C., $Et_2O$, then 3 N NaOH, 30% $H_2O_2$; (b) TBSOTf, 2,6-lutidine, $CH_2Cl_2$ (74% for two steps, 87% ee); (c) $O_3$, $CH_2Cl_2$/MeOH, $-78°$ C., then DMS, (82%); (d) t-butyl isobutyrylacetate, NaH, BuLi, $0°$ C., then 6 (60%, 10:1); (e) $Me_4$NBH(OAc)$_3$, $-10°$ C. (50%, 10:1 $\alpha/\beta$) or $NaBH_4$, MeOH, THF, $0°$ C., (88%, 1:1 $\alpha/\beta$); (f) TBSOTf, 2,6-lutidine, $-40°$ C., (88%); (g) Dess-Martin periodinane, (90%); (h) Pd(OH)$_2$, $H_2$, EtOH (96%); (1) DMSO, oxalyl chloride; $CH_2Cl_2$, $-78°$ C. (78%); (0) Methyl triphenylphosphonium bromide, NaHMDS, THF, $0°$ C. (85%); (k) TBSOTf, 2,6-lutidine, $CH_2Cl_2$, rt (87%).

FIGS. 22(A), 22(B) and 22(C) show a synthetic pathway to prepare epothilone analogue 27D.

FIGS. 39(A) and 39(B) show epothilone A and epothilone analogues #1–7. Potencies against human leukemia CCRF-CEM (sensitive) and CCRF-CEM/VBL MDR (resistant) sublines are shown in round and square brackets, respectively.

FIGS. 41(A) and 41(B) show epothilone analogues #17–25. Potencies against human leukemia CCRF-CEM (sensitive) and CCRF-CEM/VBL MDR (resistant) sublines are shown in round and square brackets, respectively.

FIGS. 42(E) shows epothilone analogues #47–49.

FIG. 45(B) shows comparative therapeutic effect of desoxyepothilone B and taxol on nude mice bearing MX-1 xenoplant. Tumor, s.c.; drug administered i.p., Q2Dx5, start on day 7. control (♦); Taxol (□; 5 mg/kg, one half of LD$_{50}$, given on days 7, 9, 11, 13, 15; then 6 mg/kg, given on days 17, 19, 23, 24, 25); desoxyepothilone B (n–3; Δ, x, *; 25 mg/kg, nontoxic dose, given to three mice on days 7, 9, 11, 13, 15; then 35 mg/kg, given on days 17, 19, 23, 24, 25).

DETAILED DESCRIPTION OF THE INVENTION

Figure 1A:
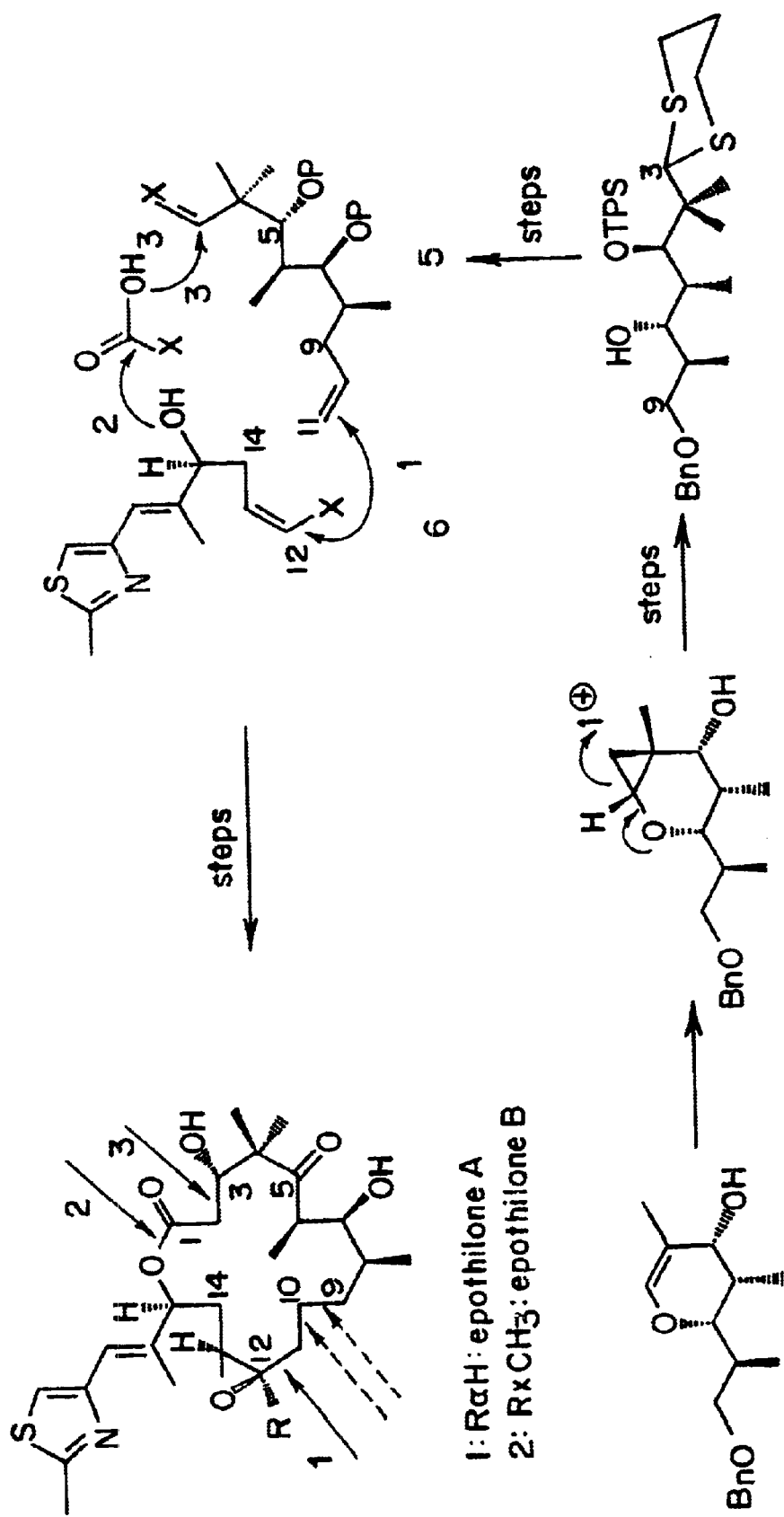
FIG. 1(A) shows a retrosynthetic analysis for epothilone A and B.
Figure 2:
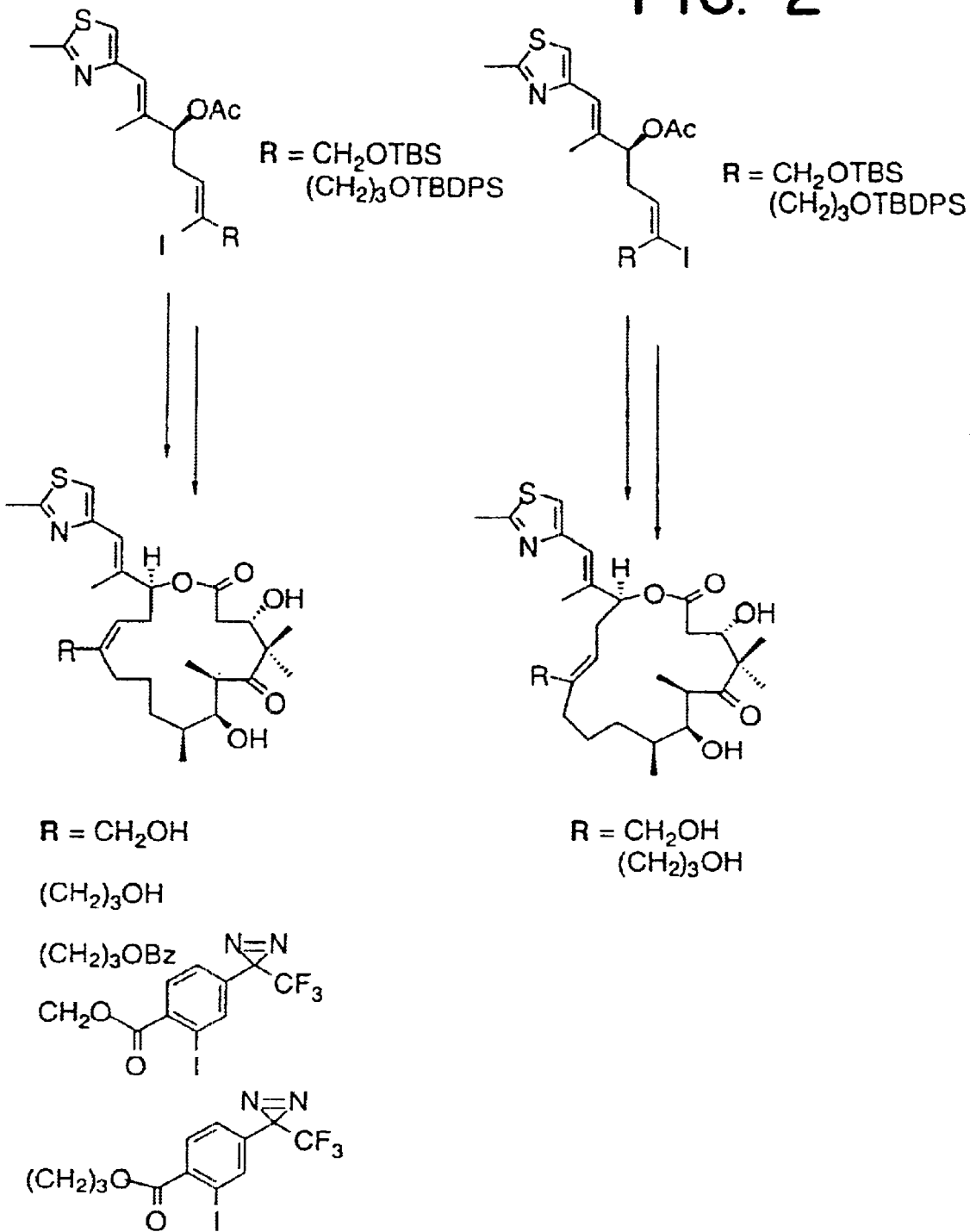
FIG. 2 provides key intermediates in the preparation of 12,13-E- and -Z-deoxyepothilones.
Figure 3A:
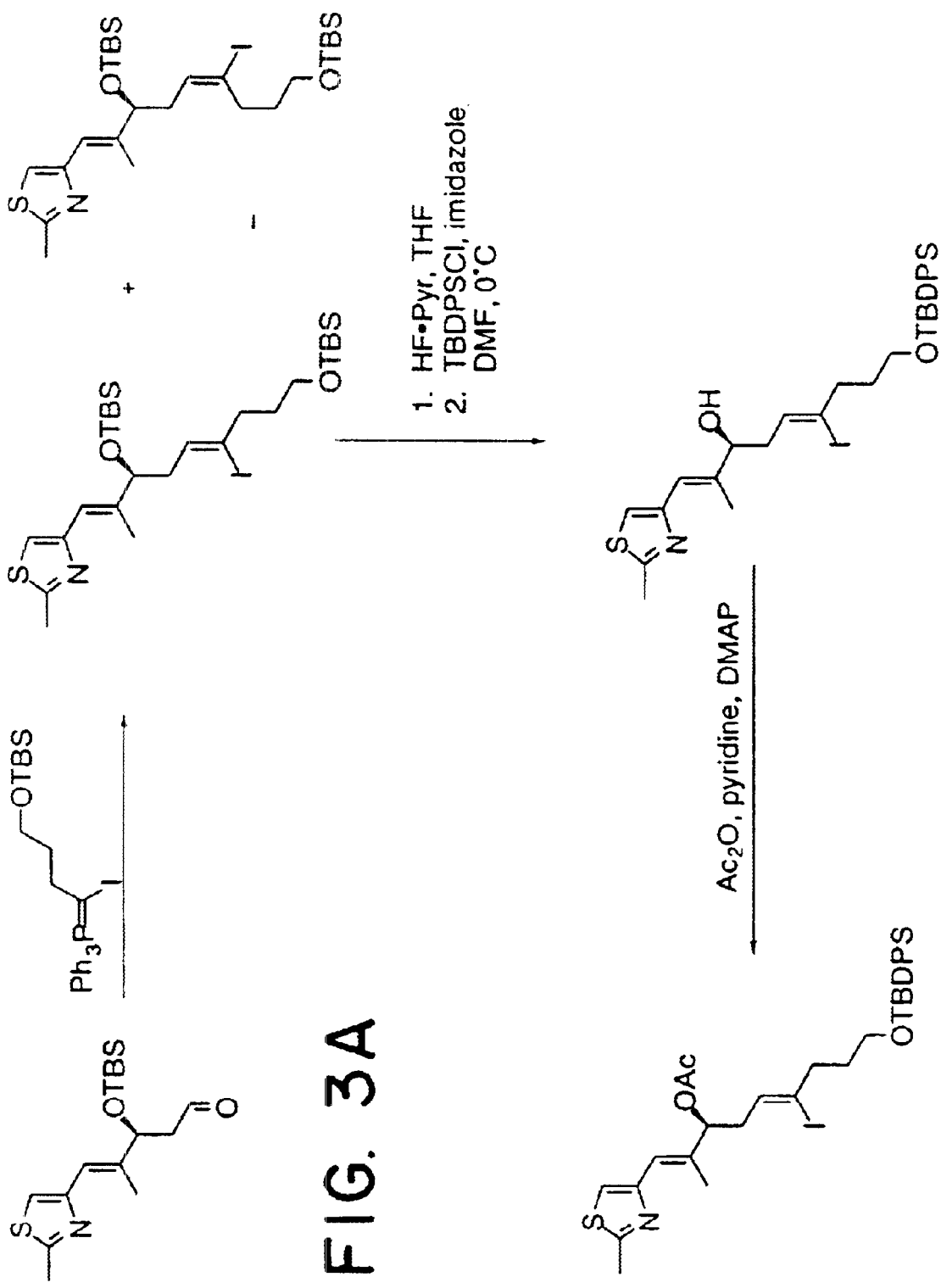
FIGS. 3(A) and 3(B) provide syntheses of key iodinated intermediates used to prepare hydroxymethylene- and hydroxypropylene-substituted epothilone derivatives.
Figure 3B:
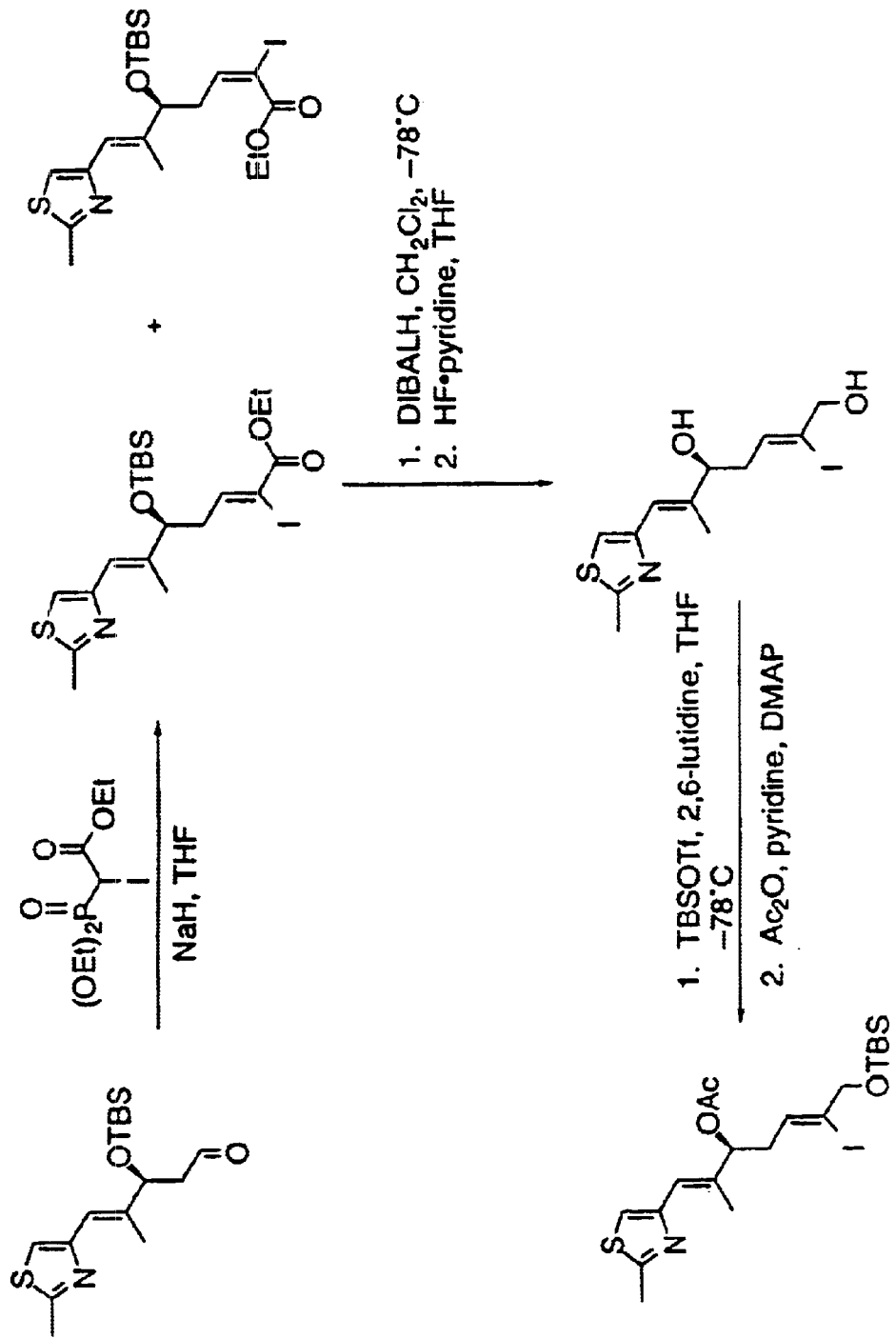
Figure 3C:
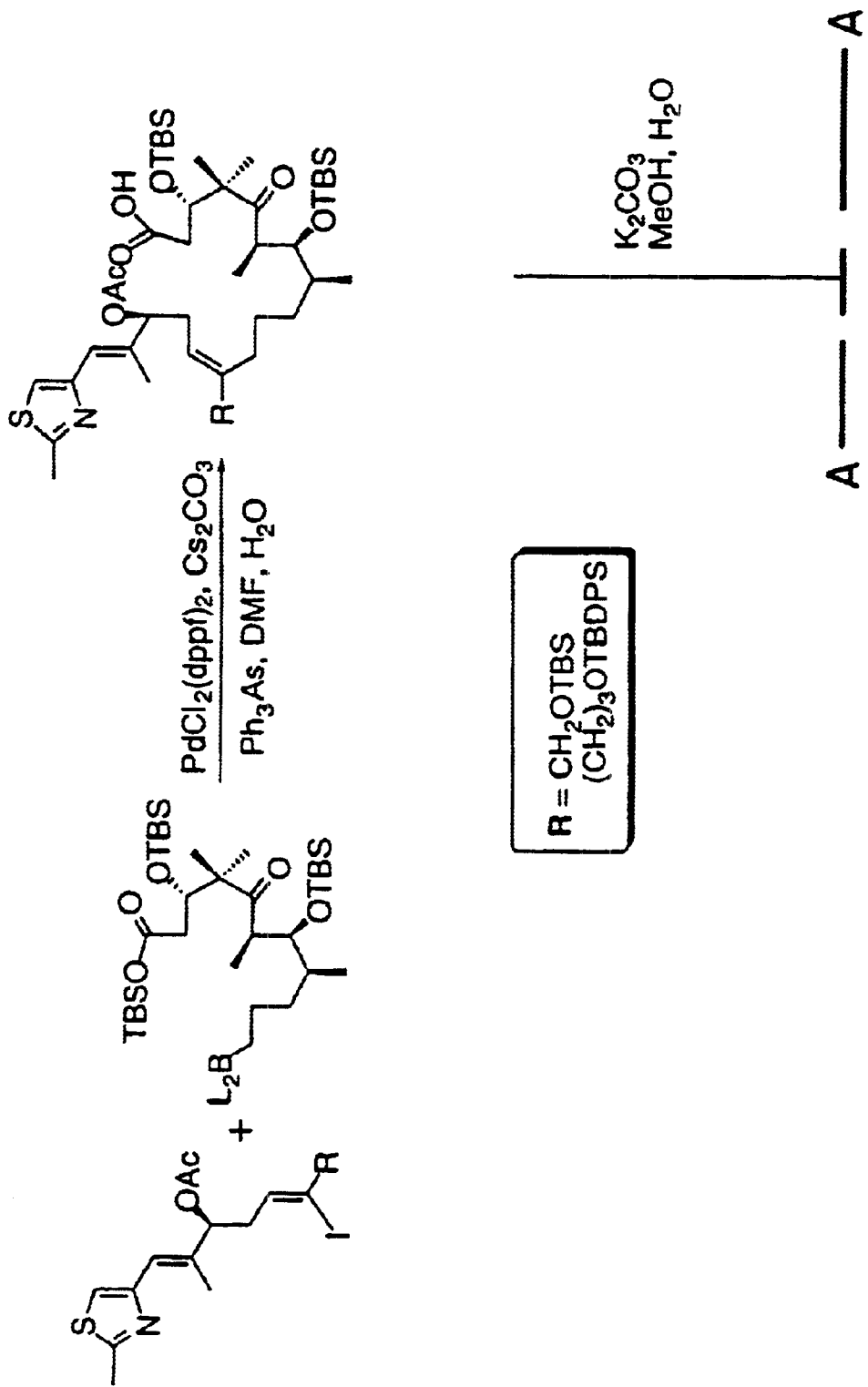
FIGS. 3(C) and 3(D) provide methods of preparing hydroxymethylene- and hydroxypropylene-substituted epothilone derivatives, said methods being useful generally to prepare 12,13-E epothilones wherein R is methyl, ethyl, n-propyl, and n-hexyl from the corresponding E-vinyl iodides.
Figure 3D:
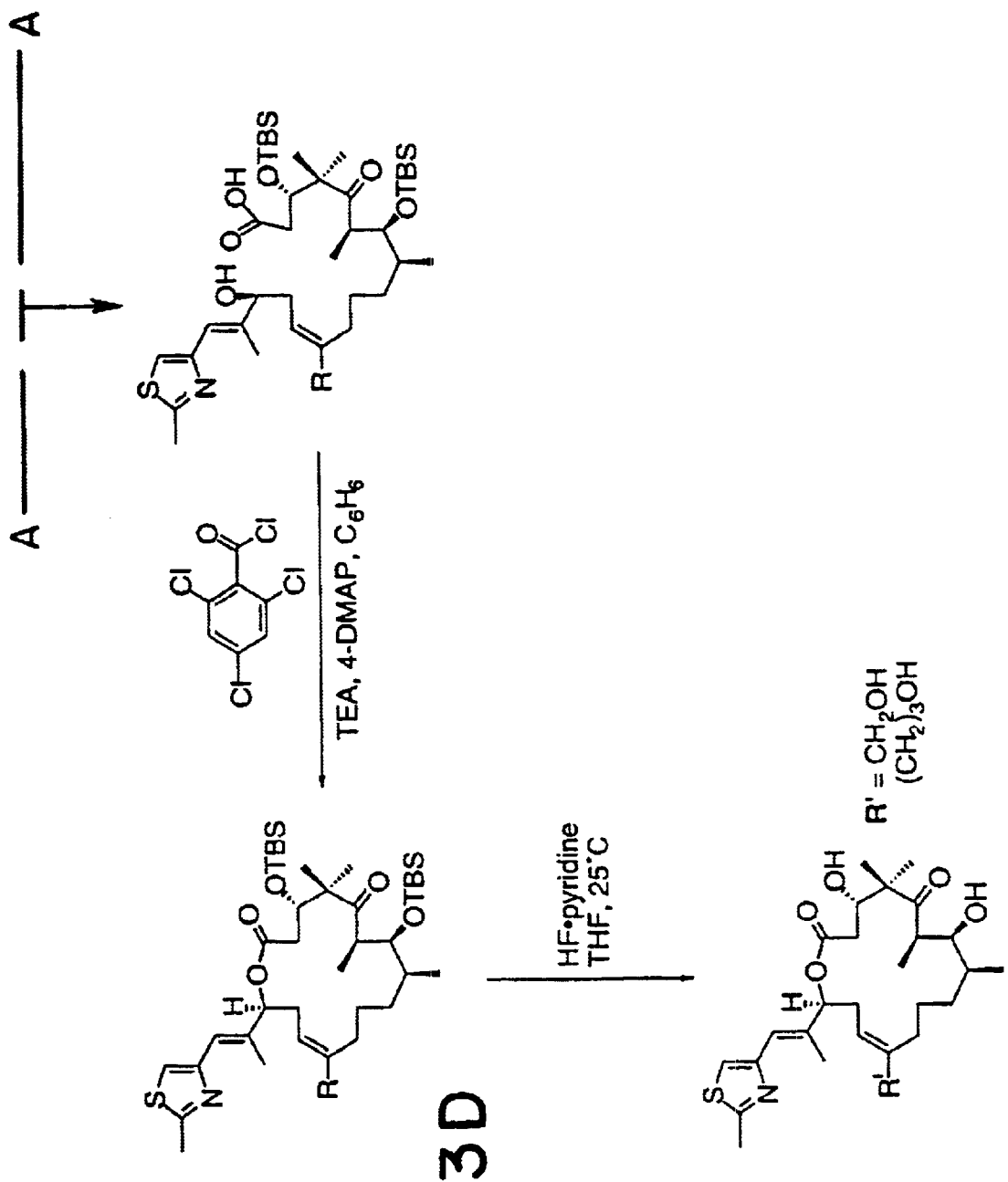
Figure 3E:
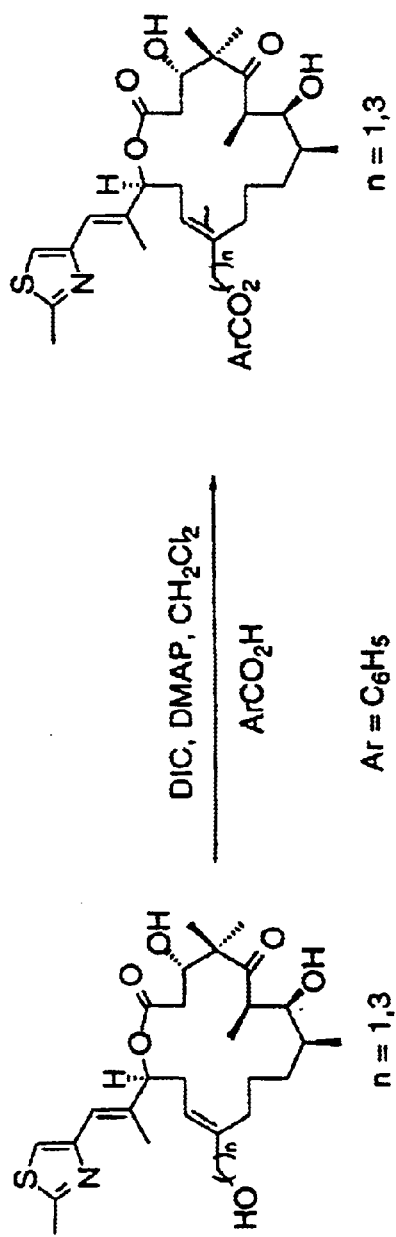
FIGS. 3(E) and 3(F) show reactions leading to benzoylated hydroxymethyl-substituted desoxyepothilone and hydroxymethylene-substituted epothilone (epoxide).
Figure 3F:
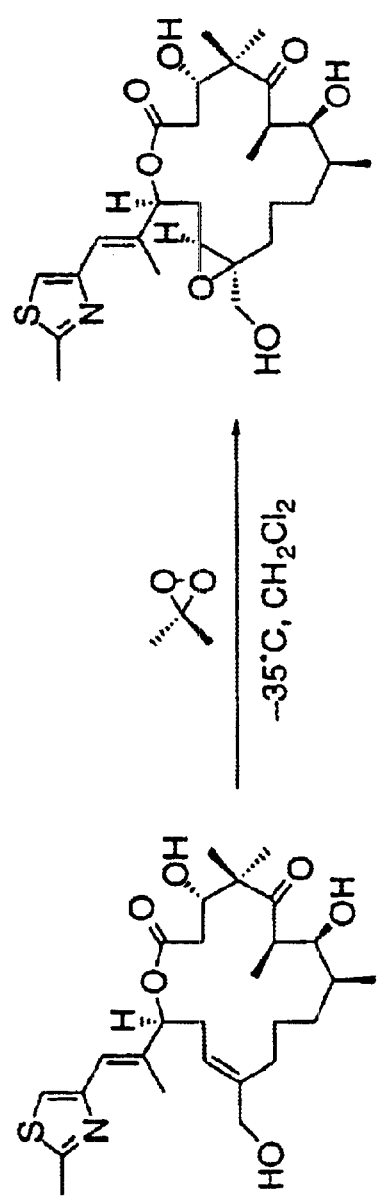

As used herein, the term "linear or branched chain alkyld" encompasses, but is not limited to, methyl, ethyl, propyl, isopropyl, t-butyl, sec-butyl, cyclopentyl or cyclohexyl. The alkyl group may contain one carbon atom or as many as fourteen carbon atoms, but preferably contains one carbon atom or as many as nine carbon atoms, and may be substituted by various groups, which include, but are not limited to, acyl, aryl, alkoxy, aryloxy, carboxy, hydroxy, carboxamido and/or N-acylamino moieties.

As used herein, the terms "alkoxycarbonyl", "acyl" and "alkoxy" encompass, but are not limited to, methoxycarbonyl, ethoxycarbonyl, propoxycarbonyl, n-butoxycarbonyl, benzyloxycarbonyl, hydroxypropylcarbonyl, aminoethoxycarbonyl, sec-butoxycarbonyl and cyclopentyloxycarbonyl. Examples of acyl groups include, but are not limited to, formyl, acetyl, propionyl, butyryl and penanoyl. Examples of alkoxy groups include, but are not limited to, methoxy, ethoxy, propoxy, n-butoxy, sec-butoxy and cyclopentyloxy.

As used herein, an "aryl" encompasses, but is not limited to, a phenyl, pyridyl, pyrryl, indolyl, naphthyl, thiophenyl or furyl group, each of which may be substituted by various groups, which include, but are not limited to, acyl, aryl alkoxy, aryloxy, carboxy, hydroxy, carboxamido or N-acylamino moieties. Examples of aryloxy groups include, but are not limited to, a phenoxy, 2-methylphenoxy, 3-methylphenoxy and 2-naphthoxy. Examples of acyloxy groups include, but are not limited to, acetoxy, propanoyloxy, butyryloxy, pentanoyloxy and hexanoyloxy.

The subject invention provides chemotherapeutic analogues of epothilone A and B, including a compound having the structure:

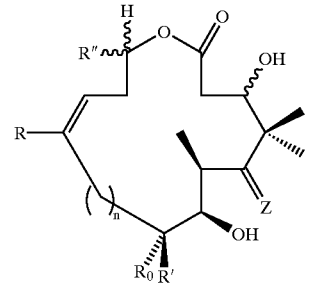

wherein R, R$_0$, and R' are independently H, linear or branched chain alkyl, optionally substituted by hydroxy, alkoxy, fluorine, NR$_1$R$_2$, N-hydroximino, or N-alkoxyimino, wherein R$_1$ and R$_2$ are independently H, phenyl, benzyl, linear or branched chain alkyl; wherein R" is —CHY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; and wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein Z is O, N(OR$_3$) or N—NR$_4$R$_5$, wherein R$_3$, R$_4$ and R$_5$ are independently H or a linear or branched alkyl; and wherein n is 0, 1, 2, or 3. In one embodiment, the invention provides the compound having the structure:

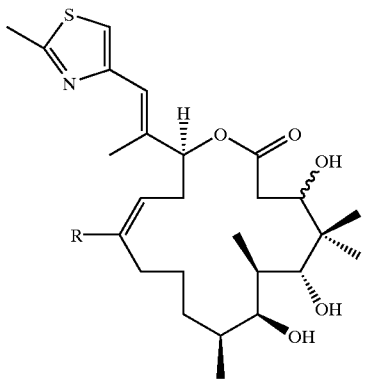

wherein R is H, methyl, ethyl, n-propyl, n-butyl, n-hexyl, CH₂OH, or (CH₂)₃OH.

The invention also provides a compound having the structure:

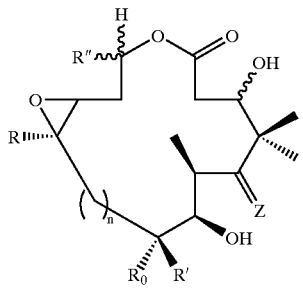

wherein R, R₀, and R' are independently H, linear or branched chain alkyl, optionally substituted by hydroxy, alkoxy, fluorine, NR₁R₂, N-hydroximino, or N-alkoxyimino, wherein R₁ and R₂ are independently H, phenyl, benzyl, linear or branched chain alkyl; wherein R" is —CHY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; and wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6indolyl; wherein Y is H or linear or branched chain alkyl; wherein Z is O, N(OR₃) or N—NR₄R₅ wherein R₃, R₄ and R₅ are independently H or a linear or branched chain alkyl; and wherein n is 0, 1, 2, or 3. In a certain embodiment, the invention provides a compound having the structure:

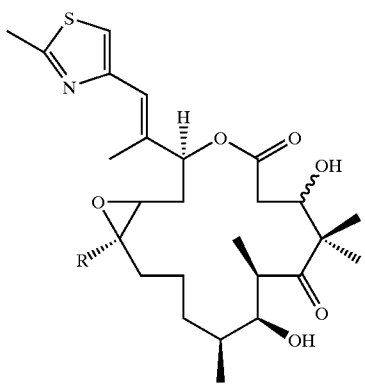

wherein R is H, methyl, ethyl, n-propyl, n-butyl, n-hexyl or CH₂OH.

In addition, the invention provides a compound having the structure:

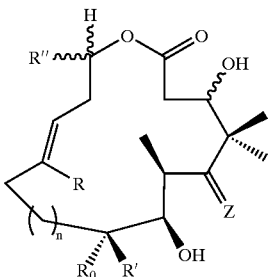

wherein R, R₀, and R' are independently H, linear or branched chain alkyl, optionally substituted by hydroxy, alkoxy, fluorine, NR₁R₂, N-hydroximino, or N-alkoxyimino, wherein R₁ and R₂ are independently H, phenyl, benzyl, linear or branched chain alkyl; wherein R" is —CHY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; and wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein Z is O, N(OR₃) or N—NR₄R₅, wherein R₃, R₄ and R₅ are independently H or a linear or branched chain alkyl; and wherein n is 0, 1, 2, or 3. In particular, the invention provides a compound having the structure:

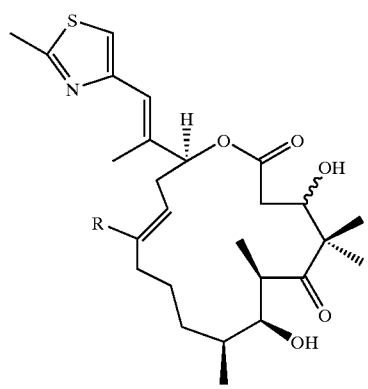

wherein R is H, methyl, ethyl, n-propyl, n-butyl, CH₂OH or (CH₂)₃OH.

The invention further provides a compound having the structure:

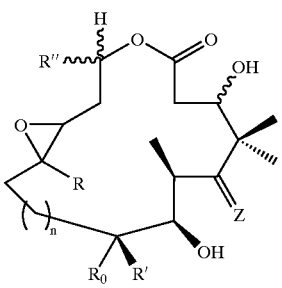

wherein R, $R_5$ and R' are independently H, linear or branched chain alkyl, optionally substituted by hydroxy, alkoxy, fluorine, $NR_1R_2$, N-hydroximino or N-alkoxyimino, wherein $R_1$ and $R_2$ are independently H, phenyl, benzyl, linear or branched chain alkyl; wherein R" is —CHY=CHX, or H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; and wherein X is H, linear or branched chain alkyl, phenyl, 2-methyl-1,3-thiazolinyl, 2-furanyl, 3-furanyl, 4-furanyl, 2-pyridyl, 3-pyridyl, 4-pyridyl, imidazolyl, 2-methyl-1,3-oxazolinyl, 3-indolyl or 6-indolyl; wherein Y is H or linear or branched chain alkyl; wherein Z is O, $N(OR_3)$ or $N-NR_4R_5$, wherein $R_3$, $R_4$ and $R_5$ are independently H or a linear or branched chain alkyl; and wherein n is 0, 1, 2 or 3.

The invention also provides a compound having the structure:

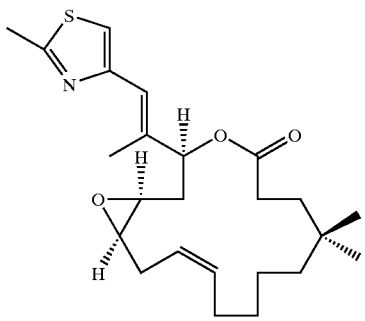

The subject invention also provides various intermediates useful for the preparation of the chemotherapeutic compounds epithilone A and B, as well as analogues thereof. Accordingly, the invention provides a key intermediate to epothilone A and its analogues having the structure:

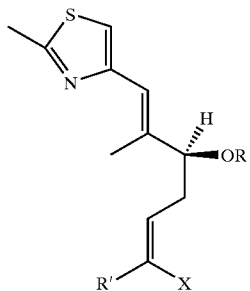

wherein R is hydrogen, a linear or branched acyl, substituted or unsubstituted aroyl or benzoyl; wherein R' is hydrogen, methyl, ethyl, n-propyl, n-hexyl,

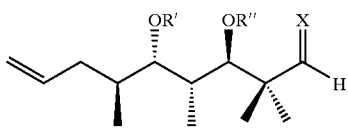

$CH_2OTBS$ or $(CH_2)_3$-OTBDPS; and X is a halide. In one embodiment, the subject invention provides a compound of the above structure wherein R is acetyl and X is iodo.

The subject invention also provides an intermediate having the structure:

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl; wherein X is oxygen, $(OR)_2$, $(SR)_2$, —(O—$(CH_2)_n$—O)—, —(O—$(CH_2)_n$—S)— or —(S—$(CH_2)_n$—S)—; and wherein n is 2, 3 or 4.

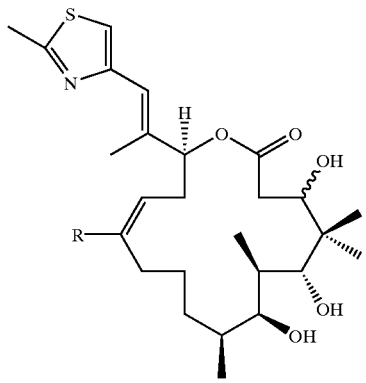

wherein R is H or methyl.

Another analogue provided by the invention has the structure:

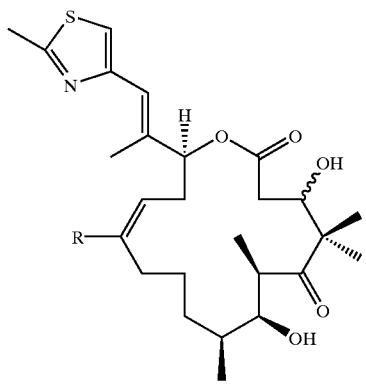

wherein R is H, methyl, ethyl, n-propyl, n-butyl, n-hexyl, $CH_2OH$, or $(CH_2)_3OH$.

Additionally, the subject invention provides an analogue having the structure:

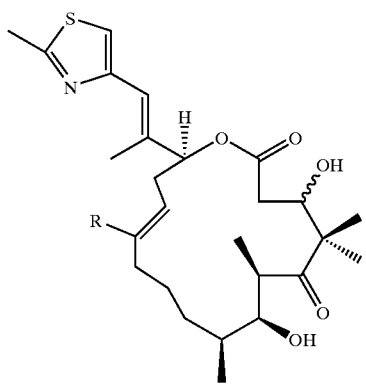

wherein R is H or methyl. The scope of the present invention includes compounds wherein the $C_3$ carbon therein possesses either an R or S absolute configuration, as well as mixtures thereof.

The subject invention further provides an analogue of epothilone A having the structure:

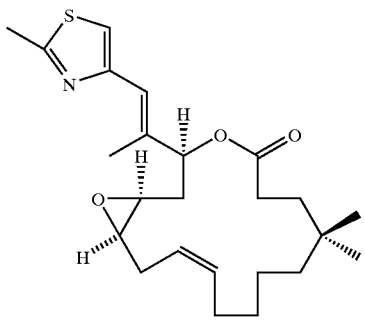

The subject invention also provides synthetic routes to prepare the intermediates for preparing epothilones. Accordingly, the invention provides a method of preparing a Z-iodoalkene ester having the structure:

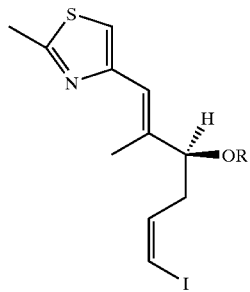

wherein R is hydrogen, a linear or branched alkyl, alkoxyalkyl, substituted or unsubstituted aryloxyalkyl, linear or branched acyl, substituted or unsubstituted aroyl or benzoyl, which comprises (a) coupling a compound having the structure:

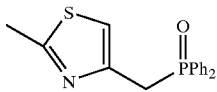

with a methyl ketone having the structure:

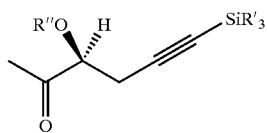

wherein R' and R" are independently a linear or branched alkyl, alkoxyalkyl, substituted or unsubstituted aryl or benzyl, under suitable conditions to form a compound having the structure:

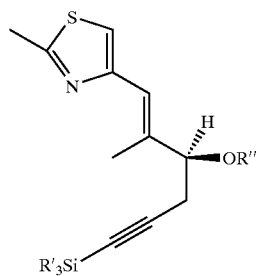

(b) treating the compound formed in step (a) under suitable conditions to form a Z-iodoalkene having the structure:

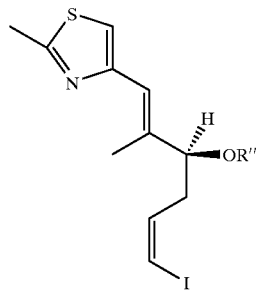

and (c) deprotecting and acylating the Z-iodoalkene formed in step (b) under suitable conditions to form the Z-iodoalkene ester. The coupling in step (a) may be effected using a strong base such as n-BuLi in an inert polar solvent such as tetrahydrofuran (THF) at low temperatures, typically below −50° C., and preferably at −78° C. The treatment in step (b) may comprise sequential reaction with N-iodosuccinimide in the presence of Ag(I), such as silver nitrate, in a polar organic solvent such as acetone, followed by reduction conditions, typically using a hydroborating reagent, preferably using $Cy_2BH$. Deprotecting step (c) involves contact with a thiol such as thiophenol in the presence of a Lewis acid catalyst, such as boron trifluoride-etherate in an inert organic solvent such as dichloromethane, followed by acylation with an acyl halide, such as acetyl chloride, or an acyl anhydride, such as acetic anhydride in the presence of a mild base such as pyridine and/or 4-dimethyaminopyridine (DMAP) in an inert organic solvent such as dichloromethane.

The subject invention also provides a method of preparing a Z-haloalkene ester having the structure:

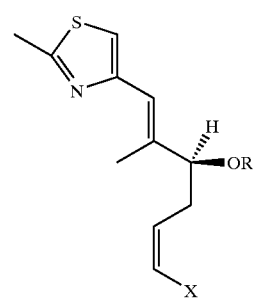

wherein R is hydrogen, a linear or branched alkyl, alkoxyalkyl, substituted or unsubstituted aryloxyalkyl, linear or branched acyl, substituted or unsubstituted aroyl or benzoyl; and wherein X is a halogen, which comprises (a) oxidatively cleaving a compound having the structure:

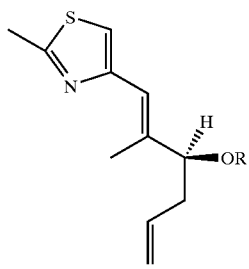

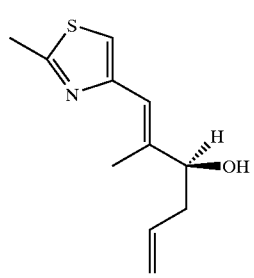

under suitable conditions to form an aldehyde intermediate; and (b) condensing the aldehyde intermediate with a halomethylene transfer agent under suitable conditions to form the Z-haloalkene ester. In one embodiment of the method, X is iodine. In another embodiment, the method is practiced wherein the halomethylene transfer agent is $Ph_3P\!=\!CHI$ or $(Ph_3P^+CH_2I)I^-$. Disubstituted olefins may be prepared using the haloalkylidene transfer agent $Ph_3P\!=\!CR'I$, wherein R' is hydrogen, methyl, ethyl, n-prop-yl, n-hexyl,

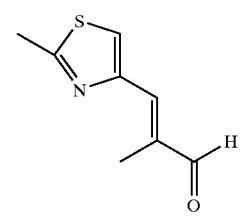

$CO_2Et$ or $(CH_2)_3OTBDPS$. The oxidative step (a) can be performed using a mild oxidant such as osmium tetraoxide at temperatures of about 0° C., followed by treatment with sodium periodate, or with lead tetraacetate/sodium carbonate, to complete the cleavage of the terminal olefin, and provide a terminal aldehyde. Condensing step (b) occurs effectively with a variety of halomethylenating reagents, such as Wittig reagents.

The subject invention further provides a method of preparing an optically pure compound having the structure:

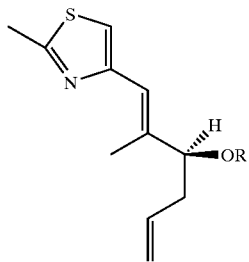

wherein R is hydrogen, a linear or branched alkyl, alkoxyalkyl, substituted or unsubstituted aryloxyalkyl; linear or branched acyl, substituted or unsubstituted aroyl or benzoyl, which comprises: (a) condensing an allylic organometallic reagent with an unsaturated aldehyde having the structure:

under suitable conditions to form an alcohol, and, optionally concurrently therewith, optically resolving the alcohol to form an optically pure alcohol having the structure:

(b) alkylating or acylating the optically pure alcohol formed in step (a) under suitable conditions to form the optically pure compound. In one embodiment of the method, the allylic organometallic reagent is an allyl(trialkyl)stannane. In another embodiment, the condensing step is effected using a reagent comprising a titanium tetraalkoxide and an optically active catalyst. In step (a) the 1,2-addition to the unsaturated aldehyde may be performed using a variety of allylic organometallic reagents, typically with an allyltrialkylstannane, and preferably with allyltri-n-butylstannane, in the presence of chiral catalyst and molecular sieves in an inert organic solvent such as dichloromethane. Preferably, the method may be practiced using titanium tetraalkoxides, such as titanium tetra-n-propoxide, and S-(-)BINOL as the optically active catalyst. Alkylating or acylating step (b) is effected using any typical alkylating agent, such as alkylhalide or alkyl tosylate, alkyl triflate or alkyl mesylate, any typical acylating agent, such as acetyl chloride, acetic anhydride, benzoyl chloride or benzoyl anhydride, in the presence of a mild base catalyst in an inert organic solvent, such as dichloromethane.

The subject invention also provides a method of preparing an open-chain aldehyde having the structure:

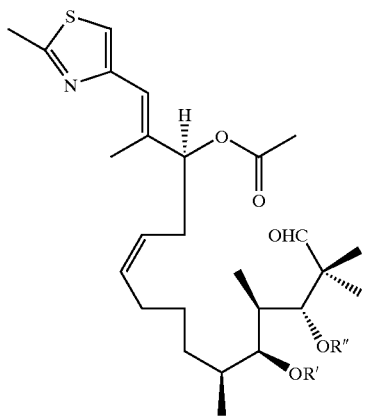

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, which comprises: (a) cross-coupling a haloolefin having the structure:

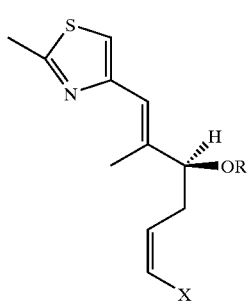

wherein R is a linear or branched alkyl, alkoxyalkyl, substituted or unsubstituted aryloxyalkyl, trialkylsilyl, aryldialkylsilyl, diarylalkylsilyl, triarylsilyl, linear or branched acyl, substituted or unsubstituted aroyl or benzoyl, and X is a halogen, with a terminal olefin having the structure:

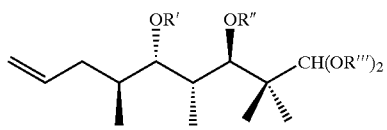

—wherein $(OR''')_2$ is $(OR_0)_2$, $(SR_0)_2$, —(O—$(CH_2)_n$—O)—, —(O—$(CH_2)_n$—S)— or —(S—$(CH_2)_n$—S)— where $R_0$ is a linear or branched alkyl, substituted or unsubstituted aryl or benzyl; and wherein n is 2, 3 or 4, under suitable conditions to form a cross-coupled compound having the structure:

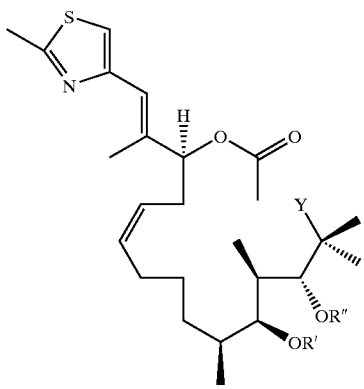

wherein Y is $CH(OR^*)_2$ where $R^*$ is a linear or branched alkyl, alkoxyalkyl, substituted or unsubstituted aryloxyalkyl; and (b) deprotecting the cross-coupled compound formed in step (a) under suitable conditions to form the open-chain compound. Cross-coupling step (a) is effected using reagents known in the art which are suited to the purpose. For example, the process may be carried out by hydroborating the pre-acyl component with 9-BBN. The resulting mixed borane may then be cross-coupled with an organometallic catalyst such as $PdCl_2(dppf)_2$, or any known equivalent thereof, in the presence of such ancillary reagents as cesium carbonate and triphenylarsine. Deprotecting step (b) can be carried out with a mild acid catalyst such as p-tosic acid, and typically in a mixed aqueous organic solvent system, such as dioxane-water. The open-chain compound can be cyclized using any of a variety of non-nucleophilic bases, such as potassium hexamethyldisilazide or lithium diethyamide.

The subject invention also provides a method of preparing an epothilone having the structure:

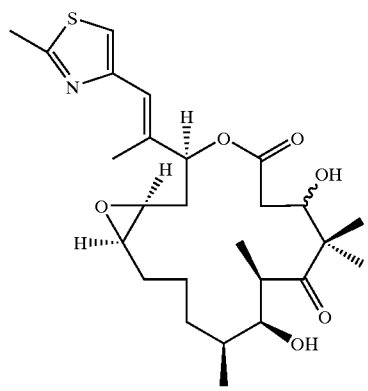

which comprises: (a) deprotecting a cyclized compound having the structure:

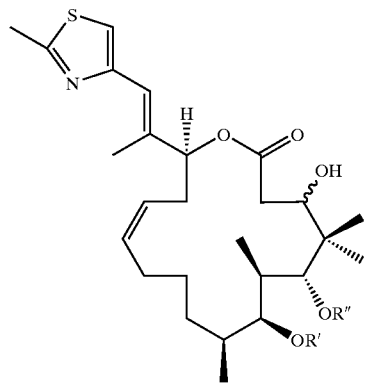

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, under suitable conditions to form a deprotected cyclized compound and oxidizing the deprotected cyclized compound under suitable conditions to form a desoxyepothilone having the structure:

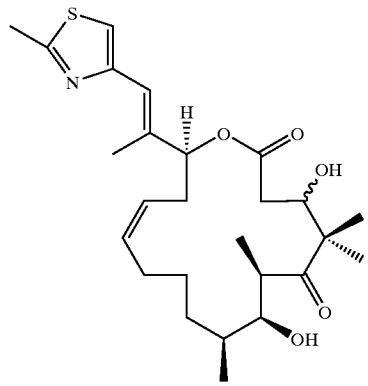

and (b) epoxidizing the desoxyepothilone formed in step (a) under suitable conditions to form the epothilone. Deprotecting step (a) is effected using a sequence of treatments comprising a catalyst such as HF-pyridine, followed by t-butyidimethylsilyl triflate in the presence of a base such as lutidine. Dess-Martin oxidation and further deprotection with a catalyst such as HF-pyridine provides the desoxyepothilone. The latter compound can then be epoxidized in step (b) using any of a variety of epoxidizing agents, such acetic peracid, hydrogen peroxide, perbenzoic acid, m-chloroperbenzoic acid, but preferably with dimethyldioxirane, in an inert organic solvent such as dichloromethane.

The subject invention further provides a method of preparing an epothilone precursor having the structure:

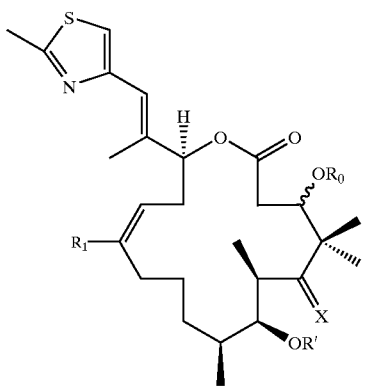

wherein $R_1$ is hydrogen or methyl; wherein X is O, or a hydrogen and OR", each singly bonded to carbon; and wherein $R_0$, R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, which comprises (a) coupling a compound having the structure:

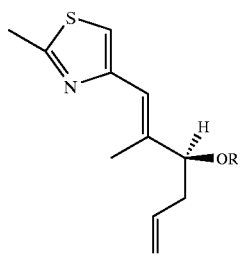

wherein R is an acetyl, with an aldehyde having the structure:

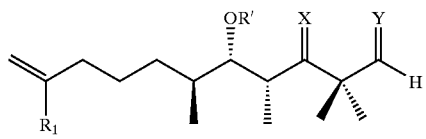

wherein Y is oxygen, under suitable conditions to form an aldol intermediate and optionally protecting the aldol intermediate under suitable conditions to form an acyclic epthilone precursor having the structure:

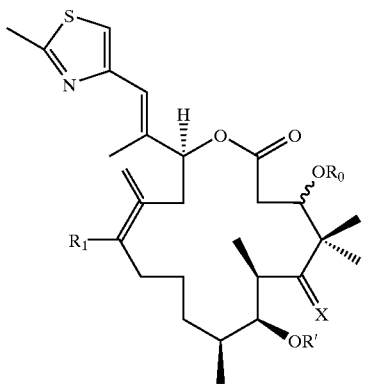

(b) subjecting the acylic epothilone precursor to conditions leading to intramolecular olefin metathesis to form the epothilone precursor. In one embodiment of the method, the conditions leading to intramolecular olefin metathesis require the presence of an organometallic catalyst. In a certain specific embodiment of the method, the catalyst contains Ru or Mo. The coupling step (a) may be effected using a nonnucleophilic base such as lithium diethylamide or lithium diisopropylamide at subambient temperatures, but preferably at about −78° C. The olefin metathesis in step (b) may be carried out using any catalyst known in the art suited for the purpose, though preferably using one of Grubbs's catalysts.

In addition, the present invention provides a compound useful as an intermediate for preparing epothilones having the structure:

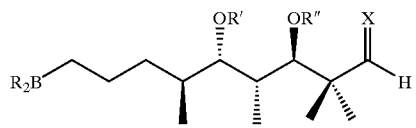

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl; wherein X is oxygen, $(OR^*)_2$, $(SR^*)_2$, $-O-(CH_2)_n-$, $-O-(CH_2)_n-S-$ or $-S-(CH_2)_n-S-$; wherein $R^*$ is a linear or branched alkyl, substituted or unsubstituted aryl or benzyl; wherein $R_2B$ is a linear, branched or cyclic boranyl moiety; and wherein n is 2, 3 or 4. In certain embodiments, the invention provides the compound wherein R' is TBS, R" is TPS and X is $(OMe)_2$. A preferred example of $R_2B$ is derived from 9-BBN.

The invention also provides the compound having the structure:

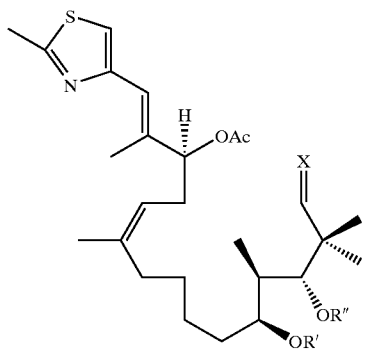

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl; wherein X is oxygen, $(OR)_2$, $(SR)_2$, $-O-(CH_2)_n-O-$, $-O-(CH_2)_n-S-$ or $-S-(CH_2)_n-S-$; and wherein n is 2, 3 or 4. In certain embodiments, the invention provides the compound wherein R' is TBS, R" is TPS and X is $(OMe)_2$.

The invention further provides a desmethylepothilone analogue having the structure:

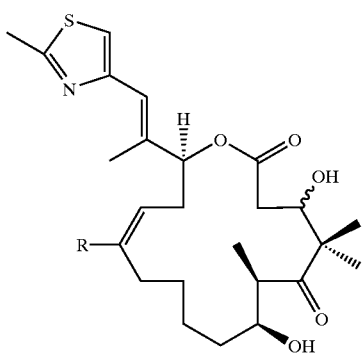

wherein R is H or methyl.

The invention provides a compound having the structure:

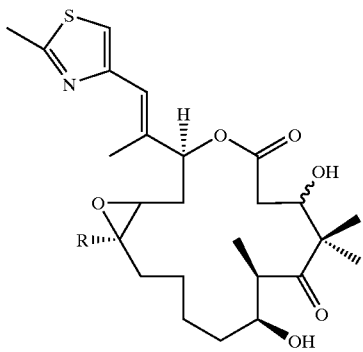

wherein R is H or methyl.

The invention also provides a trans-desmethyldeoxyepothilone analogue having the structure:

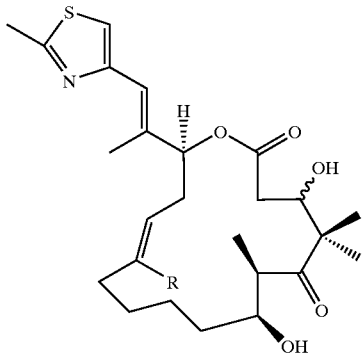

wherein R is H or methyl.

The invention also provides a trans-epothilone having the structure:

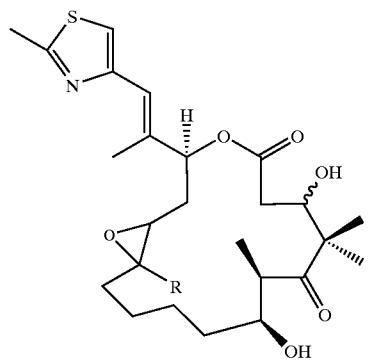

wherein R is H or methyl.

The invention also provides a compound having the structure:

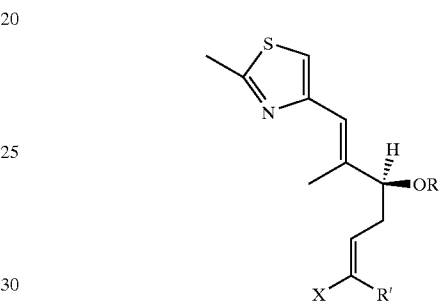

wherein R is hydrogen, a linear or branched alkyl, alkoxyalkyl, substituted or unsubstituted aryloxyalkyl, linear or branched acyl, substituted or unsubstituted aroyl or benzoyl; wherein R' is hydrogen, methyl, ethyl, n-propyl, n-hexyl,

$CO_2Et$ or $(CH_2)_3OTBDPS$.

and X is a halogen. In certain embodiments, the invention provides the compound wherein R is acetyl and X is iodine.

The invention additionally provides a method of preparing an open-chain aldehyde having the structure:

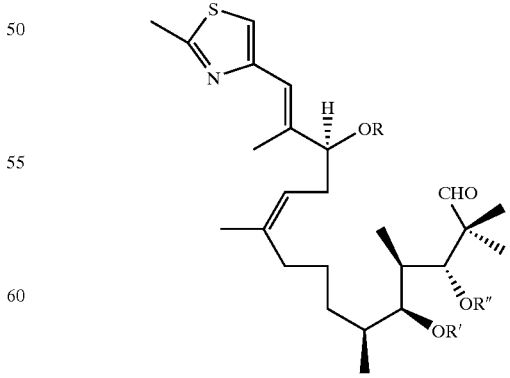

wherein R is a linear or branched alkyl, alkoxyalkyl, substituted or unsubstituted aryloxyalkyl, trialkylsilyl, aryldialkylsilyl, diarylalkylsilyl, triarylsilyl, linear or branched acyl, substituted or unsubstituted aroyl or benzoyl; and wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, which comprises:

(a) cross-coupling a haloolefin having the structure:

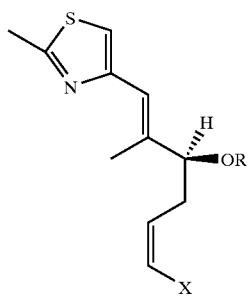

wherein X is a halogen, with a terminal borane having the structure:

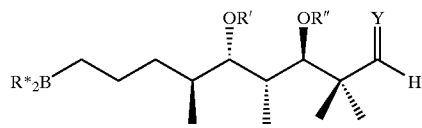

wherein $R^*_2B$ is a linear, branched or cyclic alkyl or substituted or unsubstituted aryl or benzyl boranyl moiety; and wherein Y is $(OR_0)_2$, $(SR_0)_2$, —O—$(CH_2)_n$—O—, —O—$(CH_2)_n$—S— or —S—$(CH_2)_n$—S— where $R_0$ is a linear or branched alkyl, substituted or unsubstituted aryl or benzyl; and wherein n is 2, 3 or 4, under suitable conditions to form a cross-coupled compound having the structure:

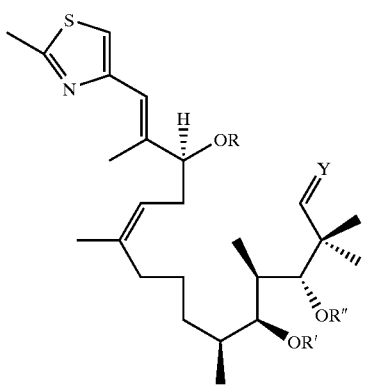

and (b) deprotecting the cross-coupled compound formed in step (a) under suitable conditions to form the open-chain aldehyde. In certain embodiments, the invention provides the method wherein R is acetyl; R' is TBS; R" is TPS; $R^*_2B$ is derived from 9-BBN; and Y is $(OMe)_2$. Cross-coupling step (a) is effected using reagents known in the art which are suited to the purpose. For example, the mixed borane may be cross-coupled with an organometallic catalyst such as $PdCl_2(dppf)_2$, or any known equivalent thereof, in the presence of such reagents as cesium carbonate and triphenylarsine. Deprotecting step (b) can be carried out using a mild acid catalyst such as p-tosic acid, typically in a mixed aqueous organic solvent system, such as dioxane-water.

The invention also provides a method of preparing a protected epothilone having the structure:

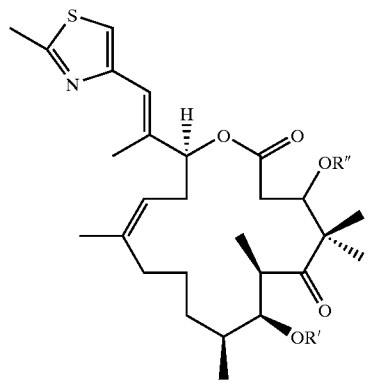

wherein R' and R" are independently hydrogen, a linear or branched alkyl, substituted or unsubstituted aryl or benzyl, trialkylsilyl, dialkyl-arylsilyl, alkyldiarylsilyl, a linear or branched acyl, substituted or unsubstituted aroyl or benzoyl, which comprises:

(a) monoprotecting a cyclic diol having the structure:

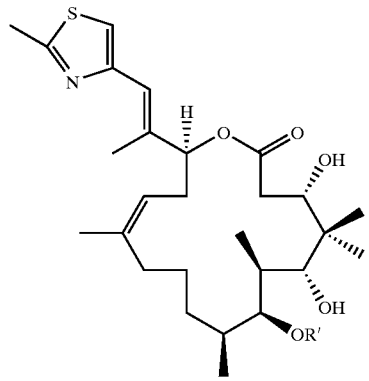

under suitable conditions to form a cyclic alcohol having the structure:

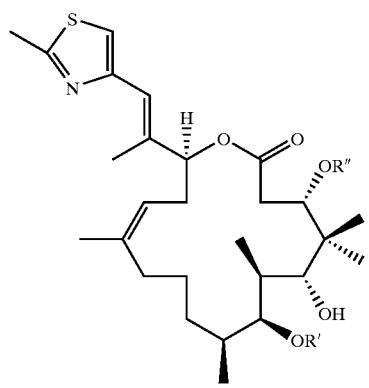

and (b) oxidizing the cyclic alcohol formed in step (a) under suitable conditions to form the protected epothilone. In certain embodiments, the invention provides the method wherein R' and R" are TBS. The monoprotecting step (a) may be effected using any of a variety of suitable reagents, including TBSOTf in the presence of a base in an inert organic solvent. The base may be a non-nucleophilic base such as 2,6-lutidine, and the solvent may be dichloromethane. The reaction is conducted at subambient temperatures, preferably in the range of −30° C. The oxidizing step (b) utilizes a selective oxidant such as Dess-Martin periodinane in an inert organic solvent such as dichloromethane. The oxidation is carried out at ambient temperatures, preferably at 20–25° C.

The invention further provides a method of preparing an epothilone having e structure:

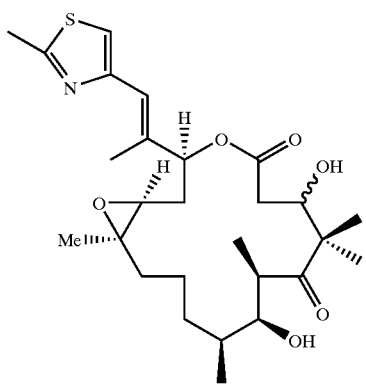

which comprises:

(a) deprotecting a protected cyclic ketone having the structure:

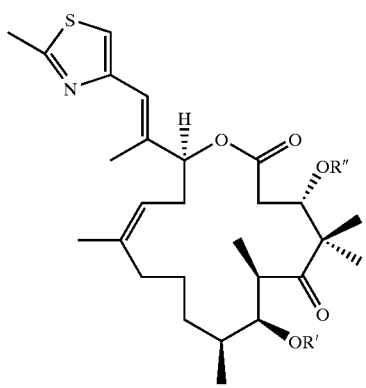

wherein R' and R" are independently hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, under suitable conditions to form a desoxyepothilone having the structure:

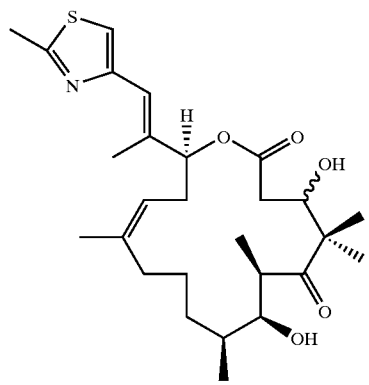

and (b) epoxidizing the desoxyepothilone formed in step (a) under suitable conditions to form the epothilone. In certain embodiments, the invention provides the method wherein R' and R" are TBS. Deprotecting step (a) is carried out by means of a treatment comprising a reagent such as HF-pyridine. The deprotected compound can be epoxidized in step (b) using an epoxidizing agent such acetic peracid, hydrogen peroxide, perbenzoic acid, m-chloroperbenzoic acid, but preferably with dimethyidioxirane, in an inert organic solvent such as dichloromethane.

The invention also provides a method of preparing a cyclic diol having the structure:

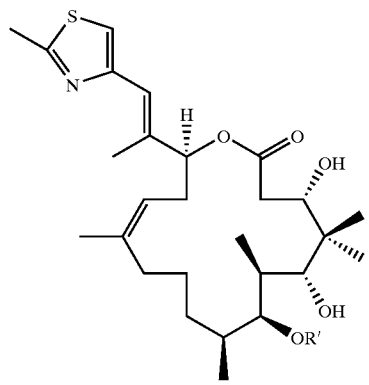

wherein R' is a hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl, which comprises:

(a) cyclizing an open-chain aldehyde having the structure:

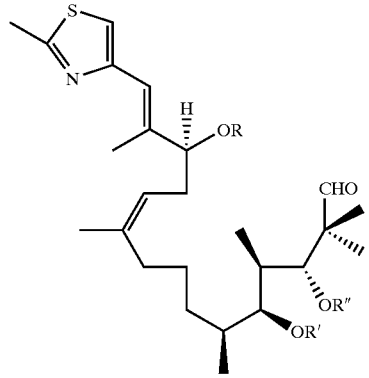

wherein R is a linear or branched alkyl, alkoxyalkyl, substituted or unsubstituted aryloxyalkyl, trialkylsilyl, aryldialkylsilyl, diarylalkylsilyl, triarylsilyl, linear or branched acyl, substituted or unsubstituted aroyl or benzoyl; and wherein R" is a hydrogen, a linear or branched alkyl, substituted or unsubstituted aryl or benzyl, trialkylsilyl, dialkylarylsilyl, alkyldiarylsilyl, a linear or branched acyl, substituted or unsubstituted aroyl or benzoyl under suitable conditions to form an enantiomeric mixture of a protected cyclic alcohol having the structure:

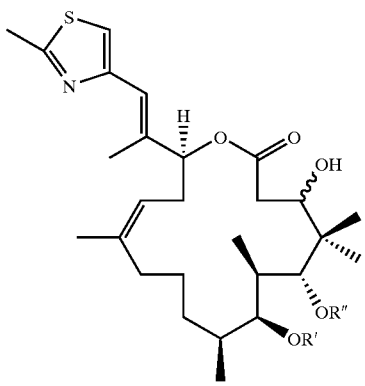

said mixture comprising an α- and a β-alcohol component;

(b) optionally isolating and oxidizing the α-alcohol formed in step (a) under suitable conditions to form a ketone and thereafter reducing the ketone under suitable conditions to form an enantiomeric mixture of the protected cyclic alcohol comprising substantially the β-alcohol; and (c) treating the protected cyclic alcohol formed in step (a) or (b) with a deprotecting agent under suitable conditions to form the cyclic diol. In certain embodiments, the invention provides the method wherein R' is TBS and R" is TPS. Cyclizing step (a) is performed using any of a variety of mild nonnucleophilic bases such as KHMDS in an inert solvent such as THF. The reaction is carried out at subambient temperatures, preferably between −90° C. and −50° C., more preferably at −78° C. Isolation of the unnatural alpha-OH diastereomer is effected by any purification method, including any suitable type of chromatography or by crystallization. Chromatographic techniques useful for the purpose include high pressure liquid chromatography, countercurrent chromatography or flash chromatography. Various column media are suited, including, inter alia, silica or reverse phase support. The beta-OH derivative is then oxidized using a selective oxidant, such as Dess-Martin periodinane. The resulting ketone is the reduced using a selective reductant. Various hydridoborane and aluminum hydride reagents are effective. A preferred reducing agent is sodium borohydride. Treating step (c) may be effected using a variety of deprotecting agents, including HF-pyridine.

In addition, the invention provides a method of treating cancer in a subject suffering therefrom comprising administering to the subject a therapeutically effective amount of any of the analogues related to epothilone B disclosed herein optionally in combination with a pharmaceutically suitable carrier. The method may be applied where the cancer is a solid tumor or leukemia. In particular, the method is applicable where the cancer is breast cancer or melanoma.

The subject invention also provides a pharmaceutical composition for treating cancer comprising any of the analogues of epothilone disclosed hereinabove, as an active ingredient, optionally though typically in combination with a pharmaceutically suitable carrier. The pharmaceutical compositions of the present invention may further comprise other therapeutically active ingredients.

The subject invention further provides a method of treating cancer in a subject suffering therefrom comprising administering to the subject a therapeutically effective amount of any of the analogues of epothilone disclosed hereinabove and a pharmaceutically suitable carrier. The method is especially useful where the cancer is a solid tumor or leukemia.

The compounds taught above which are related to epothilones A and B are useful in the treatment of cancer, and particularly, in cases where multidrug resistance is present, both in vivo and in vitro. The ability of these compounds as non-substrates of MDR in cells, as demonstrated in the Tables below, shows that the compounds are useful to treat, prevent or ameliorate cancer in subjects suffering therefrom.

The magnitude of the therapeutic dose of the compounds of the invention will vary with the nature and severity of the condition to be treated and with the particular compound and its route of administration. In general, the daily dose range for anticancer activity lies in the range of 0.001 to 25 mg/kg of body weight in a mammal, preferably 0.001 to 10 mg/kg, and most preferably 0.001 to 1.0 mg/kg, in single or multiple doses. In unusual cases, it may be necessary to administer doses above 25 mg/kg.

Any suitable route of administration may be employed for providing a mammal, especially a human, with an effective dosage of a compound disclosed herein. For example, oral, rectal, topical, parenteral, ocular, pulmonary, nasal, etc., routes may be employed. Dosage forms include tablets, troches, dispersions, suspensions, solutions, capsules, creams, ointments, aerosols, etc.

The compositions include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disintegrating agents, etc., in the case of oral solid preparations are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general compositions are prepared by uniformly and intimately admixing the active ingredient with liquid carriers, finely divided solid carriers; or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent or surface active or dispersing agent. Molded tablets may be made by molding in a suitable machine, a mixture of the powdered compound moistened with an inert liquid diluent.

The present invention will be better understood from the Experimental Details which follow. However, one skilled in the art will readily appreciate that the specific methods and results discussed are merely illustrative of the invention as described in the claims which follow thereafter. It will be understood that the processes of the present invention for preparing epothilones A and B, analogues thereof and intermediates thereto encompass the use of various alternate protecting groups known in the art. Those protecting groups used in the disclosure including the Examples below are merely illustrative.

EXAMPLE 1

THP glycidol: 13; A solution of (R)-(+)-glycidol 12 (20 g; 270 mmol) and freshly distilled 3,4-dihydro-2H-pyran (68.1 g; 810 mmol) in $CH_2Cl_2$ (900 ml) was treated with pyridinium p-toluenesulfonate (2.1 g; 8.36 mmol) at rt and the resulting solution was stirred for 16 h. Approximately 500% of the solvent was then removed in vacuo and the remaining solution was diluted with ether (1 L). The organic layer was then washed with two portions of saturated aqueous sodium bicarbonate (500 ml), dried ($Na_2SO_4$), filtered, and concentrated. Purification of the residue by flash chromatography (silica, 25→50% ether:hexanes) afforded THP glycidol 13 (31.2 g; 73%) as a colorless liquid: IR(film): 2941, 1122, 1034 $cm^{-1}$; $^1H$ NMR($CDCl_3$, 500MHz) d 4.66(t, J=3.5 Hz, 1H), 4.64 (t, J=3.5 Hz, 1H), 3.93 (dd, J=11.7, 3.1 Hz, 1H), 3.86 (m, 2H), 3.73 (dd, J=11.8, 5.03 Hz, 1H), 3.67 (dd, J=11.8, 3.4 Hz, 1H), 3.51 (m, 2H), 3.40 (dd, J=11.7, 6.4, 1H), 3.18 (m, 2H), 2.80 (m, 2H), 2.67 (dd, J=5.2 2.7 Hz, 1H), 2.58 (dd, J=5.0, 2.7 Hz, 1H), 1.82 (m, 2H), 1.73 (m, 2H), 1.52 (m, 4H); $^{13}C$ NMR ($CDCl_3$, 125 MHz) d 98.9, 98.8, 68.5, 67.3, 62.4, 62.2, 50.9, 50.6, 44.6, 44.5, 30.5, 30.4, 25.4, 19.3, 19.2; $[\alpha]_D$=+4.98 (c=2.15, $CHCl_3$).

EXAMPLE 2

Alcohol 13a: Trimethylsilylacetylene (32.3 g; 329 mmol) was added via syringe to THF (290 ml), and the resulting solution was cooled to −78° C. and treated with n-butyllithium (154 ml of a 1.6 M solution in hexanes; 246.4 mmol). After 15 min, boron trifluoride diethyl etherate (34.9 g; 246 mmol) was added, and the resulting mixture was stirred for 10 min. A solution of epoxide 13 (26 g; 164.3 mmol) in THF (130 ml) was then added via a cannula and the resulting solution was stirred for 5.5 h at −78° C. The reaction was quenched by the addition of saturated aqueous sodium bicarbonate solution (250 ml) and the solution was allowed to warm to rt. The mixture was then diluted with ether (600 ml) and washed successively with saturated aqueous sodium bicarbonate solution (250 ml), water (250 ml), and brine (250 ml). The organic layer was then dried ($Na_2SO_4$), filtered, and concentrated in vacuo. Purification of the residue by flash chromatography (silica, 20% ether:hexanes) provided alcohol 13a (34 g; 76%).

EXAMPLE 3

MOM ether 13b: A solution of alcohol 13a (24 g; 88.9 mmol) and N,N-diisopropylethylamine (108 ml; 622 mmol) in anhydrous 1,2-dichloroethane (600 ml) was treated with chloromethyl methyl ether (17 ml; 196 mmol), and the resulting mixture was heated to 55° C. for 28 h. The dark mixture was then cooled to rt and treated with saturated aqueous sodium bicarbonate solution (300 ml). The layers were separated, and the organic layer was washed successively with saturated aqueous sodium bicarbonate solution (200 ml) and brine (200 ml). The organic layer was then dried ($MgSO_4$) and filtered through a pad of silica gel (ether rinse). Purification of the residue by flash chromatography (silica, 20–30% ether:hexanes) afforded MOM ether 13b (23.7 g; 85%) as a pale yellow oil.

EXAMPLE 4

Alcohol 14: A solution of THP ether 13b (20 g; 63.7 mmol) in methanol (90 ml) was treated with pyridinium p-toluenesulfonate (4.0 g; 15.9 mmol) and the resulting mixture was stirred at rt for 16 h. The reaction was then quenched by the addition of saturated aqueous sodium bicarbonate solution (100 ml), and the excess methanol was removed in vacuo. The residue was diluted with ether (300 ml), and the organic layer was washed successively with saturated aqueous sodium bicarbonate solution (200 ml) and brine (200 ml). The organic layer was dried ($MgSO_4$), filtered, and concentrated. Purification of the residue by flash chromatography (silica, 40–50% ether:hexanes) provided alcohol 14 (13.1 g; 95%) as a colorless oil.

EXAMPLE 5

Alcohol 14a: To a cooled (−78° C.) solution of oxalyl chloride (24.04 ml of a 2.0 M solution in $CH_2Cl_2$; 48.08 mmol) in $CH_2Cl_2$ (165 ml) was added anhydrous DMSO (4.6 ml; 64.1 mmol) in dropwise fashion. After 30 min, a solution of alcohol 14 (6.93 g; 32.05 mmol) in $CH_2Cl_2$ (65 ml+10 ml rinse) was added and the resulting solution was stirred at −78° C. for 40 min. Freshly distilled triethylamine (13.4 ml; 96.15 mmol) was then added, the cooling bath was removed, and the mixture was allowed to warm to 0° C. The reaction mixture was then diluted with ether (500 ml), and washed successively with two portions of water (250 ml) and one portion of brine (250 ml). The organic layer was then dried ($MgSO_4$), filtered, and concentrated.

The crude aldehyde (6.9 g) prepared in the above reaction was dissolved in ether (160 ml) and cooled to 0° C. Methylmagnesium bromide (32.1 ml of a 3.0 M solution in butyl ether; 96.15 mmol) was then added, and the solution was allowed to warm slowly to rt. After 10 h, the reaction mixture was cooled to 0° C. and the reaction was quenched by the addition of saturated aqueous ammonium chloride solution. The mixture was diluted with ether (200 ml) and washed successively with water (150 ml) and brine (150 ml). The organic layer was dried ($MgSO_4$), filtered, and concentrated. Purification of the residue by flash chromatography (silica, 40–50% ether:hexanes) provided alcohol 14a (6.3 g; 85% from 14).

EXAMPLE 6

Ketone 15: A solution of alcohol 14 (1.0 g; 4.35 mmol), 4 Å mol. sieves, and N-methylmorpholine-N-oxide (1.0 g;

8.7 mmol) in CH$_2$Cl$_2$ (20 ml) at rt was treated with a catalytic amount of tetra-n-propylammonium perruthenate, and the resulting black suspension was stirred for 3 h. The reaction mixture was then filtered through a pad of silica gel (ether rinse), and the filtrate was concentrated in vacuo. Purification of the residue by flash chromatography (silica, 10% ether:hexanes) afforded ketone 15 (924 mg; 93%) as a light yellow oil.

EXAMPLE 7

Alkene 17: A cooled (−78° C.) solution of phosphine oxide 16 (1.53 g; 4.88 mmol) in THF (15.2 ml) was treated with n-butyllithium (1.79 ml of a 2.45 M solution in hexanes). After 15 min, the orange solution was treated with a solution of ketone 15 (557 mg; 2.44 mmol) in THF (4.6 ml). After 10 min, the cooling bath was removed, and the solution was allowed to warm to rt. The formation of a precipitate was observed as the solution warmed. The reaction was quenched by the addition of saturated aqueous ammonium chloride solution (20 ml). The mixture was then poured into ether (150 ml) and washed successively with water (50 ml) and brine (50 ml). The organic layer was dried (Na$_2$SO$_4$), filtered, and concentrated. Purification of the residue by flash chromatography (silica, 10% ether:hexanes) afforded alkene 17 (767 mg; 97%) as a colorless oil: IR(film): 2956, 2177, 1506, 1249, 1149, 1032, 842, cm$^{-1}$; $^1$H NMR(CDCl$_3$, 500MHz) d 6.95(s, 1H), 6.53(s, 1H), 4.67 (d, 16.7 Hz, 1H), 4.57 (d, J=6.8 Hz, 1H), 4.29 (dd, 8.1, 5.4 Hz, 1H), 3.43 (s, 3H), 2.70 (s, 3H), 2.62 (dd, J=16.9, 8.2 Hz, 1H), 2.51 (dd, J=17.0,5.4 Hz, 1H), 2.02 (s, 3H); $^3$C NMR (CDCl$_3$, 125 MHz) d 164.4, 152.5, 137.1, 121.8, 116.2, 103.7, 93.6, 86.1, 79.6, 55.4, 25.9, 19.1, 13.5; [α]$_D$=−27.3 (c=2.2, CHCl$_3$).

EXAMPLE 8

Alkynyl iodide formation: To a solution of the alkyne 17 (3.00 g, 9.29 mmol) in acetone (100 mL) at 0° C. was added NIS (2.51 g; 11.2 mmol) and AgNO$_3$ (0.160 g; 0.929 mmol). The mixture was then slowly warmed to rt. After 1.5 h, the reaction was poured into Et$_2$O (250 mL) and washed once with sat bisulfite (40 mL), once with sat NaHCO$_3$ (40 mL), once with brine (40 mL) and dried over anhydrous MgSO$_4$. Purification by flash chromatography on silica gel using gradient elution with hexanes/ethyl acetate (10:1-7:1) gave 2.22 g (64%) of the iodide 17a as an amber oil.

EXAMPLE 9

Reduction of the alkynyl iodide: BH$_3$.DMS (0.846 mL, 8.92 mmol) was added to a solution of cyclohexene (1.47 mL, 17.9 mmol) in Et$_2$O (60 mL) at 0° C. The reaction was then warmed to rt. After 1 h, the iodide x (2.22 g, 5.95 mmol) was added to Et$_2$O. After 3 h, AcOH (1.0 mL) was added. After 30 additional min, the solution was poured into sat NaHCO$_3$ and extracted with Et$_2$O (3×100 mL). The combined organics were then washed once with brine (50 mL) and dried over anhydrous MgSO$_4$. Purification by flash chromatography on silica gel eluting with hexanes/ethyl acetate (6:1) gave 1.45 g (65%) of the vinyl iodide 18 as a yellow oil.

EXAMPLE 10

MOM removal: To a solution of iodide 18 (1.45 g, 3.86 mmol) in CH$_2$Cl$_2$ (40 mL) at rt was added thiophenol (1.98 mL, 19.3 mmol) and BF$_3$∘Et$_2$O (1.90 mL, 15.43 mmol). After 22 h, the reaction was poured into EtOAc (150 mL) and washed with 1 N NaOH (2×50 mL) and dried over anhydrous MgSO$_4$. Purification by flash chromatography on silica gel using gradient elution with hexanes/ethyl acetate (4:1–2:1–1:1) gave 1.075 g (86%) of the alcohol 18a as a pale yellow oil.

EXAMPLE 11

Acetate formation: To a solution of alcohol 18a (1.04 g, 3.15 mmol) in CH$_2$Cl$_2$ (30 mL) was added pyridine (2.52 mL, 25.4 mmol), acetic anhydride (1.19 mL, 12.61 mmol) and DMAP (0.005 g). After 1 h, the volatiles were removed in vacuo. Purification of the resulting residue by flash chromatography on silica gel eluting with hexanes/ethyl acetate (7:1) gave 1.16 g (99%) of the acetate 19 as a pale yellow oil. IR(film):1 737, 1368, 1232, 1018 cm$^{-1}$; $^1$H NMR (CDCl$_3$, 500 MHz) d 6.97 (s, 1H), 6.53 (s, 1H), 6.34 (dd, J=17.5, 1.0 Hz, 1H), 6.18 (dd, J=13.7, 6.9 Hz, 1 h), 5.40 (t, J=6.4 Hz, 1H), 2.70 (s, 3 h), 2.61 (m, 2H), 2.08 (2b, 6H). $^{13}$C NMR (CDCl$_3$, 125 MHz) d 169.8, 164.4, 152.2, 136.4, 136.1, 120.6, 116.4, 85.1, 38.3, 21.0, 19.1, 14.7; [α]$_D$−28.8 (c=1.47, CHCl$_3$).

EXAMPLE 12

To a solution of alcohol 4 (2.34 g, 3.62 mmol) and 2,6-lutidine (1.26 mL, 10.86 mmol) in CH$_2$Cl$_2$ (23 mL) at 0° C. was treated with TBSOTf (1.0 mL, 4.34 mmol). After stirrring for 1.5 h at 0° C. the reaction mixture was quenched with MeOH (200 uL) and the mixture stirred an additional 5 min. The reaction mixture was diluted with Et$_2$O (100 mL) and washed successively with 1N HCl (25 mL), water (25 mL), and brine (25 mL). The solution was dried over MgSO$_4$, filtered, and concentrated. The residue was purified by flash chromatography on silica gel eluting with 5% Et$_2$O in hexanes to provide compound 7 (2.70 g, 98%) as a colorless foam.

EXAMPLE 13

A solution of compound 7 (2.93 g, 3.85 mmol) in CH$_2$Cl$_2$/H$_2$O (20:1, 80 mL) was treated with DDQ (5.23 g, 23.07 mmol) and the resulting suspension was stirred at room temperature for 24 h. The reaction mixture was diluted with Et$_2$O (200 mL) and washed with aqueous NaHCO$_3$ (2×40 mL). The aqueous layer was extracted with Et$_2$O (3×40 mL) and the combined organic fractions were washed with brine (50 mL), dried over MgSO$_4$, filtered, and concentrated. Purification of the crude oil by flash chromatography on silica gel eluting with 30% ether in hexanes afforded alcohol 7A (2.30 g, 89%) as a colorless oil: IR (film) 3488, 1471, 1428,1115, 1054 cm$^{-1}$; $^1$H NMR (CDCl$_3$, 500 MHz) d 7.70 (6H, dd, J=8.0, 1.5 Hz), 7.44 (9H, s), 4.57 (1H, d, J=3.5 Hz), 4.19 (1H, s), 3.67 (1H, d, J=8.5 Hz), 3.06 (1H, dd, J=11.5, 5.0 Hz), 2.89 (1H, dd, J=11.5, 5.0 Hz), 2.68 (1H, d, J=13.5 Hz), 2.59 (1H, d, J=13.5 Hz), 2.34 (1H, dt, J=12.0, 2.5 Hz), 2.11 (1H, m), 1.84 (1H, dt, J=12.0, 2.5 Hz), 1.76 (2H, m), 1.59 (2H, m), 1.34 (3H, s), 1.13 (3H, d, J=7.5 Hz), 1.10 (3H, s), 0.87 (9H, s), 0.84 (3H, d, J=12.0 Hz), 0.02 (3H, s), 0.01 (3H, s); $^{13}$C NMR (CDCl$_3$, 125 MHz) d 136.18, 134.66, 130.16, 127.84, 78.41, 75.91, 63.65, 59.69, 45.43, 45.09, 37.72, 30.84, 30.50, 26.23, 25.89, 22.42, 21.05, 18.40, 15.60, 14.41, −3.23, −3.51; [α]$_D$−0.95 (c=0.1 73, CHCl$_3$).

EXAMPLE 14

To a solution of oxalyl chloride (414 μL, 4.74 mmol) in CH$_2$Cl$_2$ (40 mL) at −78° C. was added dropwise DMSO (448 uL, 6.32 mmol) and the resulting solution was stirred at −78 DC for 30 min. Alcohol 7a (2.12 g, 3.16 mmol) in $CH_2Cl_2$ (20 mL) was added and the resulting white suspension was stirred at −78° C. for 45 min. The reaction mixture was quenched with $Et_3N$ (2.2 mL, 15.8 mmol) and the solution was allowed to warm to 0° C. and stirred at this temperature for 30 min. The reaction mixture was diluted with $Et_2O$ (100 mL) and washed successively with aqueous $NH_4Cl$ (20 mL), water (20 mL), and brine (20 mL). The crude aldehyde was purified by flash chromatography on silica gel eluting with 50% $Et_2O$ in hexanes to provide aldehyde 8 (1.90 g, 90%) as a colorless oil.

EXAMPLE 15

A solution of (methoxymethyl)triphenylphosphonium chloride (2.97 g, 8.55 mmol) in THF (25 mL) at 0° C. was treated with $KO^tBu$ (8.21 mL, 1M in THF, 8.1 mmol). The mixture was stirred at 0° C. for 30 min. Aldehyde 8 (3.1 g, 4.07 mmol) in THF (10 mL) was added and the resulting solution was allowed to warm to room temperature and stirred at this temperature for 2 h. The reaction mixture was quenched with aqueous $NH_4Cl$ (40 mL) and the resulting solution extracted with $Et_2O$ (3×30 mL). The combined $Et_2O$ fractions were washed with brine (20 ml), dried over $MgSO_4$, filtered, and concentrated. The residue was purified by flash chromatography on silica gel eluting with 5% $Et_2O$ in hexanes to yield compound 9 (2.83 g, 86%) as a colorless foam.

EXAMPLE 16

To a solution of compound 9 (2.83 g, 3.50 mmol) in dioxane/$H_2O$ (9:1, 28 mL) was added $pTSA.H_2O$ (1.0 g, 5.30 mmol) and the resulting mixture was heated to 50° C. for 2 h. After cooling to room temperature the mixture was diluted with $Et_2O$ (50 mL) and washed with aqueous $NaHCO_3$ (15 mL), brine (20 ml), dried over $MgSO_4$, filtered, and concentrated to provide aldehyde 9a (2.75 g, 99%) as a colorless foam.

EXAMPLE 17

Methyltriphenylphosphonium bromide (1.98 g, 5.54 mmol) in THF (50 mL) at 0° C. was treated with lithium bis(trimethylsilyl)amide (5.04 mL, 1M in THF, 5.04 mmol) and the resulting solution was stirred at 0° C. for 30 min. Aldehyde 9a (2.0 g, 2.52 mmol) in THF (5.0 mL) was added and the mixture was allowed to warm to room temperature and stirred at this temperature for 1 h. The reaction mixture was quenched with aqueous $NH_4Cl$ (15 mL) and extracted with $Et_2O$ (3×20 mL). The combined $Et_2O$ fractions were washed with brine (15 mL), dried over $MgSO_4$, filtered, and concentrated. The residue was purified by flash chromatography on silica gel eluting with 5% $Et_2O$ in hexanes to afford compound 10 (1.42 g, 76%) as a colorless foam.

EXAMPLE 18

A solution of compound 10 (1.0 g, 1.34 mmol) in MeOH/THF (2:1, 13 mL) was treated with [bis(trifluoroacetoxy)iodobenzene] (865 mg, 2.01 mmol) at room temperature. After 15 min the reaction mixture was quenched with aqueous $NaHCO_3$ (25 mL). The mixture was extracted with $Et_2O$ (3×25 mL) and the combined $Et_2O$ fractions were washed with brine, dried over $MgSO_4$, filtered, and concentrated. Purification of the residue by flash chromatography on silica gel eluting with 5% $Et_2O$ in hexanes provided compound 11 (865 mg, 92%) as a colorless foam: IR (film) 1428, 1252, 1114, 1075, 1046 $cm^{-1}$; $^1H$ NMR ($CDCl_3$, 500 MHz) d 7.61 (6H, dd, J=7.9, 1.4 Hz), 7.38 (9H, s), 5.47 (1H, m), 4.87 (1H, d, J=10.0 Hz), 4.76 (1H, d, J=15.9 Hz), 4.30 (1H, d, J=3.7 Hz), 3.95 (1H, s), 3.56 (1H, dd, J=7.5, 1.4 Hz), 3.39 (3H, s), 2.84 (3H, s), 2.02 (1H, m), 1.64 (2H, m), 1.34 (1H, m), 1.11 (3H, s), 1.02 (3H, d, J=7.4 Hz), 0.90 (3H, s), 0.85 (9H, s), 0.62 (3H, d, J=6.8 Hz), −0.04 (3H, s), −0.05 (3H, s); $^3C$ NMR ($CDCl_3$, 125 MHz) d 138.29, 135.79, 135.04, 129.86, 127.78, 114.98, 110.49, 60.11, 55.57, 46.47, 43.91, 36.82, 34.21, 26.26, 19.60, 18.60, 17.08, 16.16, 13.92, −2.96, −3.84; $[\alpha]_D$=+1.74 (c=0.77, $CHCl_3$).

EXAMPLE 19

Suzuki Coupling: To a solution of olefin 11 (0.680 g, 1.07 mmol) in THF (8.0 mL) was added 9-BBN (0.5M soln in THF, 2.99 mL, 1.50 mmol). In a separate flask, the iodide 19 (0.478 g, 1.284 mmol) was dissolved in DMF (10.0 mL). $CsCO_3$ (0.696 g, 2.14 mmol) was then added with vigorous stirring followed by sequential addition of $Ph_3As$ (0.034 g, 0.111 mmol), $PdCl_2(dppf)_2$ (0.091 g, 0.111 mmol) and $H_2O$ (0.693 mL, 38.5 mmol). After 4 h, then borane solution was added to the iodide mixture in DMF. The reaction quickly turned dark brown in color and slowly became pale yellow after 2 h. The reaction was then poured into $H_2O$ (100 mL) and extracted with $Et_2O$ (3×50 mL). The combined organics were washed with $H_2O$ (2×50 mL), once with brine (50 mL) and dried over anhydrous $MgSO_4$. Purification by flash chromatography on silica gel eluting with hexanes/ethyl acetate (7:1) gave 0.630 g (75%) of the coupled product 20 as a pale yellow oil.

EXAMPLE 20

Hydrolysis of dimethyl acetal 21: The acetate 20 (0.610 g, 0.770 mmol) was dissolved in dioxane/$H_2O$ (9:1, 15 mL) and $pTSA.H_2O$ (0.442 g, 2.32 mmol) was added. The mixture was then heated to 55° C. After 3 h, the mixture was cooled to rt and poured into $Et_2O$. This solution was washed once with sat $NaHCO_3$ (30 mL), once with brine (30 mL) and dried over anhydrous $MgSO_4$. Purification by flash chromatography on silica get eluting with hexanes/ethyl acetate (7:1) gave 0.486 g (85%) of the aldehyde 21 as a pale yellow oil. IR (film) 1737, 1429, 1237, 1115, 1053 $cm^{-1}$; $^1H$ NMR ($CDCl_3$, 500 MHz) d 9.74 (1H, s), 7.61 (6H, dd, J=7.8, 1.2 Hz), 7.38 (9H, m), 6.94 (1H, s), 6.53 (1H, s), 5.39 (1H, m) 5.31 (1H, m), 5.29 (1H, t, J=6.9 Hz), 4.61 (1H, d, J=4.3 Hz), 3.50 (1H, dd, J=5.2, 2.6 Hz), 2.70 (3H, s), 2.48 (2H, m), 2.14 (1H, m), 2.09 (3H, s), 2.07 (3H, s), 1.83 (2, m), 1.41 (1H, m), 1.18 (1H, m), 1.01 (3H, s), 0.99 (3H, s), 0.91 (3H, d, J=7.4 Hz), 0.85 (9H, s), 0.69 (1H, m), 0.58 (3H, d, J=6.8 Hz), −0.05 (3H, s), −0.06 (3H, s); $^{13}C$ NMR ($CDCl_3$, 125 MHz) d 205.46, 170.01, 164.49, 152.46, 137.10, 135.60, 134.22, 132.55, 130.65, 127.84, 123.82, 120.66, 116.19, 81.09, 78.47, 76.73, 51.66, 43.14, 38.98, 30.99, 30.42, 27.63, 26.10, 21.15, 20.92, 20.05, 19.15, 18.49, 15.12, 14.70, 12.75, −3.25, −4.08; $[\alpha]_D$=−18.7 (c=0.53, $CHCl_3$).

EXAMPLE 21

Aldol: To a solution of the acetate-aldehyde 21 (84 mg, 0.099 mmol) in THF at −78° C. was added KHMDS (0.5M in toluene, 1.0 ml, 0.5 mmol)) dropwise. The resulting solution was stirred at −78° C. for 30 min. Then the reaction mixture was cannulated to a short pad of silica gel and washed with ether. The residue was purified by flash chromatography (silica, 12% EtOAc in hexane) to give the lactone 22 (37 mg of 3-S and 6 mg of 3-R5, 51%) as white foam.

EXAMPLE 22

Monodeprotection: Lactone 22 (32 mg, 0.0376 mmol) was treated with 1 ml of pyridine buffered HF-pyridine—

THF solution at room temperture for 2 h. The reaction mixture was poured into saturated aqueous $NaHCO_3$ and extracted with ether. The organic layer was washed in sequence with saturated $CuSO_4$ (10 ml×3) and saturated $NaHCO_3$ (10 ml), then dried over $Na_2SO_4$ and concentrated under vacuum. The residue was purified by flash chromatography (silica, 25% EtOAc in hexane) and to give diol 22a (22 mg, 99%) as white foam.

EXAMPLE 23

TBS-protection: To a cooled (−30° C.) solution of diol 22a (29 mg, 0.0489 mmol) and 2,6-lutidine (0.017 ml, 0.147 mmol) in anhydrous $CH_2Cl_2$ (1 ml) was added TBSOTf (0.01 5 ml, 0.0646 mmol). The resulting solution was then stirred at −30° C. for 30 min. The reaction was quenched with 0.5M HCl (10 ml) and extracted with ether (15 ml). Ether layer was washed with saturated $NaHCO_3$, dried ($Na_2SO_4$) and concentrated in vacuo. Purifiction of the residue by flash chromatogrphy (silica, 8% EtOAc in hexane) afforded TBS ether 22B (32 mg, 93%) as white foam.

EXAMPLE 24

Ketone Formation: To a solution of alcohol 220 (30 mg, 0.0424 mmol) in $CH_2Cl_2$ (2.0 mL) at 25° C. was added Dess-Martin periodinane (36 mg, 0.0848 mmol) in one portion. The resulting solution was then allowed to stir at 25° C. for 1.5 h. The reaction was quenched by the addition of 1:1 saturated aqueous sodium bicarbonate: sodium thiosulfate (10 ml) and stirred for 5 min. The mixture was then extracted with ether (3×15 ml). The organic layer was dried ($Na_2SO_4$), filtered, and concentrated in vacuo. Purification of the residue by flash chromatography (silica, 8% EtOAc in hexane) provided ketone 22C (25 mg, 84%) as white foam. IR(film): 2928, 1745, 1692, 1254, 1175, 836 cm$^{-1}$; $^1$H NMR(CDCl$_3$, 500 MHz) d 6.97 (s, 1H), 6.57 (s, 1H), 5.53 (dt, J=3.4, 11.1 Hz, 1H), 5.37 (dd, J=16.4, 9.9 Hz, 1H), 5.00 (d, J=10.3 Hz, 1H), 4.02 (d, J=9.7 Hz, 1H), 3.89 (d, J=8.7 Hz, 1H), 3.00 (m, 1H), 2.82 (d, J=6.5 Hz, 1H), 2.71 (m, 5H), 2.36 (q, J=10.7 Hz, 1H), 2.12 (, 3H), 2.07 (dd, J=8.2, 1H), 1.87 (bs, 1H), 1.49 (m, 3H), 1.19 (m, 5H), 1.14 (s, 3H), 1.08 (d, J=6.8 Hz, 3H), 0.94 (m, 12H), 0.84 (s, 9H), 0.12 (s, 3H), 0.10 (s, 3H), 0.07 (s, 3H), −0.098 (s, 3H); $^{13}$C NMR (CDCl$_3$, 125 MHz) d 218.7, 170.1, 164.5, 152.6, 137.9, 133.9, 124.8, 119.6, 115.9, 72.7, 53.2, 43.9, 41.0, 40.3, 32.9, 32.3, 28.4, 27.1, 26.3, 26.1, 26.0, 19.2, 19.1, 18.3, 18.2, 17.1, 16.0, 15.2, 14.3, −4.2, −4.4, 4.6, −4.8; $[\alpha]_D$−21.93 (c=1.4, CHCl$_3$).

EXAMPLE 25

Desoxy compound: To a solution of TBS ether 22C (27 mg, 0.038 mmol) in THF(1 ml) at 25° C. in a plastic vial was added dropwise HF.pyridine (0.5 ml). The resulting solution was allowed to stir at 25° C. for 2 h. The reaction mixture was diluted with chloroform (2 ml) and very slowly added to satured sodium bicarbonate (20 ml). The mixture was extracted with CHCl$_3$ (20ml×3). The organic layer was dried (Na$_2$SO$_4$), filtered, and concentrated in vacuo. Purification of the residue by flash chromatography (silica, 30% EtOAc in hexane) provided diol 23 (18 mg, 99%) as white foam: IR(film): 3493, 2925, 1728, 1689, 1249 cm$^{-1}$; $^1$H NMR (CDCl$_3$, 500 MHz) d 6.96 (s, 1H), 6.59 (s, 1H), 5.44 (dt, J=4.3, 10.4 Hz, 1H), 5.36 (dt, J=5.1, 10.2 Hz, 1H), 5.28 (dd, J=1.7, 9.8 Hz, 1H), 4.11 (d, J=7.2 Hz, 1H), 3.74 (s, 1H), 3.20 (d, J=4.5 Hz, 1H), 3.14 (dd, J=2.2, 6.8 Hz, 1H), 3.00 (s, 1H), 2.69 (m, 4H), 2.49 (dd, J=11.3, 15.1 Hz, 1H), 2.35 (dd, J−2.5, 15.1 Hz, 1H), 2.27 (m, 1H), 2.05 (m, 1H), 2.04 (s, 3H), 2.01 (m, 1H) 1.75 (m, 1H), 1.67 (m, 1H), 1.33 (m, 4H), 1.21 (s, 1H), 1.19 (m, 2H), 1.08 (d, J=7.0 Hz, 3H), 1.00 (s, 3H), 0.93 (d, J=7.1 Hz, 3H); $^{13}$C NMR (CDCl$_3$, 125 MHz) d 226.5, 176.5, 171.1, 158.2, 144.7, 139.6, 131.1, 125.7, 122.0, 84.6, 80.2, 78.6, 59.4, 47.9, 45.4, 35 44.6, 38.5, 37.9, 33.7, 33.6, 28.7, 25.1, 25.0, 21.9, 21.7, 19.6; $[\alpha]_D$=−84.7 (c=0.85, CHCl$_3$).

EXAMPLE 26

Epothilone: To a cooled (−50° C.) solution of desoxyepothilone (9 mg, 0.0189 mmol) in dry CH$_2$Cl$_2$ (1 ml) was added freshly prepared dimethyldioxirane (0.95 ml, 0.1 M in acetone). The resulting solution was allowed to warm up to −30° C. for 2 h. A stream of nitrogen was then bubbled through the solution to remove excess DMDO. The residue was purified by flash chromatography (silica, 40% EtOAc in hexane) and afforded epothilone A (4.6 mg, 49%) as colorless solid and 0.1 mg of cis-epoxide diastereomer. This material was identical with the natural epothilone A in all respects.

EXAMPLE 27

Procedure for Ring-closing Olefin Metathesis:

To a stirred solution of diene 24 (5 mg, 0.0068 mmol) in dry benzene (1.5 mL) was added Grubbs's catalyst (2.8 mg, 0.0034 mmol). After 12 h, an additional portion of catalyst was added (2.8 mg). After an additional 5 h, the reaction was concentrated. Purification by silica gel chromatography eluting with hexanes/ethyl acetate (11:1) gave the lactone 23 (3.5 mg, 94%, 2:1 E/Z).

EXAMPLE 28

Preparation of Compound 19:

Alcohol 2A: A mixture of (S)-(−)-1,1'-bi-2-naphthol (259 mg. 0.91 mmoL), Ti(O-i-Pr)$_4$ (261 μL;0.90 mmol), and 4 Å sieves (3.23g) in CH$_2$Cl$_2$ (16 mL) was heated at reflux for 1 h. The mixture was cooled to rt and aldehyde 1 was added. After 10 min. the suspension was cooled to −78° C., and allyl tributyltin (3.6 mL; 11.60 mmol) was added. The reaction mixture was stirred for 10 min at −78° C. and then placed in a −20° C. freezer for 70 h. Saturated NaHCO$_3$ (2 mL) was added, and the mixture was stirred for 1 h, poured over Na$_2$SO$_4$, and then filtered through a pad of MgSO$_4$ and celite. The crude material was purified by flash chromatography (hexanes/ethyl acetate, 1:1) to give alcohol 2A as a yellow oil (1.11g; 60%).

EXAMPLE 29

Acetate 3A: To a solution of alcohol 2A (264 mg; 1.26 mmol) in CH$_2$Cl$_2$ (12 mL) was added DMAP (15 mg: 0.098 mmol), Et$_3$N (0.45 mL; 3.22 mmol), and Ac$_2$O (0.18 mL; 1.90 mmol). After 2 h, the reaction mixture was quenched by 20 mL of H$_2$O, and extracted with EtOAC (4×20 mL). The combined organic layer was dried with MgSO$_4$, filtered, and concentrated. Flash chromatrography (EtOAC/hexanes, 1:3) afforded acetate 3A as a yellow oil (302 mg; 96%).

EXAMPLE 30

Vinyl Iodide 19: To a solution of acetate 3A (99 mg; 0.39 mmol) in acetone at 0° C. was added H$_2$O (4 drops), OsO$_4$ (2.5% wt. in butyl alcohol; 175 μL; 0.018 mmol), and N-methyl-morpholine-N-oxide (69 mg; 0.59 mmol). The mixture was stirred at 0° C. for 2 h and 45 min and then quenched with Na$_2$SO$_3$. The solution was poured to 10 mL of H$_2$O and extracted with EtOAc (5×10 mL). The combined organic layer was dried over MgSO4, filtered, and concentrated.

To a solution of this crude product in THF/H$_2$O (4 mL, 3:1) was added NaIO$_4$ (260 mg; 1.22 mmol). After 1.25 h, the reaction mixture was then quenched with 10 mL of H$_2$O and concentrated. The residue was extracted with EtOAc (5×10 mL). The organic layer was dried over MgSO$_4$, filtered, and concentrated. Flash chromatography (EtOAc/hexanes, 1:1) gave a yellow oil (80 mg) which contained unidentified by-product(s). This mixture was used without further purification.

To a solution of (Ph$_3$P$^+$CH$_2$I)I$^-$ (100 mg; 0.19 mmol) in 0.25 mL of THF at rt was added 0.15 mL (0.15 mmol) of NaHMDS (1M in THF). To the resulting solution at −78° C. was added HMPA (22 μL; 0.13 mmol) and the product from previous step (16 mg) in THF (0.25 mL). The reaction mixture was then stirred at rt for 30 min. After the addition of hexanes (10 mL), the solution was extracted with EtOAc (4×10 mL). The combined EtOAC layer was dried (MgSO$_4$), filtered, and concentrated. Preparative TLC (EtOAc/hexanes, 2.3) afforded vinyl iodide 19 as a yellow oil (14 mg; 50% for three steps).

EXAMPLE 31

Iodoolefin acetate 8C: To a suspension of ethyltriphenylphosphonium iodide (1.125 g, 2.69 mmol) in THF (10 mL) was added nBuLi (2.5M soln in hexanes, 1.05 mL, 2.62 mmol) at rt. After disappearance of the solid material, the solution was added to a mixture of iodine (0.613 g, 2.41 mmol) in THF (20 mL) at −78° C. The resulting suspension was vigorously stirred for 5 min at −78° C., then warmed up −20° C., and treated with sodium hexamethyldisilazane (1M soln in THF, 2.4 mL, 2.4 mmol). The resulting red solution was stirred for 5 min followed by the slow addition of aldehyde 9C (0.339 g, 1.34 mmol). The mixture was stirred at −20° C. for 40 min, diluted with pentane (50 mL), filtered through a pad of celite, and concentrated. Purification of the residue by flash column chromatography (hexanes/ethyl acetate, 85:15) gave 0.202 g (25% overall from vinyl acetate 10C) of the vinyl iodide 8C as a yellow oil. IR (film): 2920, 1738, 1234 cm$^{-1}$; $^1$H NMR (CDCl$_3$): δ 6.98 (s, 1H), 6.56 (s, 1H), 5.42 (dd, J=5.43, 6.57 Hz, 1H), 5.35 (t, J=6.6 Hz, 1H), 2.71 (s, 3H), 2.54 (q, J=6.33, 2H), 2.50 (s, 3H), 2.09 (s, 6H); $^{13}$C NMR (CDCl$_3$): 6170.1, 164.6, 152.4, 136.9, 130.2, 120.6, 116.4, 103.6, 40.3, 33.7, 21.2, 19.2, 14.9; [α]$_D$−20.7° (c=2.45, CHCl$_3$).

EXAMPLE 32

Acetal 13C: To a solution of olefin "7C" (0.082 g, 0.13 mmol) in THF (0.5 mL) was added 9-BBN (0.5 M soln in THF, 0.4 mL, 0.2 mmol). After stirring at rt. for 3.5 h, an additional portion of 9-BBN (0.5 M soln in THF, 0.26 mL, 0.13 mmol) was added. In a separate flask, iodide 8C (0.063 g, 0.16 mmol) was dissolved in DMF (0.5 mL). Cs$_2$CO$_3$ (0.097 g, 0.30 mmol) was then added with vigorous stirring followed by sequential addition of PdCl$_2$(dppf)$_2$ (0.018 g, 0.022 mmol), Ph$_3$As (0.0059 g, 0.019 mmol), and H$_2$O (0.035 mL, 1.94 mmol). After 6 h, then borane solution was added to the iodide mixture in DMF. The reaction quickly turned dark brown in color and slowly became pale yellow after 3 h. The reaction was then poured into H$_2$O (10 mL) and extracted with Et$_2$O (3×15 mL). The combined organic layers were washed with H$_2$O (3×15 mL), brine (1×20 mL), dried over MgSO$_4$, filtered, and concentrated. Flash column chromatography (hexanes/ethyl acetate, 9:1) gave 0.089 g (77%) of the coupled product 13C as a yellow oil.

EXAMPLE 33

Aldehyde 14C: Acetal 13C (0.069 g, 0.077 mmol) was dissolved in dioxane/H$_2$O (9:1, 1 mL) and pTSA.H$_2$O (0.045 g, 0.237 mmol) was added. The mixture was then heated to 55° C. After 3 h, the mixture was cooled to rt, poured into Et$_2$O, and extracted with Et$_2$O (4×15 mL). The combined ether solutions were washed with sat NaHCO$_3$ (1×30 mL), brine (1×30 mL), dried over MgSO$_4$, filtered, and concentrated. Flash column chromatography (hexanes/ethyl acetate, 3:1) gave 0.046 g (71%) of the aldehyde 14C as a pale yellow oil.

EXAMPLE 34

Macrocycle 15C-(SR): To a solution of aldehyde 14C (0.021 g, 0.024 mmol) in THF (5 mL) at −78° C. was added KHMDS (0.5M soln in toluene, 0.145 mL, 0.073 mmol). The solution was stirred at −78° C. for 1 h, then quenched with sat'd N H$_4$Cl, and extracted with ether (3×15 mL). The combined organic layers were dried with MgSO$_4$, filtered, and concentrated. Flash column chromatography (hexanes/ethyl acetate, 7:1) gave 0.008 g of the desired α-alcohol 15C-(S) and 0.006 g of P-alcohol 15C-(R) (67% total ) as pale yellow oils.

EXAMPLE 35

Macrocycle 15C4S): To a solution of β-alcohol 1C-(R) (0.006 g, 0.0070 mmol) in 0.5 mL of CH$_2$Cl$_2$ at rt. was added Dess-Martin periodinane (0.028 g, 0.066 mmol). After 0.5 h, an additional portion of Dess-Martin periodinane (0.025 mg, 0.059 mmol) was added. The resulting solution was stirred at rt for additional 1 h, then treated with ether (2 mL) and sat'd Na$_2$S$_2$O$_3$/sat'd NaHCO$_3$ (3 mL, 1:1), poured into H$_2$O (20 mL), and extracted with ether (3×15 mL). The combined ether solutions were washed with H$_2$O (1×30 mL), brine (1×30 mL), dried with MgSO$_4$, filtered, and concentrated. To a solution of crude ketone 15C' in MeOH/THF (2 mL, 1:1) at −78° C. was added NaBH$_4$ (0.015 g, 0.395 mmol). The resulting solution was stirred at rt for 1 h, quenched with sat NH$_4$Cl, and extracted with ether (3×15 mL). The organic layers were dried with MgSO$_4$, filtered, and concentrated. Flash column chromatography (hexanes/ethyl acetate, 9:1) gave 0.0040 g (67%) of the α-alcohol 15C-(S) as a pale yellow oil and 0.0006 g of α-alcohol 15C-(R).

EXAMPLE 36

Diol 15C": The silyl ether 15C-(S) (0.010 g, 0.012 mmol) was dissolved in HF.pyridine/pyridine/THF (1 mL). The solution was stirred at rt. for 2 h, then diluted with Et$_2$O (1 mL), poured into a mixture of Et$_2$O/sat. NaHCO$_3$ (20 mL, 1:1), and extracted with Et$_2$O (4×10 mL). The Et$_2$O solutions were washed with sat CuSO$_4$ (3×30 mL), sat NaHCO$_3$ (1×30 mL), brine (1×30 mL), dried with MgSO$_4$, filtered, and concentrated. Flash column chromatography (hexanes/ethyl acetate, 9:1) gave 0.0066 g (93%) of the diol 15C" as a pale yellow oil.

EXAMPLE 37

Alcohol 15C'": To a solution of diol 15C" (0.0066 g, 0.011 mmol) in 0.5 mL of CH$_2$Cl$_2$ at −78° C. was added 2,6-lutidine (7 μL, 0.060 mmol) and TBSOTf (5 μL, 0.022 mmol). The resulting solution was stirred at −30° C. for 0.5 h, then quenched with H$_2$O (5 mL), and extracted with Et$_2$O (4×10 mL). The ether solutions were washed with 0.5M HCl (1×10 mL), sat'd NaHCO$_3$ (1×10 mL), dried over MgSO$_4$, filtered, and concentrated. Flash column chromatography (hexanes/ethyl acetate, 93:7) gave 0.0070 g (89%) of the alcohol 15C'" as a pale yellow oil.

EXAMPLE 38

Ketone 16C: To a solution of alcohol 15C'" (0.006 g, 0.0083 mmol) in 0.5 mL of CH$_2$Cl$_2$ at rt. was added Dess-Martin periodinane (0.030 g, 0.071 mmol). After 1.25 h, another portion of Dess-Martin periodinane (0.025 mg, 0.059 mmol) was added. The resulting solution was stirred at rt for additional 0.75 h, treated with ether (1 mL) and sat'd $Na_2S_2O_3$/sat'd $NaHCO_3$ (2 mL, 1:1), poured into $H_2O$ (20 mL), and extracted with ether (4×10 mL). The ether solution was washed with sat $NaHCO_3$ (1×20 mL), dried with $MgSO_4$, filtered, and concentrated. Flash column chromatography (hexanes/ethyl acetate, 9:1) gave 0.0040 g (67%) of the ketone 16C as a pale yellow oil.

EXAMPLE 39

Desoxyepothilone B (2C): To a solution of ketone 16C (0.004 g, 0.0056 mmol) in THF (0.35 mL) was added HF.pyridine (0.25 mL) dropwise over 20 min. The solution was stirred at rt for 1.5 h, diluted with $CHCl_3$ (2 mL), poured into sat'd $NaHCO_3$/$CHCl_3$ (20 mL, 1:1) slowly, and extracted with $CHCl_3$ (4×10 mL). The combined $CHCl_3$ layers were dried with $MgSO_4$, filtered, and concentrated. Flash column chromatography (hexanes/ethyl acetate, 3:1) gave 0.0022 g (80%) of the desoxyepothilone B 2C as a pale yellow oil.

EXAMPLE 40

Epothilone B (2): To a solution of desoxyepothilone B (0.0022 g, 0.0041 mmol) in $CH_2Cl_2$ (0.25 mL) at −50° C. was added dimethyldioxirane (0.1 mL, 0.0095 mmol) dropwise. The resulting solution was stirred at −50° C. for 1 h. The dimethyldioxirane and solvent were removed by a stream of $N_2$. The residue was purified by flash column chromatography (hexanes/ethyl acetate, 1:1) gave 0.0015 g (70%) of epothiolone B (2) as a pale yellow oil which was identical with an authentic sample in $^1H$ NMR, IR, mass spectrum, and $[\alpha]_D$.

EXAMPLE 41

8-Desmethylepothilone A

Crotylation product: To a stirred mixture of potassium tert-butoxide (1.0M soln in THF, 50.4 mL, 50.4 mmol), THF (14 mL), and cis-2-butene (9.0 mL, 101 mmol) at −78° C. was added n-BuLi (1.6M, in hexanes, 31.5 mL, 50.4 mmol). After complete addition of n-BuLi, the mixture was stirred at 45° C. for 10 min and then cooled to −78° C. (+)-B-Methoxydiisopinocampheylborane (19.21 g, 60.74 mmol) was then added dropwise in $Et_2O$ (10 mL). After 30 min, $BF_3Et_2O$ (7.47 mL, 60.74 mmol) was added followed by aldehyde 4D (9.84 g, 60.74 mmol) in THF (15 mL) generating a viscous solution which could not be stirred. The mixture was shaken vigorously every 10 min to ensure homogeneity. After 3 h at −78° C., the reaction was treated with 3N NaOH (36.6 mL, 110 mmol) and 30% $H_2O_2$ (15 mL) and the solution brought to reflux for 1 h. The reaction was poured into $Et_2O$ (300 mL) and washed with $H_2O$ (100 mL), brine (30 mL) and dried over anhydrous $MgSO_4$. The crude material was placed in a bulb-to-bulb distillation apparatus to remove the ligand from the desired product. Heating at 80° C. at 2 mm Hg removed 90% of the lower boiling ligand. Further purification of the alcohol 4D was achieved by flash chromatography on silica gel eluting with $Et_2O$ in $CH_2Cl_2$ (2%–4%) to give pure alcohol 4D as a clear oil. The erythro selectivty was >50:1 as judged by $^1H$ NMR spectroscopy. The product was determined to be 87% ee by formation of the Mosher ester: IR (film): 3435, 2861, 1454, 1363, 1099 cm$^{-1}$; $^1H$ NMR (CDCl$_3$, 400 MHz) δ 7.34 (5H, m), 5.80 (1H, m), 5.09 (1H, dd, J=1.6, 8.3 Hz), 5.04 (1H, d, J=1.6 Hz), 4.52 (2H, s), 3.51 (2H, t, J=5.8 Hz), 3.47 (1H, m), 2.27 (2H, m), 1.73 (3H, m), 1.42 (1H, m), 1.04 (3H, d, J=6.9 Hz); $^{13}C$ NMR (CDCl$_3$, 100 MHz) δ 141.1, 138.2, 128.3, 127.6, 127.5, 115.0, 74.5, 72.9, 70.4, 43.7, 31.3, 26.5, 14.6.

EXAMPLE 42

TBS ether SD: Alcohol 4D (5.00 g, 21.4 mmol) was dissolved in $CH_2Cl_2$ (150 mL) and 2,6-lutidine (9.97 mL, 85.6 mmol) was added. The mixture was cooled to 0° C. and TBSOTf (9.83 mL, 42.8 mmol) was slowly added. The reaction was then warmed to rt. After 1 h, the reaction was poured into $Et_2O$ (300 mL) and washed once with 1N HCl (50 mL), once with sat $NaHCO_3$ (50 mL), once with brine (30 mL) and dried over anhydrous $MgSO_4$. Purification by flash chromatography on silica gel eluting with hexanes/diethyl ether (97:3) gave 6.33 g (85%) of pure olefin 5D as a clear oil: IR (film): 1472, 1361, 1255, 1097, 1068 cm$^{-1}$; $^1H$ NMR (CDCl$_3$, 400 MHz) δ 7.30 (5H, m), 5.81 (1H, m), 4.97 (1H, dd, J=1.4, 4.8 Hz), 4.94 (1H, d, J=1.1 Hz), 3.51 (1H, q, J=5.1 Hz), 3.41 (2H, dt, J=2.1, 6.6 Hz), 2.27 (1H, q, J=5.5 Hz), 1.68 (1 h, m), 1.55 (1H, m), 1.41 (2H, m), 0.93 (3H, dd, J=6.9 Hz), 0.85 (9H, s), −0.01 (6H, s); $^{13}C$ NMR (CDCl$_3$, 100 MHz) δ 141.2, 138.6, 128.3, 127.6, 127.4, 113.9, 75.6, 72.7, 70.6, 42.7, 30.1, 25.9, 25.4, 18.1, 15.1, −4.3, −4.4.

EXAMPLE 43

Aldehyde 6D: The olefin 5 (4.00 g, 11.49 mmol) was dissolved in 1:1 MeOH/$CH_2Cl_2$ (100 mL). Pyridine (4.0 mL) was then added and the mixture cooled to −78° C. Ozone was then bubbled through the reaction for 10 minutes before the color turned light blue in color. Oxygen was then bubbled through the reaction for 10 min. Dimethyl sulfide (4.0 mL) was then added and the reaction slowly warmed to rt. The reaction was stirred overnight and then the volatiles were removed in vacuo. Purification by flash chromatography on silica gel eluting with hexanes/ethyl acetate (9:1) gave 3.31 g (82%) of the aldehyde 6D as a clear oil: IR (film): 2856, 1727, 1475, 1361, 1253, 1102 cm$^{-1}$; $^1H$ NMR (CDCl$_3$, 400 MHz) δ 9.76 (1 H, s), 7.33 (5H, m), 4.50 (2H, s), 4.11 (1H, m), 3.47 (2H, m), 2.46 (1H, m), 1.50–1.70 (4H, band), 1.05 (3H, d, J=7.0 Hz), 0.86 (9H, s), 0.06 (3H, s), 0.03 (3H, s); $^{13}C$ NMR (CDCl$_3$, 100 MHz) δ 204.8, 138.3, 128.2, 127.4, 127.3, 72.7, 71.7, 69.9, 51.1, 31.1, 25.9, 25.6, 17.8, 7.5, −4.4, −4.8.

EXAMPLE 44

Dianion addition product 7D: The tert-butyl isobutyrylacetate (0.653 g, 3.51 mmol) was added to a suspension of NaH (60% in mineral oil, 0.188 g, 4.69 mmol) in THF (50 mL) at rt. After 10 min, the mixture was cooled to 0° C. After an additional 10 min, n-BuLi (1.6M in hexanes, 2.20 mL, 3.52 mmol) was slowly added. After 30 min, the aldehyde 6D (1.03 g, 2.93 mmol) was added neat. After 10 min, the reaction was quenched with $H_2O$ (10 mL) and extracted with $Et_2O$ (2×75 mL). The combined organics were washed once with brine (30 mL) and dried over anhydrous $MgSO_4$. The crude reaction mixture contained a 15:1 ratio of diastereomers at C5. Purification by flash chromatography on silica gel eluting with hexanes/ethyl acetate (9:1–7:1) gave 0.723 g (47%) of the desired alcohol 7D as a clear oil: IR (film): 3531, 2953, 1739, 1702, 1367, 1255, 1153 cm$^{-1}$; $^1H$ NMR (CDCl$_3$, 400 MHz) δ 7.33 (5H, m), 4.49 (2H, s), 3.75 (1H, d, J=2.6 Hz), 3.71 (1H, m), 3.62 (1H, d, J=16.0 Hz), 3.53(1H, d, J=16.0 Hz), 3.44(2H, t, J=5.1 Hz), 2.70 (1H, d, J=2.6 Hz), 1.83 (1H, m), 1.55 (4H, m), 1.46 (9H, s), 1.17 (3H, s), 1.11 (3H, s), 0.89 (9H, s), 0.82 (3H, d, J=7.0 Hz), 0.09 (6H, s); $^{13}C$ NMR (CDCl$_3$, 100 MHz) δ 208.9, 167.3, 138.4, 128.3, 127.6, 127.5, 81.3, 79.5, 78.7, 72.8, 70.1, 52.4, 47.6, 35.8, 30.6, 28.2, 25.9, 25.8, 22.6, 20.5, 17.9, 7.05, −4.0, −4.5.

EXAMPLE 45

Directed reduction: To a solution of tetramethylammonium triacetoxyborohydride (1.54 g, 5.88 mmol) in acetonitrile (4.0 mL) was added anhydrous AcOH.(4.0 mL). The mixture was stirred at rt for 30 min before cooling to −10° C. A solution of the ester 7D (0.200 g, 0.39 mmol) in acetonitrile (1.0 mL) was added to the reaction and it was stirred at −10° C. for 20 h. The reaction was quenched with 1N sodium-potassium tartrate (10 mL) and stirred at rt for 10 min. The solution was then poured into sat $NaHCO_3$ (25 mL) and neutralized by the addition of solid $Na_2CO_3$. The mixture was then extracted with EtOAc (3×30 mL) and the organics were washed with brine (20 mL) and dried over anydrous $MgSO_4$. Purification by flash chromatography on silica gel eluting with hexanes/ethyl acetate (4:1) gave 0.100 g (50%) of the diol as 10:1 ratio of diastereomeric alcohols.

EXAMPLE 46

Monoprotection of the diol: The diol (1.76 g, 3.31 mmol) was dissolved in $CH_2Cl_2$ (100 mL) and cooled to 0° C. 2,6-lutidine (12.2 mL, 9.92 mmol) was added followed by TBSOTf (1.14 mL, 4.96 mmol) and the reaction slowly warmed to rt. After 1 h, the reaction was poured into $Et_2O$ (300 mL) and washed once with 1N HCl (50 mL), once with sat $NaHCO_3$ (50 mL), once with brine (30 mL) and dried over anhydrous $MgSO_4$. Purification by flash chromatography on silica gel eluting with hexanes/ethyl acetate (20:1→15:1) gave 2.03 g (95%) of the alcohol 8D as a clear oil, which was used as a mixture of diastereomers.

EXAMPLE 47

C5 Ketone formation: The alcohol 8D (2.03 g, 3.14 mmol) was dissolved in $CH_2Cl_2$ (50 mL) and Dess-Martin periodinane (2.66 g, 6.28 mmol) was added. After 2 h, a 1:1 mixture of sat'd $NaHCO_3$/sat $Na_2S_2O_3$ (20 mL) was added. After 10 min, the mixture was poured into $Et_2O$ (300 mL) and the organic layer was washed with brine (30 mL) and dried over anhydrous $MgSO_4$. Purification by flash chromatography on silica gel eluting with hexanes/ethyl acetate (15:1) gave 1.85 g (91%) of the ketone (benzyl ether) as a clear oil, which was used as a mixture of diastereomers.

EXAMPLE 48

Debenzylation: The ketone (benzyl ether) (1.85 g, 2.87 mmol) was dissolved in EtOH (50 mL), and $Pd(OH)_2$ (0.5 g) was added. The mixture was then stirred under an atmosphere of $H_2$. After 3 h, the reaction was purged with $N_2$ and then filtered through a pad of celite rinsing with $CHCl_3$ (100 mL). Purification by flash chromatography on silica gel eluting with ethyl acetate in hexanes (12%→15%) gave 1.43 g (90%) of the diastereomeric alcohols as a clear oil. The C3 diastereomers were separated by flash chromatography on TLC-grade $SiO_2$ eluting with ethyl acetate in hexanes (155%):

Alpha isomer: IR (film): 3447, 1732, 1695, 1254, 1156 $cm^{-1}$; $^1H$ NMR ($CDCl_3$, 400 MHz) δ 4.24 (1H, dd, J=3.6, 5.8 Hz), 3.83 (1H, m), 3.53 (1H, m), 3.06 (1H, t, J=7.1 Hz), 2.36 (1H, dd, J=3.6, 17.2 Hz), 2.12 (1H, dd, J=3.9, 17.2 Hz), 1.68 (1H, t, J=5.4 Hz), 1.54 (2H, m), 1.41 (1H, m), 1.37 (9H, s), 1.31 (1H, m), 1.16 (3H, s), 1.02 (3H, s,), 0.99 (3H, d, J=6.8 Hz), 0.84 (9H, s), 0.81 (9H, s), 0.05 (3H, s), 0.01 (6H, s), −0.01 (3H, s); $^{13}C$ NMR ($CDCl_3$, 100 MHz) δ 217.7, 171.3, 80.57, 73.5, 73.1, 63.0, 53.4, 26.8, 41.2, 32.1, 28.1, 28.0, 26.0, 25.9, 23.1, 19.8, 18.1 (overlapping), 15.3, −4.0, −4.3 (overlapping), −4.8.

Beta isomer: IR (film): 3442, 2857, 1732, 1700, 1472, 1368, 1255 $cm^{-1}$; $^1H$ NMR ($CDCl_3$, 400 MHz) δ 4.45 (1H, t, J=5.3 Hz), 3.86 (1H, m), 3.52 (2H, q, J=5.9 Hz), 3.01 (1H, m), 2.28 (1H, dd, J=4.3, 17.1 Hz), 2.16 (1H, dd, J=5.5, 17.1 Hz), 1.67 (1H, t, J=5.6 Hz), 1.56 (2H, m), 1.44 (1H, m), 1.37 (9H, s), 1.34 (1H, m), 1.13 (3H, s), 0.97 (3H, d, J=7.4 Hz), 0.96 (3H, s), 0.83 (9H, s), 0.79 (9H, s), 0.01 (3H, s), 0.00 (6H, s), −0.07 (3, s); $^{13}C$ NMR ($CDCl_3$, 100 MHz) δ 217.1, 171.2, 80.6, 73.5, 72.1, 62.9, 63.9, 46.4, 41.2, 32.0, 28.1, 28.0, 26.0, 25.9, 21.5, 19.5, 18.2, 18.1, 15.8, −4.0, −4.3, −4.4, −4.7.

EXAMPLE 49

Aldehyde formation: DMSO (0.177 mL, 2.50 mmol) was added to a mixture of oxalyl chloride (0.11 mL, 1.25 mmol) in $CH_2Cl_2$ (15 mL) at −78° C. After 10 min, the alcohol (0.531 g, 0.96 mmol) was added in $CH_2Cl_2$ (4 mL). After 20 min, TEA (0.697 mL, 5.00 mmol) was added to the reaction followed by warming to rt. The reaction was then poured into $H_2O$ (50mL) and extracted with $Et_2O$ (3×50 mL). The organics were washed once with $H_2O$ (30 mL), once with brine (30 mL) and dried over anhydrous $MgSO_4$. The aldehyde was used in crude form.

EXAMPLE 50

Wittig olefination to give 9D: NaHMDS (1.0 M soln in THF, 1.54 mL, 1.54 mmol) was added to a suspension of methyl triphenylphosphonium bromide (0.690 g, 1.92 mmol) in THF (20 mL) at 0° C. After 1 h, the crude aldehyde (0.96 mmol) was added in THF (5 mL). After 15 min at 0° C., $H_2O$ (0.1 mL) was added and the reaction poured into hexanes (50 mL). This was filtered through a plug of silica gel eluting with hexanes/$Et_2O$ (9:1, 150 mL). The crude olefin 9D was further purified by flash chromatography on silica gel eluting with ethyl acetate in hexanes (5%) to give 0.437 g (83% for two steps) of the olefin 9D as a clear oil: IR (film): 2857, 1732, 1695, 1472, 1368, 1255, 1156 $cm^{-1}$; $^1H$ NMR ($CDCl_3$, 400 MHz) δ 5.72 (1H, m), 4.91 (2H, m), 4.25 (1H, dd, J=3.9, 5.4 Hz), 3.81 (1H, m), 3.05 (1H, m), 2.38 (1H, dd, J=7.9, 17.2 Hz), 2.12 (1H, dd, J=6.6, 17.2 Hz), 2.04 (2H, q, J=7.5 Hz), 1.47 (1H, m), 1.39 (9H, s), 1.34 (1H, m), 1.20 (3H, s), 1.00 (3H, s), 3.00 (3H, d, J=6.7 Hz), 0.85 (9H, s), 0.83 (9H, s), 0.07 (3H, s), 0.00 (6H, s), −0.05 (3H, s); $^{13}C$ NMR ($CDCl_3$, 100 MHz) δ 217.5, 172.1, 137.9, 114.0, 80.4, 74.0, 73.0, 53.0, 46.9, 41.3, 35.1, 29.0, 28.1, 26.0, 25.9, 22.8, 20.2, 18.2 (overlapping), 14.9, −4.1, −4.2, −4.3, −4.8.

EXAMPLE 51

TBS ester 10D: The olefin 9D (0.420 g, 0.76 mmol) was dissolved in $CH_2Cl_2$ (15 mL) and treated successively with 2,6-lutidine (1.33 mL, 11.4 mmol) and TBSOTf (1.32 mL, 5.73 mmol). After 7 h, the reaction was poured into $Et_2O$ (100 mL) and washed successively with 0.2N HCl (25 mL), brine (20 mL) and dried over anhydrous $MgSO_4$. The residue was purified by flash chromatography on a short pad of silica gel with fast elution with hexanes/ethyl acetate (20:1) to give the TBS ester 10D as a clear oil. The purification must be done quickly to avoid hydrolysis of the silyl ester: IR (film): 2930, 1721, 1695, 1472, 1254, 1091 $cm^{-1}$; $^1H$ NMR ($CDCl_3$, 400 MHz) δ 5.73 (1H, m), 4.91 (2H, m), 4.25 (1H, dd, J=3.8, 5.4 Hz) 3.80 (1H, q, J=6.8 Hz), 3.06 (1H, m), 2.50 (1H, dd, J=3.7, 17.3 Hz), 2.19 (1H, dd, J=5.7, 17.3 Hz), 2.04 (2H, dd, J=7.6, 15.3 Hz), 1.49 (1H, m), 1.36 (1H, m), 1.21 (3H, s), 1.00 (3H, d, J=6.8 Hz), 0.88 (9H, s), 0.85 (9H, s), 0.83 (9H, s), 0.22 (3H, s), 0.22 (3H, s), 0.21

(3H, s), 0.06 (3H, s), 0.01 (6H, s), −0.05 (3H, s); $^{13}$C NMR (CDCl$_3$, 100 MHz) δ 217.3 172.3, 138.5, 114.4, 74.5, 73.0, 53.2, 46.9, 41.8, 35.1, 29.0, 26.0, 25.7, 25.5, 22.8, 20.4, 18.2, 18.1, 17.5, 14.9, −2.9, −4.0, −4.2, −4.3, −4.8, −4.9.

EXAMPLE 52

Suzuki coupling: The acetate acid 13D was purified by flash chromatography on silica gel eluting with hexanes/ethyl acetate (7:1–4:1). This was further purified by preparative-TLC eluting with hexanes/ethyl acetate (2:1) to remove unreacted vinyl iodide 12D from the acetate acid 13D. Isolated yield of the acid was 0.297 g (62% based on 90% purity with borane residues).

EXAMPLE 53

Hydrolysis of acetate acid 13D: The acetate 13D (0.220 g, 0.297 mmol) was dissolved in MeOH/H$_2$O (2:1, 15 mL) and K$_2$CO$_3$ (0.300 g) was added. After 3 h, the reaction was diluted with sat NH$_4$Cl (20 mL) and extracted with CHCl$_3$ (5×20 mL). The hydroxy-acid 14D was purified by flash chromatography on silica gel eluting with hexanes/ethyl acetate (4:1–2:1) to give 0.146 g (70%) of the pure hydroxy acid 14D. IR (film): 3510–2400, 1712, 1694, 1471, 1254, 1093 cm$^{-1}$; $^1$H NMR (CDCl$_3$, 400 MHz) 6 6.96 (1H, s), 6.66 (1H, s), 5.55 (1H, m), 5.38 (1H, m), 4.38 (1H, dd, J=3.4, 6.1 Hz), 4.19 (1H, t, J=7.5 Hz), 3.84 (1H, m), 3.05 (1H, t, J=7.0 Hz), 2.72 (3H, s), 2.49 (1H, dd, 3.2, 16.4 Hz), 2.42 (2H, m), 2.33 (1H, dd, J=6.2, 16.4 Hz), 2.07 (2H, m), 2.02 (3H, s), 1.33 (4H, m), 1.19 (3H, s), 1.14 (3H, s), 1.06 (3H, d, J=6.7 Hz), 0.89 (9H, s), 0.88 (9H, s), 0.11 (3H, s), 0.07 (3H, s), 0.04 (6H, s); $^{13}$C NMR (CDCl$_3$, 100 MHz) δ 217.8, 176.6, 164.9, 152.5, 141.7, 132.9, 125.0, 119.0, 115.3, 73.5, 73.3, 53.4, 47.0, 40.1, 35.8, 33.2, 29.8, 27.4, 26.0, 25.9, 24.5, 19.0, 18.1, 15.2, 25 14.3, −4.0, −4.2, −4.2, −4.7.

EXAMPLE 54

Macrolactonization: DCC (0.150 g, 0.725 mmol), 4-DMAP (0.078 g, 0.64 mmol) and 4-DMAP.HCl (0.110 g, 0.696 mmol) were dissolved in CHCl$_3$ (80 mL) at 80° C. To this refluxing solution was added by syringe pump the hydroxy acid 14D (0.020 g, 0.029 mmol) and DMAP (0.010 g) in CHCl$_3$ (10 mL) over 20 h. The syringe needle was placed at the base of the condensor to ensure proper addition. After 20 h, the reaction was cooled to 50° C. and AcOH (0.046 mL, 0.812 mmol) was added. After 2 h, the reaction was cooled to rt and washed with sat NaHCO$_3$ (30 mL), brine (30 mL) and dried over anhydrous Na$_2$SO$_4$. The lactone 15D was purified by flash chromatography on silica gel eluting with hexanes/ethyl acetate (20:1→15:1) to give 0.014 g (75%): IR (film): 2929, 1741, 1696, 1254, 1097 cm$^{-1}$; $^1$H NMR (CDCl$_3$, 400 MHz) δ 6.95 (1H, s), 6.55 (1H, s), 5.48 (1H, m), 5.37 (1H, m), 5.16 (1H, d, J=9.8 Hz), 4.17 (1H, d, J=8.3 Hz), 4.07 (1H, t, J=7.2 Hz), 3.02 (1H, t, J=7.2 Hz), 2.77(1H, m), 2.70(3H, s), 2.64 (2H, m), 2.29 (1H, m), 2.15 (1H, m), 2.12 (3H, s), 1.92 (1H, m), 1.71 (1H, m), 1.44 (2H, m), 1.26 (1H, m), 1.17 (3H, s), 1.12 (3H, s), 1.11 (3H, d, J=7.0 Hz), 0.91 (9H, s), 0.85 (9H, s), 0.09 (3H, s), 0.06 (6H, s), −0.04 (3H, s); $^{13}$C NMR (CDCl$_3$, 100 MHz) δ 215.2, 171.9, 164.5, 152.5, 138.0, 133.5, 123.8, 120.0, 116.7, 79.4, 76.2, 72.5, 53.5, 47.4, 39.9, 34.5, 31.9, 31.5, 30.2, 27.7, 26.1, 25.9, 24.1, 23.8, 23.1, 22.6, 19.2, 18.5, 18.2, 16.3, 14.9, 14.1, −3.7, −4.2, −4.7, −5.2.

EXAMPLE 55

Desmethyidesoxyepothilone A (16D): To the lactone 15D (0.038 g, 0.056 mmol) in THF (2.0 mL) was added HF.pyridine (1.0 mL). After 2 h, the reaction was poured into sat NaHCO$_3$ (30 mL) and extracted with CHCl$_3$ (5×20 mL). The organics were dried over Na$_2$SO$_4$. The crude diol 16D was purified by flash chromatography on silica gel eluting with hexanes/ethyl acetate (3:1→2:1) to give 0.023 g (89%): IR (film): 3501, 2933, 1734, 1684, 1290, 1248, 1045 cm$^{-1}$; $^1$H NMR (CDCl$_3$, 400 MHz) δ 6.95 (1H, s), 6.59 (1H, s), 5.40 (2H, m), 5.23 (1H, dd, J=1.4, 9.5 Hz), 4.38 (1H, bd, J=11.1 Hz), 3.78 (1H, t, J=6.9 Hz), 3.59 (1H, bs), 3.47 (1H, s), 2.99 (1H, q, 7.0 Hz), 2.68 (3H, s), 2.66 (1H, m), 2.46 (1H, dd, J=11.4, 14.4 Hz), 2.26 (1H, dd, J=2.2, 14.4 Hz), 2.22 (1H, m), 2.06 (3H, s), 1.96 (1H, m), 1.49 (3H, m), 1.35 (3H, m), 1.30 (3H, s), 1.15 (3H, d, J=6.9 Hz), 1.06 (3H, s); $^{13}$C NMR (CDCl$_3$, 100 MHz) δ 221.5, 170.3, 165.1, 151.8, 139.1, 132.8, 125.2, 119.1, 115.5, 78.4, 72.5, 70.8, 53.8, 42.7, 39.6, 32.3, 31.8, 28.3, 26.8, 24.8, 23.1, 19.0, 17.2, 16.0, 11.1.

EXAMPLE 56

Epoxide formation: Diol 16D (0.008 g, 0.017 mmol) was dissolved in CH$_2$Cl$_2$ (1.0 mL) and cooled to −60° C. Dimethyldioxirane (0.06 M, 0.570 mL, 0.0034 mmol) was then slowly added. The reaction temperature was slowly warmed to −25° C. After 2 h at −25° C., the volatiles were removed from the reaction at −25° C. under vacuum. The resulting residue was purified by flash chromatography on silica gel eluting with MeOH in CH$_2$Cl$_2$ (1%→2%) to give a 1.6:1 mixture of cis-epoxides 3D and the diastereomeric cis-epoxide (0.0058 g, 74%). The diastereomeric epoxides were separated by preparative-TLC eluting with hexanes/ethyl acetate (1:1) after 3 elutions to give pure diastereomers:

Beta epoxide 3D: IR (film): 3458, 2928, 1737, 1685, 1456, 1261, 1150, 1043, 1014 cm$^{-1}$; $^1$H NMR (CD$_2$Cl$_2$, 500 MHz) δ 7.01 (1H, s), 6.56 (1H, s), 5.35.(1H, dd, J=2.3, 9.6 Hz), 4.30 (1H, dd, J=3.0, 5.7 Hz), 3.85 (1H, m), 3.81 (1H, d, J=5.7 Hz), 3.42 (1H, d, J=2.0 Hz), 3.03 (1H, q, J=6.8 Hz), 2.97 (1H, m), 2.88 (1H, m), 2.67 (3H, s), 2.46 (1H, dd, J=9.0, 14.5 Hz), 2.33 (1H, dd, J=2.6, 14.5 Hz), 2.13 (1H, dt, J=3.0, 15.0 Hz), 2.08 (3H, s), 1.82 (1H, m), 1.52 (6H, m), 1.41 (1H, m), 1.33 (3H, s), 1.21 (4H, m), 1.12 (3H, d, J=7.0 Hz), 1.06 (3H, s); $^{13}$C NMR (CD$_2$Cl$_2$, 125 MHz) δ 221.9, 170.6, 165.6, 152.2, 138.3, 120.2, 116.6, 77.3, 73.4, 69.9, 57.7, 55.3, 43.7, 39.7, 32.6, 32.0, 29.8, 27.2, 25.7, 24.7, 22.5,19.2, 19.0, 15.6, 15.6, 11.5;

Alpha epoxide: IR (film): 3439, 2918, 1735, 1684, 1455, 1262, 1048, 1014 cm$^{-1}$; $^1$H NMR (CD$_2$Cl$_2$, 500 MHz) δ 7.02 (1H, 5), 6.56 (1H, s), 5.62 (1H, d, J=8.1 Hz), 4.33 (1H, dd, J=2.7, 11.0 Hz), 3.85 (1H, t, J=5.9 Hz), 3.27 (1H, d, J=5.3 Hz), 3.11 (1H, m), 3.07 (1H, d, J=7.0 Hz), 3.04 (1H, s), 2.87 (1H, m), 2.68 (3H, s), 2.46 (1H, dd, J=11.1, 14.1 Hz), 2.35 (1H, dd, J=2.3, 14.1 Hz), 2.11 (3H, s), 2.06 (1H, ddd, J=1.9, 4.5, 15.1 Hz), 1.87 (1H, m), 1.52 (6H, m), 1.38 (2H, m), 1.29 (3H, s), 1.08 (3H, d, J=6.9 Hz), 103 (3H, s); $^{13}$C NMR (CD$_2$Cl$_2$, 125 MHz) δ 222.1, 170.2, 165.3, 152.5, 137.6, 119.7, 116.7, 76.7, 72.9, 70.6, 57.1, 55.1, 44.7, 40.0, 32.1, 31.4, 30.0, 26.6, 25.5, 24.7, 21.3, 19.3, 18.7, 15.7, 11.5.

EXAMPLE 57

Experimental Data for C-12 Hydroxy Epothilone Analogs

Propyl hydroxy compound 43: $^1$H NMR (CDCl$_3$, 400 MHz) d 6.96 (1H, s), 6.59 (1H, s), 5.16–5.23 (2H, band), 4.28 (1H, m), 3.72 (1H, m), 3.63 (2H, t, J=6.3 Hz), 3.17 (1H, dq, J=2.2, 0.5 Hz), 3.02 (1H, s), 2.70 (3H, s), 2.65 (2H, m), 2.46 (1H, dd, J=10.9 14.6 Hz), 2.29 (2H, m), 1.98–2.09 (6H, band), 1.60–1.91 (6H, band), 1.35 (3H, s), 1.33 (3H, s), 1.18 (3H, d, J=6.8 Hz), 1.07 (3H, s), 1.01 (3H, d, J=7.1 Hz); $^{13}$C NMR (CDCl$_3$, 100 MHz) d 220.69, 170.29, 165.00, 151.81, 141.63, 138.93, 120.64, 118.81, 115.52, 78.53, 77.23, 73.93, 71.85, 62.26, 53.63, 41.57, 39.54, 37.98, 32.33, 32.14, 31.54, 30.75, 29.67, 25.27, 22.89, 18.92, 17.67, 15.98, 15.74, 13.28; MS e/m 536.2, calc 535.29.

Hydroxy methyl compound 46: $^1$H NMR (CDCl$_3$, 400 MHz) d 6.97 (1H, s), 6.63 (1H, s), 5.43 (1H, dd, J=5.7, 9.1 Hz), 5.24 (1H, d, J=7.4 Hz), 4.31 (1H, d, J=9.7 Hz), 4.05 (2H, dd, J=7.3, 31.0 Hz), 3.87 (1H, bs), 3.69 (1H, bs), 3.17 (1H, dd, J=2.0, 6.9 Hz), 3.03 (1H, s), 2.69 (3H, s), 2.63 (1H, m), 2.45 (1H, dd, J=11.2, 14.6 Hz), 2.37 (1H, m), 2.25 (2H, m), 2.11 (1H, m), 2.05 (3H, s), 1.78 (1H, m), 1.70 (1H, m), 1.35 (3H, s), 1.34 (2H, m), 1.29 (1H, m), 1.18 (3H, d, J=6.8 Hz), 1.06 (3H, s), 1.00 (3H, d, J=7.0 Hz); $^{13}$C NMR (CDCl$_3$, 100 MHz) d 220.70, 170.16, 165.02, 151.63, 141.56, 138.41, 121.33, 118.65, 115.33, 77.74, 77.25, 74.11, 71.37, 65.75, 53.86, 41.52, 39.52, 37.98, 31.46, 27.70, 25.10, 22.86, 18.74, 17.20, 16.17, 15.63, 13.41.

Discussion

Total Synthesis of (−)-Epothilone A.

The first known method for preparing epothilone A (1) is provided by this invention. Carbons 9 through 11 insulate domains of chirality embracing carbons 3 through 8 on the acyl side of the macrolactone, and carbons 12 through 15 on the alkyl side. Transmitting stereochemical information from one of the segments to the other is unlikely. Thus, the approach taken deals with the stereochemistry of each segment individually. In the acyl segment, this strategy required knowledge of both the relative and absolute configurations of the "polypropionate-like" network. In the alkyl segment, two possibilities emerge. In one instance, the C12–C13 epoxide would be included in the construct undergoing merger with the acyl related substructure. In that case it would be necessary to secure the relative stereochemical relationship of carbons 15, 13 and 12. It was necessary to consider the the possibility that the epoxide would be deleted from the alkyl-side moiety undergoing coupling. This approach would only be feasible if the epoxide could be introduced with acceptable stereocontrol after closure of the macrocycle. The synthesis of compound 4, which contains most of the requisite stereochemical information required for the acyl fragment, is described above. This intermediate is prepared by a novel oxidatively induced solvolytic cleavage of the cyclopropanopyran 3. Also described above is a construct containing the alkyl side coupling partner embodying the absolute and relative stereochemistry at carbons 15, 13 and 12, which differs from the alternative approach set forth below.

In considering the union of the alkyl and acyl domains, several potential connection sites were available. At some point, an acylation would be required to establish an ester (or lactone) bond (see bold arrow 2). Furthermore, an aldol construction was required to fashion a C2–C3 connection. Determining the exact timing of this aldol step required study. It could be considered in the context of elongating the C3–C9 construct to prepare it for acylation of the C-15 hydroxyl. Unexpectedly, it was discovered that the macrolide could be closed by an unprecedented macroaldolization. (For a previous instance of a keto aldehyde macroaldolization, see: C. M. Hayward, et al., J. Am. Chem. Soc., 1993, 115, 9345.) This option is implied by bold arrow 3 in FIG. 1(A).

The first stage merger of the acyl and alkyl fragments (see bold arrow 1) posed a difficult synthetic hurdle. It is recognized in the art (P. Bertinato, et al., J. Org. Chem., 1996, 61, 8000; vide infra) that significant resistance is encountered in attempting to accomplish bond formation between carbons 9 and 10 or between carbons 10 and 11, wherein the epoxide would be included in the alkyl coupling partner. These complications arose from unanticipated difficulties in fashioning acyl and alkyl reactants with the appropriate complementarity for merger across either of these bonds. An initial merger between carbons 11 and 12 was examined. This approach dictated deletion of the oxirane linkage from the O-alkyl coupling partner. After testing several permutations, generalized systems 5 and 6 were examined to enter the first stage coupling reaction. The former series was to be derived from intermediate 4. A de novo synthesis of a usable substrate corresponding to generalized system 5 would be necessary (FIG. 1(B)).

The steps leading from 4 to 11 are shown in Scheme 2. Protection of the future C-7 alcohol (see compound 7) was followed by cleavage of the benzyl ether and oxidation to aldehyde 8. Elongation of the aldehyde to the terminal allyl containing fragment 10 proceeded through end ether 9 (mixture of E and Z geometrical isomers). Finally, the dithiane linkage was oxidatively cleaved under solvolytic trapping conditions, giving rise to specific coupling component 11. G. Stork; K. Zhao, Tetrahedron Lett. 1989, 30, 287.

Figure 4A:
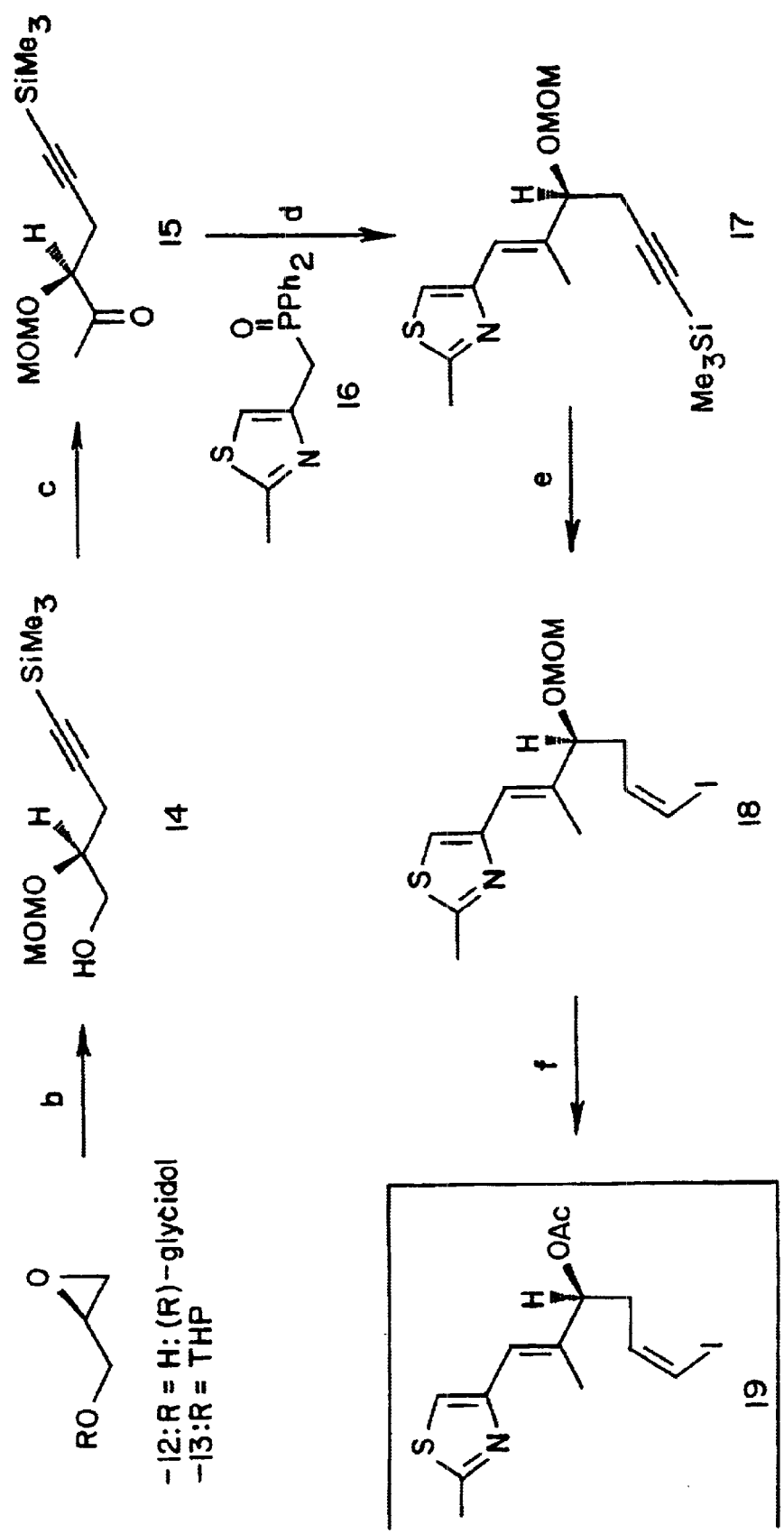
FIG. 4(A) provides synthesis of compound 19. (a) DHP, PPTS, $CH_2Cl_2$, rt: (b) (1) $Me_3SiCCLi$, $BF_3.OEt_2$, THF, $-78°$ C.; (2) MOMCl, I-$Pr_2$NEt, Cl$(CH_2)_2$Cl, $55°$ C.; (3) PPTS, MeOH, rt; (c) (1) $(COCl)_2$, DMSO, $CH_2Cl_2$, $-78°$ C.; then $Et_3N$, $-78°$ C.→rt; (2) MeMgBr, $Et_2O$, $0°$ C.→rt, (3) TRAP, NMO, 4 Å mol. sieves, $CH_2Cl_2$, $0°$ C.→rt,; (d) 16, n-BuLi, THF, $-78°$ C.; then 15, THF, $-78°$ C.→rt; (e) (1) N-iodosuccinimide, $AgNO_3$, $(CH_3)_2CO$; (2) $Cy_2BH$, $Et_2O$, AcOH; (f) (1) PhSH, $BF_3.OEt_2$, $CH_2Cl_2$, rt; (2) $Ac_2O$, pyridine, 4-DMAP, $CH_2Cl_2$, rt.

The synthesis of the alkyl fragment started with commercially available (R)-glycidol 12 which was converted, via its THP derivative 13, to alcohol 14. After cleavage of the tetrahydropyran blocking group, the resultant alcohol was smoothly converted to the methyl ketone 15, as shown. The latter underwent an Emmons-type homologation with phosphine oxide 16. D. Meng et al., J. Org. Chem., 1996, 61, 7998. This Emmons coupling provided a ca. 8:1 mixture of olefin stereoismoers in favor of trans-17. The resultant alkyne 17 was then converted, via compound 18 to Z-iodoalkene 19 (see FIG. 4(A)). E. J. Corey et al., J. Am. Chem. Soc., 1985, 107, 713.

Figure 4B:
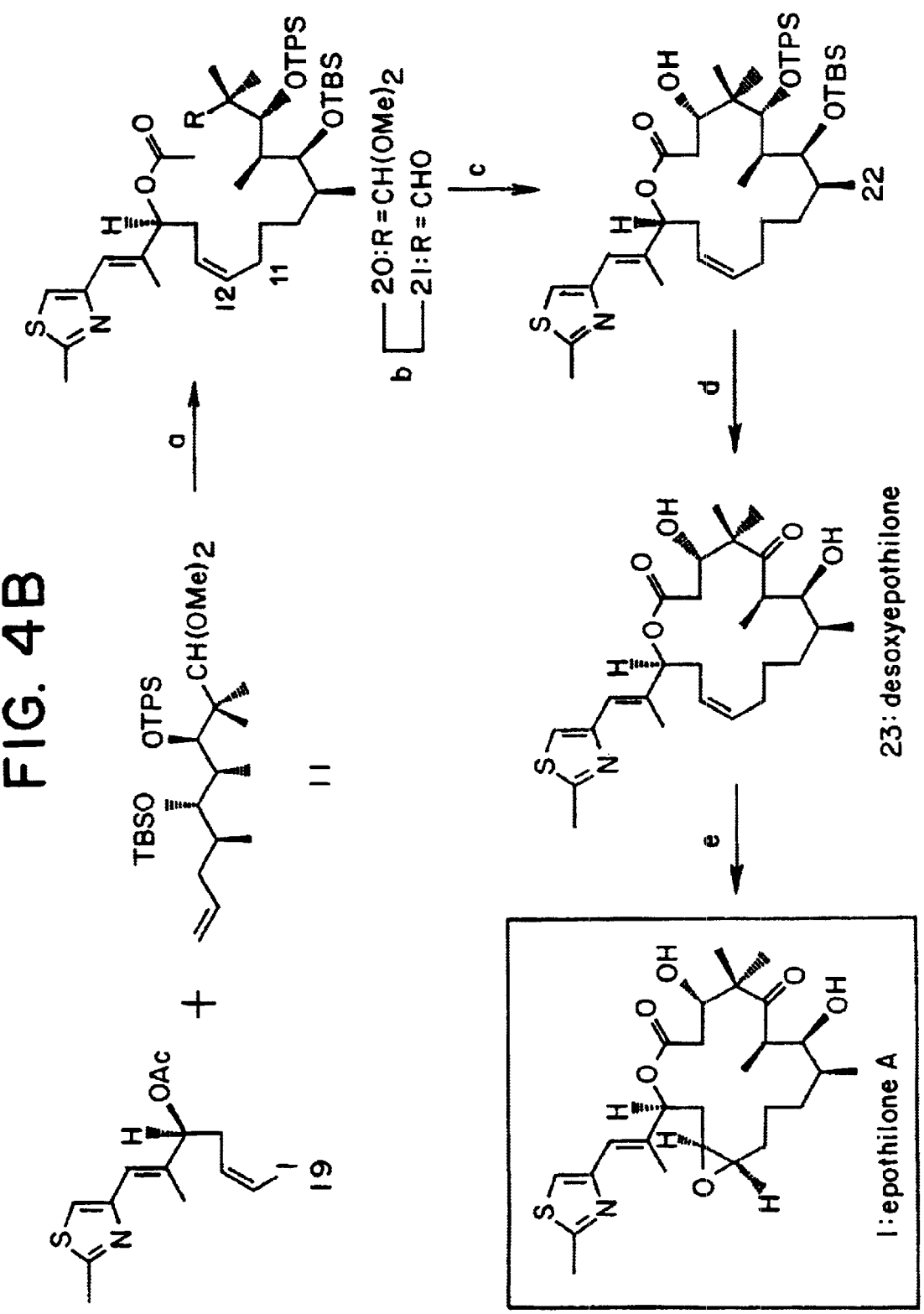
FIG. 4(B) presents synthesis of compound 1. (a) 11, 9-BBN, THF, rt; then $PdCl_2(dppf)_2$, $Cs_2CO_3$, $Ph_3As$, $H_2O$, DMF, 19, rt, 71%; (b) p-TsOH, dioxane/$H_2O$, $50°$ C.; (c) KHMDS, THF, $-78°$ C., 51%; (d) (1) HF-pyridine, pyridine, THF, rt, 97%; (2) t-$BuMe_2$ SiOTf, 2,6-lutidine, $CH_2Cl_2$, $-25°$ C., 93%; (3) Dess-Martin periodinane, $CH_2Cl_2$, 87%; (4) HF-pyridine, THF, rt, 99%; (e) dimethyidioxirane, $CH_2Cl_2$, 0.5 h, $-50°$ C., 45% ($\geq$20: 1).
Figure 5:
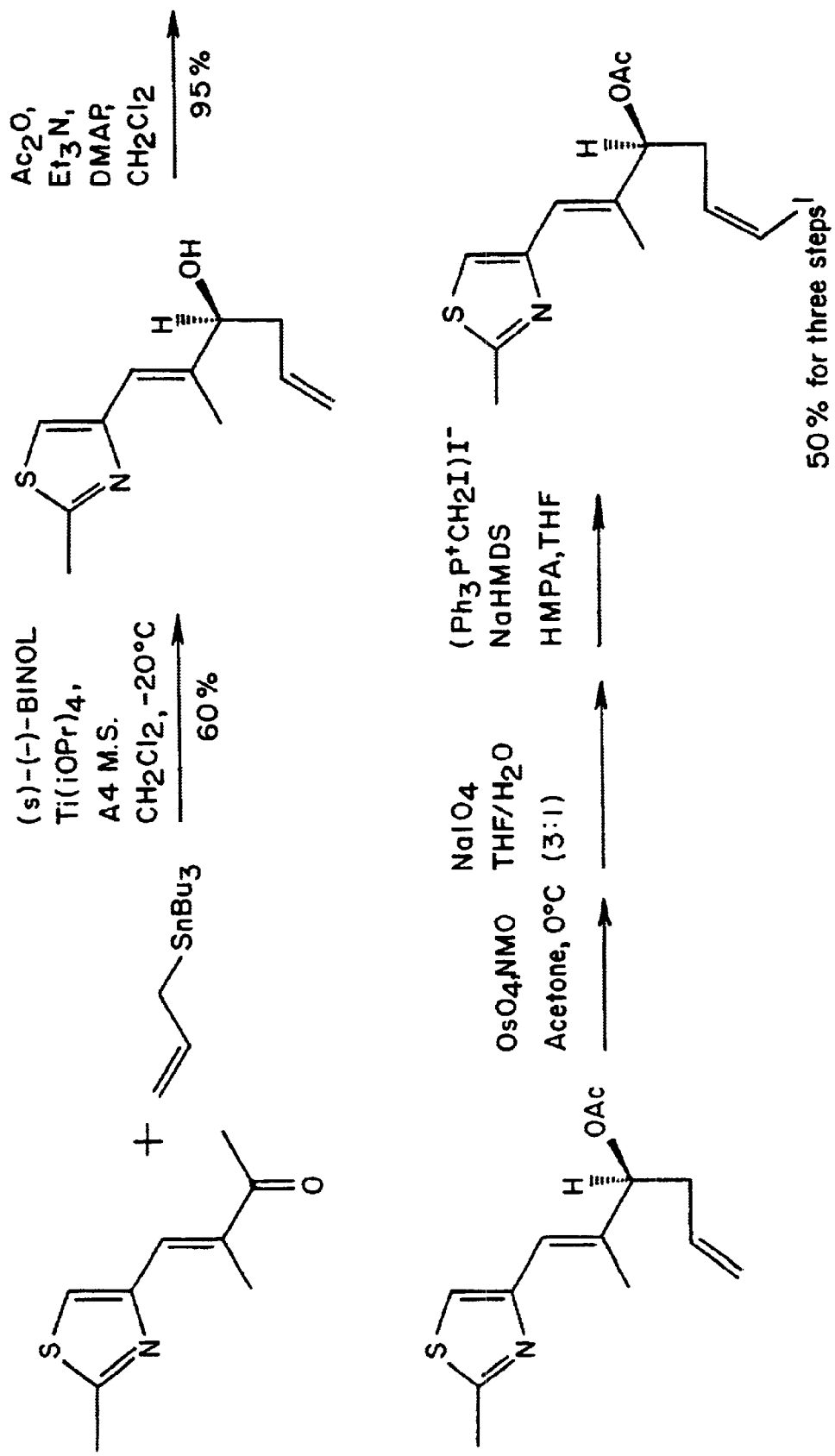
FIG. 5 shows a scheme of the synthesis of the "left wing" of epothilone A.
Figure 6A:
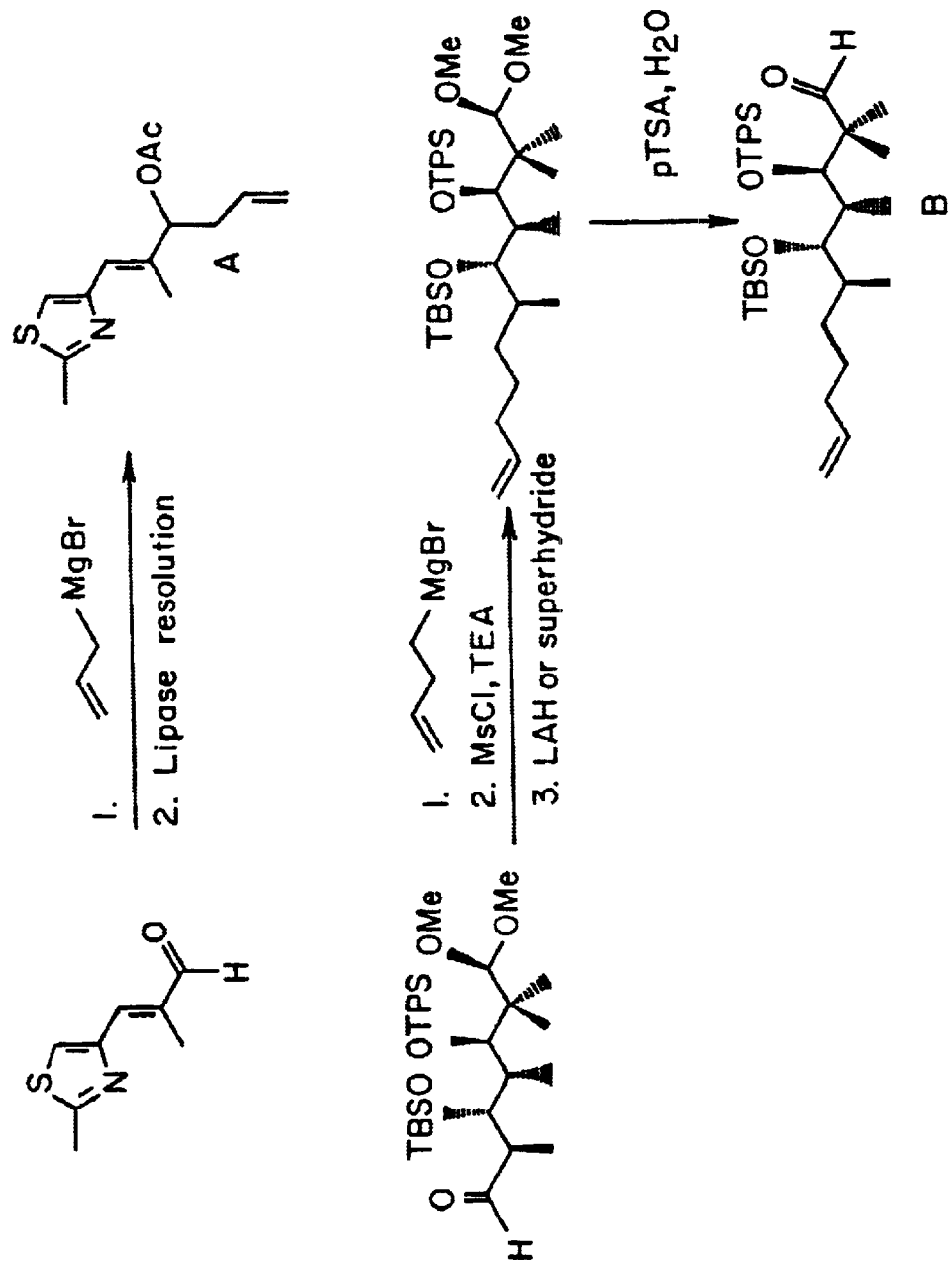
FIGS. 6(A) and 6(B) provide a scheme of an olefin metathesis route to epothilone A and other analogues.
Figure 6B:
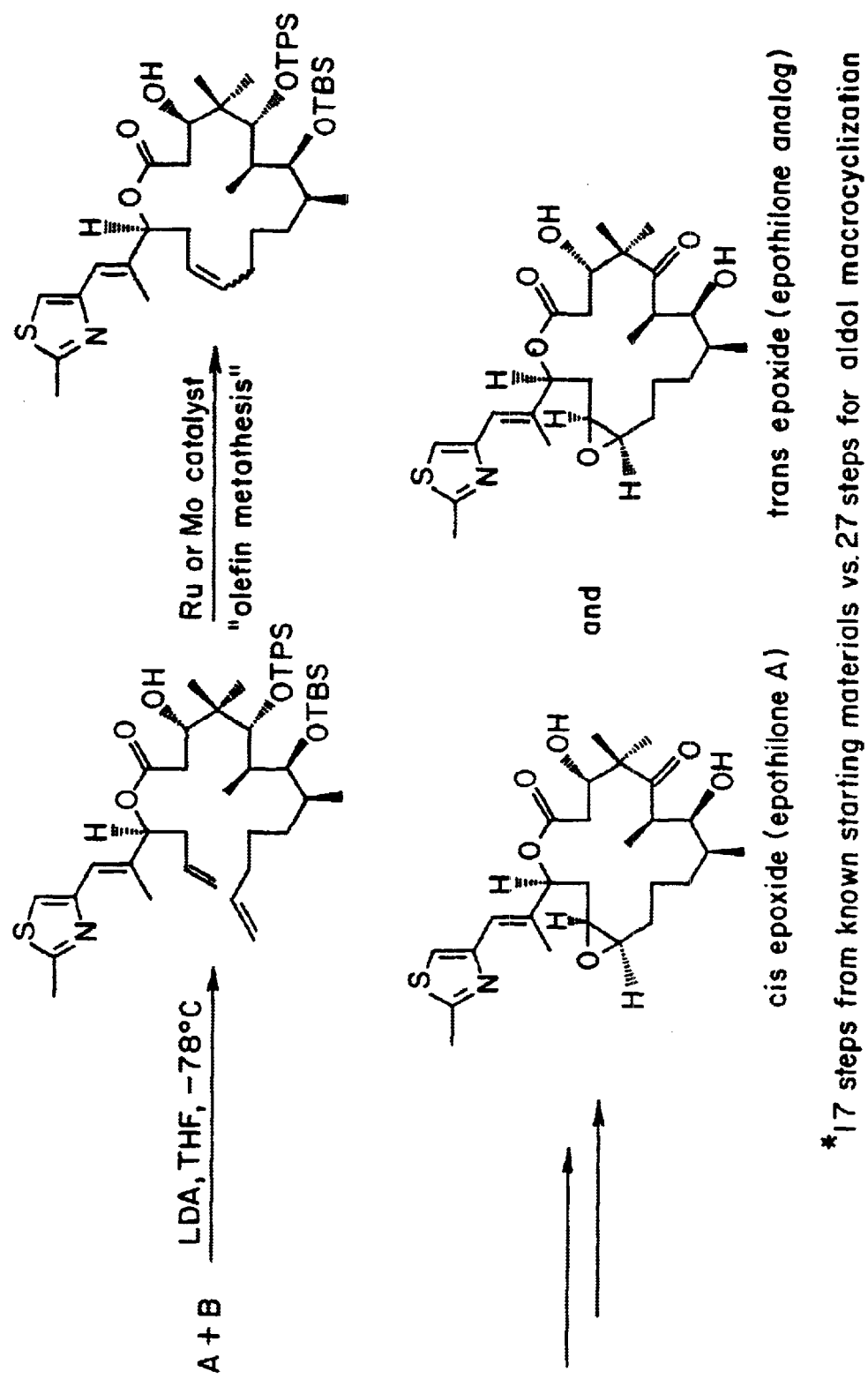

The critical first stage coupling of the two fragments was achieved by a B-alkyl Suzuki carbon—carbon bond construction. N. Miyaura et al., J. Am. Chem. Soc., 1989, 111, 314; N. Miyaura and A. Suzuki, Chem. Rev., 1995, 95, 2457. Thus, hydroboration of the pre-acyl fragment 11 was accomplished by its reaction with 9-BBN. The resultant mixed borane cross-coupled to iodoolefin 19, under the conditions indicated, to give 20 in 71% yield. (FIG. 4(B)) Upon cleavage of the acetal, aldehyde 21 was in hand.

The availability of 21 permitted exploration of the strategy in which the methyl group of the C-1 bound acetoxy function would serve as the nucleophilic component in a macroaldolization. Cf. C. M. Hayward et al., supra. Deprotonation was thereby accomplished with potassium hexamethyldisilazide in THF at −78° C. Unexpectedly, these conditions give rise to a highly stereoselective macroaldolization, resulting in the formation of the C-3 (S)-alcohol 22, as shown. The heavy preponderance of 22 was favored when its precursor potassium aldolate is quenched at ca. 0° C. When the aldolate was protonated at lower temperature, higher amounts of the C-3 (R) compound were detected. In fact, under some treatments, the C-3 (R) epimer predominates. It is therefore possible to generate highly favorable C-3(R):C-3(S) ratios in analytical scale quenches. In preparative scale experiments, the ratio of 22 to its C-3 epimer is 6:1.

With compound 22 in ready supply, the subgoal of obtaining desoxyepothilone (23) was feasible. This objective was accomplished by selective removal of the triphenylsilyl (TPS) group in 22, followed, sequentially, by selective silylation of the C-3 alcohol, oxidation of the C-5 alcohol, and, finally, fluoride-induced cleavage of the two silyl ethers.

Examination of a model made possible by the published crystal structure of epothilone (Höfle et al., supra), suggested that the oxirane is disposed on the convex periphery of the macrolide. Oxidation of 23 was carried out with dimethyl dioxirane under the conditions shown. The major product of this reaction was (−)epothilone A (1), the identity of which was established by nmr, infrared, mass spectral, optical rotation and chromotaraphic comparisons with authentic material. Höfle et al., supra. In addition to epothilone A (1), small amounts of a diepoxide mixture, as well as traces of the diastereomeric cis C12–C13 monoepoxide ($\geq$20:1) were detected.

The method of synthesis disclosed herein provides workable, practical amounts of epothilone A. More importantly, it provides routes to congeners, analogues and derivatives not available from the natural product itself. Studies Toward a Synthesis of Epothilone A: Use of Hydropyran Templates For the Management of Acyclic Stereochemical Relationships.

The synthesis of an enantiomerically pure equivalent of the alkoxy segment (carbons 9–15) was carried out in model studies. The key principle involves transference of stereochemical bias from an (S)-lactaldehyde derivative to an emerging dihydropyrone. The latter, on addition of the thiazole moiety and disassembly, provides the desired acyclic fragment in enantiomerically pure form.

Figure 14A:
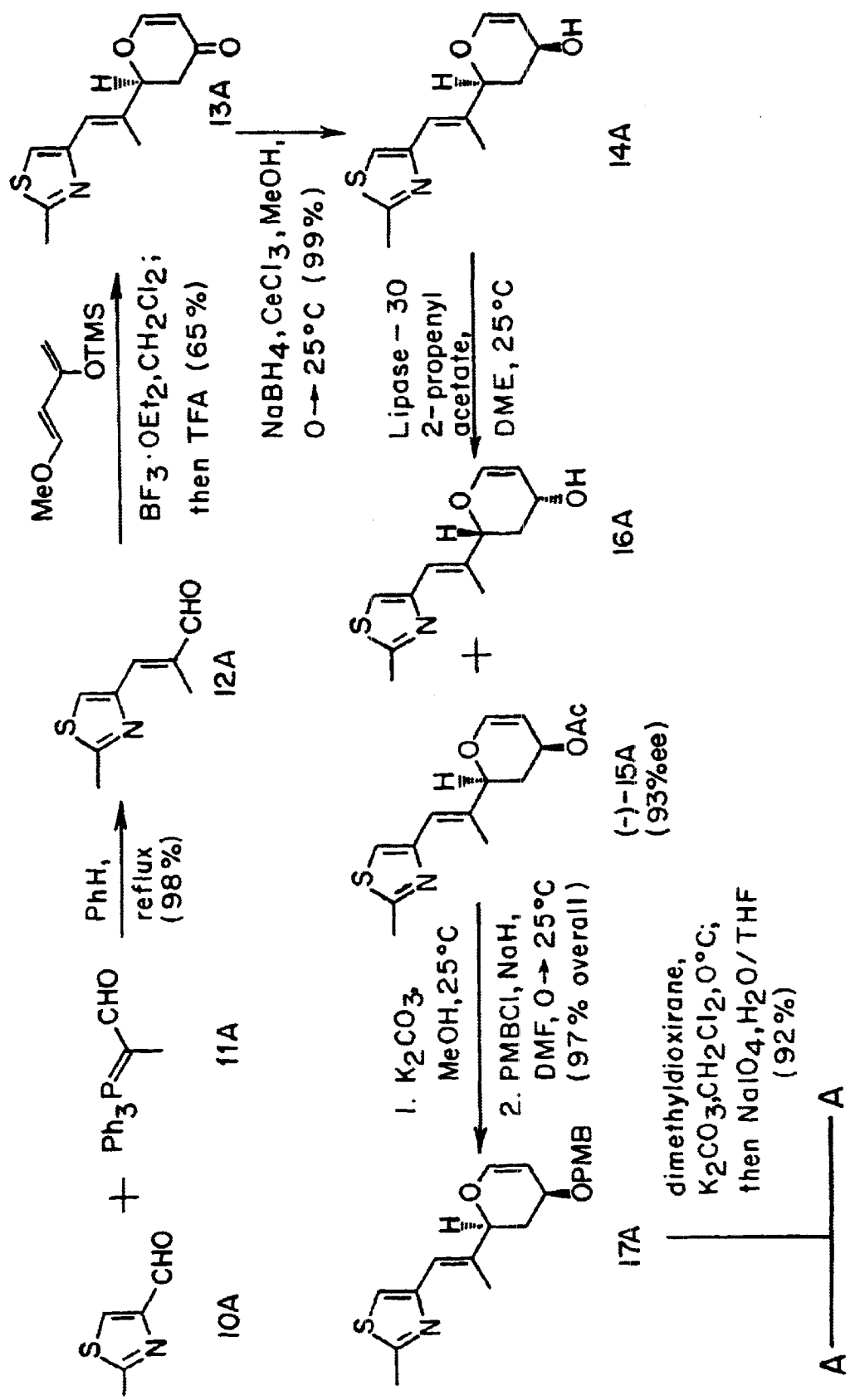
FIGS. 14(A) and 14(B) show the preparation of intermediate 4A.
Figure 14B:
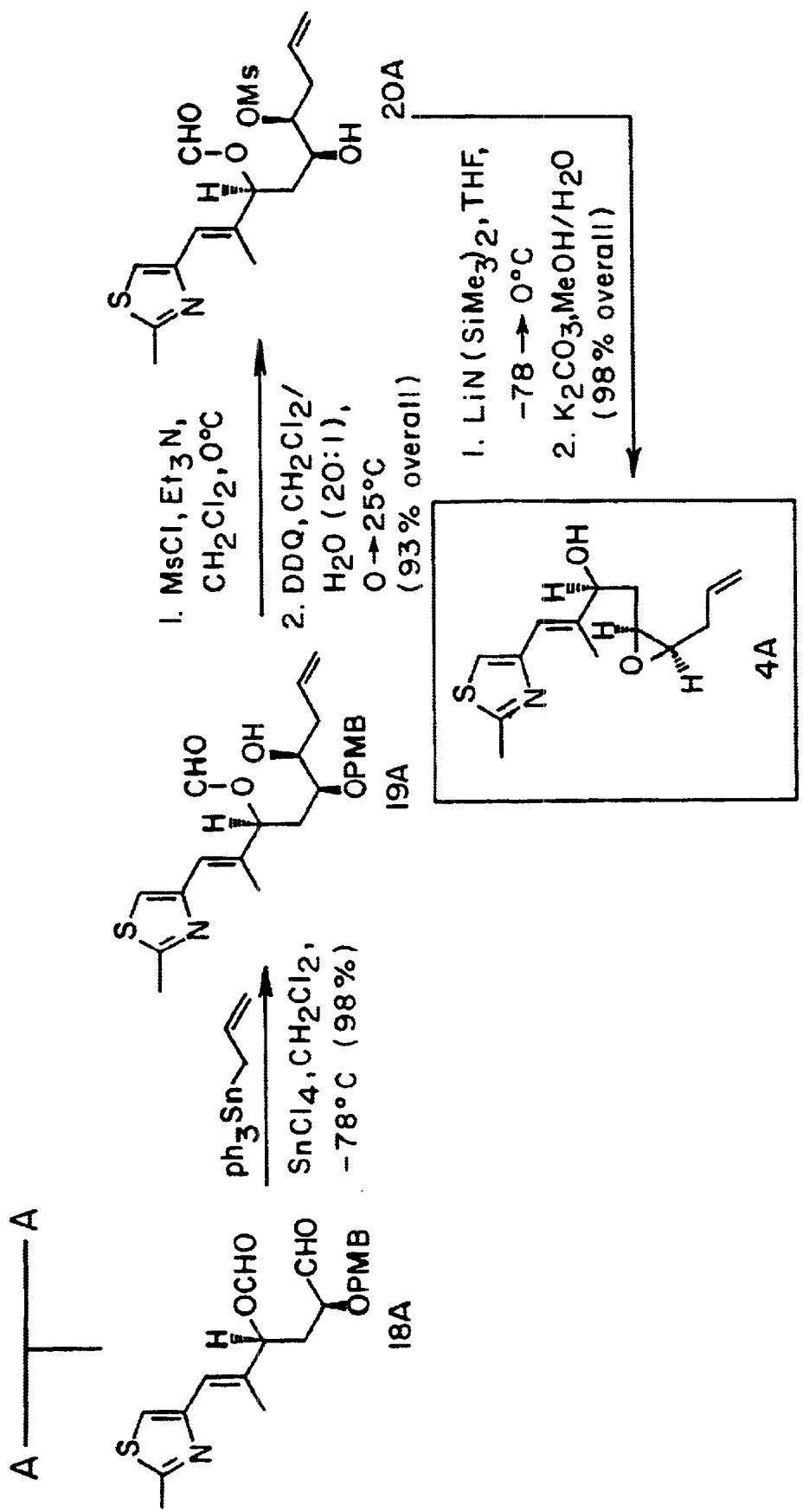

Various novel structural features of the epothilones make their synthesis challenging. The presence of a thiazole moiety, as well as a cis epoxide, and a geminal dimethyl grouping are key problems to be overcome. An intriguing feature is the array of three contiguous methylene groups which serves to insulate the two functional domains of the molecules. The need to encompass such an achiral "spacer element" actually complicates prospects for continuous chirality transfer and seems to call for a strategy of merging two stereochemically committed substructures. The present invention provides a synthesis of compound 4A (FIG. 14), expecting that, in principle, such a structure could be converted to the epothilones themselves, and to related screening candidates.

Figure 13:
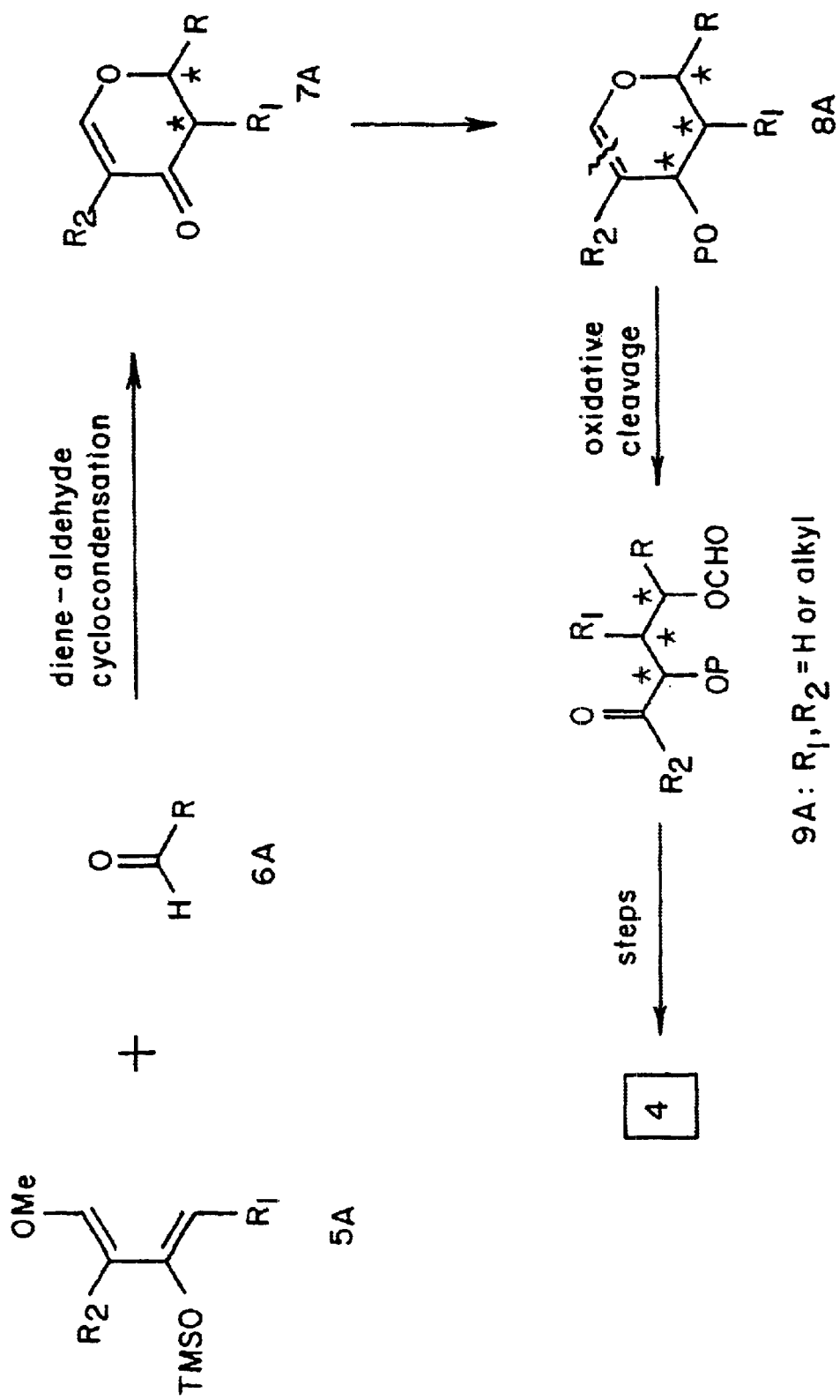
FIG. 13 shows a method of elaborating acyclic stereochemical relationships based on ghydropyrone matrices.

The identification of compound 4A as a synthetic intermediate served as an opportunity to illustrate the power of hydropyran matrices in addressing problems associated with the control of stereochemistry in acyclic intermediates. The synthesis of dihydropyrones was previously disclosed through what amounts to overall cyclocondensation of suitably active dienes and aldehydic heterodienophiles. Danishefsky, S. J. *Aldrichimica Acta*, 1986, 19, 59. High margins of steroselectivity can be realized in assembling (cf. 5A+6A→7A) such matrices (FIG. 13). Moreover, the hydropyran platforms service various stereospecific reactions (see formalism 7A→8A). Furthermore, the products of these reactions are amenable to ring opening schemes, resulting in the expression of acyciic fragments with defined stereochemical relationships (cf. 8A→9A). Danishefsky, S. J. *Chemtracts*, 1989, 2, 273.

The present invention provides the application of two such routes for the synthesis of compound 4A. Route 1, which does not per se involve control of the issue of absolute configuration, commences with the known aldehyde 10A. Shafiee, A., et al., *J. Heterocyclic Chem.*, 1979, 16, 1563; Schafiee, A.; Shahocini, S. *J. Heterocyclic Chem.*, 1989, 26, 1627. Homologation, as shown, provided enal 12A. Cyclocondensation of 12A with the known diene (Danishefsky, S. J.; Kitahara, T. *J. Am. Chem. Soc.*, 1974, 96, 7807), under $BF_3$ catalysis, led to racemic dihydropyrone 13A. Reduction of 13A under Luche conditions provided compound 14A. Luche, J.-L. *J. Am. Chem. Soc.*, 1978, 100, 2226. At this point it was feasible to take advantage of a previously introduced lipase methodology for resolution of glycal derivatives through enzymatically mediated kinetic resolution. Berkowitz, D. B. and Danishefsky, S. J. *Tetrahedron Lett.*, 1991, 32, 5497; Berkowitz, D. B.; Danishefsky, S. J.; Schulte, G. K. *J. Am. Chem. Soc.*, 1992, 114, 4518. Thus, carbinol 14A was subjected to lipase 30, in the presence of isopropenyl acetate, following the prescriptions of Wong (Hsu, S.-H., et al., *Tetrahedron Lett.*, 1990, 31, 6403)to provide acetate 15A in addition to the enantiomerically related free glycal 16A. Compound 15A was further advanced to the PMB protected system 17A. At this juncture, it was possible to use another reaction type previously demonstrated by the present inventors. Thus, reaction of 17A with dimethyidioxirane (Danishefsky, S. J.; Bilodeau, M. T. *Angew. Chem. Int. Ed. Engl.*, 1996, 35, 1381) generated an intermediate (presumably the corresponding glycal epoxide) which, upon treatment with sodium metaperiodate gave rise to aldehyde formate 18A. Allylation of 18A resulted in the formation of carbinol 19A in which the formate ester had nicely survived. (For a review of allylations, see: Yamamoto, Y.; Asao, N. *Chem. Rev.* 1993, 93, 2207) However, 19A was accompanied by its anti stereoisomer (not shown here) [4:1]. Mesylation of the secondary alcohol, followed by deprotection (see 19A→20A) and cyclization, as indicated, gave compound 4A.

Figure 15:
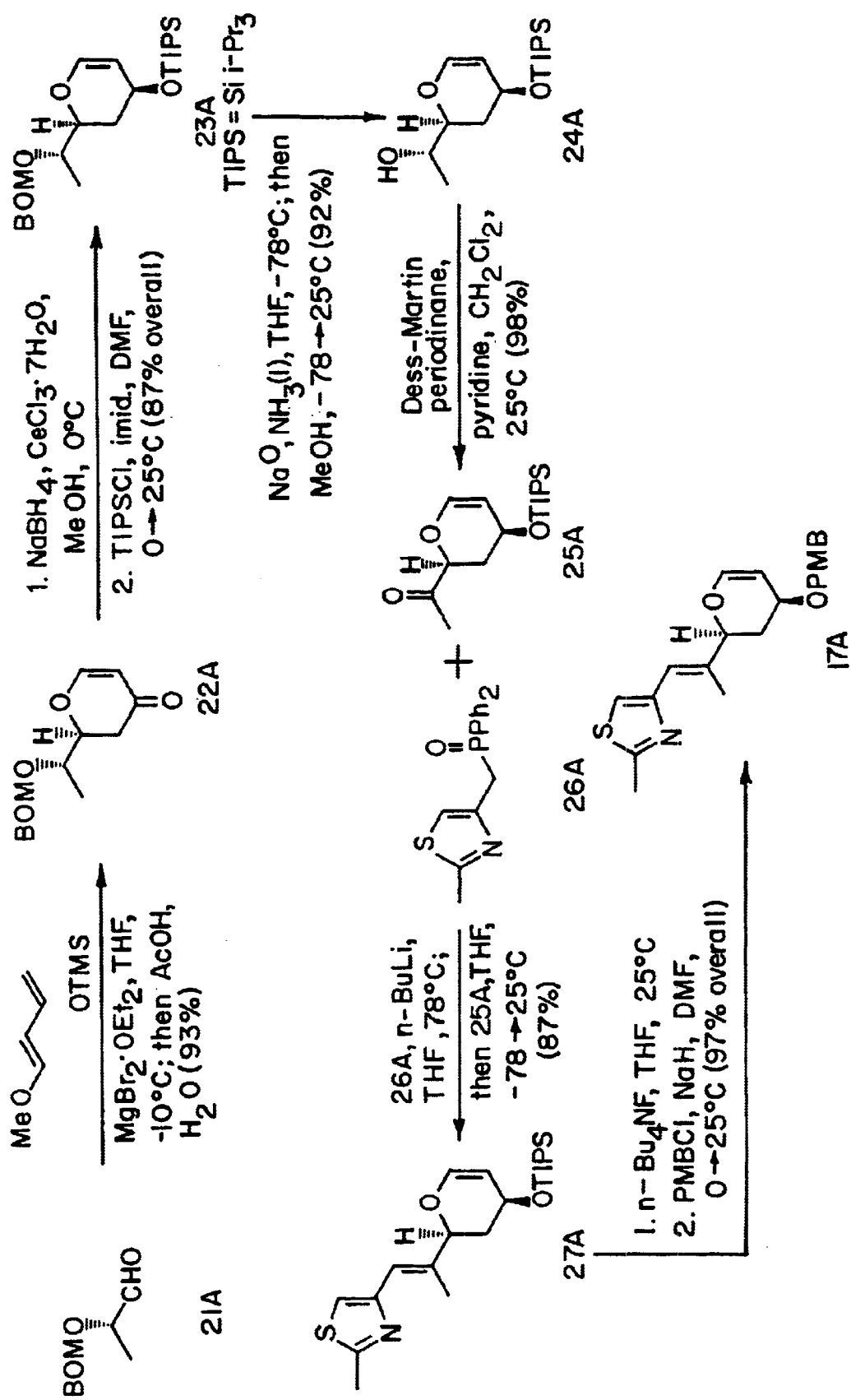
FIG. 15 shows an alternative enantioselective synthesis of compound 17A.

In this synthesis, only about half of the dihydropyrone was secured through the process of kinetic resolution. While, in theory, several of the synthetic stratagems considered contemplate use of each enantiomer of 15A to reach epothilone itself, another route was sought to allow for full enantiomeric convergence. The logic of this route is that the chirality of a "dummy" asymmetric center is communicated to the emerging pyran following previously established principles of tunable diastereoselection in the cyclocondensation reaction. (Danishefsky, supra) Cyclo-condensation of lactaldehyde derivative 21A (Heathcock, C. H., et al.,*J. Org. Chem.*, 1980, 45, 3846) with the indicated diene, under ostensible chelation control, afforded 22A. The side chain ether could then be converted to the methyl ketone 25A as shown (see 22A→23A→24A→25A). Finally, an Emmons condensations (for example, see: Lythgoe, B., et al., *Tetrahedron Lett.*, 1975, 3863; Toh, H. T.; Okamura, W. H. *J. Org. Chem.*, 1983, 48, 1414; Baggiolini, E. G., et al., *J. Org. Chem.*, 1986, 51, 3098) of 25A with the phoshphine oxide 26A was transformed to phosphine oxide 26A according to the procedure described in Toh, supra) as shown in FIG. 15 gave rise to 27A. (The known 2-methyl-4-chloromethylthiazole (see Marzoni, G. J. *Heterocyclic Chem.*, 1986, 23, 577). A straightforward protecting group adjustment then afforded the previously encountered 17A. This route illustrates the concept of stereochemical imprinting through a carbon center which eventually emerges in planar form after conferring enantioselection to subsequently derived stereocenters. The use of the dihydropyrone based logic for securing the stereochemical elements of the epothilones, as well as the identification of a possible strategy for macrocyclization will be described in the following section.

Studies Toward a Synthesis of Epothilone A: Sterocontrolled Assembly of the Acyl Region and Models for Macrocyclization.

Ring-forming olefin metathesis has been employed to construct 16-membered ring congeners related to epothilone A. A stereospecific synthesis of the C3–C9 sector of the acyl fragment was achieved by exploiting a novel oxidative opening of a cyclopropanated glycal.

Figure 7:
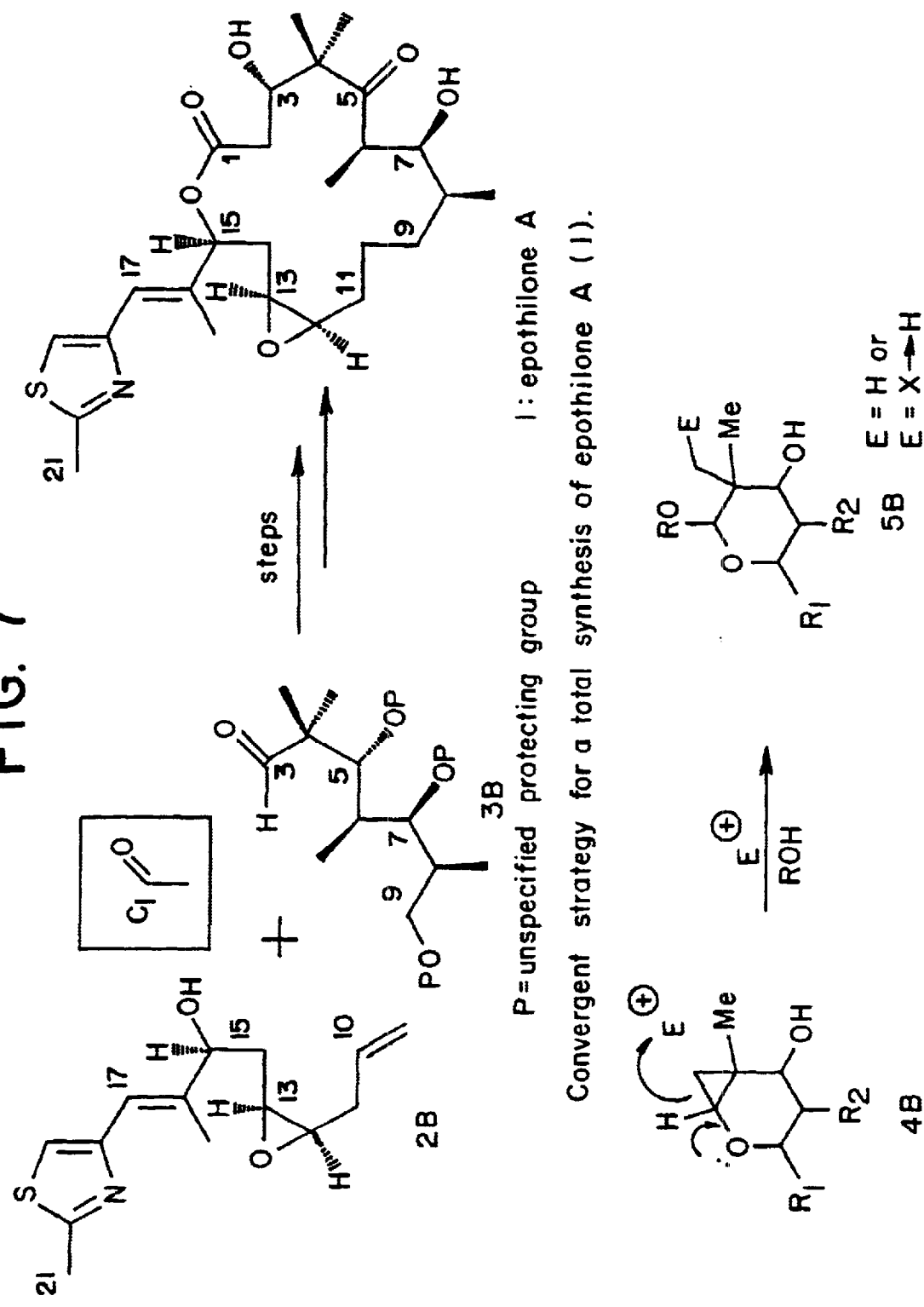
FIG. 7 illustrates a convergent strategy for a total synthesis of epothilone A (1) and the glycal cyclopropane solvolysis strategy for the introduction of geminal methyl groups.

Disclosed in the previous section is a synthesis of the "alkoxy" segment of epothilone (1) (see compound 2B, FIG. 7) encompassing carbons 10 to 21. In this section the synthesis of another fragment encoding the stereochemical information of acyl section carbons 3 to 9. It was envisioned that the aldehydo center ($C_3$) of the formal target 3B would serve as an attachment site to a nucleophilic construct derived from compound 2B (requiring placement of a 2 carbon insert, as suggested in FIG. 7), through either inter- or intramolecular means. In such a context, it would be necessary to deal independently with the stereochemistry of the secondary alcohol center eventually required at $C_3$. One of the interesting features of system 3B is the presence of geminal methyl groups at carbon 4 (epothilone numbering). Again, use is made of a dihydropyran strategy to assemble a cyclic matrix corresponding, after appropriate disassembly, to a viable equivalent of system 3B. The expectation was to enlarge upon the dihydropyran paradigm to include the synthesis of gem-dimethyl containing cyclic and acyclic fragments. The particular reaction type for this purpose is generalized under the heading of transformation of 4B→5B (see FIG. 7). Commitment as to the nature of the electrophile E is avoided. Accordingly, the question whether a reduction would or would not be necessary in going from structure type 5B to reach the intended generalized target 3B is not addressed.

Figure 8:
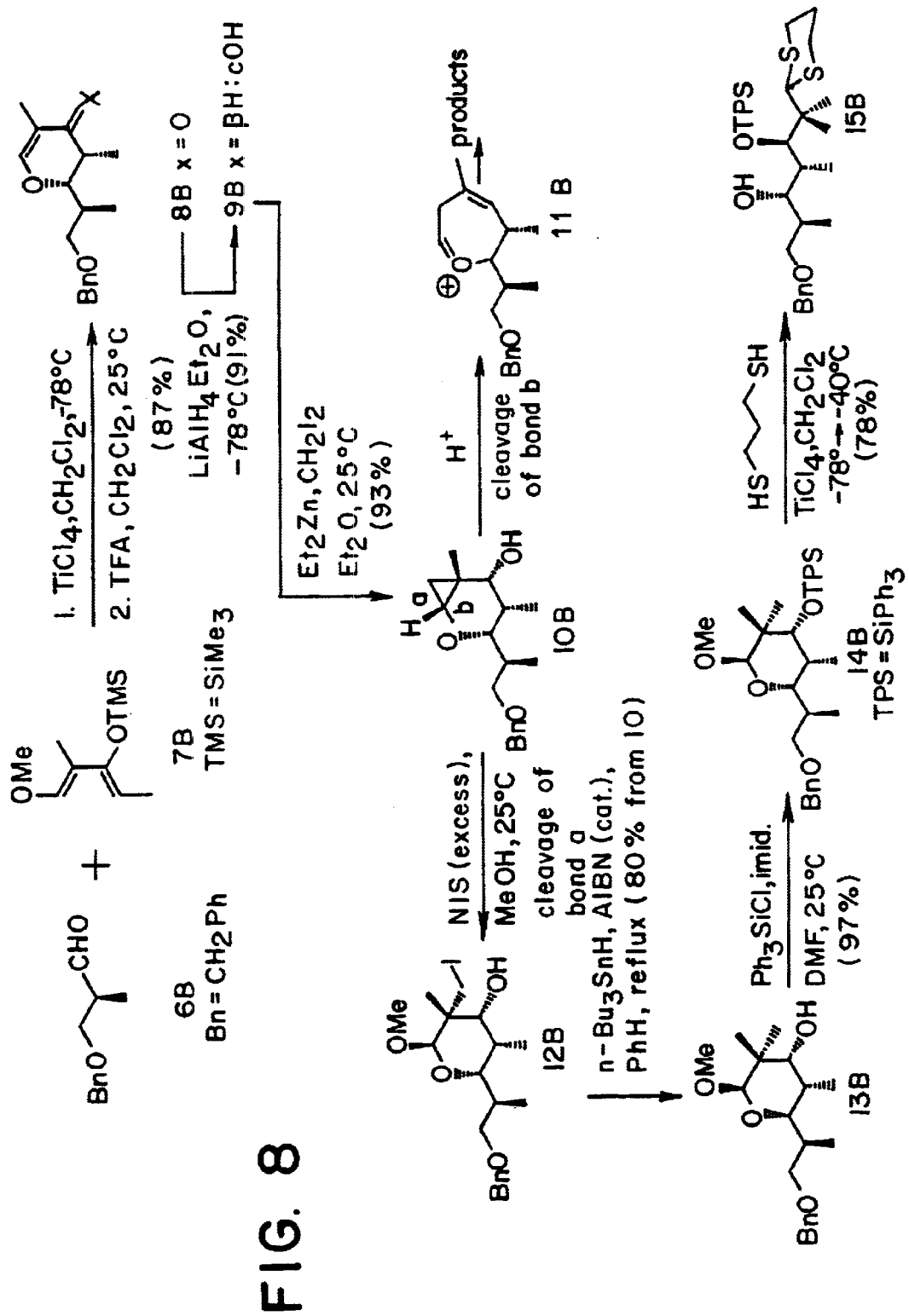
FIG. 8 provides an enantioselective synthesis of compound 15B.

The opening step consisted of a stereochemically tuneable version of the diene-aldehyde cyclocondensation reaction (FIG. 8; Danishefsky, S. J., *Aldrichimica Acta*, 1986, 19, 59), in this instance drawing upon chelation control in the merger of the readily available enantiomerically homogenous aldehyde 6B with the previously known diene 7B. Danishefsky, S. J., et al., *J. Am. Chem. Soc.* 1979, 101, 7001. Indeed, as precedent would have it, under the influence of titanium tetrachloride there was produced substantially a single isomer shown as compound 8B. In the usual and stereochemically reliable way (Danishefsky, S. J., *Chemtracts Org. Chem.* 1989, 2, 273), the dihydropyrone was reduced to the corresponding glycal, 9B. At this point, it was feasible to utilize a directed Simmons-Smith reaction for the conversion of glycal 9B to cyclopropane 10B. Winstein, S.; Sonnenberg, J. *J. Am. Chem. Soc.*, 1961, 83, 3235; Dauben, W. G.; Berezin, G. H. *J. Am. Chem. Soc.*, 1963, 85, 468; Furukawa, J., et al., *Tetrahedron*, 1968, 24, 53; For selected examples, see Soeckman, R. K. Jr.: Charette, A. B.; Asberom, T.; Johnston, B. H. *J. Am. Chem. Soc.*, 1991, 113, 5337; Timmers, C. M.; Leeuwenurgh, M. A.; Verheijen, J. C.; Van der Marel, G. A.; Van Boom, J. H. *Tetrahedron: Asymmetry*, 1996, 7, 49. This compound is indeed an interesting structure in that it corresponds in one sense to a cyclopropano version of a C-glycoside. At the same time, the cyclopropane is part of a cyclopropylcarbinyl alcohol system with attendant possibilities for rearrangement. Wenkert, E., et al., *J. Amer. Chem. Soc.*, 1970, 92, 7428. It was intended to cleave the C-glycosidic bond of the cyclopropane in a fashion which would elaborate the geminal methyl groups, resulting in a solvent-derived glycoside with the desired aidehyde oxidation state at C-3 (see hypothesized transformation 4B→5B, FIG. 7). In early efforts, the non-oxidative version of the projected reaction (i.e. $E^+=H^+$) could not be reduced to practice. Instead, products clearly attributable to the ring expanded system 11 were identified. For example, exposure of 10B to acidic methanol gave rise to an epimeric mixture of seven-membered mixed-acetals, presumably through the addition of methanol to oxocarbenium ion 11B.

However, the desired sense of cyclopropane opening, under the influence of the ring oxygen, was achieved by subjecting compound 10B to oxidative opening with N-iodosuccinimide. (For interesting Hg(ll)-induced solvolyses of cyclopropanes that are conceptually similar to the conversion of 10B to 12B, see: Collum, D. B.; Still, W. C.; Mohamadi, F. *J. Amer. Chem. Soc.*, 1986, 108, 2094; Collum, D. B.; Mohamadi, F.; Hallock, J. S.; *J. Amer. Chem. Soc.*, 1983, 105, 6882. Following this precedent, a Hg(ll)-induced solvolysis of cyclopropane 10B was achieved, although this transformation proved to be less efficient than the reaction shown in FIG. 8). The intermediate iodomethyl compound, obtained as a methyl glycoside 12B, when exposed to the action of tri-n-butyltinhydride gave rise to pyran 13B containing the geminal methyl groups. Protection of this alcohol (see 13B→14B), followed by cleavage of the glycosidic bond, revealed the acyclic dithiane derivative 15B which can serve as a functional version of the hypothetical aldehyde 3B.

Possible ways of combining fragments relating to 2B and 3B in a fashion to reach epothilone and congeners thereof were examined. In view of the studies of Schrock (Schrock, R. R., et al., *J. Am. Chem. Soc.*, 1990, 112, 3875) and Grubbs (Schwab, P. et al., *Angew. Chem. Int. Ed. Engl.*, 1995, 34, 2039; Grubbs, R. H.; Miller, S. J. Fu, G. C. *Acc. Chem. Res.*, 1995, 28, 446; Schmalz, H.-G., *Angew. Chem. Int. Ed. Engl.*, 1995, 34, 1833) and the disclosure of Hoveyda (Houri, A. F., et al., *J. Am. Chem. Soc.*, 1995, 117, 2943), wherein a complex lactam was constructed in a key intramolecular olefin macrocyclization step through a molybdenum mediated intramolecuar olefin in metathesis reaction (Schrock, supra; Schwab, supra), the possibility of realizing such an approach was considered. (For other examples of ring-closing metathesis, see: Martin, S. F.; Chen, H.-J.; Courtney, A. K.; Lia, Y.; Pätzel, M.; Ramser, M N.; Wagman, A. S. *Tetrahedron*, 1996, 52, 7251; Furstner, A.; Langemann, K. *J. Org. Chem.*, 1996, 61, 3942.)

Figure 9:
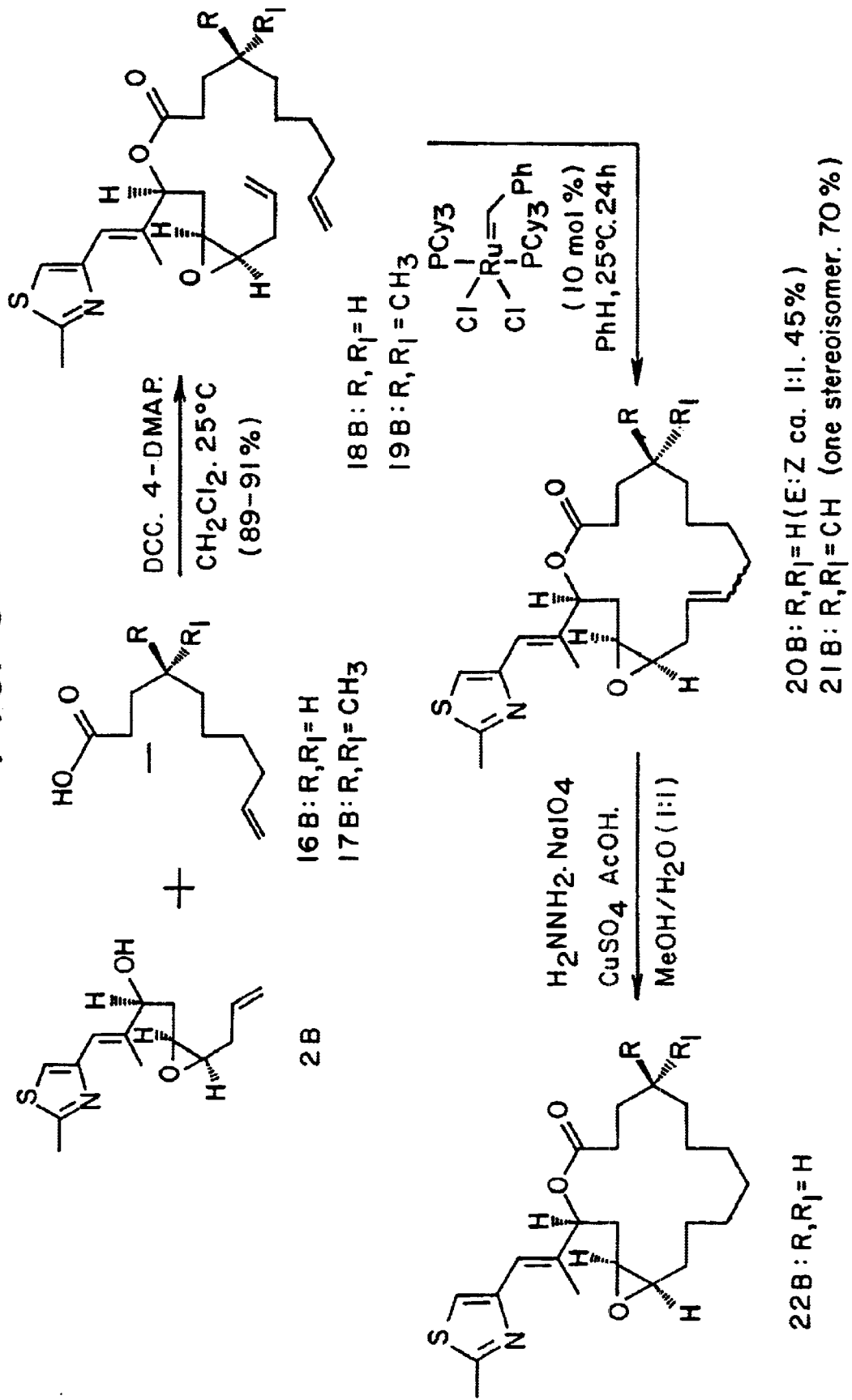
FIG. 9 shows the construction of epothilone model systems 20B, 21B, and 22B by ring-closing olefin metathesis.
Figure 10:
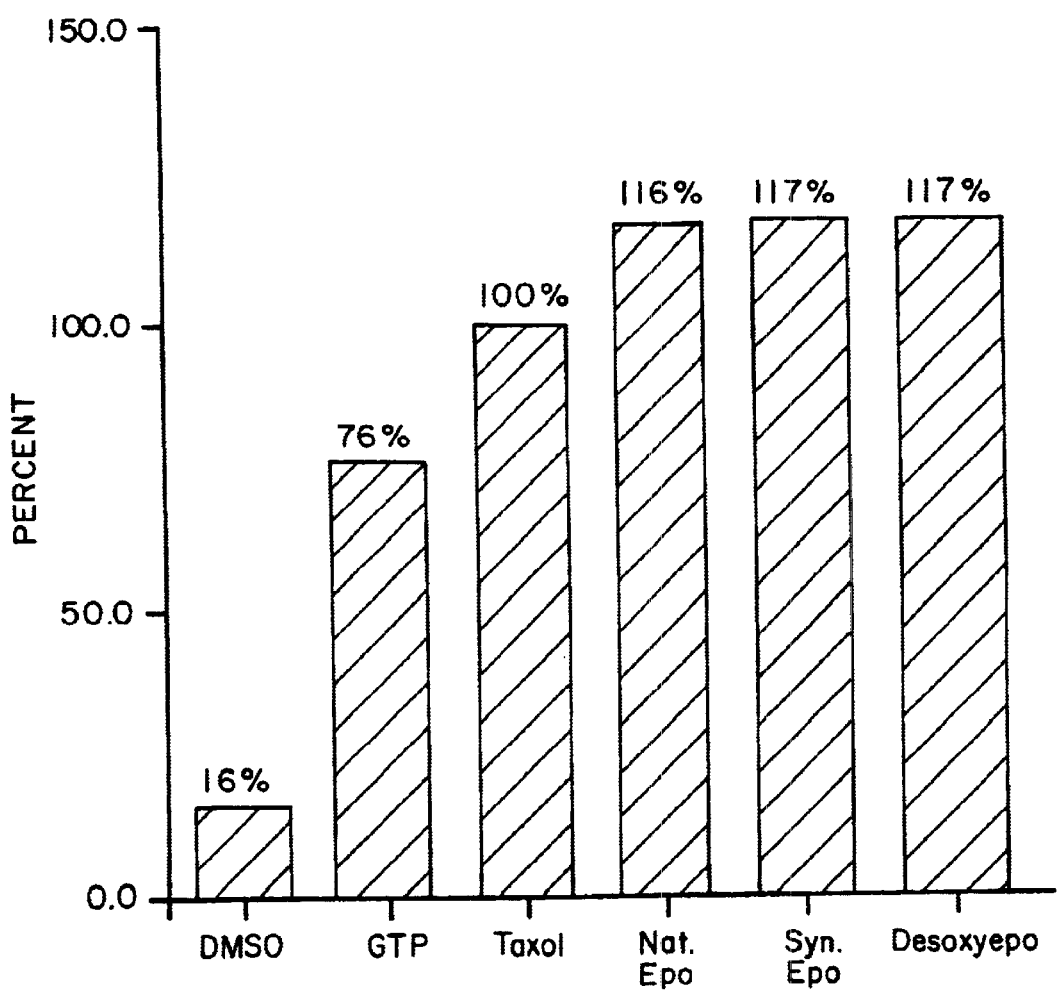
FIG. 10 illustrates a sedimentation test for natural, synthetic and desoxyepothilone A.
Figure 11:
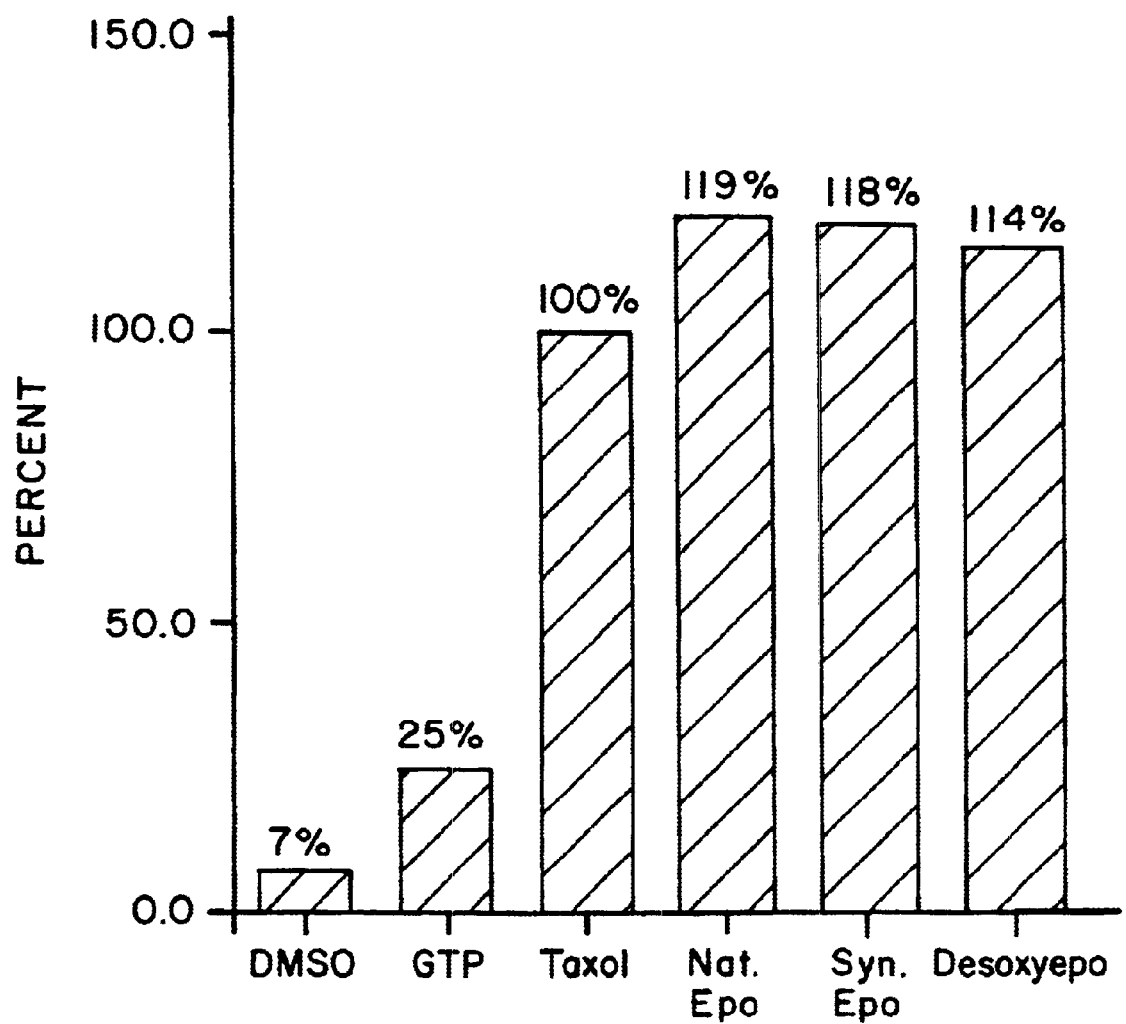
FIG. 11 illustrates a sedimentation test for natural, synthetic and desoxyepothilone A after cold treatment at $4°$ C.

The matter was first examined with two model ω-unsaturated acids 16B and 17B which were used to acylate alcohol 2B to provide esters 18B and 19B, respectively (see FIG. 9). These compounds did indeed undergo olefin metathesis macrocyclization in the desired manner under the conditions shown. In the case of substrate 18B, compound set 208 was obtained as a mixture of E- and Z-stereoisomers [ca. 1:1]. Diimide reduction of 20B was then conducted to provide homogeneous 22B. The olefin metathesis reaction was also extended to compound 19B bearing geminal methyl groups corresponding to their placement at C4 of epothilone A. Olefin metathesis occurred, this time curiously producing olefin 21B as a single entity in 70% yield (stereochemisty tentatively assigned as Z.) Substantially identical results were obtained through the use of Schrock's molybdenum alkylidene metathesis catalyst.

As described above, olefin metathesis is therefore amenable to the challenge of constructing the sixteen membered ring containing both the required epoxy and thiazolyl functions of the target system. It is pointed out that no successful olefin metathesis reaction has yet been realized from seco-systems bearing a full compliment of functionality required to reach epothilone. These negative outcomes may merely reflect a failure to identify a suitable functional group constraint pattern appropriate for macrocylization.

The Total Synthesis of Epothilone B: Extension of the Suzuki Coupline Method

The present invention provides the first total synthesis of epothilone A (1). D. Meng, et al., *J. Org. Chem*, 1996, 61, 7998 P. Bertinato, et al., *J. Org. Chem*, 1996, 61, 8000. A. Balog, et al., *Angew. Chem. Int. Ed. Engl.*, 1996, 35, 2801. D. Meng, et al., *J. Amer. Chem. Soc.*, 1997, 119, 10073. (For a subsequent total synthesis of epothilone A, see: Z. Yang, et al., *Angew. Chem. Int. Ed. Engl.*, 1997, 36, 166.) This synthesis proceeds through the Z-desoxy compound (23) which underwent highly stereoselective epoxidation with 2,2-dimethyldioxirane under carefully defined conditions to yield the desired β-epoxide. The same myxobacterium of the genus Sorangium which produces 23 also produces epothilone B (2). The latter is a more potent agent than 23, both in antifungal screens and in cytotoxicity/cell nucleus disintegration assays. G. Höfle, et al., *Angew. Chem. Int. Ed. Engl.* 1996, 35, 1567; D. M. Bollag, et al., *Cancer Res.* 1995, 55, 2325.

An initial goal structure was desoxyepothilone B (2C) or a suitable derivative thereof. Access to such a compound would enable the study of the regio- and stereoselectivity issues associated with epoxidation of the C12→C13 double bond. A key issue was the matter of synthesizing Z-tri-substituted olefinic precursors of 2C with high margins of stereoselection. A synthetic route to the disubstituted system (A. Balog, et al., *Agnew. Chem. Int. Ed. Engl.*, 1996, 35, 2801) employed a palladium-mediated B-alkyl Suzuki coupling (N. Miyaura, et al., *J. Am. Chem. Soc.* 1989, 111, 314. (For a review, see: N.

Miyaura, A. Suzuki, *Chem. Rev.* 1995, 95, 2457) of the Z-vinyl iodide 19 (FIG. 4(A)) with borane 7C derived from hydroboration of compound 11 (FIG. 1(A)) with 9-BBN (FIG. 4(B)).)

A preliminary approach was to apply the same line of thinking to reach a Z-tri-substituted olefin (FIG. 17) en route to 2C. Two issues had to be addressed. First, it would be necessary to devise a method to prepare vinyl iodide 8C, the tri-substituted analog of 19. If this goal could be accomplished, a question remained as to the feasibility of conducting the required B-alkyl Suzuki coupling reaction to reach a Z-tri-substituted olefin. The realization of such a transformation with a "B-alkyl" (as opposed to a "B-alkenyl" system) at the inter-molecular level, and where the vinyl iodide is not of the β-iodoenoate (or β-iodoenone) genre, was not precedented. (For some close analogies which differ in important details from the work shown here, see: N. Miyaura, et al., *Bull. Chem. Soc. Jpn.* 1982, 55, 2221; M. Ohba, et al., *Tetrahedron Lett.*, 1995, 36, 6101; C. R. Johnson, M. P. Braun, *J. Am. Chem. Soc.* 1993, 115, 11014.)

Figure 16:
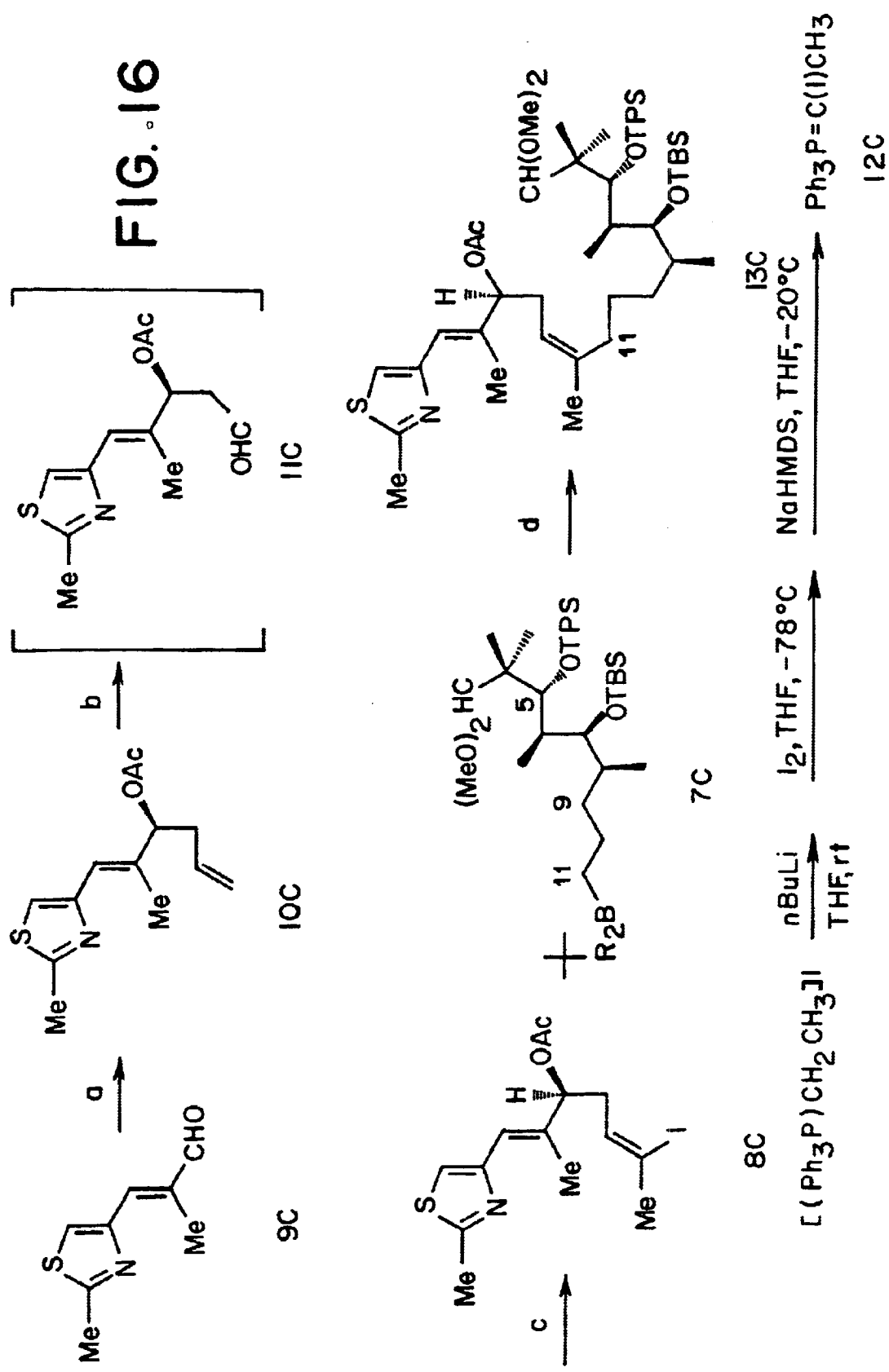
FIG. 16 provides a synthetic pathway to intermediate 13C. (a) 1. tributyl allyltin, (S)-(-)-BINOL, Ti(Oi-Pr)$_4$, $CH_2Cl_2$, $-20°$ C., 60%, >95% e.e.; 2. $Ac_2O$, $Et_3N$, DMAP, $CH_2Cl_2$, 95%; (b) 1. $OsO_4$, NMO, acetone/$H_2O$, $0°$ C.; 2. $NaIO_4$, THF/$H_2O$; (c) 12, THF, $-20°$ C., Z isomer only, 25% from 10; (d) Pd(dppf)$_2$, $Cs_2CO_3$, $Ph_3As$, $H_2O$, DMF, rt. 77%.

The synthesis of compound 8C is presented in FIG. 16. The route started with olefin 10C which was prepared by catalytic asymmetric allylation of 9C (G. E. Keck, et al., *J. Am. Chem. Soc.*, 1993, 175, 8467) followed by acetylation. Site-selective dihydroxylation of 10C. followed by cleavage of the glycol generated the unstable aidehyde 11C. Surprisingly, the latter reacted with phosphorane 12C (J. Chen, et al., *Tetrahedron Lett.*, 1994, 35, 2827) to afford the Z-iodide 8C albeit in modest overall yield. Borane 7C was generated from 11 as described herein. The coupling of compound 7C and iodide 8C (FIG. 16) could be conducted to produce the pure Z-olefin 13C.

Figure 17:
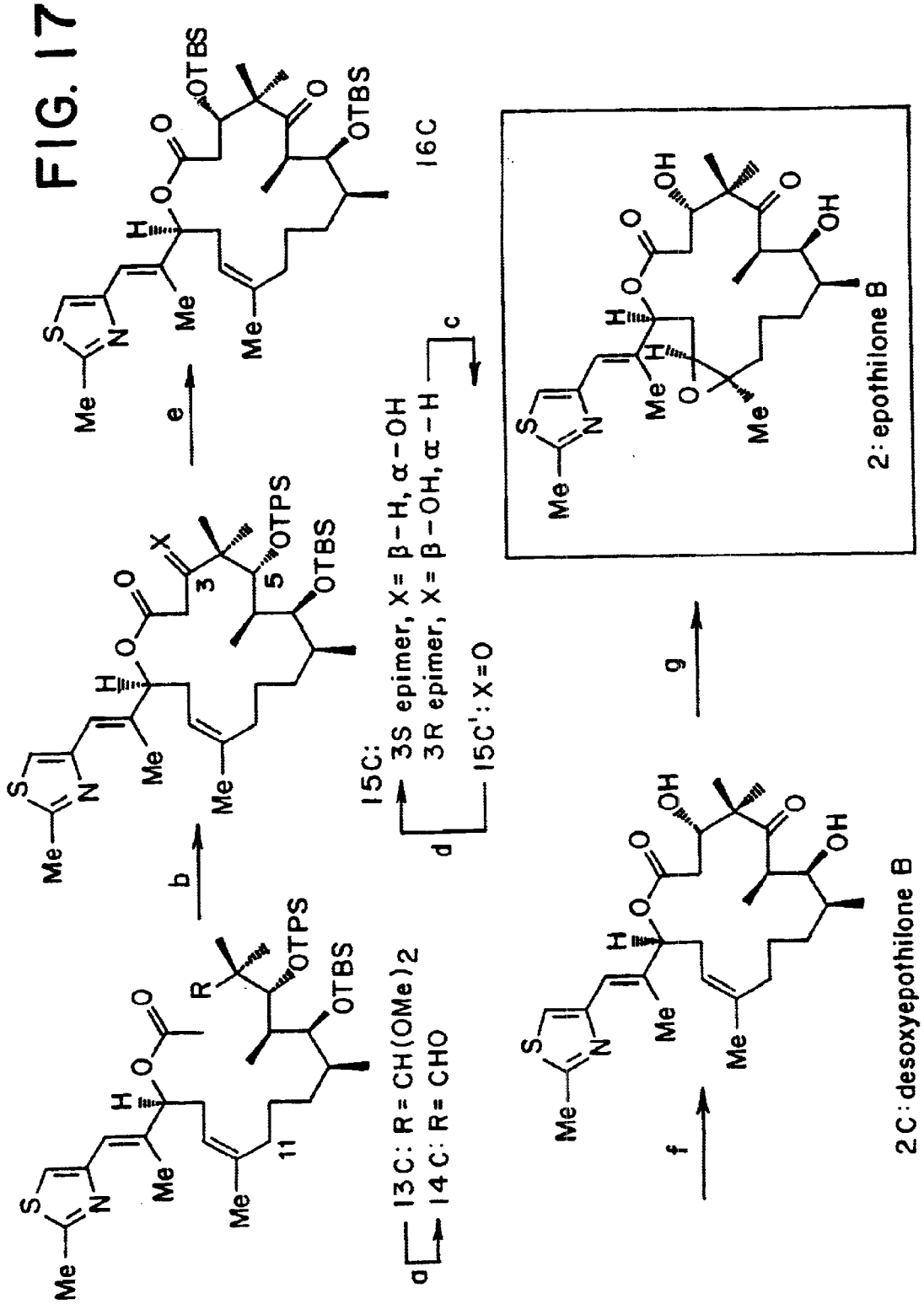
FIG. 17 provides a synthetic pathway to intermediate epothilone B (2). (a) p-TsOH, dioxane/$H_2O$, $55°$ C., 71%; (b) KHMDS, THF, $-78°$ C., 67%, $\alpha/\beta$: 1.5:1; (c) Dess-Martin periodinane, $CH_2Cl_2$; (d) $NaBH_4$, MeOH, 67% for two steps; (e) 1. HF-pyridine, pyridine, THF, rt, 93%; 2. TBSOTf, 2,6-lutidine, $CH_2Cl_2$, $-30°$ C., 89%; 3. Dess-Martin periodinane, $CH_2Cl_2$, 67%; (f) HF-pyridine, THF, rt, 80%; (g) dimethyldioxirane, $CH_2Cl_2$, $-50°$ C., 70%.
Figure 18A:
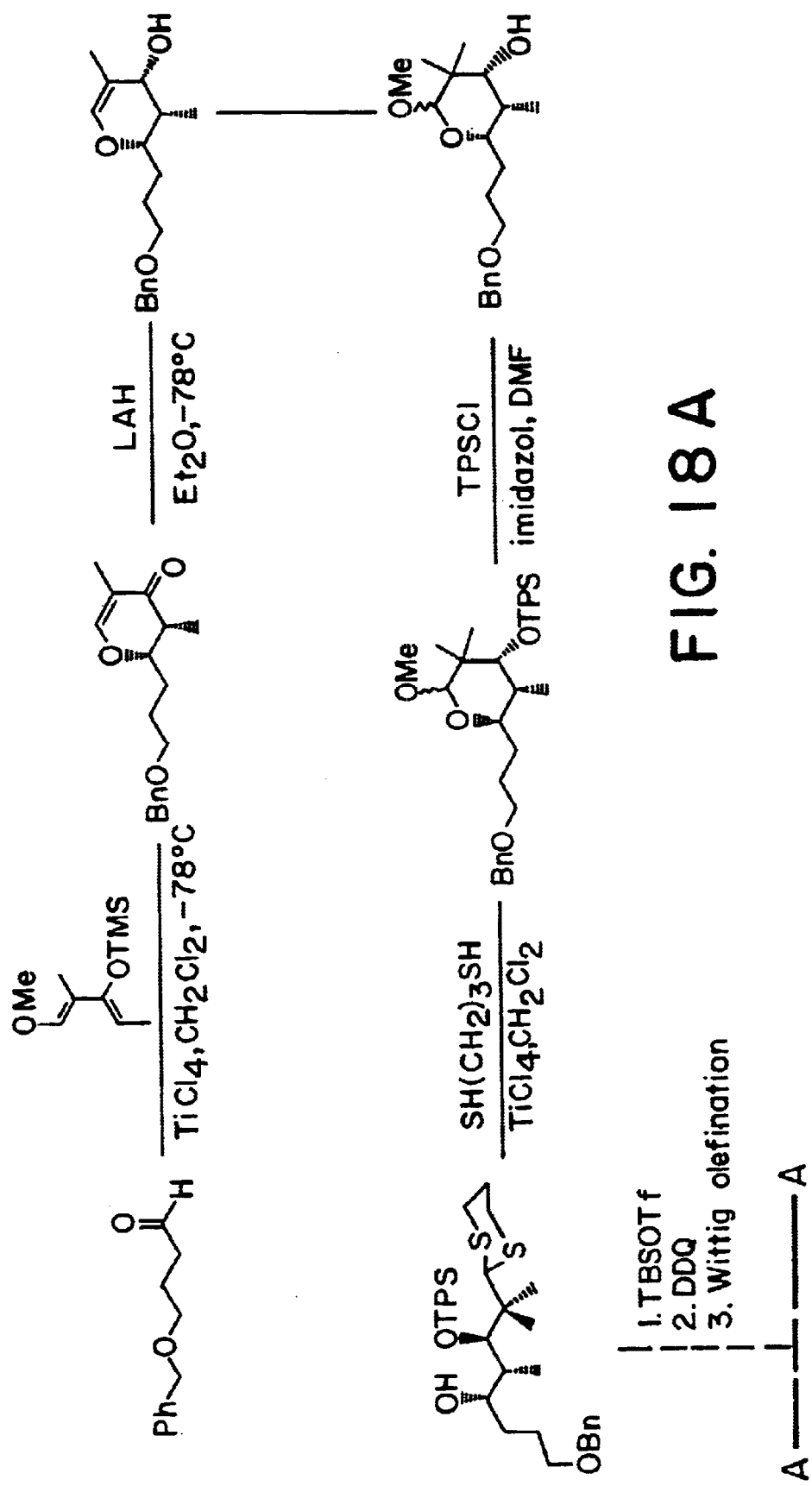
FIGS. 18(A) and 18(B) provide a synthetic pathway to a protected intermediate for 8-desmethyl deoxyepothilone A.
Figure 18B:
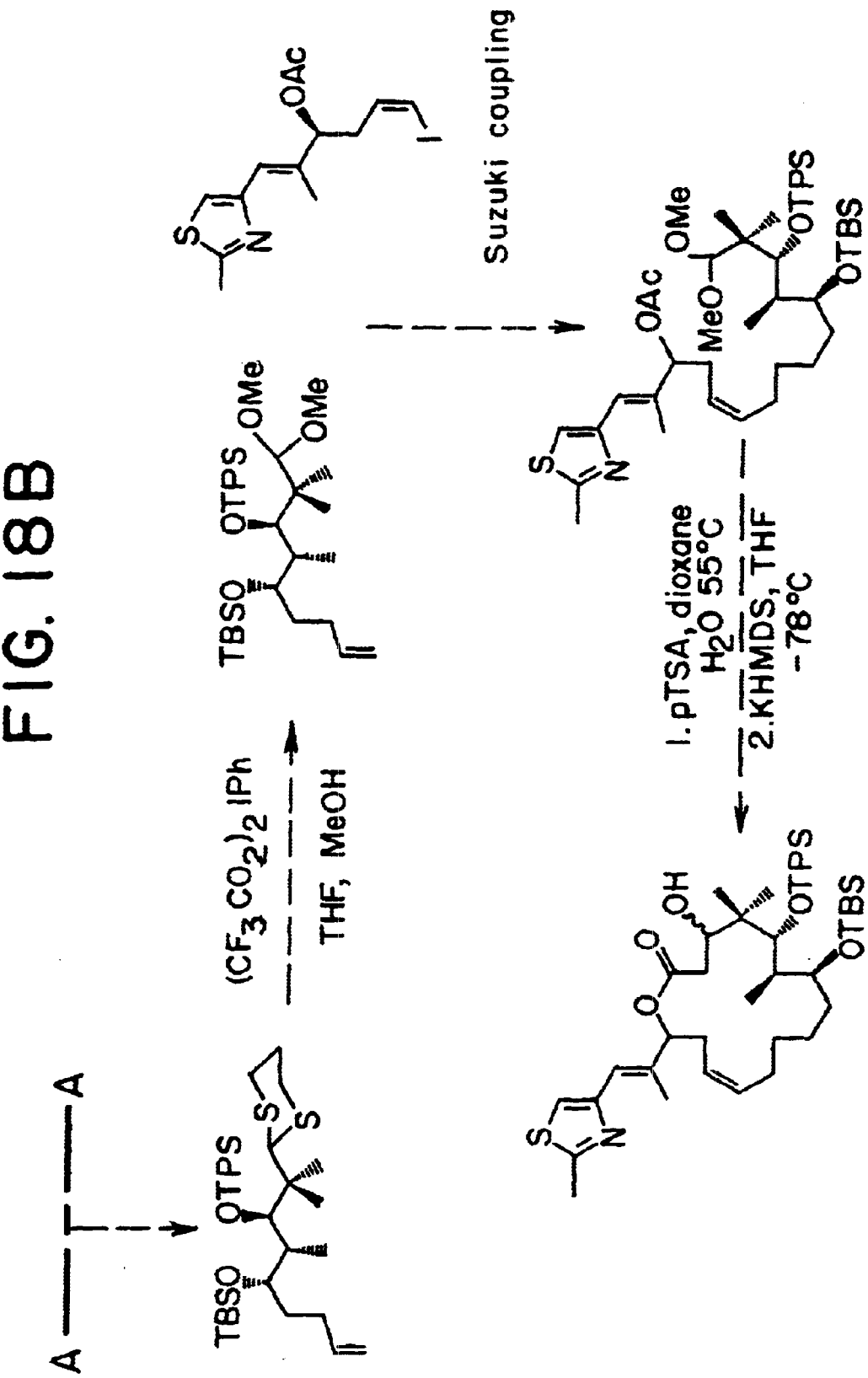
Figure 19A:
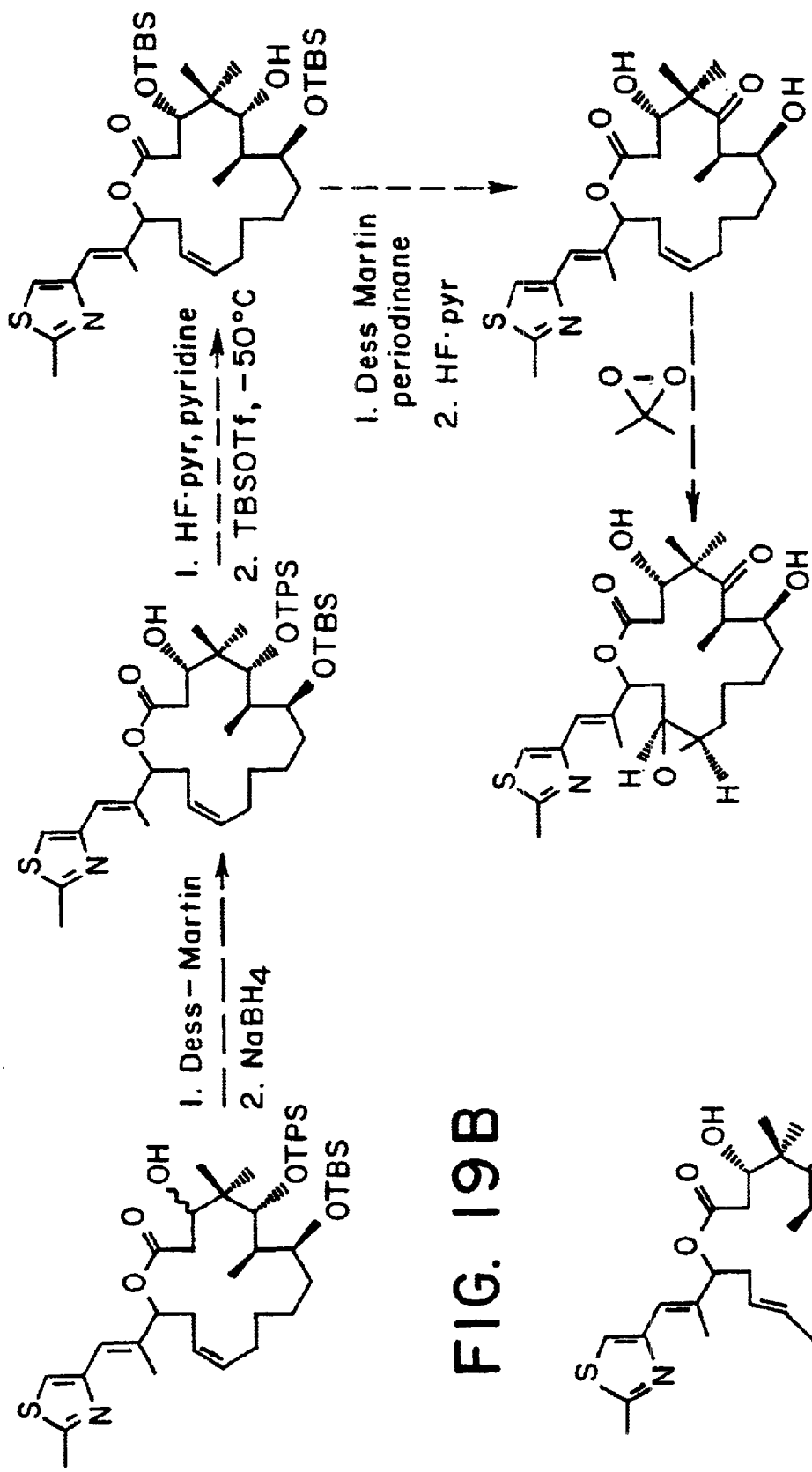
Figure 19B:
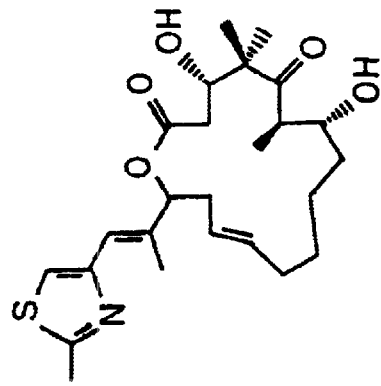

With compound 13C in hand, protocols similar to those employed in connection with the synthesis of 23 could be used. (A. Balog, et al., *Angew. Chem. Int. Ed. Engl.*, 1996, 35, 2801). Thus, cleavage of the acetal linkage led to aldehyde 14C which was now subjected to macroaldolization (FIG. 17). The highest yields were obtained by carrying out the reaction under conditions which apparently equilibrate the C3 hydroxyl group. The 3R isomer was converted to the required 3S epimer via reduction of its derived C3-ketone (see compound 15C). The kinetically controlled aldol condensation leading to the natural 3S configuration as described in the epothilone A series was accomplished. However, the overall yield for reaching the 3S epimer is better using this protocol. Cleavage of the C-5 triphenyisilyl ether was followed sequentially by monoprotection (t-butyldimethylsilyi) of the C3 hydroxyl, oxidation at C5 (see compound 16C), and, finally, cleavage of the silyl protecting groups to expose the C3 and C7 alcohols (see compound 2C).

It was found that Z-desoxyepothilone B (2C) undergoes very rapid and substantially regio- and stereoselective epoxidation under the conditions indicated (although precise comparisons are not available, the epoxidation of 2C appears to be more rapid and regioselective than is the case with 23) (A. Balog, et al., *Angew. Chem. Int. Ed. Engl.*, 1996, 35, 2801), to afford epothilone B (2) identical with an authentic sample ($^1$H NMR, mass spec, IR, $[\alpha]_D$). Accordingly, the present invention dislcoses the first total synthesis of epothilone B. Important preparative features of the present method include the enantioselective synthesis of the trisubstituted vinyl iodide 8C, the palladium-mediated stereospecific coupling of compounds 7C and 8C to produce compound 13C (a virtually unprecedented reaction in this form), and the amenability of Z-desoxyepothilone B (2C) to undergo regio- and stereoselective epoxidation under appropriate conditions.

Desmethylepothilone A

Total syntheses of epothilones A and B have not been previously disclosed. Balog, A., et al., *Angew. Chem., Int. Ed. Engl.* 1996, 35, 2801; Nicolaou, K. C., et al., *Angew. Chem., Int. Ed. Engl.* 1997, 36, 166. Nicolaou, K. C., et al., *Angew. Chem., Int. Ed. Engl.* 1997, 36, 525; Schinzer, D., et al., *Angew. Chem., Int. Ed. Engl.* 1997, 36, 523. Su, D. -S., et al., *Angew. Chem. Int. Ed. Engl.* 1997, 36, 757. The mode of antitumor action of the epothilones closely mimics that of Taxol™. Höfle, G., et al., *H. Angew. Chem., Int. Ed. Engl.* 1996, 35, 1567. Although Taxol™ (paclitaxel) is a clinically proven drug, its formulation continues to be difficult. In addition, taxol induces the multidrug resistance (MDR) phenotype. Hence, any novel agent that has the same mechanism of action as taxol and has the prospect of having superior therapeutic activity warrants serious study. Bollag, D. M., et al., *Cancer Res.* 1995, 55, 2325.

The present invention provides epothilone analogs that are more effective and more readily synthesized than epothilone A or B. The syntheses of the natural products provide ample material for preliminary biological evaluation, but not for producing adequate amounts for full development. One particular area where a structural change could bring significant relief from the complexities of the synthesis would be in the deletion of the C8 methyl group from the polypropionate domain (see target system 3D). The need to deal with this C8 chiral center complicates all of the syntheses of epothilone disclosed thus far. Deletion of the C8 methyl group prompts a major change in synthetic strategy related to an earlier diene-aldehyde cyclocondensation route. Danishefsky, S. J. *Chemtracts* 1989, 2, 273; Meng, D., et al., *J. Org. Chem.* 1996, 61, 7998; Bertinato, P., et al., *J. Org. Chem.* 1996, 61, 8000.

As shown in FIG. 20, asymmetric crotylation (87% ee) of 4D (Brown, H. C.; Bhat, K. S. *J. Am. Chem. Soc.* 1986, 108, 5919), followed by protection led to TBS ether 5D. The double bond was readily cleaved to give aldehyde 6D. The aldehyde was coupled to the dianion derived from t-butyl isobutyrylacetate to provide 7D. The ratio of the $C_{5S}$ (7D): $C_{5R}$ compound (not shown) is ca 10:1. That the Weiler-type β-ketoester dianion chemistry (Weiler, L. *J. Am. Chem. Soc.* 1970, 92, 6702.; Weiler, L.; Huckin, S. N. *J. Am. Chem. Soc.* 1974, 96, 1082) can be conducted in the context of the isobutyryl group suggested several alternate approaches for still more concise syntheses. Directed reduction of the $C_3$ ketone of 7D following literature precedents (Evans, D. A., et at., *J. Org. Chem.* 1991, 56, 741), followed by selective silylation of the $C_3$ hydroxyl gave a 50% yield of a 10:1 ratio of the required $C_{3S}$ (see compound 8D) to $C_{3R}$ isomer (not shown). Reduction with sodium borohydride afforded a ca. 1:1 mixture of $C_3$ epimers. The carbinol, produced upon debenzylation, was oxidized to an aldehyde which, following methylenation through a simple Wittig reaction, afforded olefin 9D. Treatment of this compound with TBSOTf provided ester 10D which was used directly in the Suzuki coupling with the vinyl iodide 12D.

Figure 21:
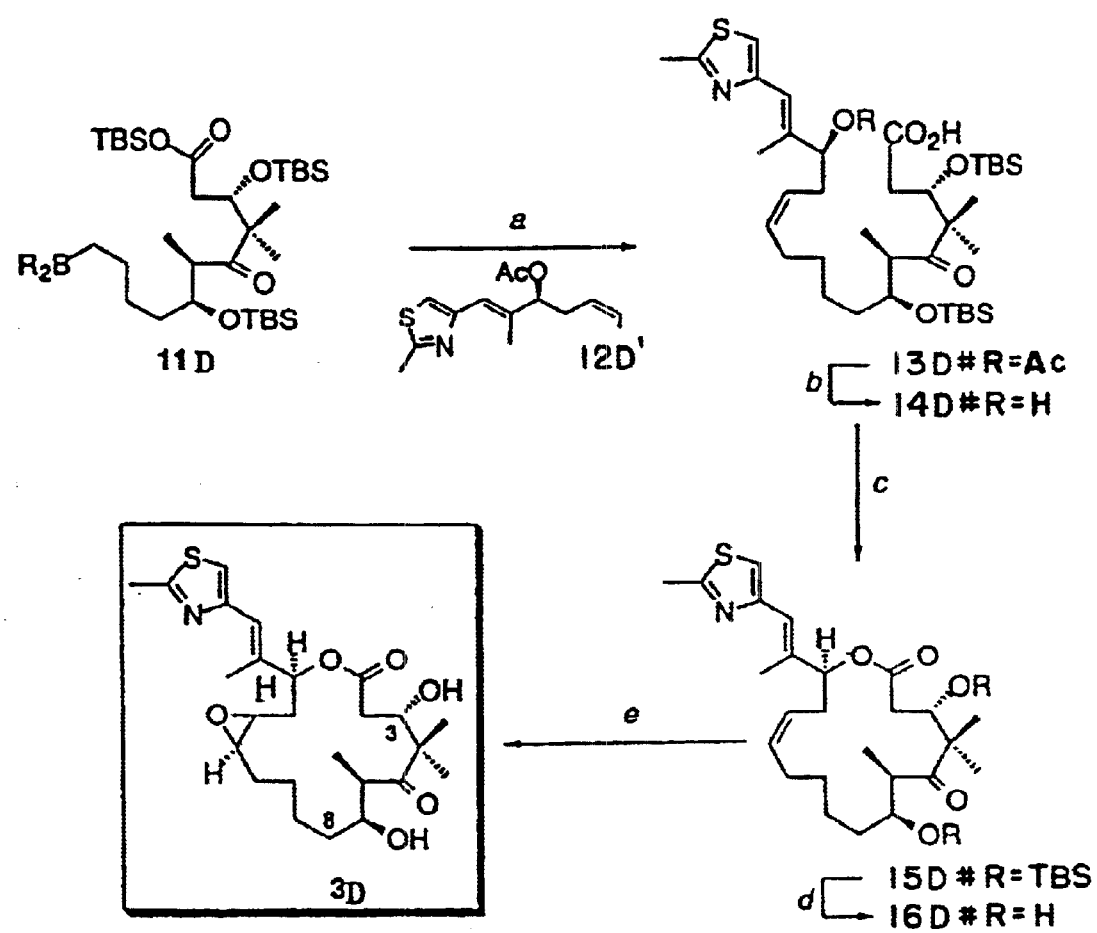
FIG. 21 shows a synthetic pathway to 8-desmethyiepothilone A. (a) Pd(dppf)$_2$Cl$_2$, Ph$_3$As, CS$_2$CO, H$_2$O, DMF, rt (62%); (b) K$_2$CO$_3$, MeOH, H$_2$O (78%); (c) DCC, 4-DMAP, 4-DMAP.HCl, CHCl$_3$ (78%); (d) HF.pyr, THF, rt (82%), (e) 3,3-dimethyl dioxirane, $CH_2Cl_2$, $-35°$ C. (72%, 1.5:1).
Figure 22C:
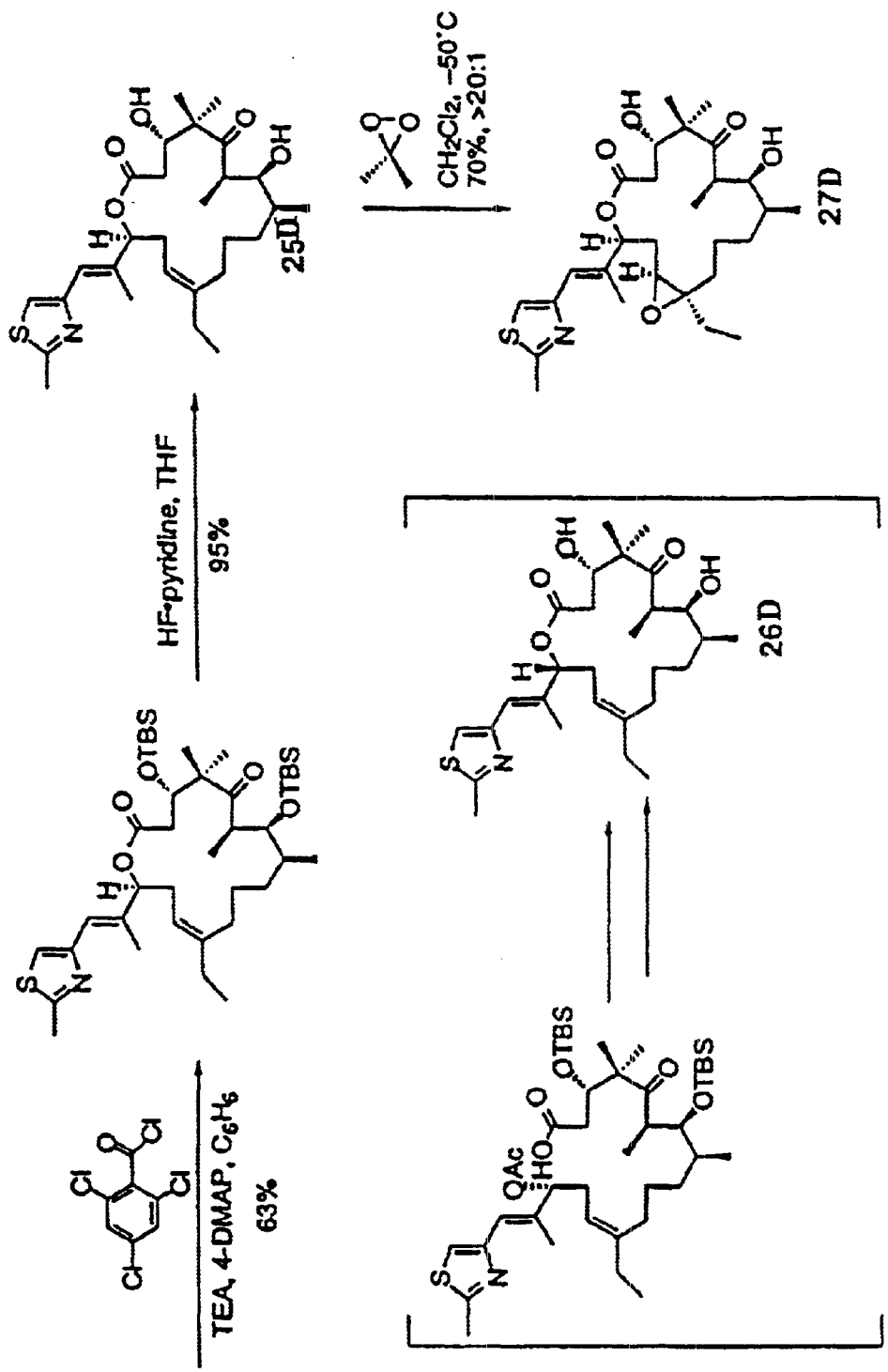
Figure 23A:
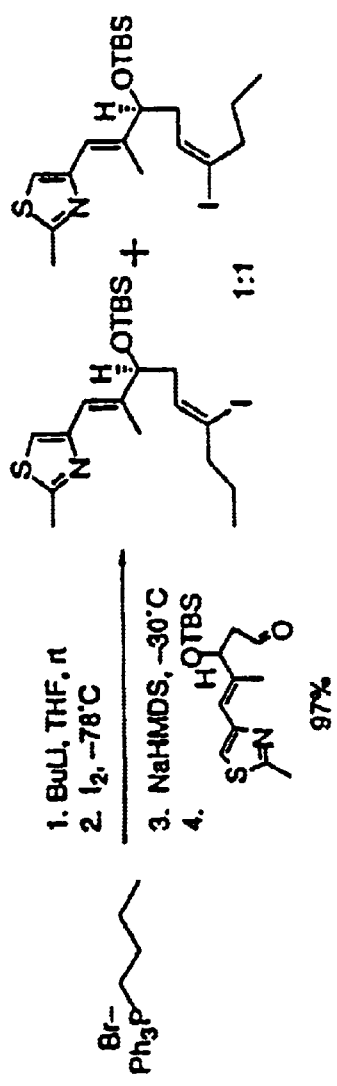
FIGS. 23(A), 23(B) and 23(C) show a synthetic pathway to prepare epothilone analogue 24D.
Figure 23B:
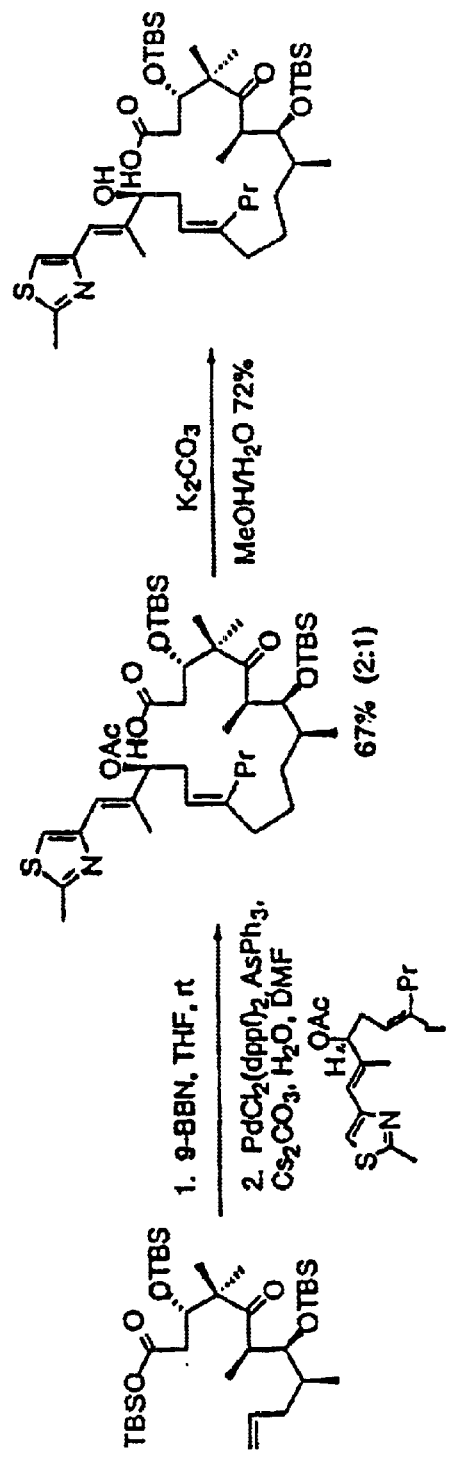
Figure 23C:
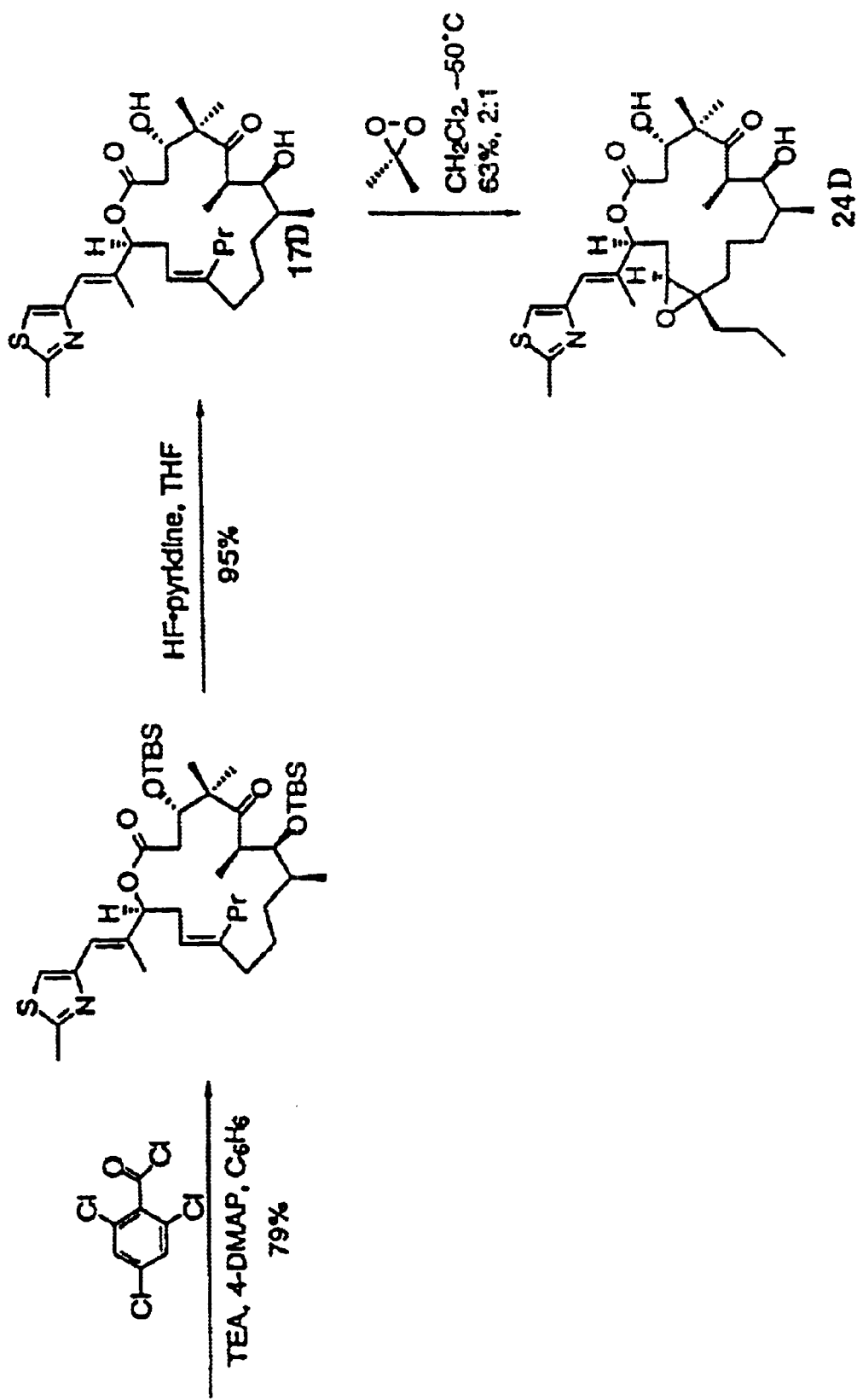
Figure 24A:
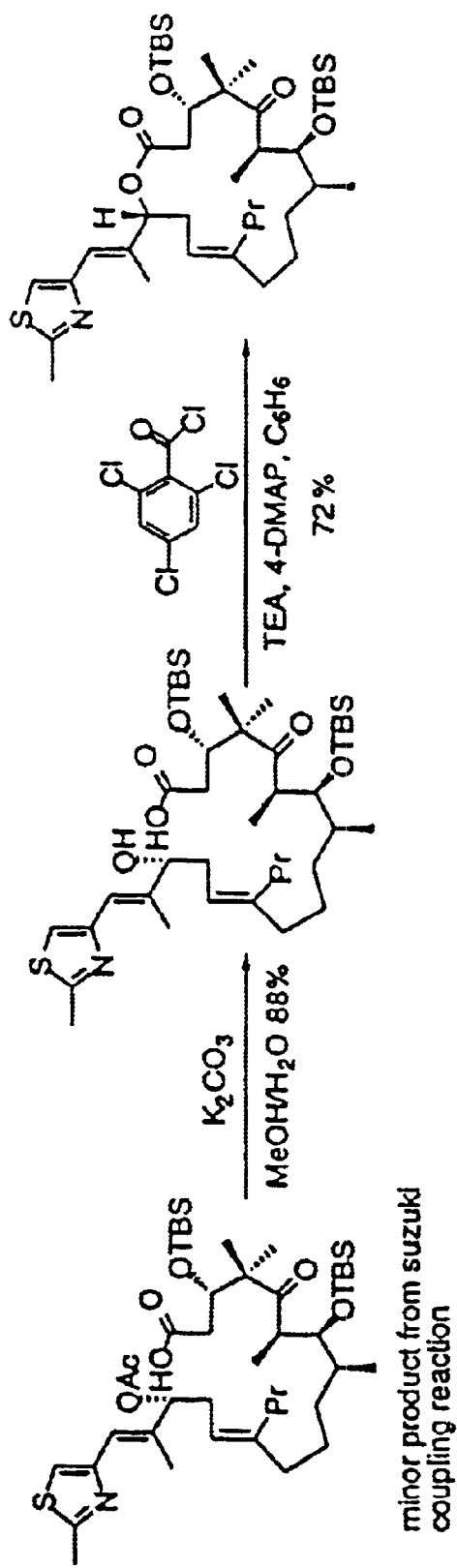
FIGS. 24(A) and 24(B) show a synthetic pathway to prepare epothilone analogue 19D.
Figure 24B:
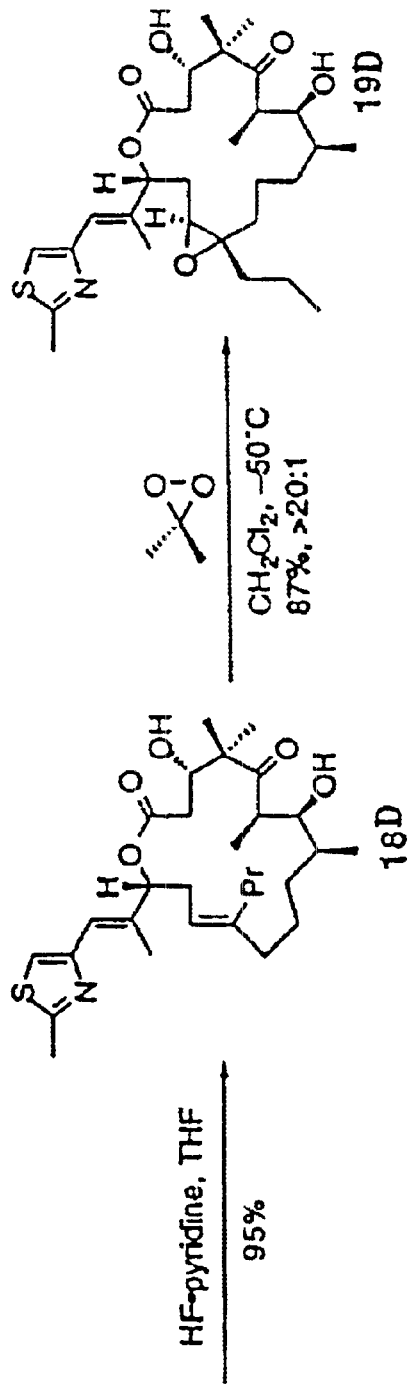
Figure 25A:
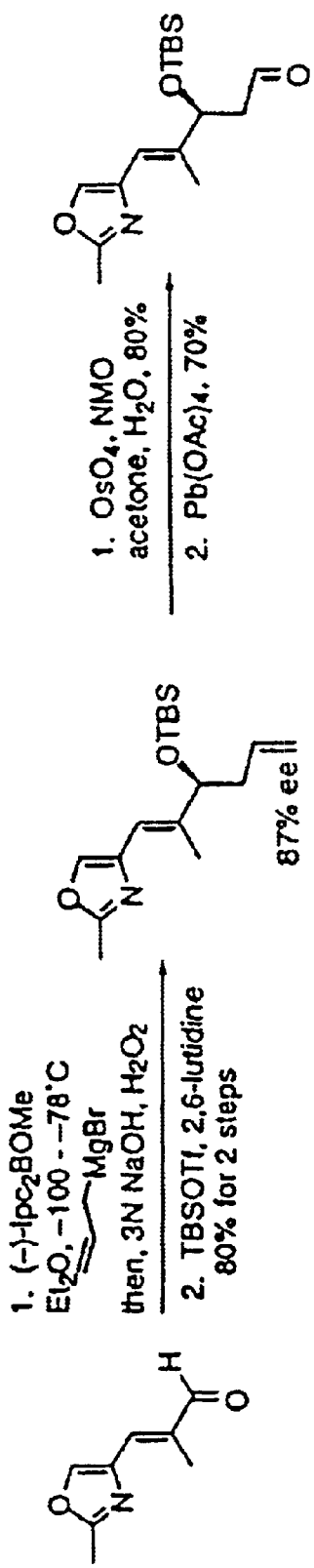
FIGS. 25(A), 25(B), 25(C) and 25(D) show a synthetic pathway to prepare epothilone analogue 20D.
Figure 25B:
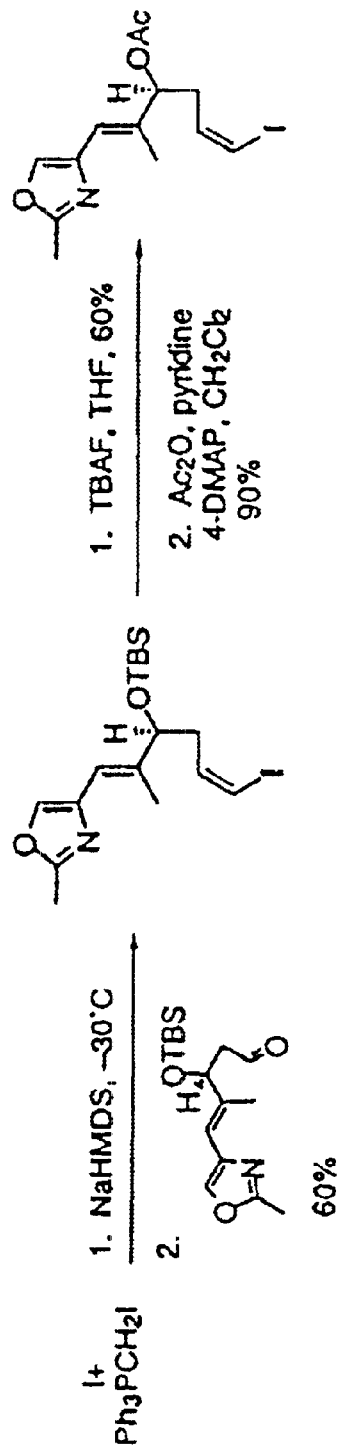
Figure 25C:
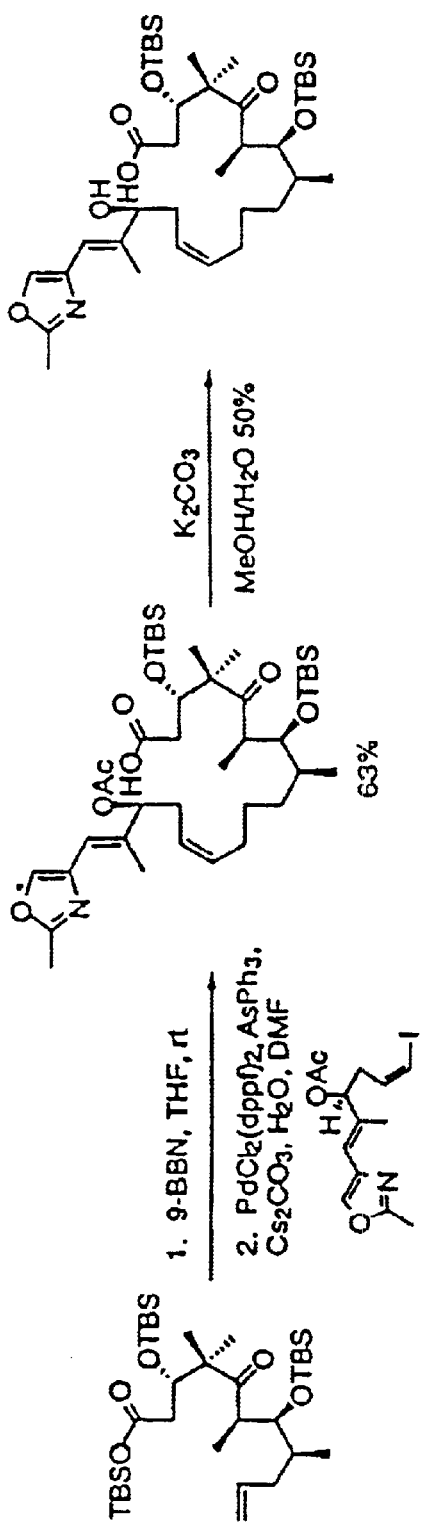
Figure 25D:
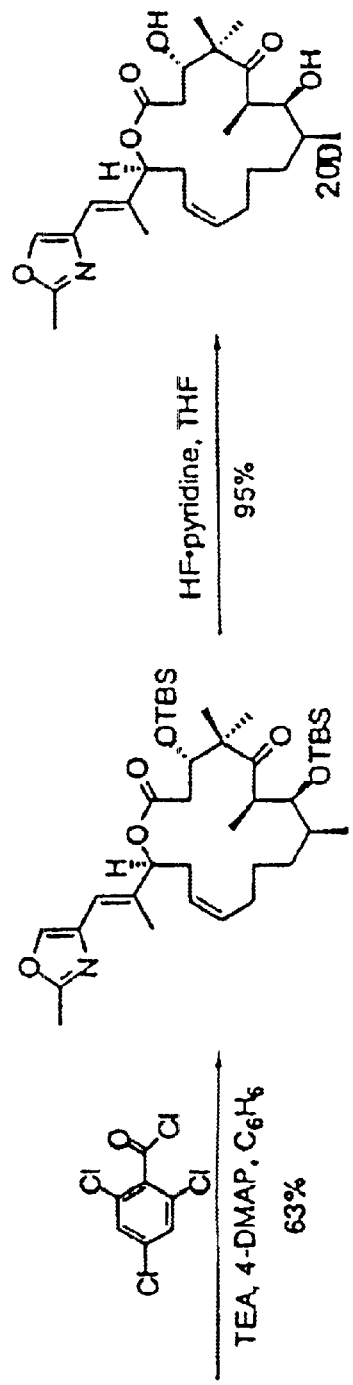
Figure 26A:
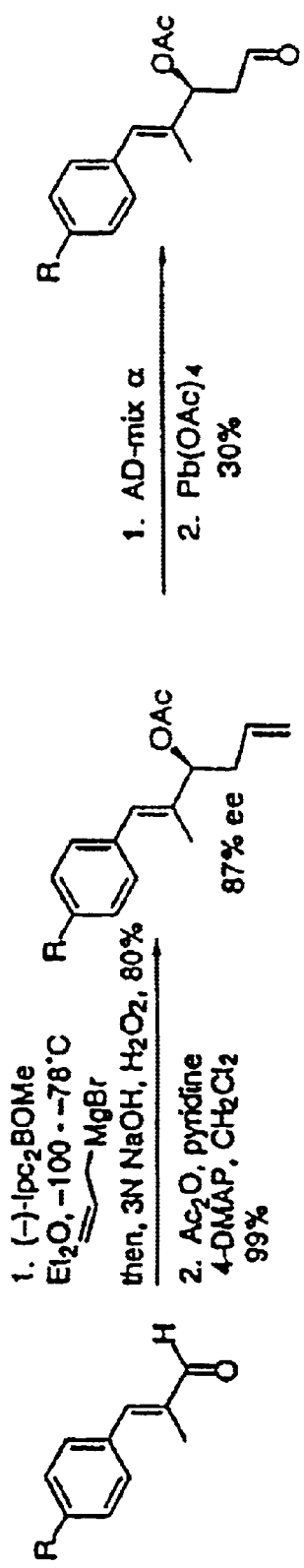
FIGS. 26(A), 26(B), 26(C) and 26(D) show a synthetic pathway to prepare epothilone analogue 22D.
Figure 26B:
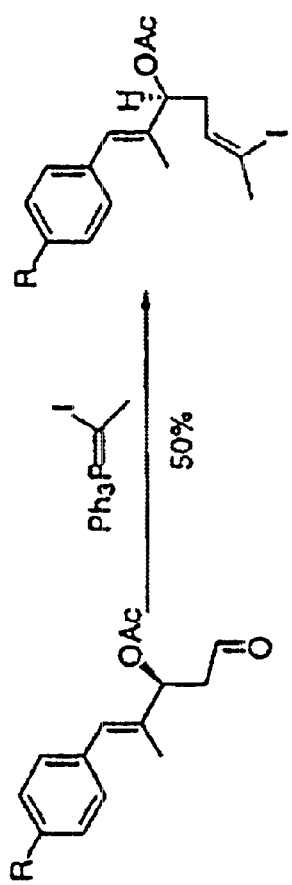
Figure 26C:
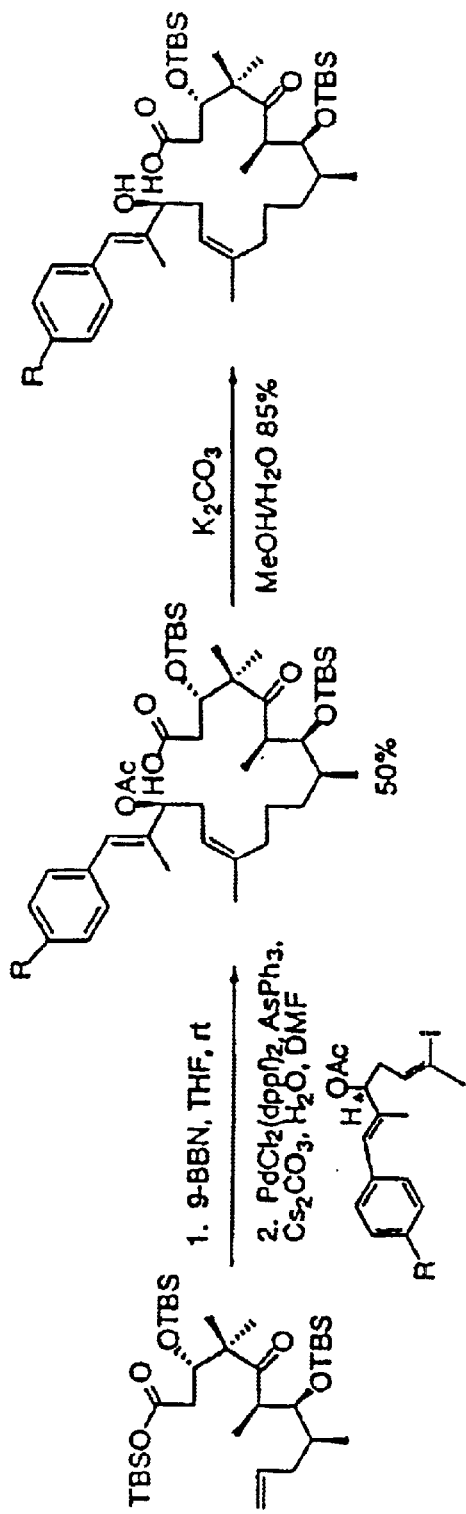
Figure 26D:
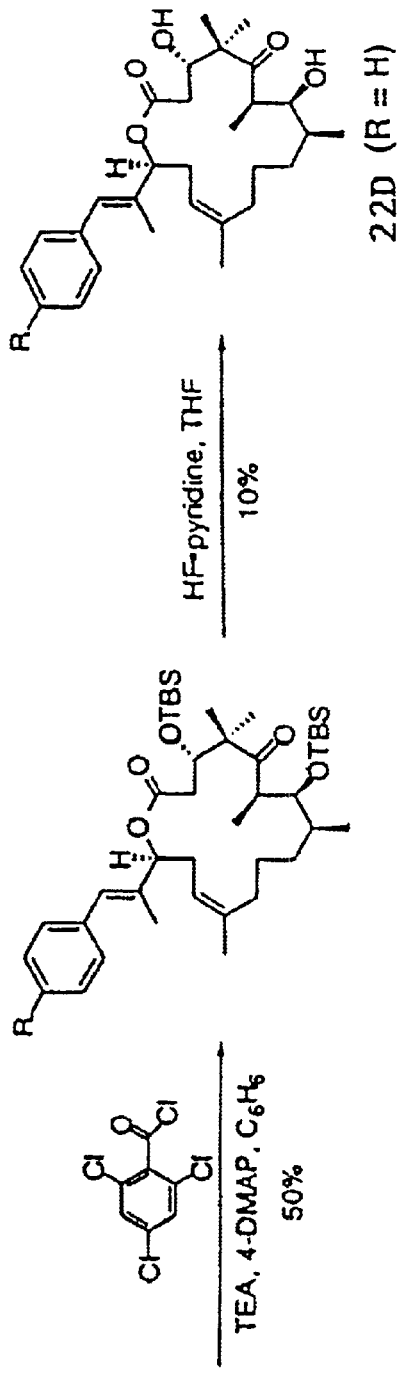
Figure 27A:
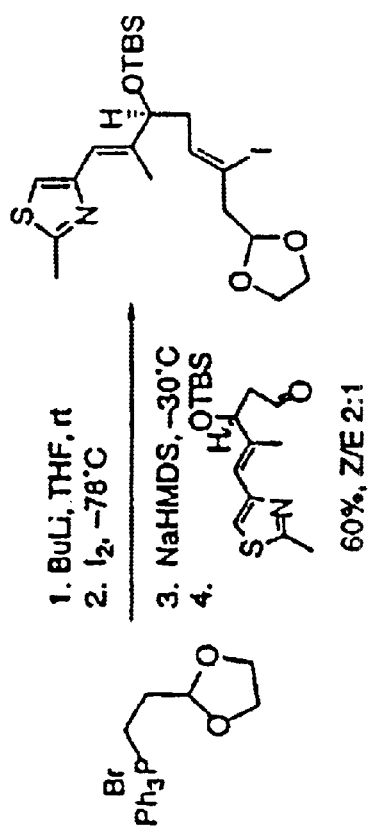
FIGS. 27(A), 27(B) and 27(C) show a synthetic pathway to prepare epothilone analogue 12-hydroxy ethyl epothilone.
Figure 27B:
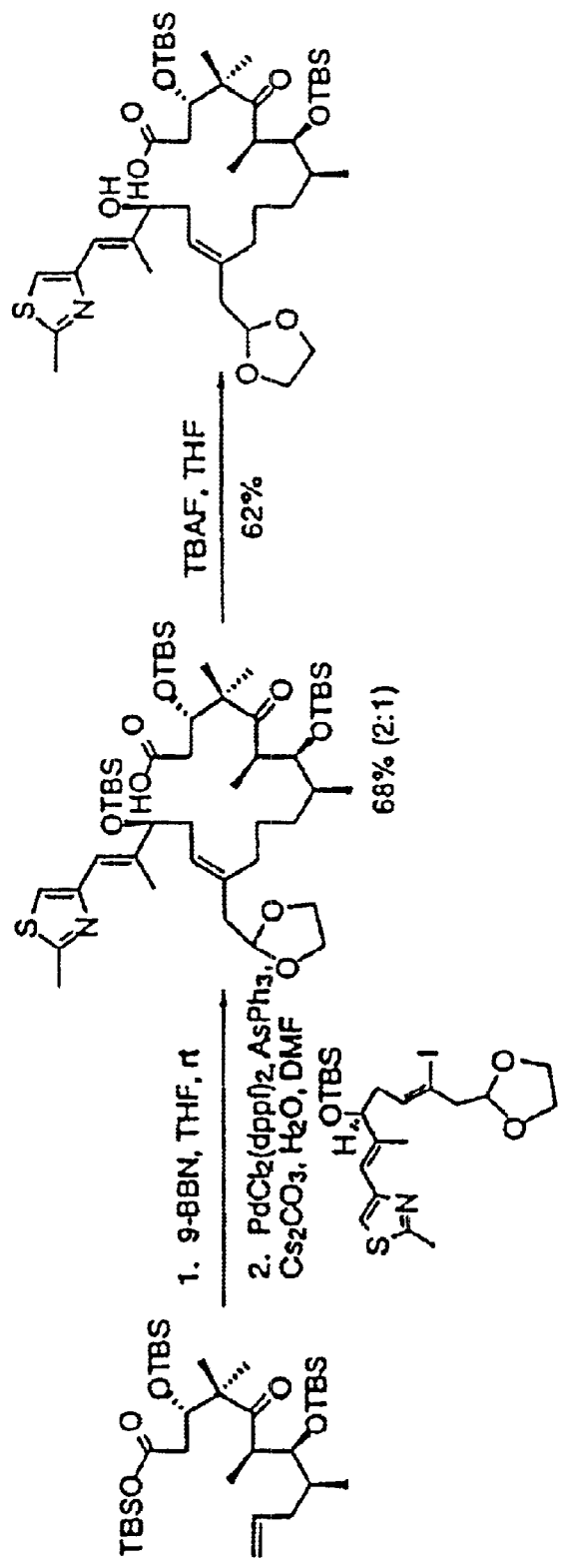
Figure 27C:
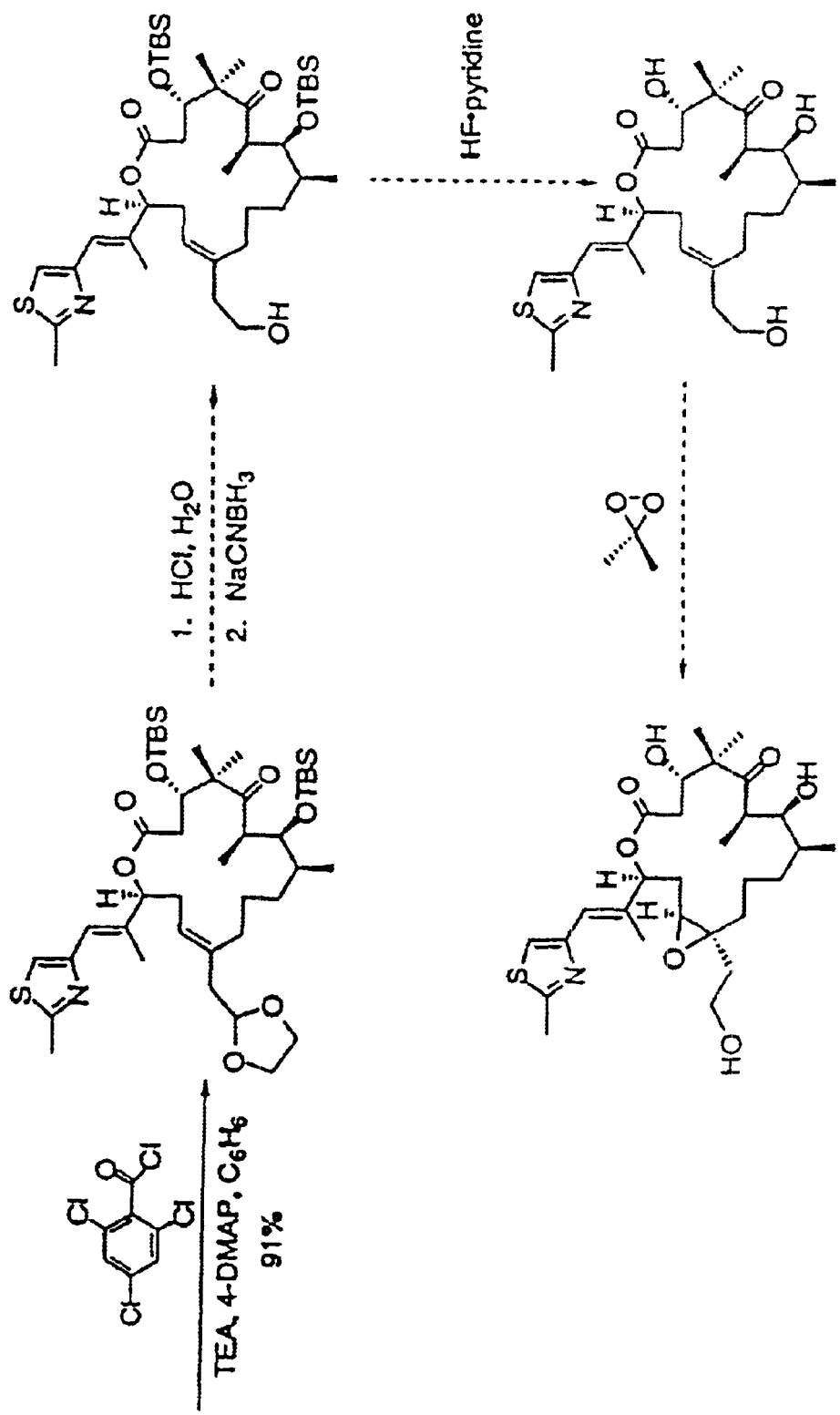
Figure 28A:
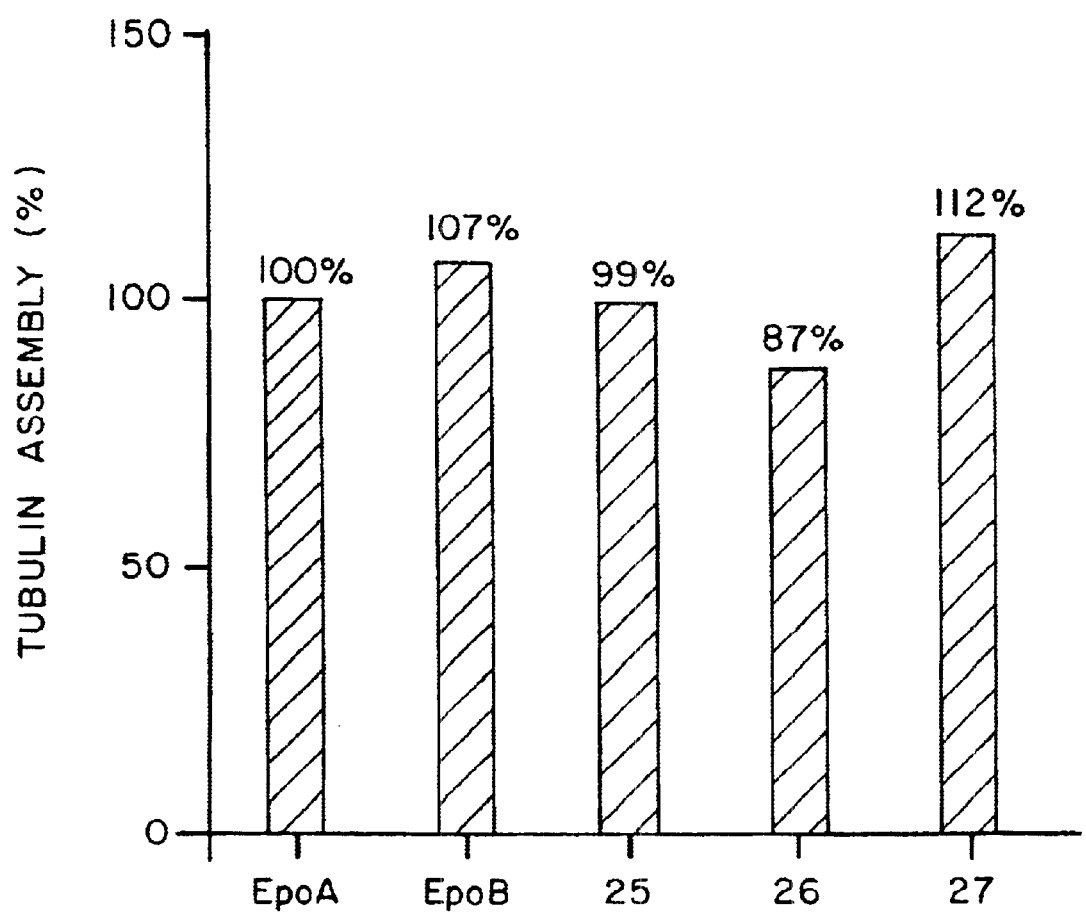
FIGS. 28(A) and 28(B) show the activity of epothilone analogues in a sedimentation test in comparison with DMSO, epothilone A and/or B. Structures 17–20, 22, and 24–27 are shown in FIGS. 29–37, respectively. Compounds were added to tubulin (1 mg/ml) to a concentration of 10 $\mu$M. The quantity of microtubules formed with epothilone A was defined as 100%.
Figure 28B:
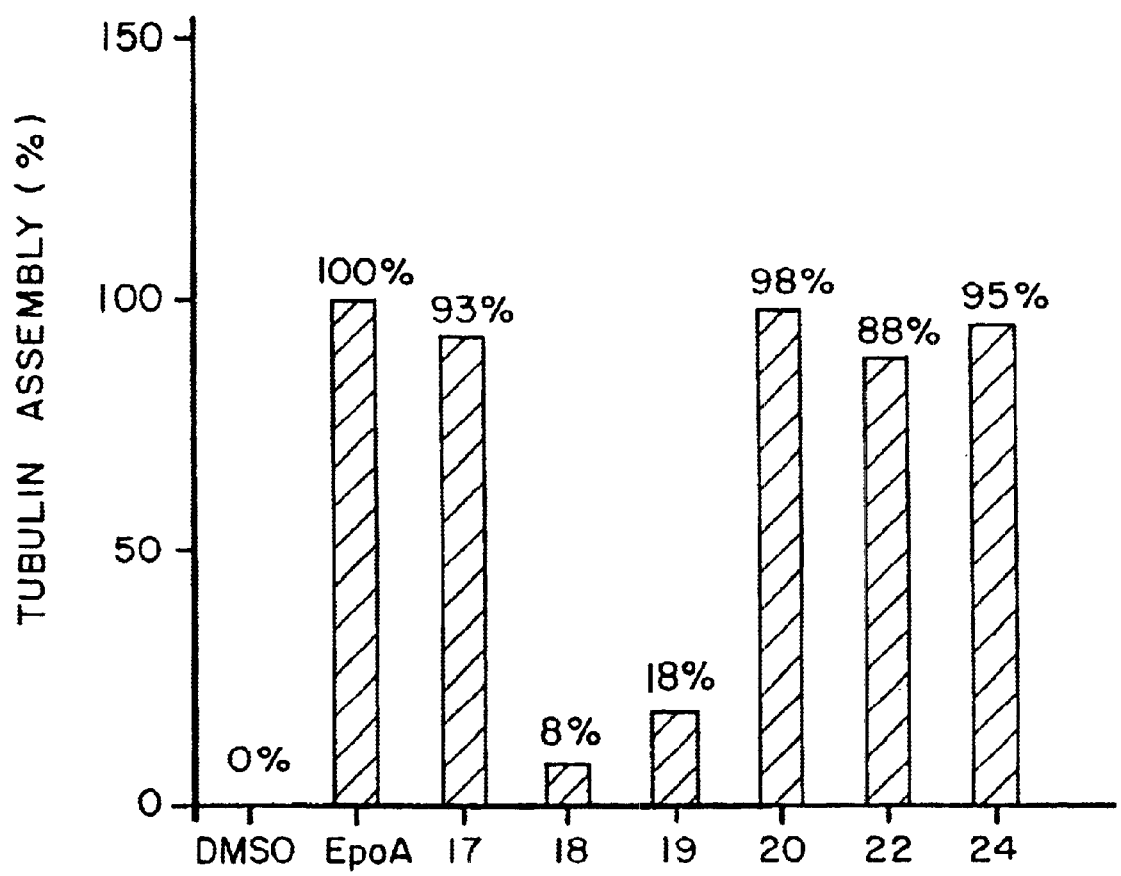
Figure 29:
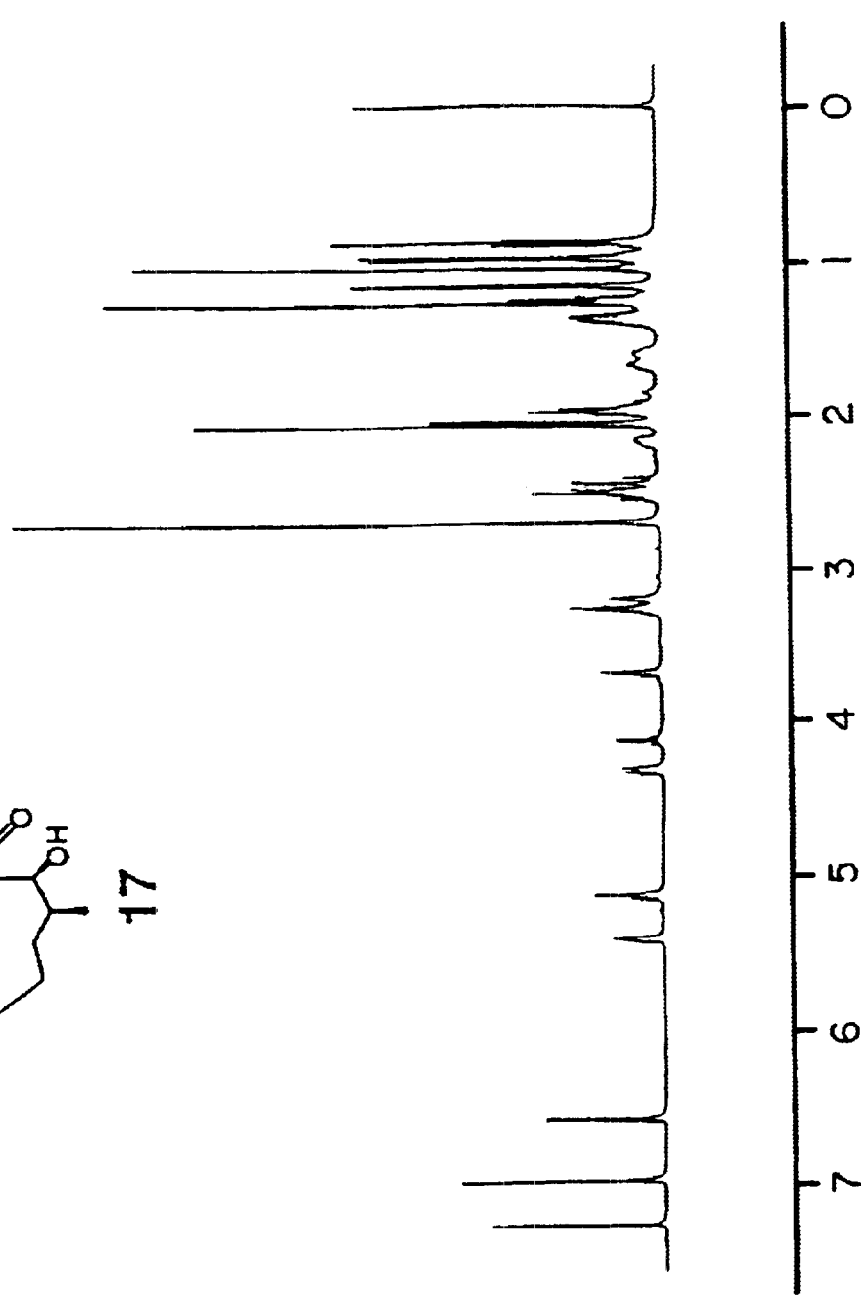
FIG. 29 shows a high resolution $^1$H NMR spectrum of epothilone analogue #17.
Figure 30:
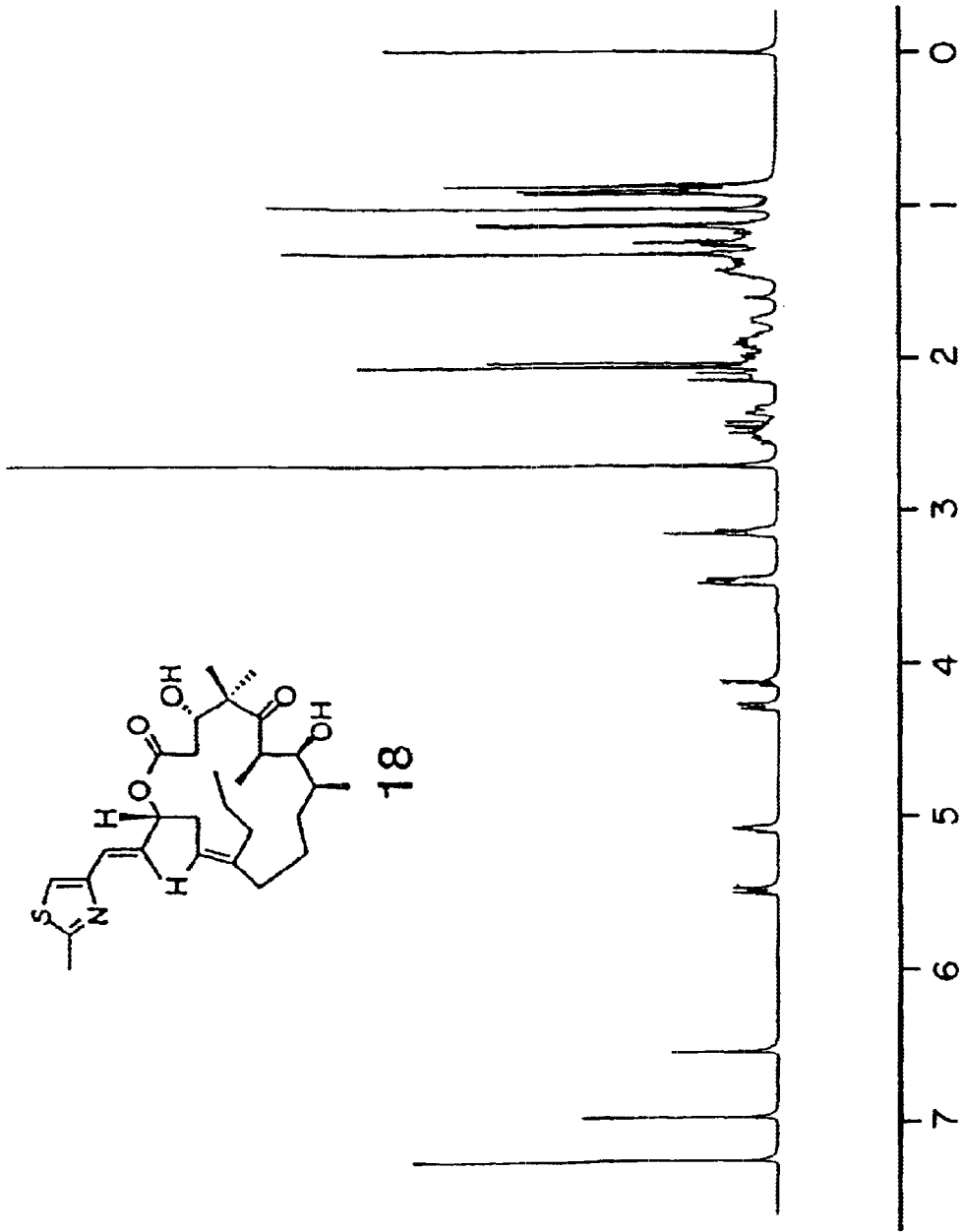
FIG. 30 shows a high resolution $^1$H NMR spectrum of epothilone analogue #18.
Figure 31:
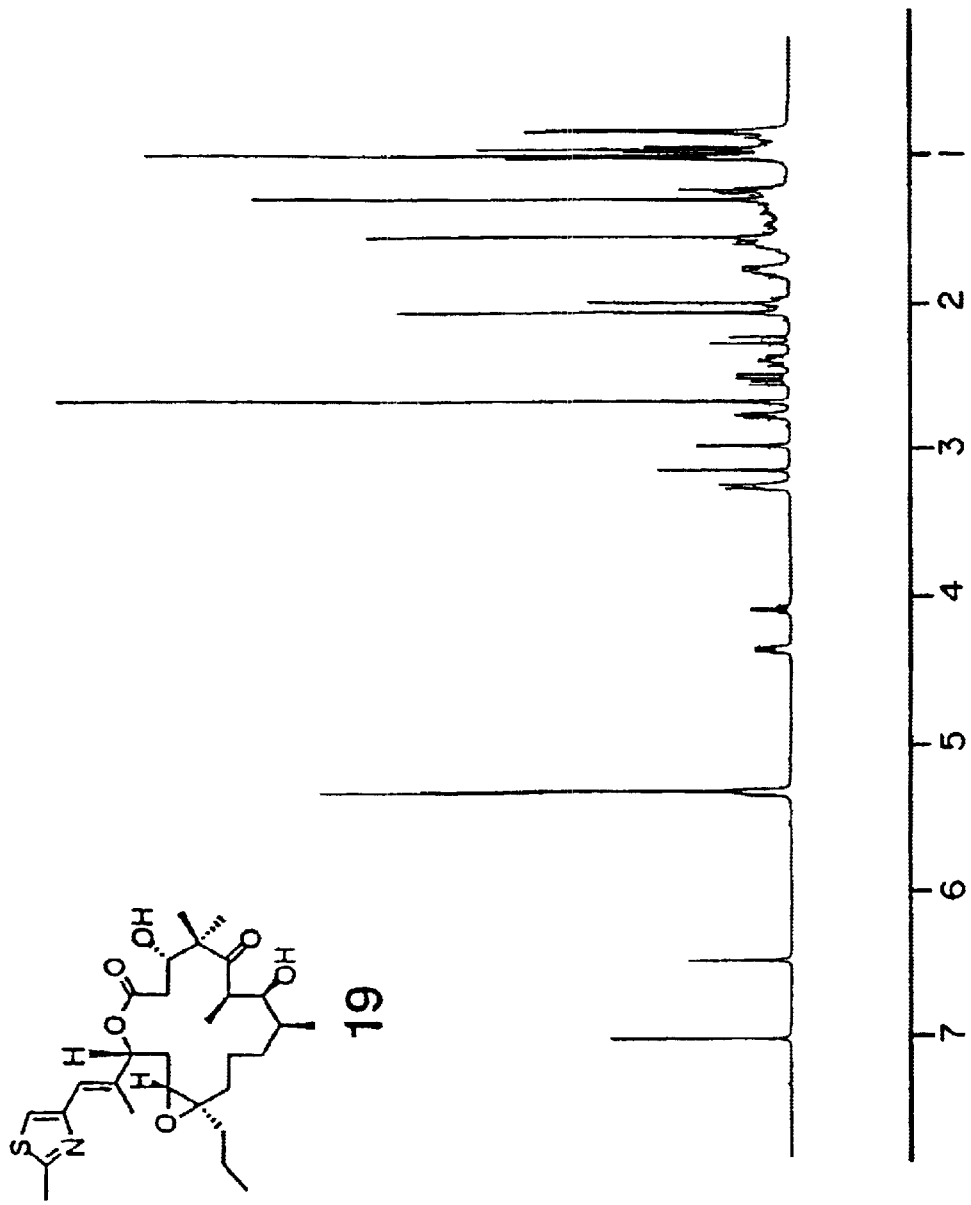
FIG. 31 shows a high resolution $^1$H NMR spectrum of epothilone analogue #19.
Figure 32:
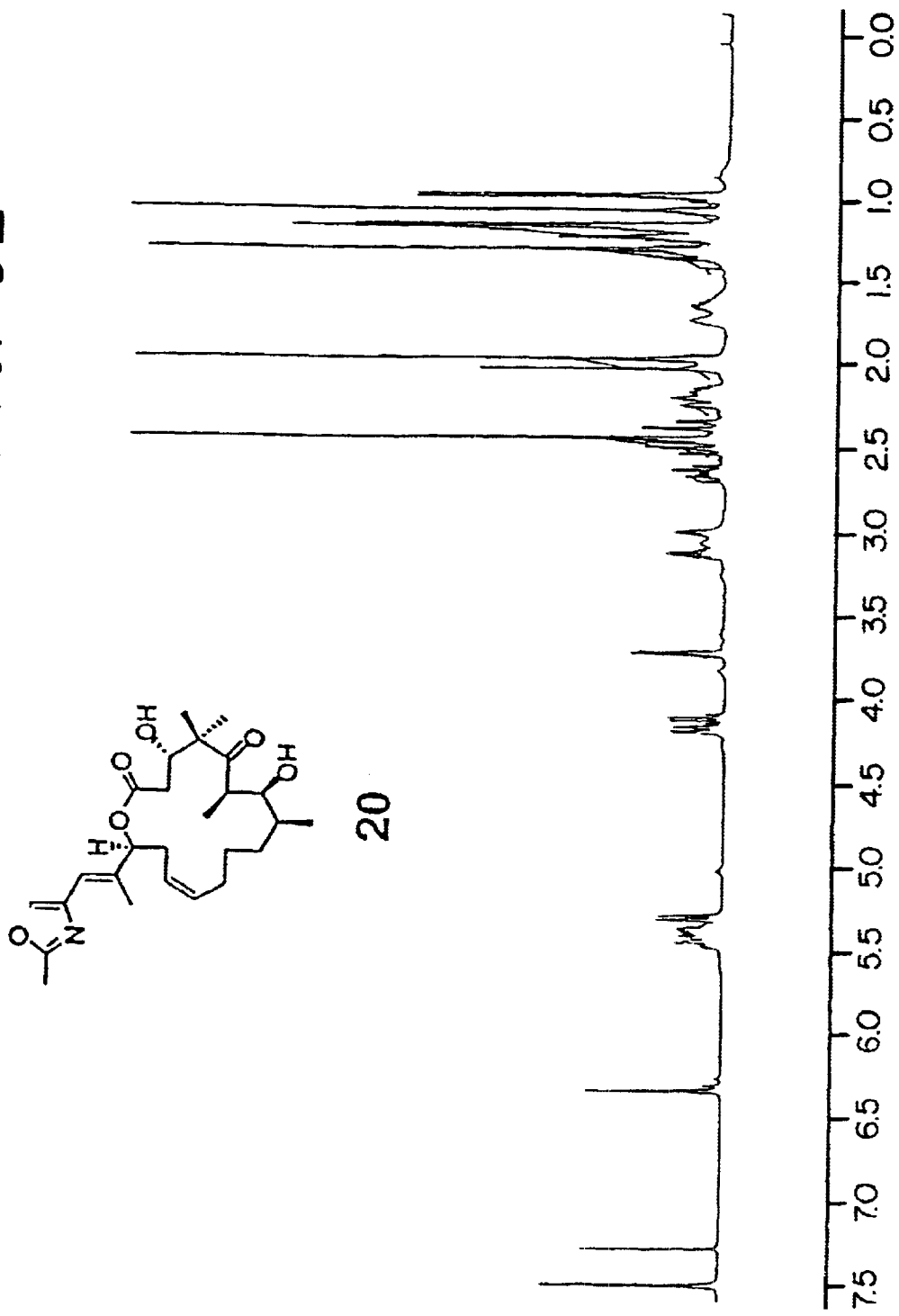
FIG. 32 shows a high resolution $^1$H NMR spectrum of epothilone analogue #20.
Figure 33:
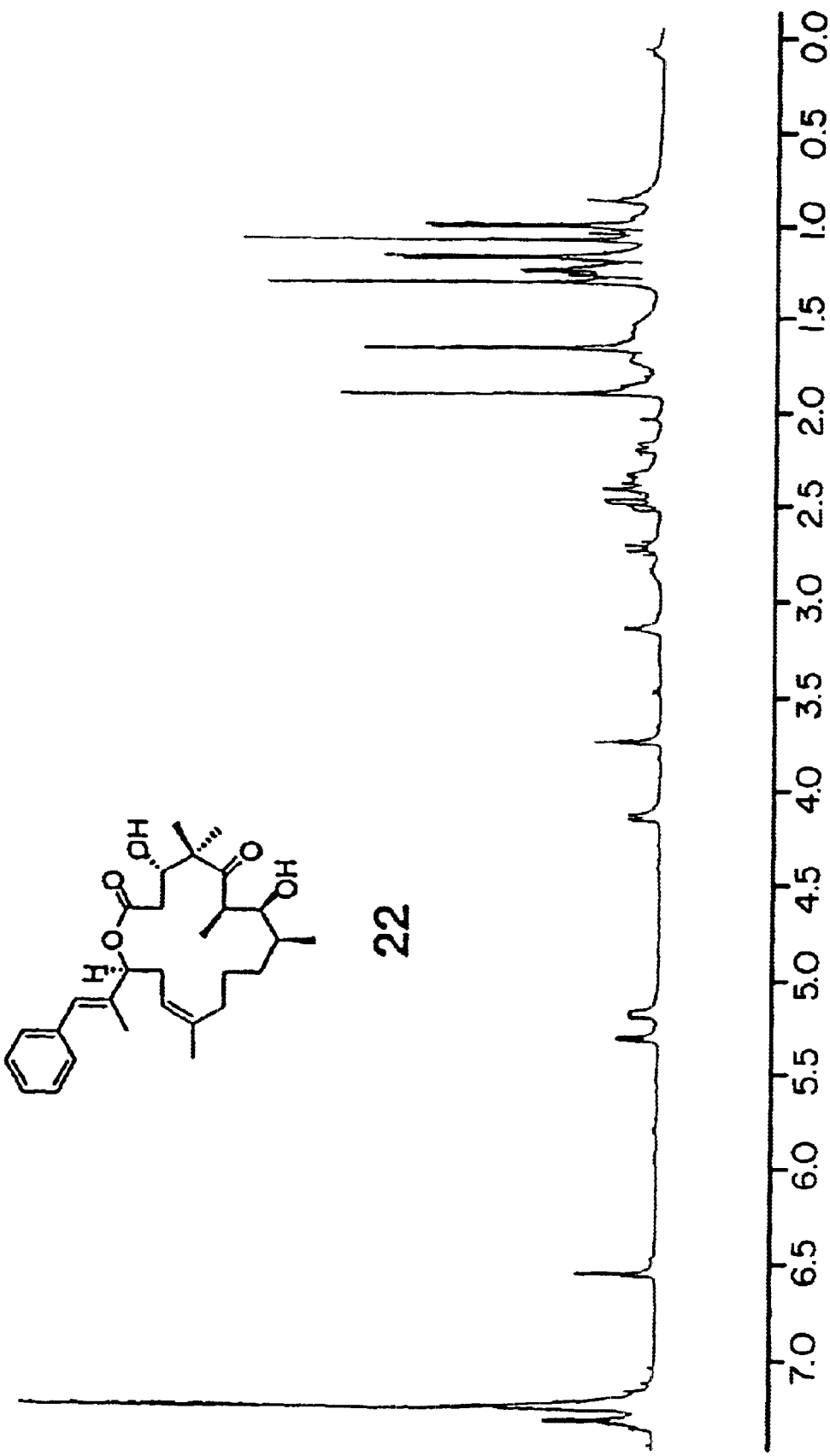
FIG. 33 shows a high resolution $^1$H NMR spectrum of epothilone analogue #22.
Figure 34:
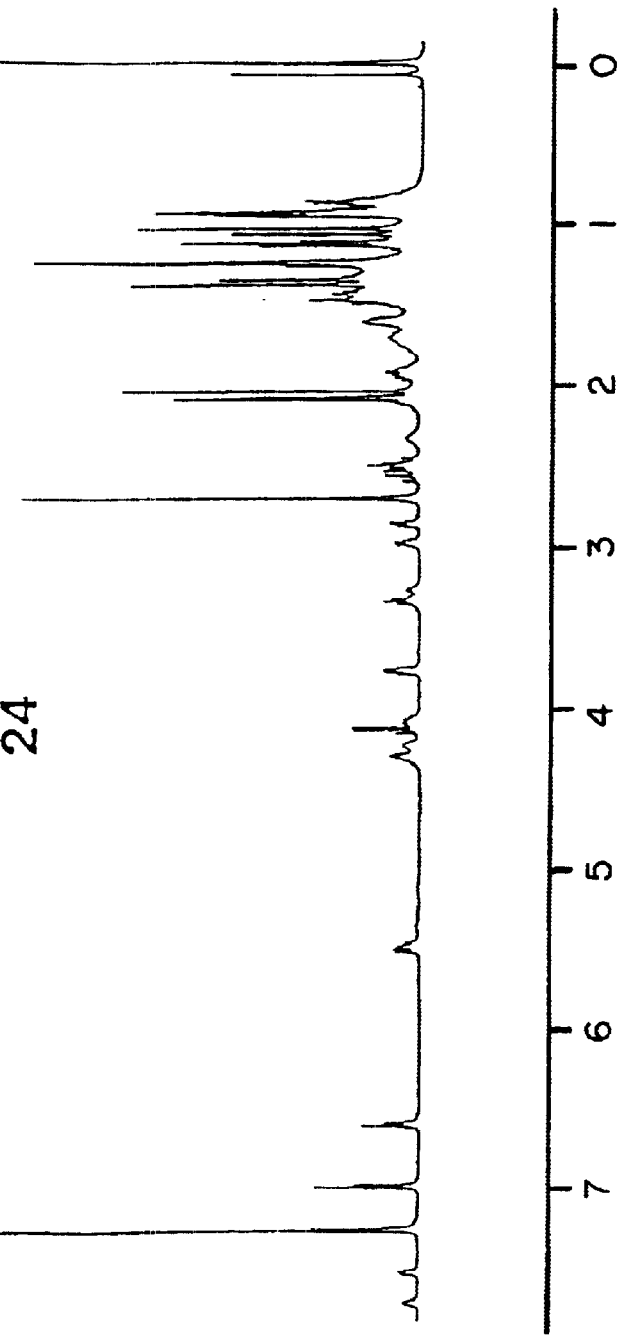
FIG. 34 shows a high resolution $^1$H NMR spectrum of epothilone analogue #24.
Figure 35:
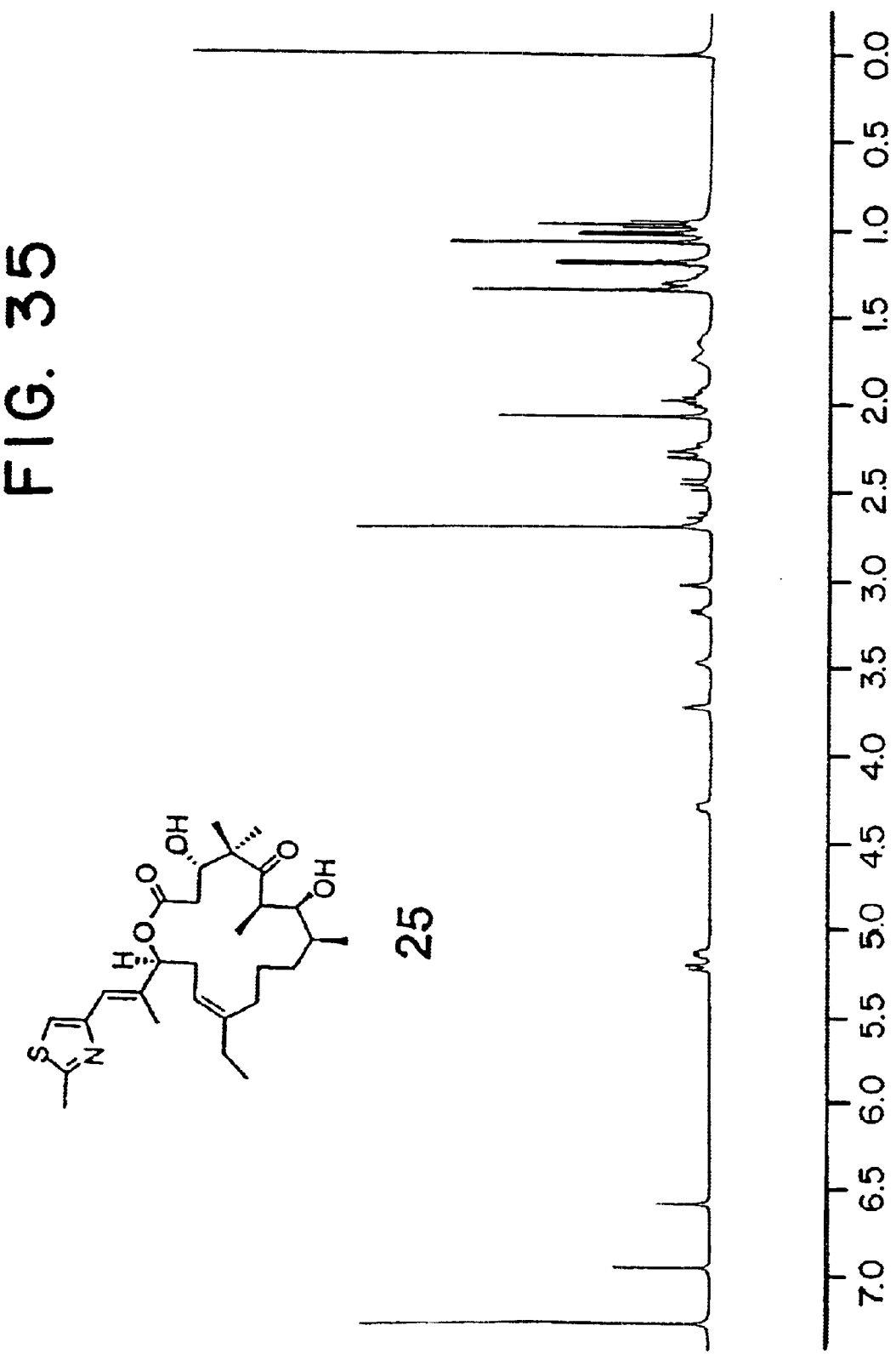
FIG. 35 shows a high resolution $^1$H NMR spectrum of epothilone analogue #25.
Figure 36:
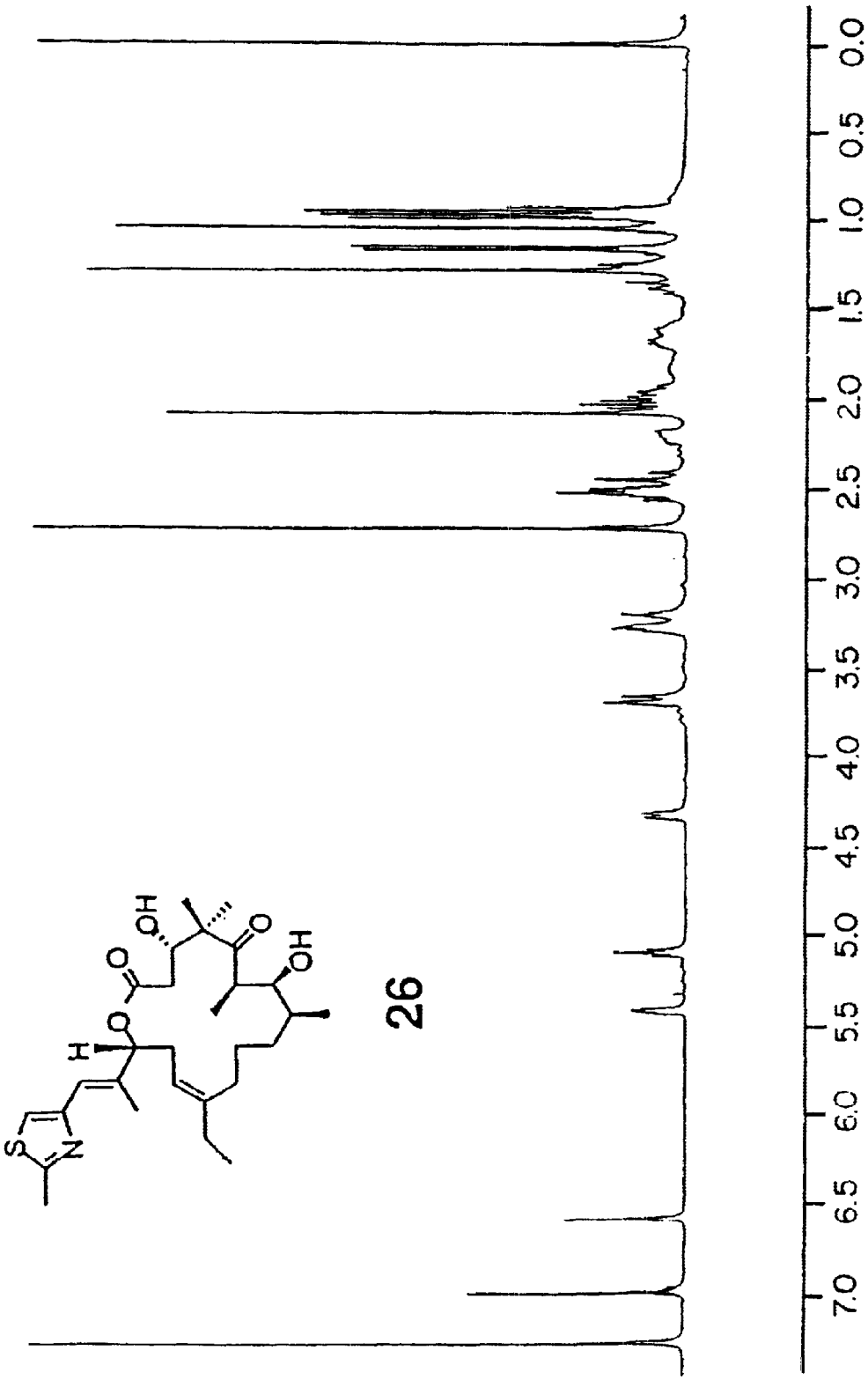
FIG. 36 shows a high resolution $^1$H NMR spectrum of epothilone analogue #26.
Figure 37:
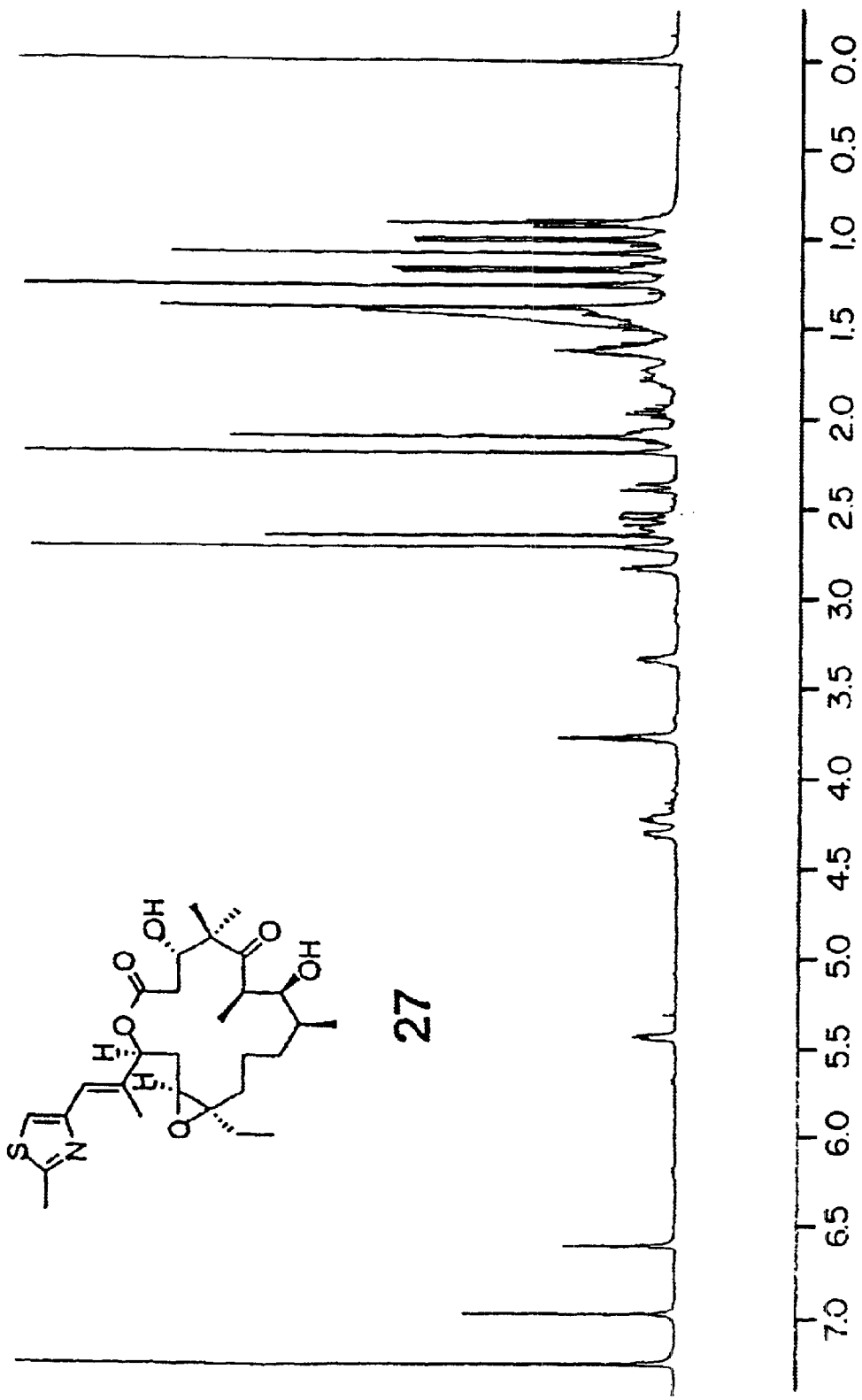
FIG. 37 shows a high resolution $^1$H NMR spectrum of epothilone analogue #27.
Figure 38:
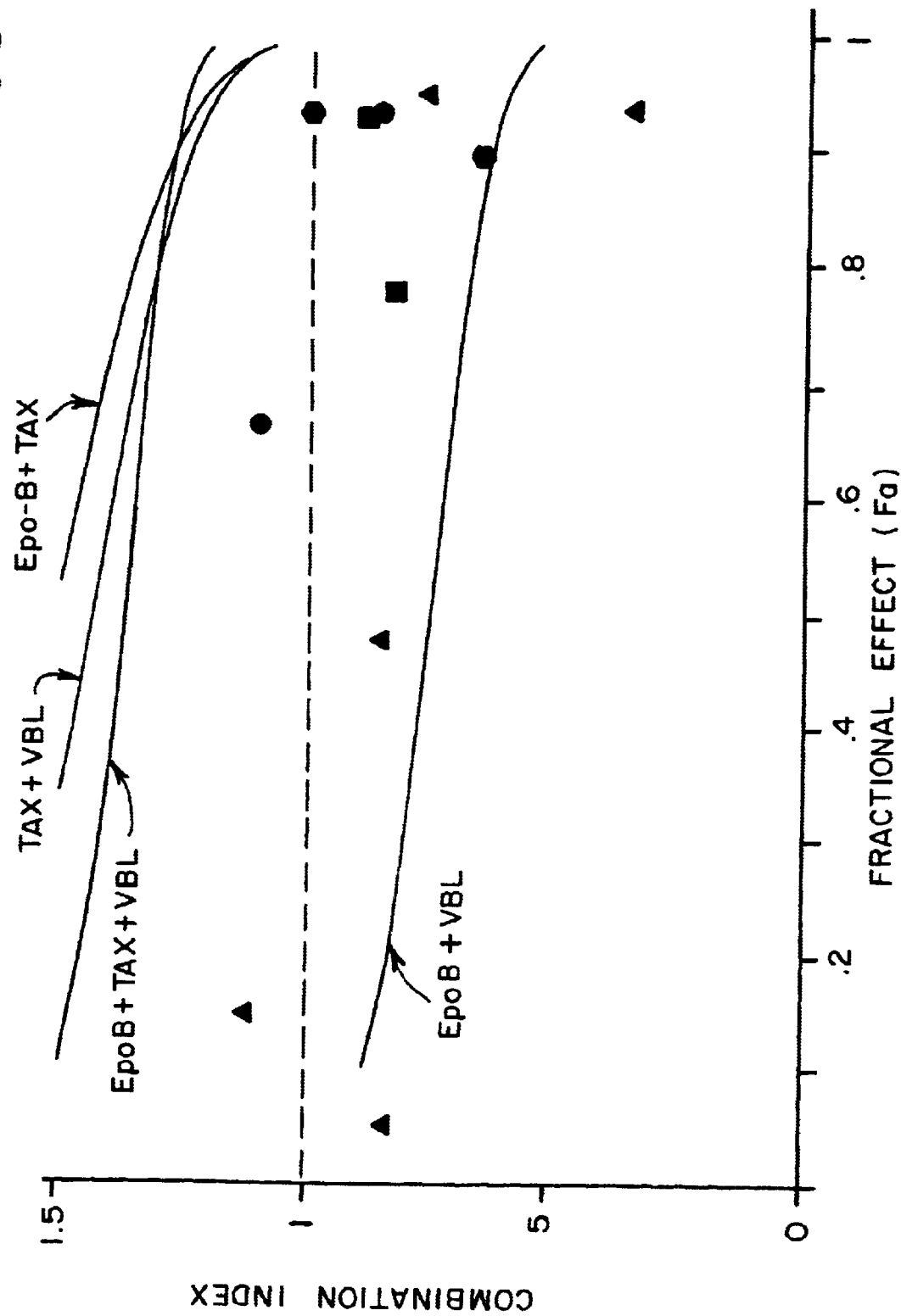
FIG. 38 provides a graphical representation of the effect of fractional combinations of cytotoxic agents.
Figure 39B:
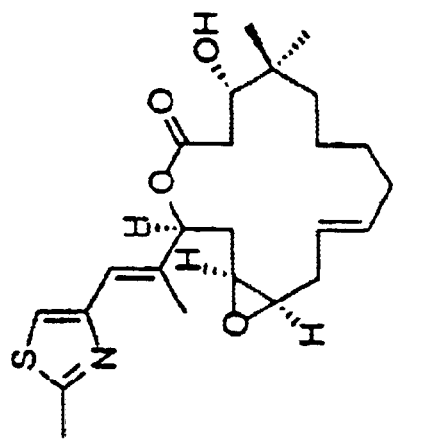
Figure 39B:
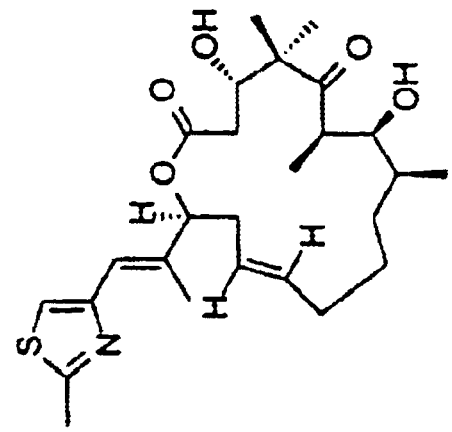
Figure 39B:
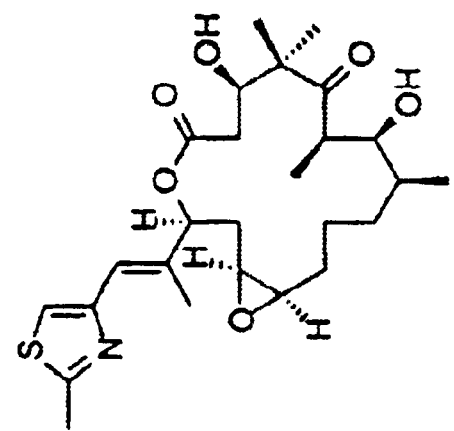
Figure 40A:
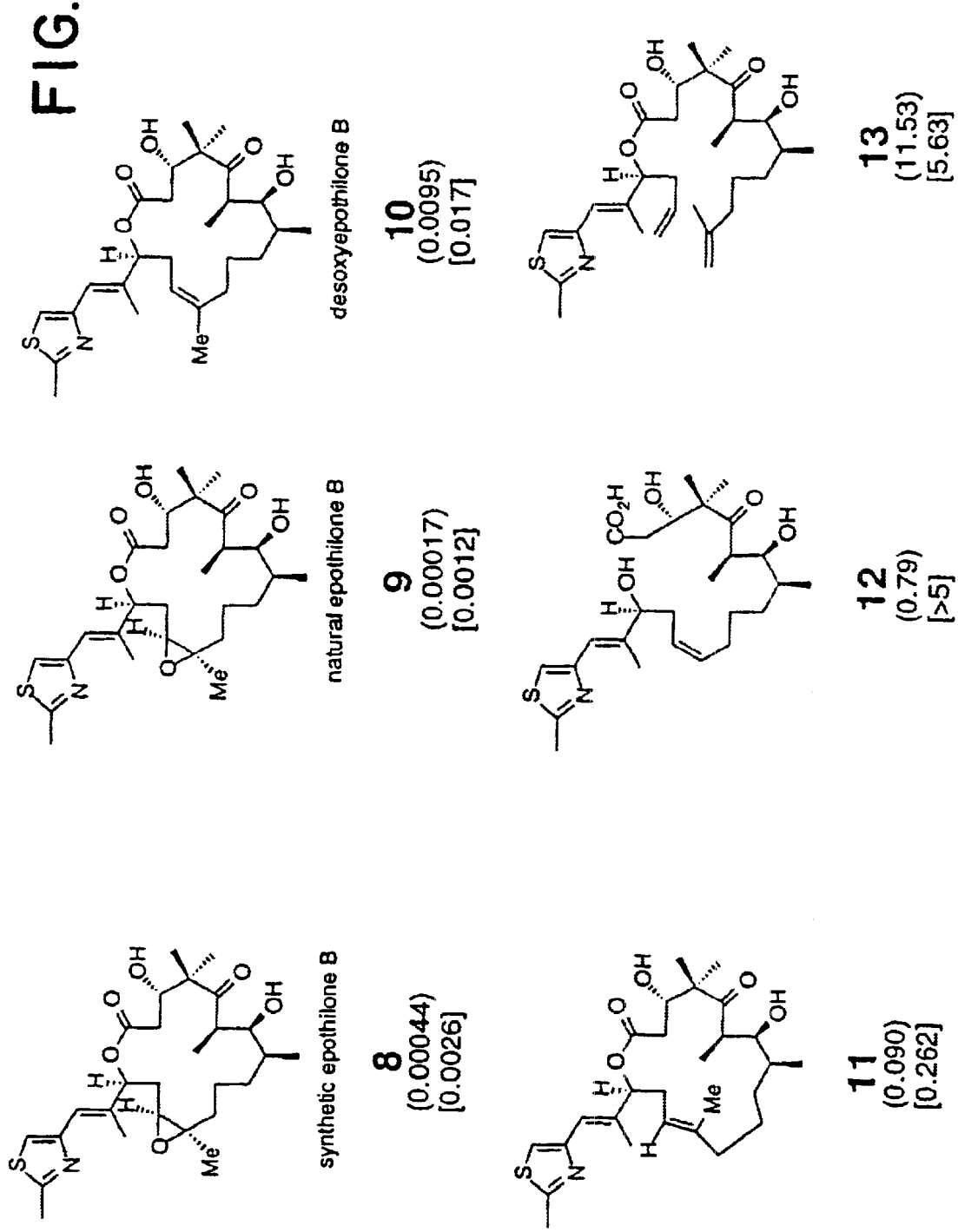
FIGS. 40(A) and 40(B) show epothilone B and epothilone analogues #8–16. Potencies against human leukemia CCRF-CEM (sensitive) and CCRF-CEM/VBL MDR (resistant) sublines are shown in round and square brackets, respectively.
Figure 40B:
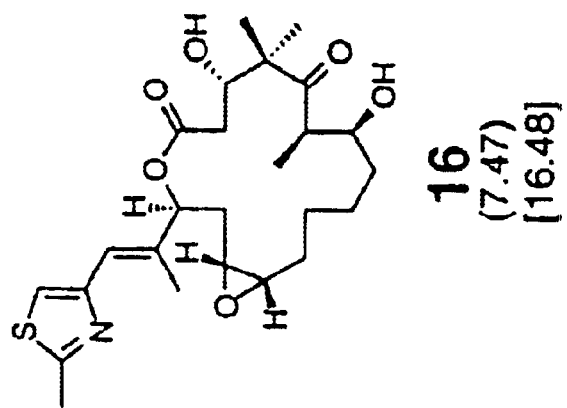
Figure 40B:
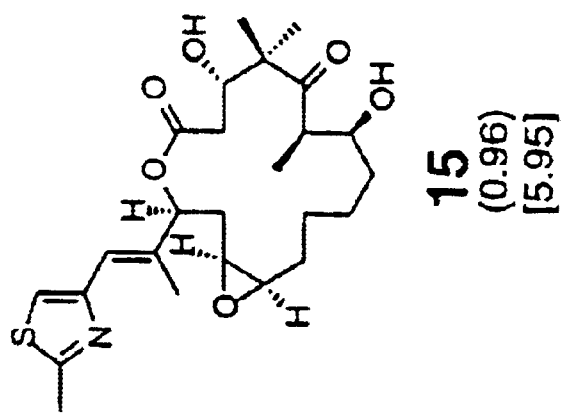
Figure 40B:
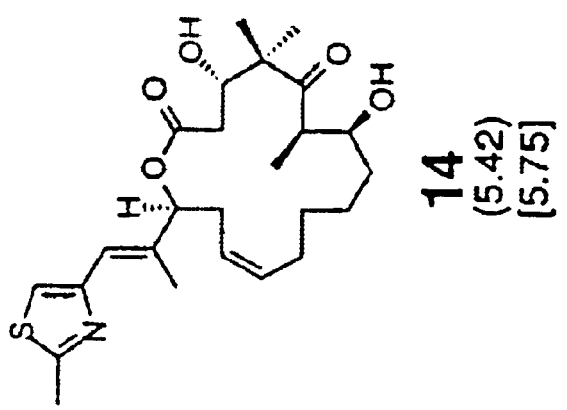
Figure 41A:
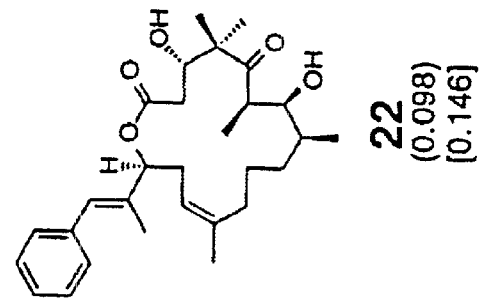
Figure 41A:
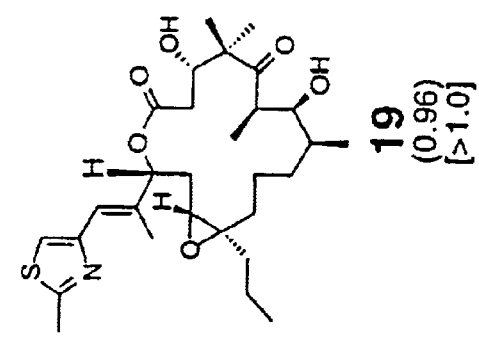
Figure 41A:
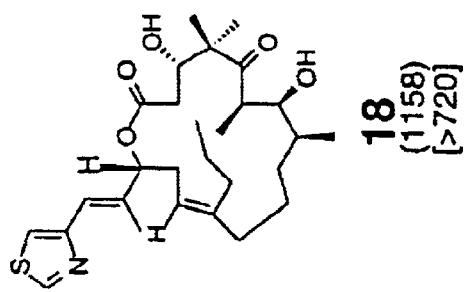
Figure 41A:
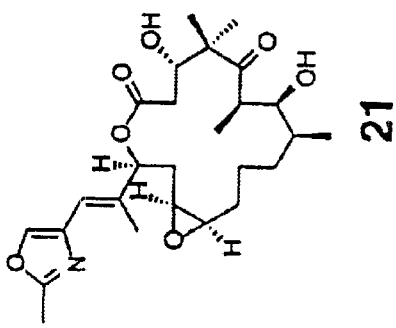
Figure 41A:
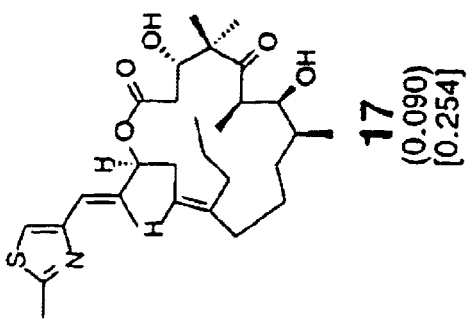
Figure 41A:
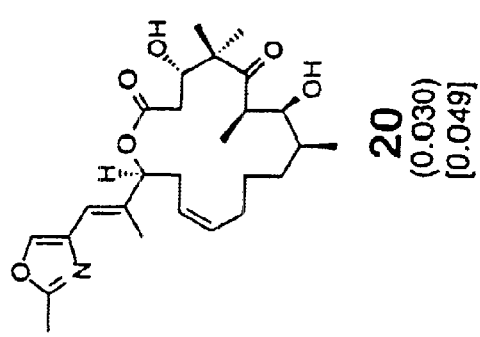
Figure 42A:
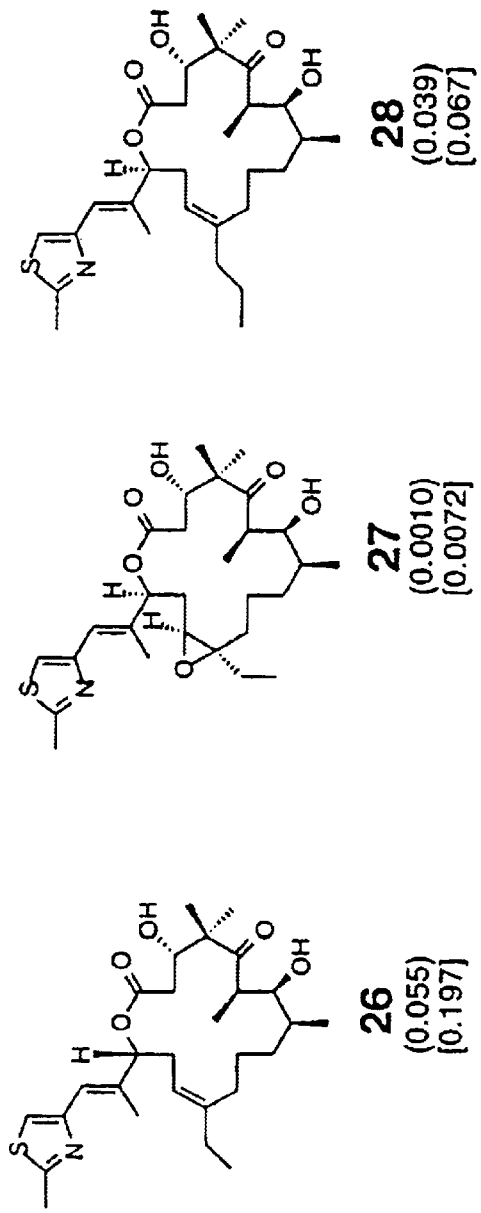
FIGS. 42(A) and 42(B) show epothilone analogues #26–34. Potencies against human leukemia CCRF-CEM (sensitive) and CCRF-CEMIVBL MDR (resistant) sublines are shown in round and square brackets, respectively.
Figure 42A:
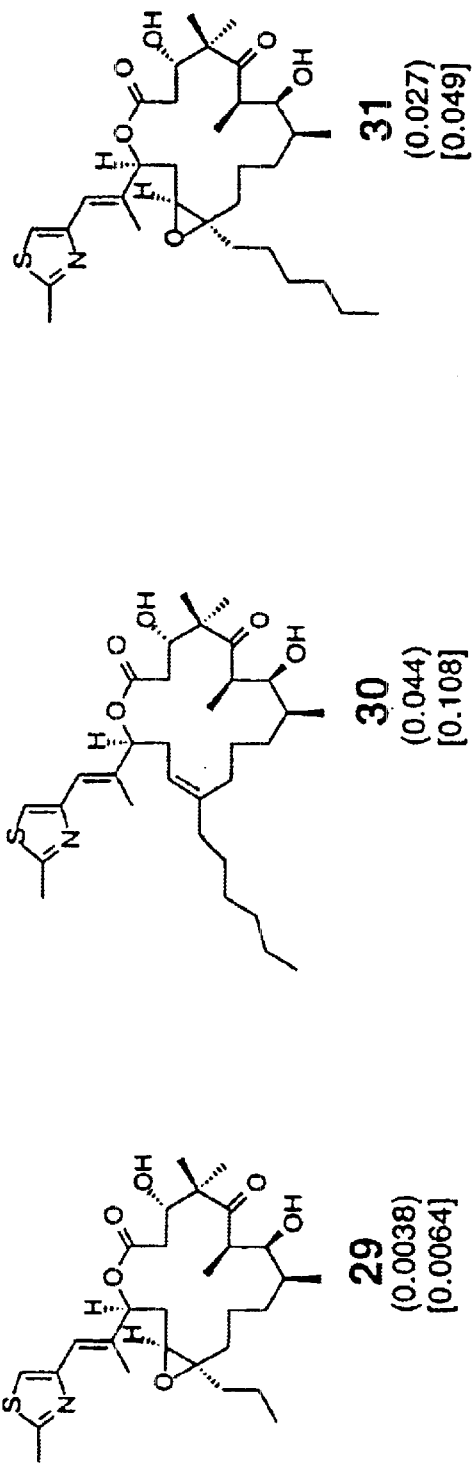
Figure 42B:
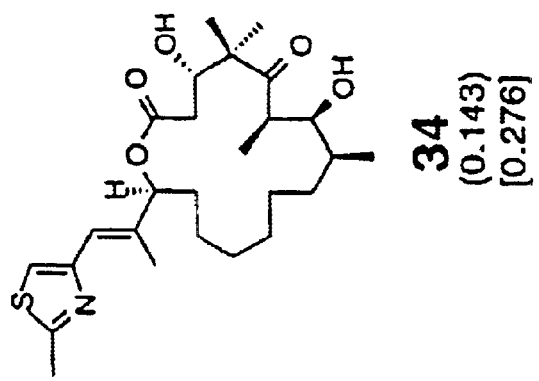
Figure 42B:
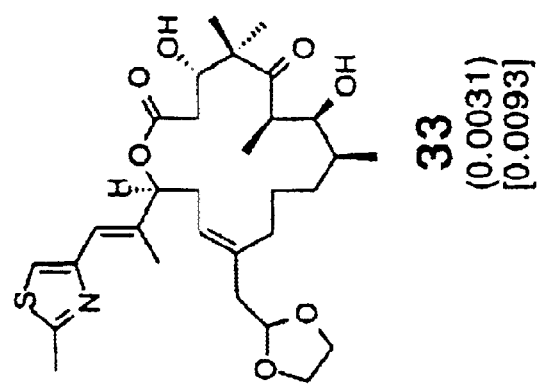
Figure 42B:
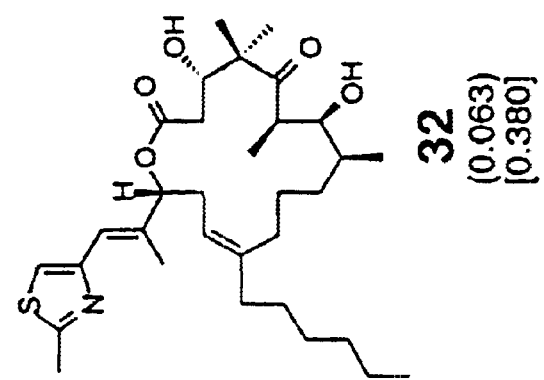
Figure 42C:
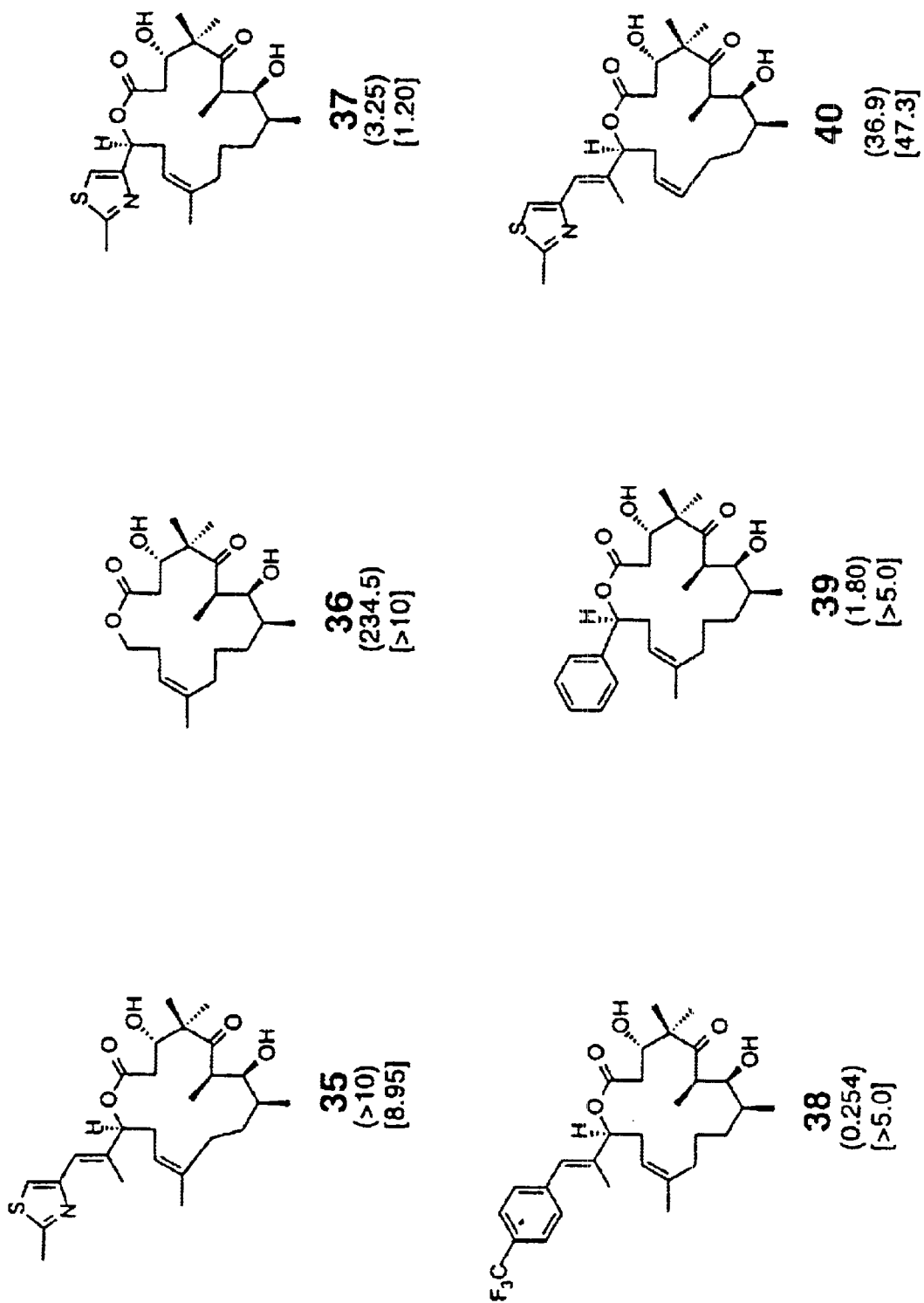
FIGS. 42(C) and 42(D) show epothilone analogues #35–46. Potencies against human leukemia CCRF-CEM (sensitive) and CCRF-CEMNVBL MDR (resistant) sublines are shown in round and square brackets, respectively.
Figure 42D:
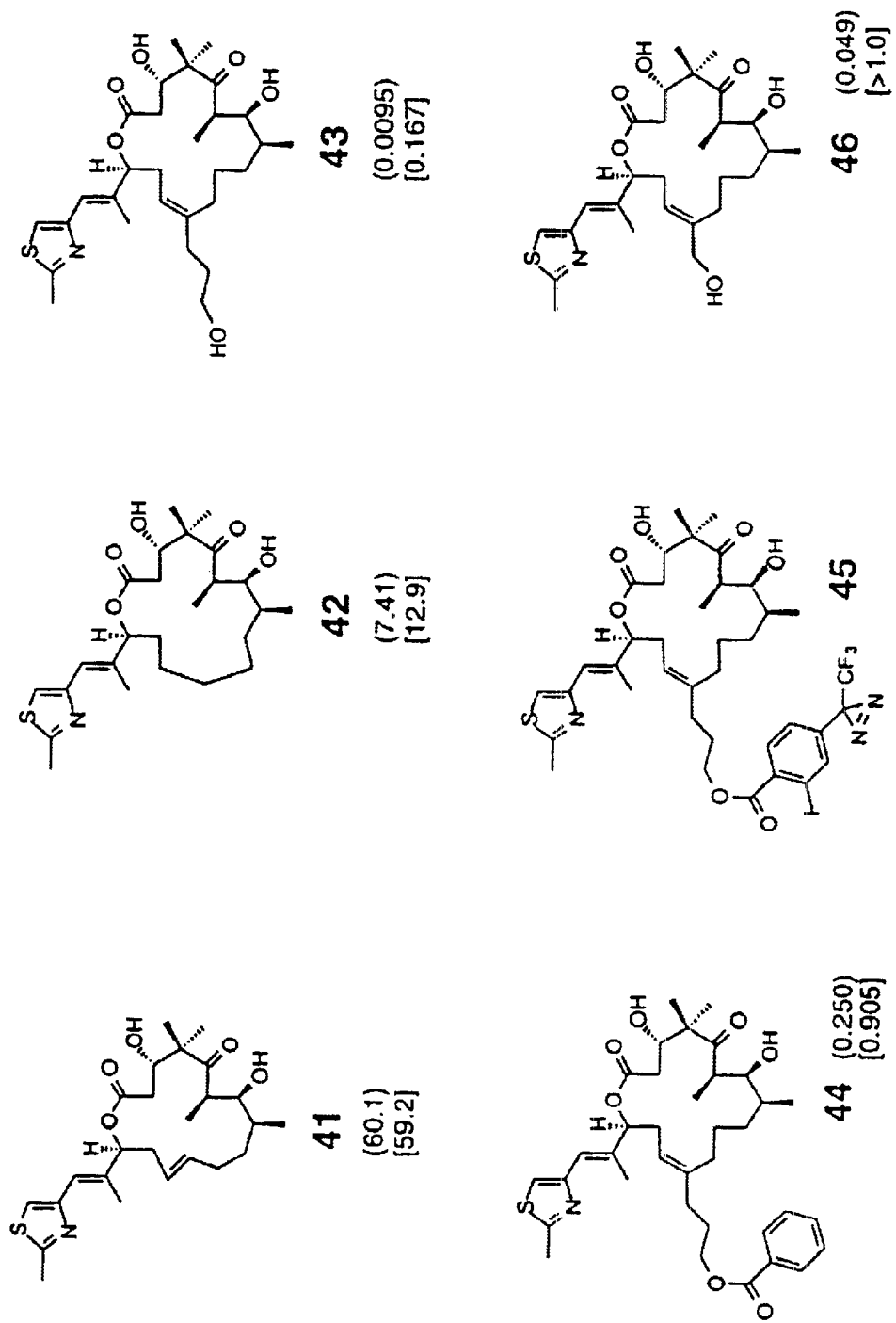
Figure 43A:
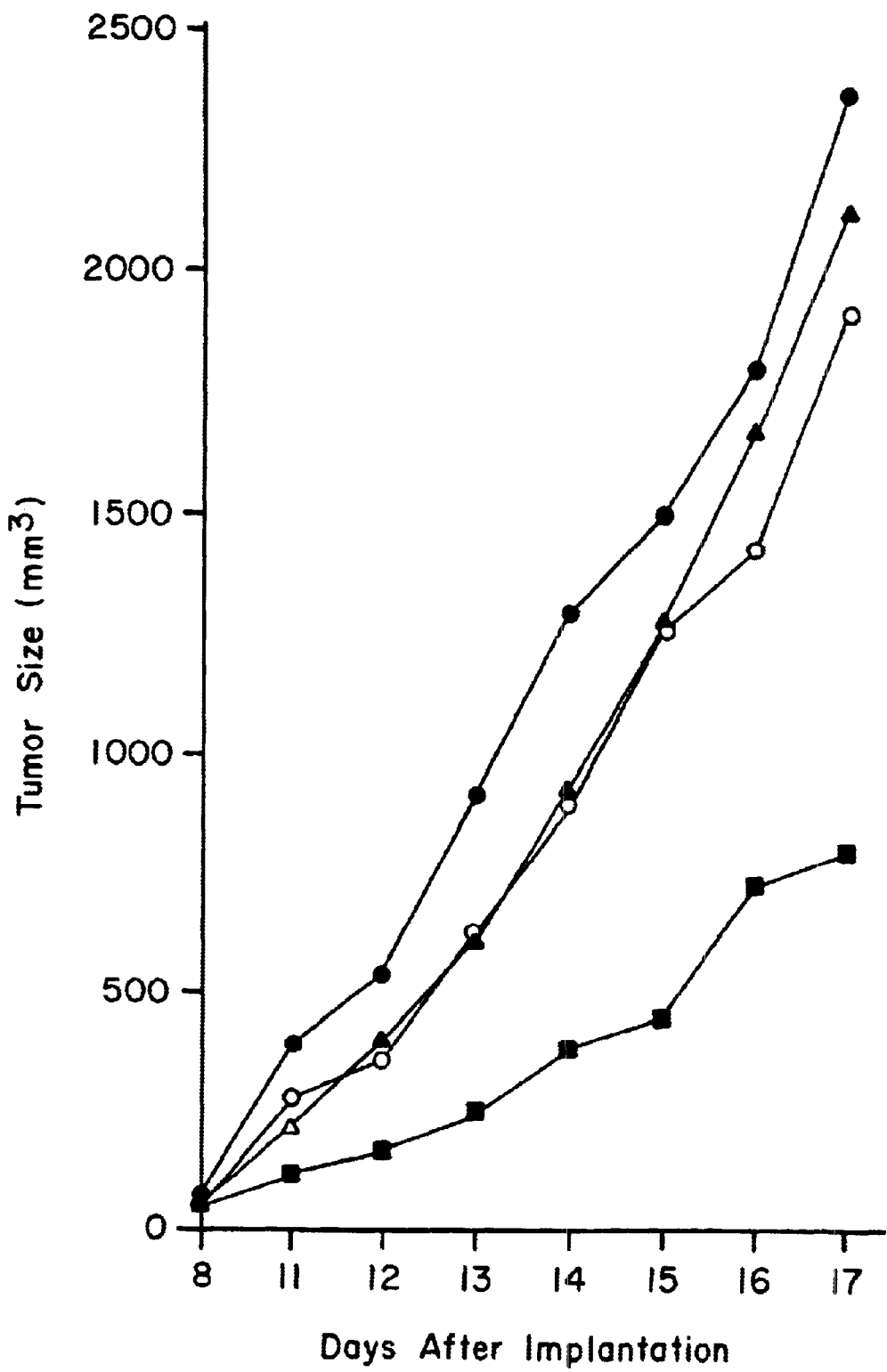
FIG. 43(A) shows antitumor activity of desoxyepothilone B against MDR MCF-7/Adr xenograft in comparison with taxol. Control (♦); desoxyepothilone B (■; 35 mg/kg); taxol (▲; 6 mg/kg); adriamycin (X;1.8 mg/kg); i.p. Q2Dx5; start on day 8.
Figure 43B:
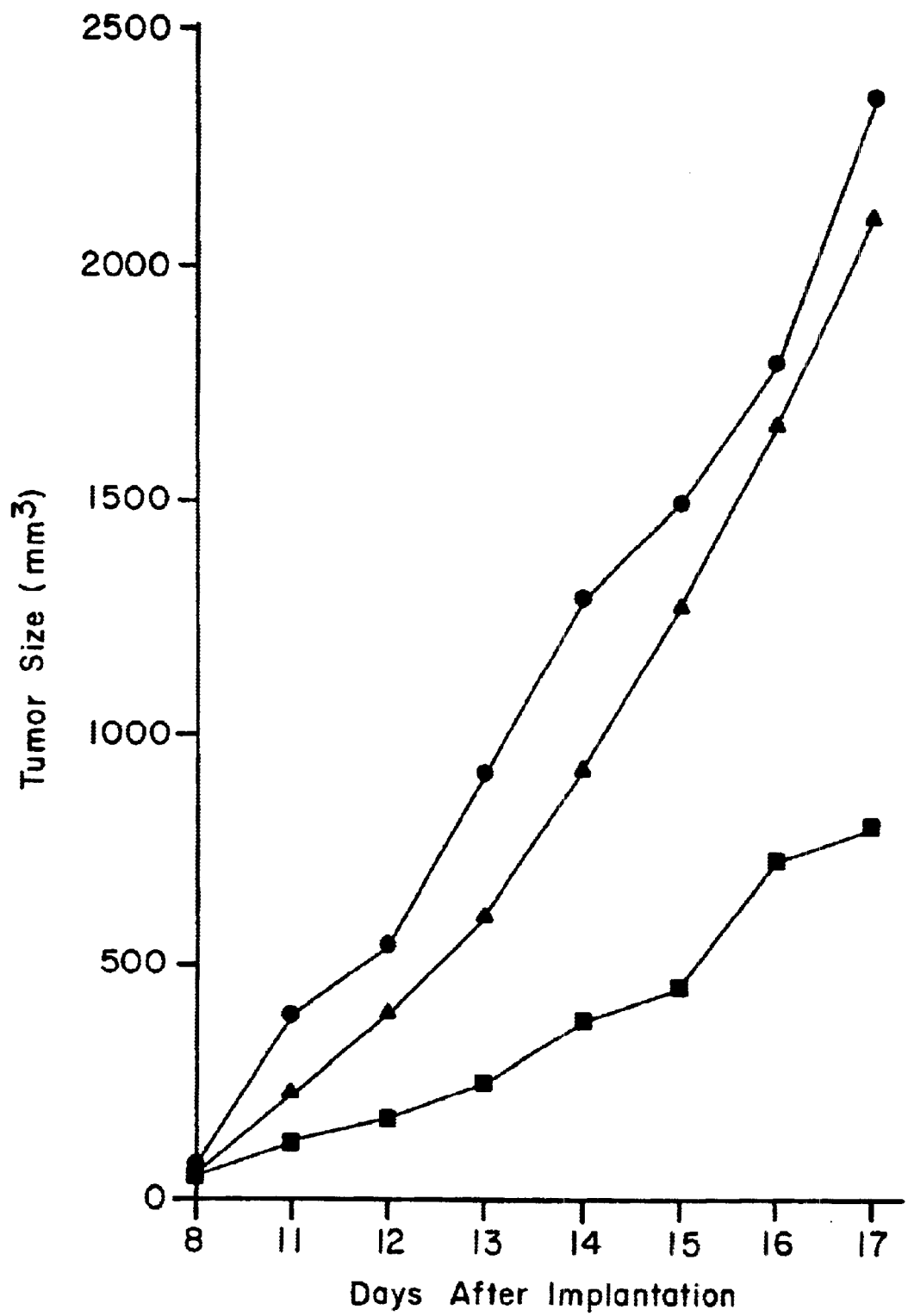
FIG. 43(B) shows antitumor activity of epothilone B against MDR MCF-7/Adr xenograft in comparison with taxol. Control (♦); epothilone B (■; 25 mg/kg; non-toxic dose); taxol (▲; 6 mg/kg; half LD$_{50}$); adriamycin (X;1.8 mg/kg); i.p. Q2Dx5; start on day 8.

The hydroboration of 10D with 9-BBN produced intermediate 11D which, on coupling with the vinyl iodide 12D and in situ cleavage of the TBS ester led to 13D (FIG. 21). After de-acetylation, the hydroxy acid 14D was in hand. Macrolactonization of this compound (Boden, E. P.; Keck, G. E. *J. Org. Chem.* 1985, 50, 2394) produced 15D which, after desilylation, afforded $C_8$-desmethyldesoxyepothilone (16D). Finally, epoxidation of this compound with dimethyldioxirane produced the goal structure 3D. The stereoselectivity of epoxidation was surprisingly poor (1.5:1) given that epoxidation of desoxyepothilone A occurred with >20:1 stereoselectivity. Deletion of the $C_8$ methyl group appears to shift the conformational distribution of 16D to forms in which the epoxidation by dimethyl dioxirane is less β-selective. It is undetermined whether the effect of the $C_8$ methyl on the stereoselectivity of epoxidation by dimethydioxirane and the dramatic reduction of biological activity are related.

Compounds 3D and 16D were tested for cytotoxicity in cell cultures and assembly of tubulin in the absence of GTP. Microtubule protein (MTP) was purified from calf brains by two cycles of temperature dependent assembly and disassembly. Weisenberg, R. C. *Science* 1972, 177, 1104. In control assembly experiments, MTP (1 mg/mL) was diluted in assembly buffer containing 0.1 M MES (2-(N-morpholino) ethanesulfonic acid), 1 mM EGTA, 0.5 mM $MgCl_2$, 1 mM GTP and 3M glycerol, pH 6.6. The concentration of tubulin in MTP was estimated to be about 85%. Assembly was monitored spectrophotometrically at 350 nm, 35° C. for 40 min by following changes in turbidity as a measure of polymer mass. Gaskin, F.; Cantor, C. R.; Shelanksi, M. L. *J. Mol. Biol.* 1974, 89, 737. Drugs were tested at a concentration of 10 µM, in the absence of GTP. Microtubule formation was verified by electron microscopy. To determine the stability of microtubules assembled in the presence of GTP or drug, turbidity was followed for 40 min after the reaction temperature was shifted to 4° C.

Cytotoxicity studies showed drastically reduced activity in the 8-desmethyl series. Compounds 3D and 16D were approximately 200 times less active than their corresponding epothilone A counterparts (see Table 1). Recalling earlier SAR findings at both $C_3$ and $C_5$, in conjunction with the findings disclosed herein, the polypropionate sector of the epothilones emerges as a particularly sensitive locus of biological function. Su, D.-S., et al., *Angew. Chem. Int. Ed. Engl.* 1997, 36, 757; Meng, D., et al., *J. Am. Chem. Soc.* 1997, 119.

TABLE 1

Relative efficacy of epothilone compounds against drug-sensitive and resistant human leukemic CCRF-CEM cell lines.[a]

| Compound | CCRF-CEM $IC_{50}$ (µM)[b] | CCRF-CEM/VBL $IC_{50}$ (µM)[b] | CCRF-CEM/$VM_1$ $IC_{50}$ (µM)[b] |
|---|---|---|---|
| 16D | 5.00 | 5.75 | 6.29 |
| 3D | 0.439 | 2.47 | 0.764 |
| epothilone A | 0.003 | 0.020 | 0.003 |
| desoxyepothilone A | 0.022 | 0.012 | 0.013 |
| epothilone B | 0.0004 | 0.003 | 0.002 |
| desoxyepothilone B | 0.009 | 0.017 | 0.014 |
| paclitaxel | 0.002 | 3.390 | 0.002 |

[a]The cytotoxicities of test compounds were determined by the growth of human lymphoblastic leukemic cells CCRF-CEM, or their sublines resistant to vinblastine and taxol (CCRF-CEM/VBL) or resistant to etoposide (CCRF-CEM/VM-1). XTT-microculture tetrazolium/formazan assays were used.
[b]The $IC_{50}$ values were calculated from 5–6 concentrations based on the median-effect plot using computer software.

Biological Results

In the tables which follow, model system I is desoxyepothilone. Model system 2 has the structure:

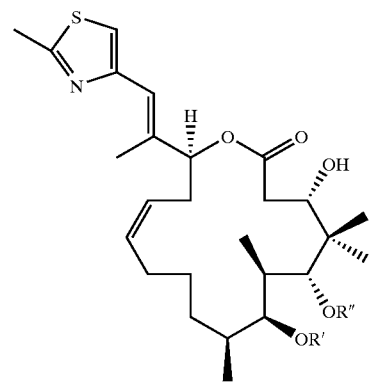

wherein R' and R" are H.

Model system 3 has the structure:

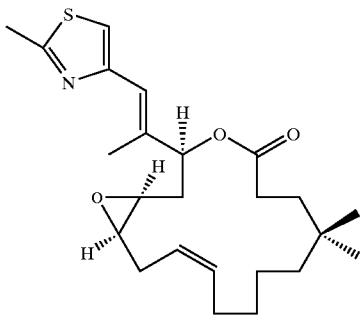

TABLE 2

Relative Efficacy of Epothilone Compound Against Human
Leukemic CCRF-CEM Cell Growth and Against
CCRF-CEM MDR Sublines Resistance to Taxol or Etoposide

| | $IC_{50}$ in $\mu M$ | | |
|---|---|---|---|
| COMPOUND | CCRF-CEM | CCRF-CEM/VLB | CCRF-CEM/VM-1 |
| EPOTHILONE A NATURAL | 0.0035 | 0.0272 | 0.0034 |
| EPOTHILONE A SYNTHETIC | 0.0029 | 0.0203 | 0.0034 |
| MODEL SYSTEM I [3] | 271.7 | 22.38 | 11.59 |
| TRIOL ANALOG [2] | 14.23 | 6.28 | 43.93 |
| DESOXY EPOTHILONE [1] | 0.002 | 0.012 | 0.013 |
| TAXOL | 0.0023 | 2.63 | 0.0030 |
| VINBLASTINE | 0.00068 | 0.4652 | 0.00068 |
| VP-16 (ETOPOSIDE) | 0.2209 | 7.388 | 34.51 |

Relative Potency of Epothilone Compounds Against Human Leukemic CCRF Sublines

| | CCRF-CEM (Parent Cell Line) | | CCRF-CEM/VBL (MDR Cell Line) (Taxol Resistant)-(1143 fold) (Vinblastine Resistant) | | | CCRF-CEM/VM, (Topo II gene mutated cell line) (Taxol Sensitive) (VP-16 resistant) | | |
|---|---|---|---|---|---|---|---|---|
| COMPOUND | $IC_{50}$ ($\mu M$) (A) | $[IC_{50}$ relative to Epothilone A] | $IC_{50}$ ($\mu M$) (B) | $[IC_{50}$ relative to Epothilone A (B)/(A)] | | $IC_{50}$ ($\mu M$) (C) | $[IC_{50}$ relative to Epothilone A (C)/(A)] | |
| TAXOL | 0.0023 | [0.72] | 2.63 | [109.6] | (1143)[a] | 0.0030 | [0.88] | (1.30)[a] |
| MODEL SYSTEM I | 271.7 | [84906] | 22.38 | [932.5] | (0.082)[b] | 11.59 | [3409] | (0.043)[b] |
| TRIAL ANALOG | 14.23 | [4447] | 6.28 | [261.71] | (0.44)[b] | 43.93 | [12920] | (3.09)[a] |
| DESOXYEPO-THILONE A | 0.022 | [6.9] | 0.012 | [0.5] | (0.55)[b] | 0.013 | [3.82] | (059)[b] |
| EPOTHILONE A | 0.0032 | [1] | 0.024 | [1] | (7.5)[a] | 0.0034 | [1] | (1.06)[a] |

[a](B)/(A) or (C)/(A) ratio >1 indicates fold of resistance when compared with the parent cell line.
[b](B)/(A) or (C)/(A) ratio <1 indicates fold of collateral sensitivity when compared with the parent cell line.

As shown in Table 2, CCRF-CEM is the parent cell line. CCRF-CEM/VBL (MDR cell line) is 1143-fold resistant to taxol. CCRF-CEM/VM (Topo II mutated cell line) only 1.3-fold resistant to taxol.

In terms of relative potency, synthetic Epothilone is roughly the same as natural Epothilone A.

For CCRF-CEM cells, the ordering is:

Taxol=Epothilone A>Desoxy Epothilone A>>Triol Analog>>Model System I

For CCRF-CEM/VBL, the relative potency ordering is:

Desoxy Epothilone A≧Epothilone A>>Taxol>Triol Analog>Model System I

For CCRF-CEM/VM, the relative potency ordering is:

Taxol=Epothilone A>Desoxy Epothilone A>>Model System I>Triol Analog

It is concluded that CCRF-CEM/VM cells are collaterally sensitive to certain epothilone compounds.

TABLE 3

Relative Efficacy of Epothilone Compounds Against
The DC-3F Hamster Lung Cell Growth and Against
DC-3F MDR Sublines Resistant Actinomylin D

| | $IC_{50}$ in $\mu M$ | | |
|---|---|---|---|
| COMPOUNDS | DC-3F | DC-3F/ADH | DC-3F/ADX |
| EPOTHILONE A NATURAL | 0.00368 | 0.01241 | 0.0533 |
| EPOTHILONE A SYNTHETIC | 0.00354 | 0.0132 | 0.070 |
| MODEL SYSTEM I [3] | 9.52 | 3.004 | 0.972 |
| TRIOL ANALOG [2] | 10.32 | 4.60 | 4.814 |
| DESOXY EPOTHILONE [1] | 0.01061 | 0.0198 | 0.042 |
| TAXOL | 0.09469 | 3.205 | 31.98 |
| VINBLASTINE | 0.00265 | 0.0789 | 1.074 |
| VP-16 (Etoposide) | 0.03386 | 0.632 | 12.06 |
| ACTINOMYCIN-D | 0.000058 (0.05816 nm) | 0.0082 | 0.486 |

Concerning Table 3, experiments were carried out using the cell lines DC-3F (parent hamster lung cells), DC-3F/ADII (moderate multidrug-resistant (MDR) cells) and DC-3F/ADX (very strong MDR cells).

The relative potency of the compounds are as follows:

DC-3F: Actinomycin D>Vinblastine≧Epothilone A (0.0036 $\mu M$)>Desoxy epothilone>VP-16>Taxol (0.09 $\mu M$)>Model system I and triol analog DC-3F/ADX: Desoxyepothilone≧Epothilone A (0.06 $\mu M$)>Actinomycin D>Model system I>Vinblastine>triol analog>viablastine>taxol (32.0 $\mu M$)

DC-3F/ADX cells (8379-fold resistant to actinomycin D) are >338 fold (ca. 8379 fold) resistant to Taxol, VP-16, Vinblastine and Actinomycin D but <20 fold resistant to epothilone compounds.

In general, these results are similar to those for CCRF-CEM cells.

TABLE 4

Three Drug Combination Analysis
(Based on the Mutually Exclusive Assumption - Classical Isobologram Method)

Drug A: EPOTHILONE B (#8) ($\mu$M)
Drug B: TAXOL ($\mu$M)
Drug C: VINBLASTINE ($\mu$M)
Conditions: CCRF-CEM, 3 DRUG COMBINATION, RATIO (A:B:C: 1:5:1); EPOTHILONE + TAXOL + VINBLASTINE; EXPOSURE TIME 72 HRS; XTT ASSAY.

| Drug | Combination Index* Values at: | | | | | Parameters | |
|---|---|---|---|---|---|---|---|
| | ED50 | ED75 | ED90 | ED95 | Dm (IC$_{50}$) ($\mu$M) | m | r |
| A | | | | | −00061 | 1.71561 | .98327 |
| B | | | | | −00109 | 2.14723 | .98845 |
| C | | | | | −00061 | 1.76186 | .9919 |
| A + B | 1.51545 | 1.38631 | 1.27199 | 1.20162 | −00146 | 2.41547 | .97168 |
| B + C | 1.43243 | 1.33032 | 1.23834 | 1.18091 | .00138 | 2.35755 | .95695 |
| A + C | .74395 | .68314 | .62734 | .59204 | .00045 | 2.0098 | .96232 |
| A + B + C | 1.37365 | 1.32001 | 1.27285 | 1.24412 | .00122 | 2.11202 | .93639 |

VBL → microtubule depolymerization
Taxol → microtubule polymerization
Epo-B → microtubule polymerization
Epothilone B and Taxol have a similar mechanism of action (polymerization) but Epothilone B synergizes VBL whereas Taxol antagonizes VBL.
Taxol + VBL → Antagonism
EpoB + Taxol → Antagonism
EpoB + VBL → Synergism
EpoB + Taxol + VBL → Antagonism

*Combination index values <1, =1, and >1 indicate synergism, additive effect, and antagonism, respectively.

TABLE 5

Relative cytotoxicity of epothilone compounds in vitro.

| | | | IC$_{50}$ in $\mu$M | | | | | |
|---|---|---|---|---|---|---|---|---|
| Compounds | | CCRF-CEM | | CCRF-CEM/VLB | | | CCRF-CEM/VM-1 | |
| VINBLASTINE | **** | 0.0008 | | 0.44 | | | 0.00049 | |
| | | 0.0006 | (0.00063 ± | 0.221 | (0.332 ± | | 0.00039 | (0.00041 ± |
| | | 0.0005 | 0.00008) | 0.336 | 0.063 | (52.7X)$^{\S}$ | 0.00036 | 0.00004) | (0.7X) |
| VP-16 | | 0.259 | | 6.02 | | | 35.05 | |
| | | 0.323 | (0.293 ± | 9.20 | (10.33 ± | | 42.24 | (34.39 ± |
| | | 0.296 | 0.019) | 15.76 | 2.87) | (35.3X) | 25.89 | 4.73) | (117.4X) |
| TAXOL | *** | 0.0021 | | 4.14 | | | 0.0066 | |
| #17 | * | | 0.090 | | 0.254 | | | |
| #18 | | | 1157.6 | | >>1 | | | |
| #19 | | | 0.959 | | >>1 | | | |
| #20 | * | | 0.030 | | 0.049 | | | |
| #21 | | | — | | — | | | |
| #22 | * | | 0.098 | | 0.146 | | | |
| #23 | | | — | | — | | | |
| #24 | *** | | 0.0078 | | 0.053 | | | |
| #25 | * | | 0.021 | | 0.077 | | | |
| #26 | * | | 0.055 | | 0.197 | | | |
| #27 | **** | | 0.0010 | | 0.0072 | | | |
| Epothilone A (Syn) | *** | | 0.0021 | | 0.015 | | | |
| Epothilone B (Syn) | **** | | 0.00042 | | 0.0017 | | | |

*Number of asterisks denotes relative potency.
$^{\S}$Number in parentheses indicates relative resistance (fold) when compared with parent cell line.

TABLE 6

Relative potency of epothilone compounds in vitro.

| Compounds | | | CCRF-CEM | | | CCRF-CEM/VBL | | | CCRF-CEM/VM-1 | |
|---|---|---|---|---|---|---|---|---|---|---|
| | | | IC$_{50}$ in $\mu$M | | | | | | | |
| Desoxy Epo. A | 1 | * | 0.022 | | | 0.012 | | | 0.013 | |
| | 2 | | 14.23 | | | 6.28 | | | 43.93 | |
| | 3 | | 271.7 | | | 22.38 | | | 11.59 | |
| | 4 | | 2.119 | | | 43.01 | | | 2.76 | |
| | 5 | | >20 | | | 35.19 | | | 98.04 | |
| Trans- A | 6 | | 0.052 | | | 0.035 | | | 0.111 | |
| | 7 | | 7.36 | | | 9.82 | | | 9.65 | |
| Syn-Epo.-B | 8 | **** | 0.00082 | | | 0.0029 | | | 0.0044 | |
| Natural B | 9 | **** | 0.00044 | | | 0.0026 | | | 0.0018 | |
| Desoxy Epo. B | 10 | *** | 0.0095 | | | 0.017 | | | 0.014 | |
| Trans. Epo. B | 11 | * | 0.090 | | | 0.262 | | | 0.094 | |
| | 12 | | 0.794 | | | >5 | | | >5 | |
| | 13 | | 11.53 | | | 5.63 | | | 14.46 | |
| 8-desmethyl desoxy-Epo | 14 | | 5.42 | | | 5.75 | | | 6.29 | |
| 8-desmethyl Mix-cis Epo | 15 | | 0.96 | | | 5.95 | | | 2.55 | |
| 8-desmethyl β-Epo | 15 | | 0.439 | | | 2.47 | | | 0.764 | |
| 8-demethyl α-Epo | 16 | | 7.47 | | | 16.48 | | | 0.976 | |
| EPOTHILONE A (Natural) | | *** | 0.0024 0.0031 | (0.0027 ± 0.0003) | 0.0211 0.0189 | (0.020 ± 0.001) | (7.4X) | 0.006 0.00625 | } | (0.00613 ± 0.0001) (2.3X) | |
| EPOTHILONE B (Natural) | | **** | 0.00017 | | | 0.0017 | (7.0X) | | 0.00077 | |
| EPOTHILONE B (Synthetic) | | | 0.00055 | | | 0.0031 | (0.00213 ± 0.00055) | | 0.0018 | (0.00126 ± 0.0003) |
| EPOTHILONE B (Synthetic, larger quantity synthesis) (25.9 mg) | | | (0.00035 ± 0.0003) 0.00033 | | | 0.0021 | (6.1X) | | 0.0012 | (3.6X) |

TABLE 7

Relative cytotoxicity of epothilone compounds in vitro.

| | IC$_{50}$ | |
|---|---|---|
| | CEM | CEM/VBL |
| epothilone A | 0.0029 $\mu$M | 0.0203 $\mu$M |
| desoxyepothilone | 0.022 | 0.012 |
| 2 | 14.2 | 6.28 |
| 3 | 271.7 | 22.4 |
| 4 | 2.1 | 43.8 |
| 5 | >20 | 35.2 |
| 6 | 0.052 | 0.035 |
| 7 | 7.4 | 9.8 |
| synthetic epothilone B | 0.00082 | 0.00293 |
| natural epothilone B | 0.00044 | 0.00263 |
| desoxyepothilone B | 0.0095 | 0.0169 |
| 11 | 0.090 | 0.262 |
| 12 | 0.794 | >5 |
| 13 | 11.53 | 5.63 |
| 14 | 5.42 | 5.75 |
| 15 | 0.439 | 2.47 |
| 16 | 7.47 | 16.48 |
| 17 | 0.090 | 0.254 |
| 18 | 1157.6 | >>1 |
| 19 | 0.959 | >>1 |
| 20 | 0.030 | 0.049 |
| 21 | Not Available | — |
| 22 | 0.098 | 0.146 |
| 23 | Not Available | — |
| 24 | 0.0078 | 0.053 |
| 25 | 0.0212 | 0.077 |
| 26 | 0.0545 | 0.197 |
| 27 | 0.0010 | 0.0072 |

TABLE 8

Chemotherapeutic Effect of Epothilone B, Taxol & Vinblastine in
CB-17 Scid Mice Bearing Human CCRF-CEM and CCRF-CEM/VBL Xenograft[1]

| Tumor | Drug[2] | Dose | Average weight change | | | | | Average tumor volume | | | |
|---|---|---|---|---|---|---|---|---|---|---|---|
| | | | Day 0 | Day 7 | Day 12 | Day 17 | Day 22 | Day 7 | Day 12 | Day 17 | Day 22 |
| CCRF-CEM | | 0 | 24.4 | +0.2 | +0.4 | +0.1 | +0.5 | 1.0[3] | 1.00 | 1.00 | 1.00 |
| | Epo B | 0.7[4] | 24.7 | −0.1 | −0.7 | −1.4 | +0.3 | 1.0 | 0.53 | 0.48 | 0.46 |
| | | 1.0[5] | 25.0 | +0.1 | −1.5 | −2.4 | +0.1 | 1.0 | 0.46 | 0.35 | 0.43 |
| | Taxol | 2.0 | 25.1 | −0.1 | −1.1 | −1.5 | −0.3 | 1.0 | 0.39 | 0.29 | 0.28 |
| | | 4.0 | 25.1 | −0.2 | −1.7 | −1.9 | −0.3 | 1.0 | 0.37 | 0.23 | 0.19 |
| | VBL | 0.2 | 25.9 | +0.2 | −0.8 | −1.5 | −0.3 | 1.0 | 0.45 | 0.25 | 0.29 |
| | | 0.4 | 25.0 | −0.1 | −1.4 | −1.8 | −0.7 | 1.0 | 0.31 | 0.27 | 0.30 |
| CCRF-CEM/ | | 0 | 26.3 | −0.3 | +0.1 | −0.3 | +0.4 | 1.0 | 1.00 | 1.00 | 1.00 |
| VBL | EpoB | 0.7 | 25.8 | +0.1 | −0.7 | −1.0 | −0.2 | 1.0 | 0.32 | 0.40 | 0.33 |
| | | 1.0[6] | 26.0 | −0.2 | −1.3 | −2.1 | −0.5 | 1.0 | 0.41 | 0.27 | 0.31 |
| | Taxol | 2.0 | 26.1 | 0 | −0.9 | −1.5 | −0.1 | 1.0 | 0.60 | 0.58 | 0.70 |
| | | 4.0 | 26.0 | 0 | −1.4 | −1.6 | −0.9 | 1.0 | 0.79 | 0.55 | 0.41 |
| | VBL | 0.2 | 25.9 | −0.3 | −0.8 | −1.4 | −0.3 | 1.0 | 0.86 | 0.66 | 0.67 |
| | | 0.4 | 25.9 | 0 | −1.2 | −1.8 | −0.5 | 1.0 | 1.02 | 0.57 | 0.62 |

[1]CCRF-CEM and CCRF-CEM/VBL tumor tissue 50 ul/mouse implanted S.C. on day 0, Treatments i.p., QD on day 7, 8, 9, 10, 14 and 15. There were seven CB-17 scid male mice in each dose group and control.
[2]Epo B, epothilone B; VBL, vinblastine.
[3]The tumor volumes for each group on day 7 was about 1 mm$^3$. The average volumes of CCRF-CEM control group on day 12, 17 and 22 were 19, 76 and 171 mm$^3$, and of CCRF-CEM/VBL control group were 35, 107 and 278 mm$^3$, respectively.
[4]Two mice died of drug toxicity on day 19 & 20.
[5]Three mice died of drug toxicity on day 18, 19 and 21.
[6]One mouse died of drug toxicity on day 17.

In summary, epothilones and taxol have similar modes of action by stabilizing polymerization of microtubules. However, epothilones and taxol have distinct novel chemical structures.

MDR cells are 1500-fold more resistant to taxol (CCRF-CEM/VBL cells), epothilone A showed only 8-fold resistance and epothilone B showed only 5-fold resistance. For CCRF-CEM cells, Epo B is 6-fold more potent than Epo A and 10-fold more potent than Taxol. Desoxyepothilone B and compd #24 are only 3–4-fold less potent than Taxol and compound #27 is >2-fold more potent than Taxol. Finally, Taxol and vinblastine showed antagonism against CCRF-CEM tumor cells, whereas the combination of Epo B+vinblastine showed synergism.

Relative Cytotoxicity of Epothilones against Human Leukemic Cells in Vitro is in the order as follows:
CCRF-CEM Leukemic Cells
Epo B ($IC_{50}$=0.00035 µM; Rel. Value=1)>VBL (0.00063;1/1.8)>#27(0.0010;1/2.9)>Taxol (0.0021; 1/6) >Epo A (0.0027; 1/7.7)>#24(0.0078; 1/22.3)>#10 (0.0095; 1/27.1)>#25 (0.021; 1/60)>#1 (0.022; 1/62.8)>#20 (0.030; 1/85.7)>#6 (0.052; 1/149)>#26 0.055; 1/157)>#17 (0.090; 1/257)>VP-16 (0.29; 1/8.29)>#15 (0.44; 1/1257)>#(0.96; 1/2943)
CCRF-CEM/VBL MDR Leukemic Cells
Epo B (0.0021; 1/6* [1]**)>#27 (0.0072; 1/20.6)>#1 (0.012; 1/34.3)>#10 (0.017; 1/48.6)>Epo A (0.020; 1/57.1 [1/9.5])>#6 (0.035)>#20 (0.049)>#24 (0.053)×#25 (0.077) >#22 (0.146)>#26 (0.197)>#17 (0.254)>#11 (0.262)>VBL (0.332; 1/948.6 [1/158.1])>Taxol (4.14; 1/11828 [1/1971.4]) >VP-16 (10.33; 1/29514 [1/4919]) *Potency in parentheses is relative to Epo B in CCRF-CEM cells. **Potency in square brackets is relative to Epo B in CCRF-CEM/VBL MDR cells.

Figure 46:
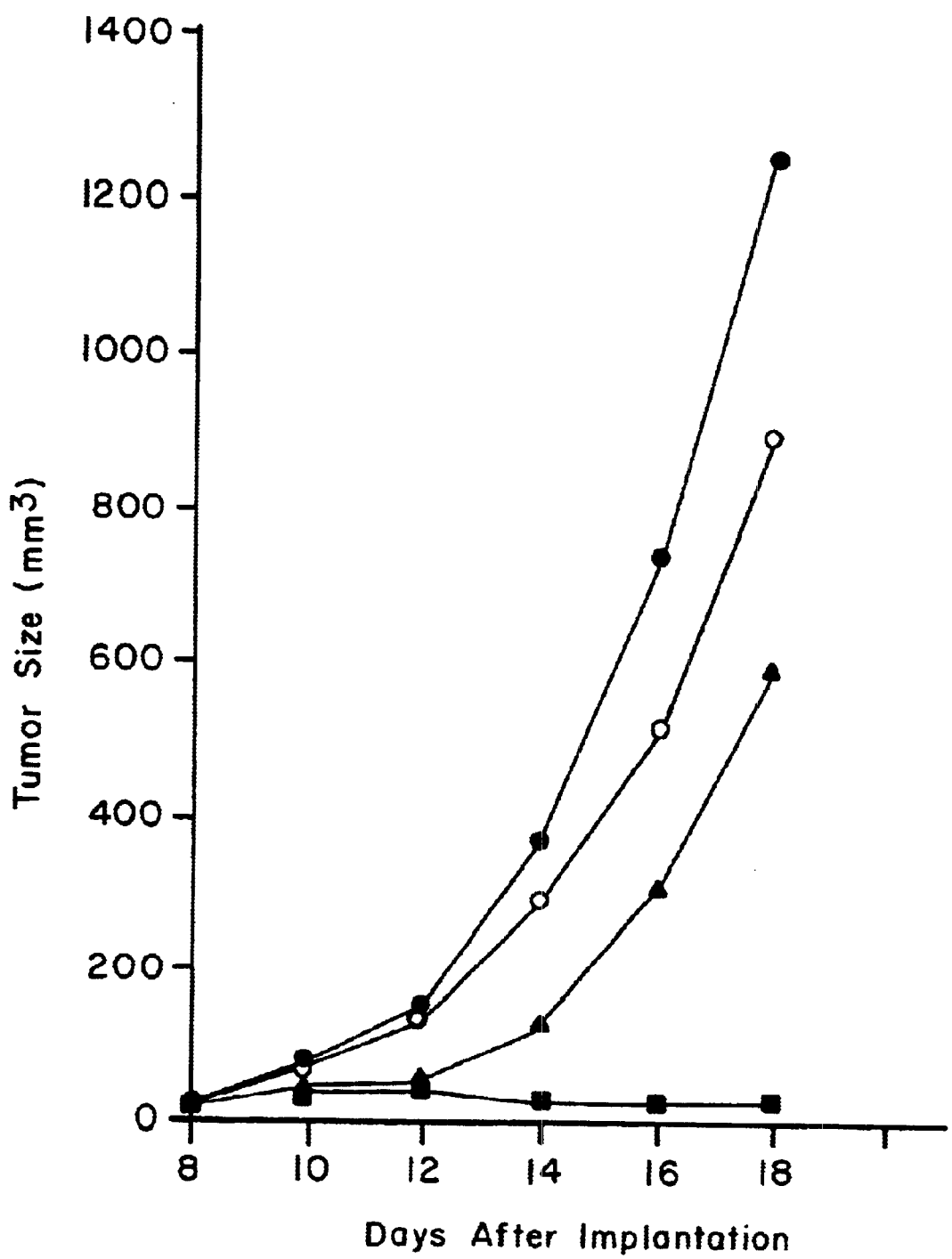
FIG. 46 shows the effect of treatment with desoxyepothilone B (35 mg/kg), taxol (5 mg/kg) and adriamycin (2 mg/kg) of nude mice bearing human MX-1 xenograft on tumor size between 8 and 18 days after implantation. Desoxyepothilone B (■), taxol (Δ), adriamycin (X), control (♦); i.p. treatments were given on day 8, 10, 12, 14 and 16.

As shown in Table 9, treatment of MX-1 xenograft-bearing nude mice with desoxyepothilone B (35 mg/kg, 0/10 lethality), taxol (5 mg/kg, 2/10 lethality; 10 mg/kg, 2/6 lethality) and adriamycin (2 mg/kg, 1/10 lethality; 3 mg/kg, 4/6 lethality) every other day, i.p. beginning day 8 for 5 doses resulted in a far better therapeutic effect for desoxyepothilone B at 35 mg/kg than for taxol at 5 mg/kg and adrimycin at 2 mg/kg with tumor volume reduction of 98%, 53% and 28%, respectively. For the desoxyepothilone B-treated group, 3 out of 10 mice were found with tumor non-detectable on day 18. (See FIG. 46)

Extended treatment with desoxyepothilone B (40 mg/kg, i.p.) beginning day 18 every other day for 5 more doses resulted in 5 out of 10 mice with tumor disappearing on day 28 (or day 31). See Table 10. By contrast, the extended treatment with taxol at 5 mg/kg for five more doses resulted in continued tumor growth at a moderate rate, and 2 out of 10 mice died of toxicity.

Figure 47:
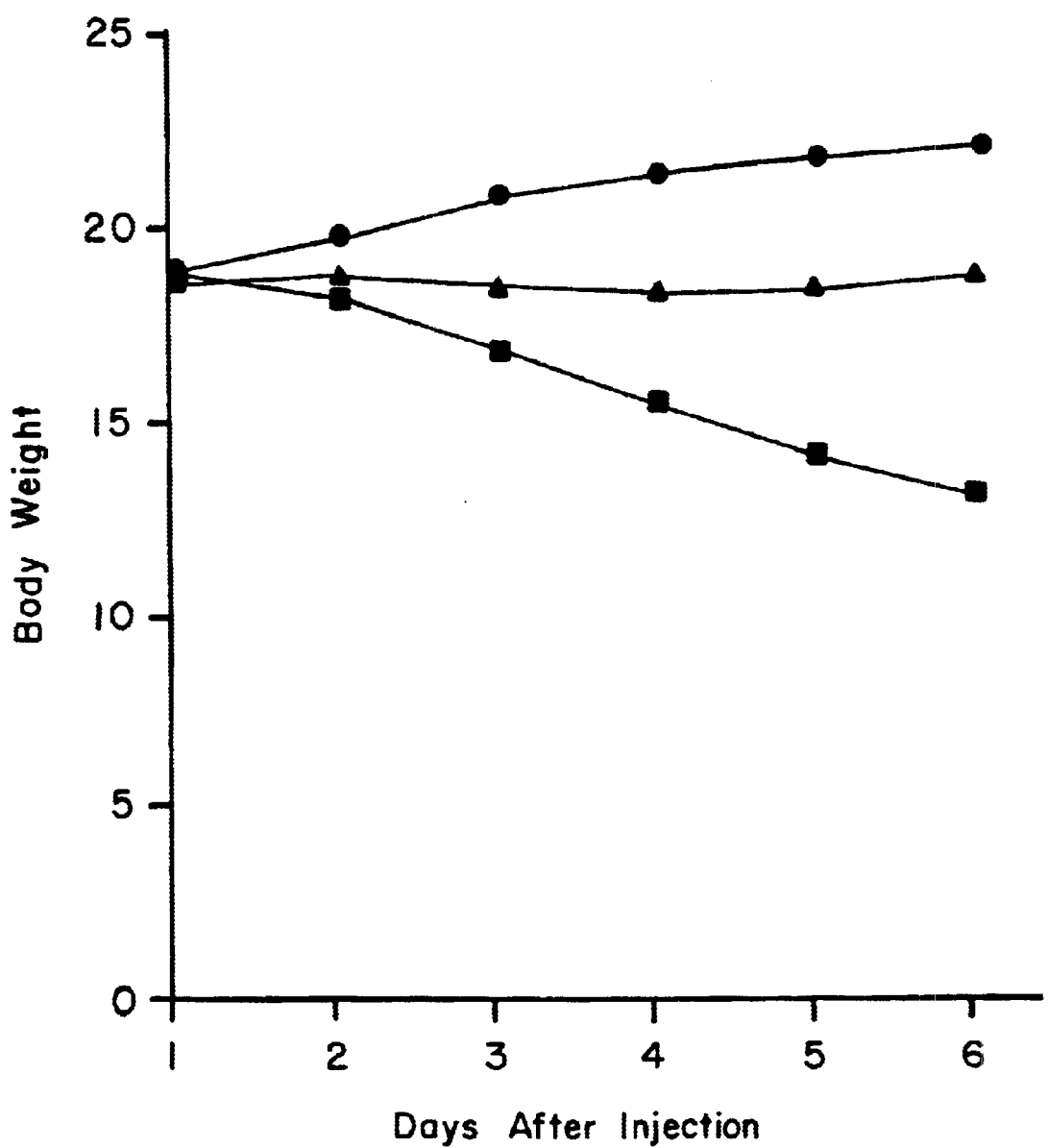
FIG. 47 shows the relative toxicity of epothilone B (□; 0.6 mg/kg QDx4; i.p.) and desoxyepothilone B (Δ; 25 mg/kg QDx4; i.p.) versus control (♦) in normal nude mice. Body weight of mice was determined daily after injection. For epothilone B, 8 of 8 mice died of toxicity on days 5, 6, 6, 7, 7, 7, 7, and 7; for desoxyepothilone B, all six mice survived.
Figure 48:
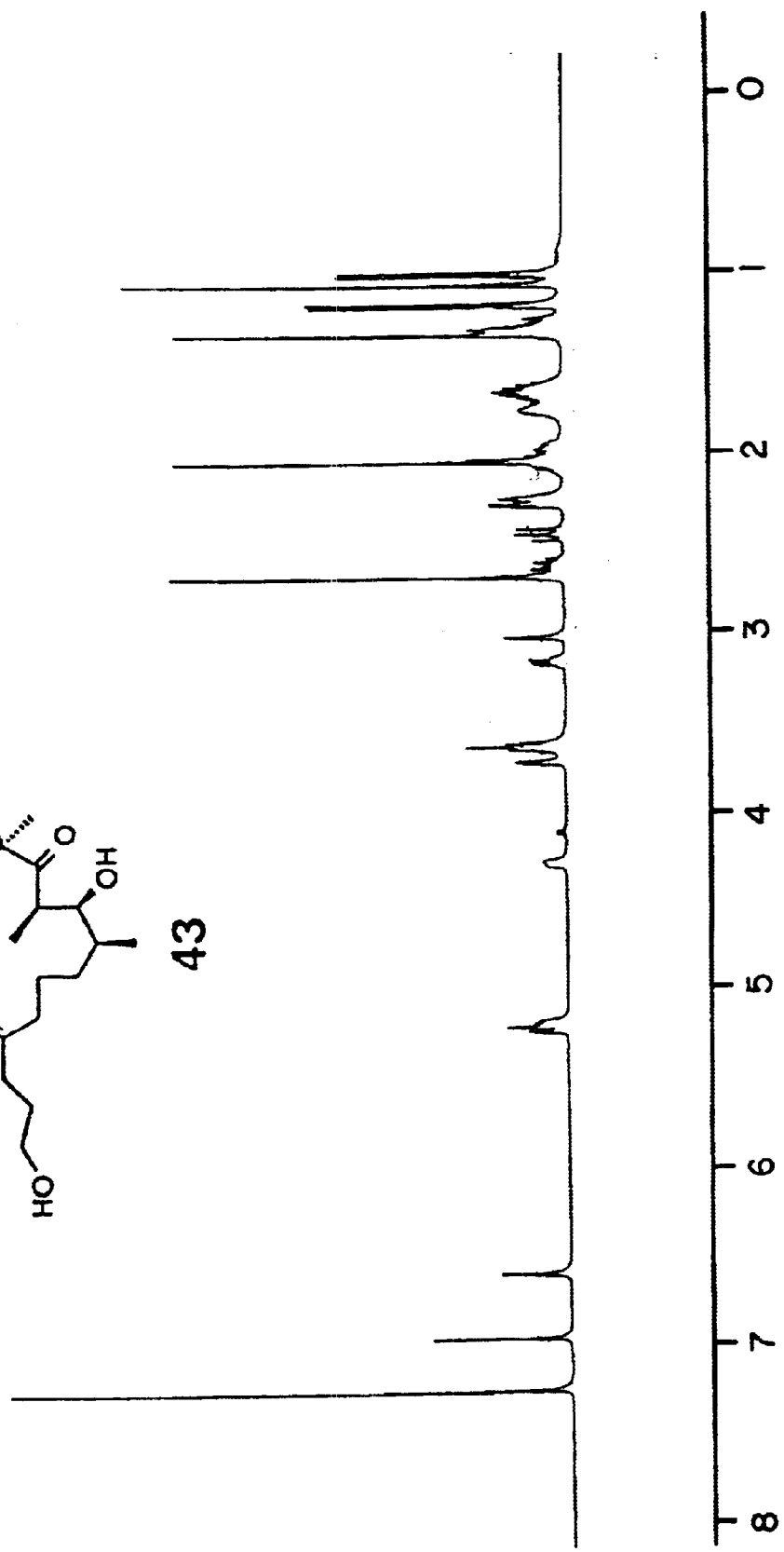
FIG. 48 shows a high resolution $^1$H NMR spectrum of epothilone analogue #43.
Figure 49:
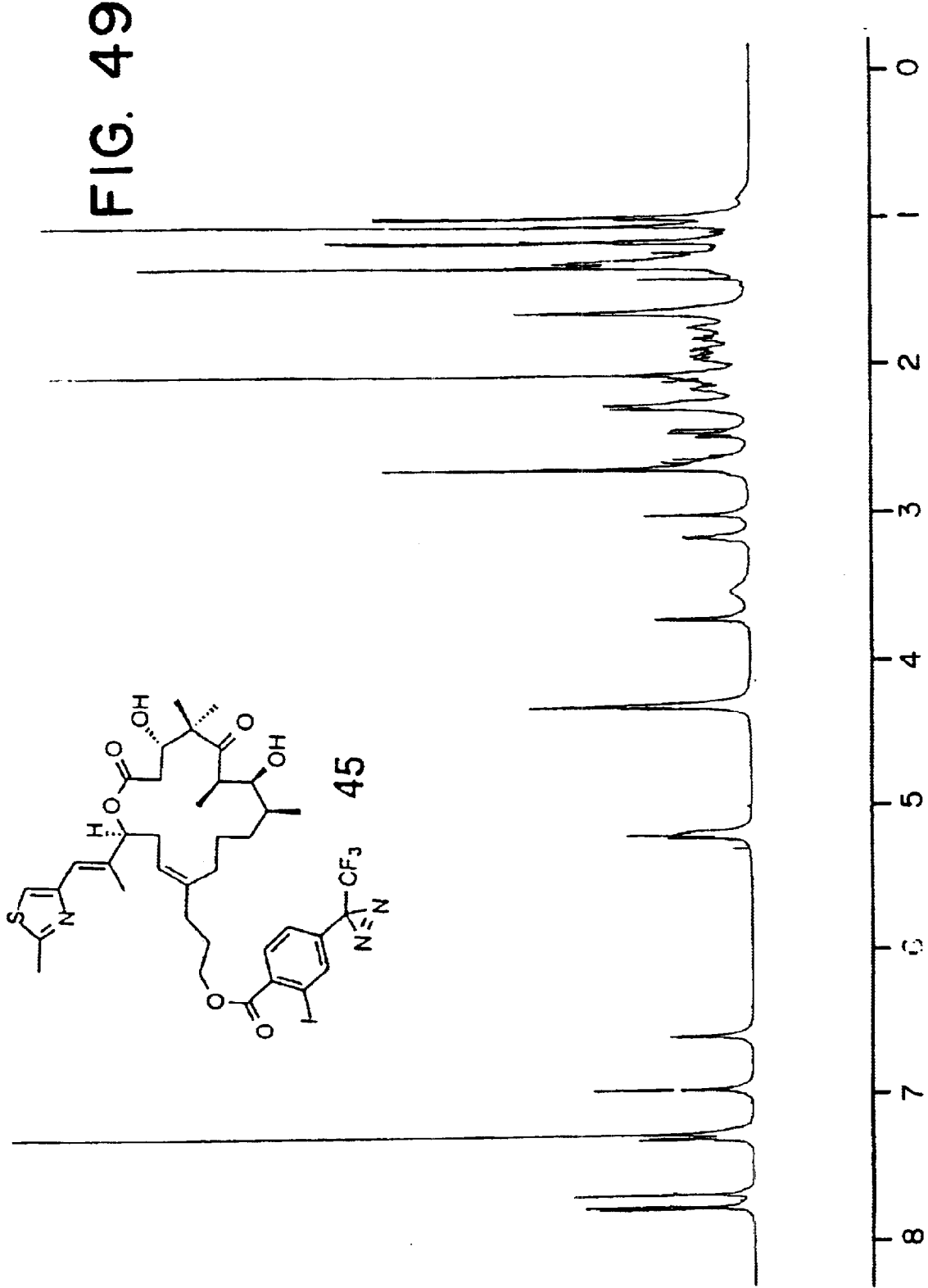
FIG. 49 shows a high resolution $^1$H NMR spectrum of epothilone analogue #45.
Figure 50:
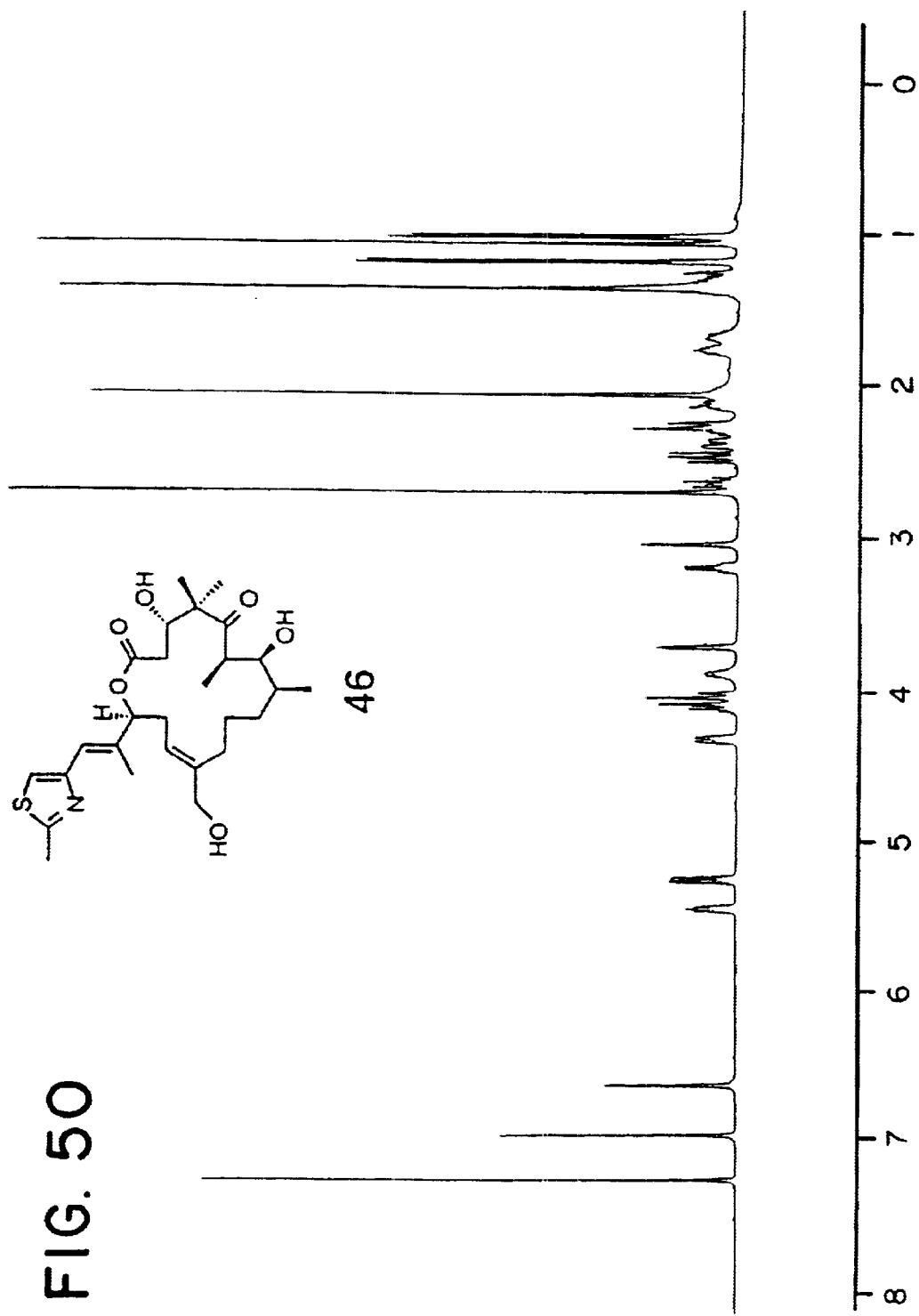
FIG. 50 shows a high resolution $^1$H NMR spectrum of epothilone analogue #46.
Figure 51:
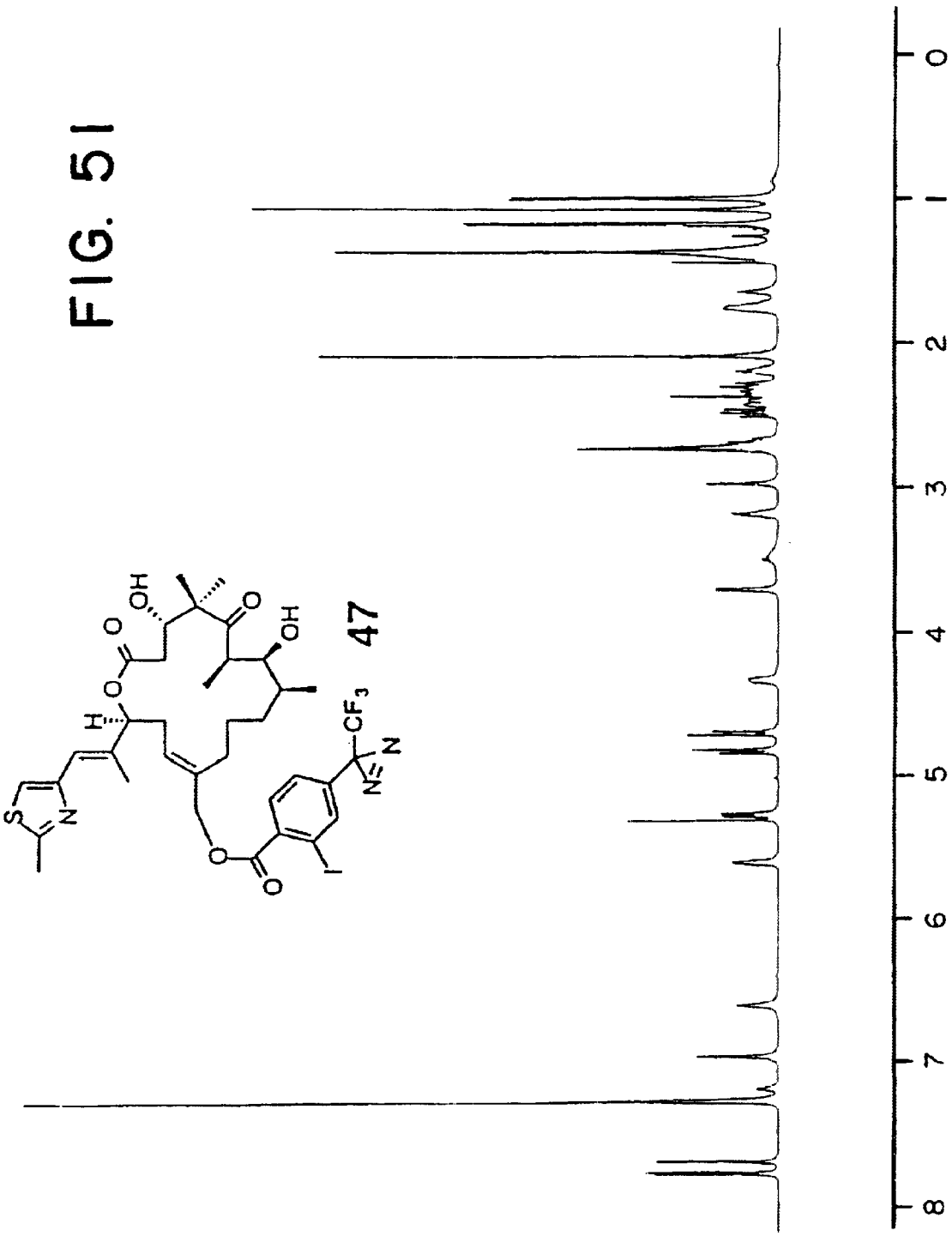
FIG. 51 shows a high resolution $^1$H NMR spectrum of epothilone analogue #47.
Figure 52:
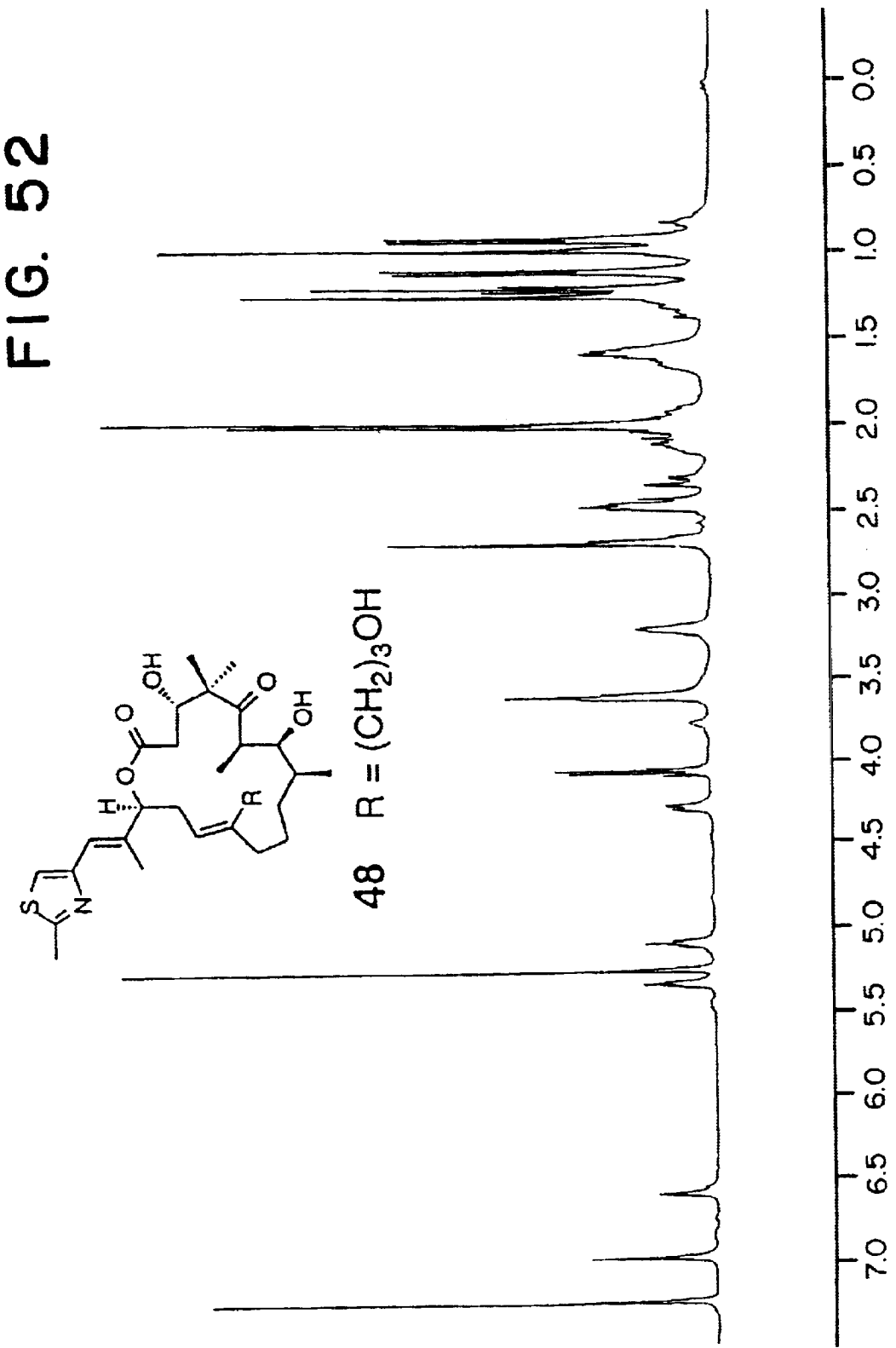
FIG. 52 shows a high resolution $^1$H NMR spectrum of epothilone analogue #48.

Toxicity studies with daily i.p. doses of desoxyepothilone B (25 mg/kg, a very effective therapeutic dose as indicated in earlier experiments) for 4 days to six mice resulted in no reduction in average body weight. (Table 13; FIG. 47) By contrast, epothilone B (0.6 mg/kg, i.p.) for 4 days to eight mice resulted in 33% reduction in average body weight; all eight mice died of toxicity between day 5 and day 7.

TABLE 9

Therapeutic Effect of Desoxyepothilone B, Taxol, and Adriamycin in Nude Mice Bearing Human MX-1 Xenograft[a]

| Drug | Dose (mg/kg) | Average Body Weight Change (g) | | | | | | Average Tumor Volume (T/C) | | | | | Died | Tumor Disappearance |
|---|---|---|---|---|---|---|---|---|---|---|---|---|---|---|
| | | Day 8 | 10 | 12 | 14 | 16 | 18 | Day 10 | 12 | 14 | 16 | 18 | | |
| Control | 0 | 24.6 | −0.1 | +1.0 | +1.0 | +1.3 | +1.8 | 1.00 | 1.00 | 1.00 | 1.00 | 1.00 | 0/10 | 0/10 |
| Desoxyepothilone B | 35 | 23.0 | −0.1 | +0.7 | −0.3 | −1.7 | −1.6 | 0.42 | 0.28 | 0.07 | 0.04 | 0.02 | 0/10 | 3/10 |
| Taxol | 5 | 24.0 | −1.3 | −0.8 | −1.4 | −1.9 | −1.8 | 0.58 | 0.36 | 0.34 | 0.42 | 0.47 | 2/10 | 0/10 |
| | 10 | 24.3 | −1.0 | −1.0 | −2.3 | −3.5 | −3.8 | 0.85 | 0.40 | 0.21 | 0.20 | 0.12 | 2/6 | 1/6 |
| Adriamycin | 2[b] | 23.9 | +0.3 | 0 | −1.4 | −1.9 | −2.0 | 0.94 | 0.88 | 1.05 | 0.69 | 0.72 | 1/10 | 0/10 |
| | 3[c] | 22.4 | +1.3 | −0.2 | −1.5 | −2.1 | −2.3 | 0.72 | 0.54 | 0.56 | 0.51 | 0.36 | 4/6 | 0/6 |

[a]MX-1 tissue 100 μl/mouse was implanted s.c on day 0. Every other day i.p. treatments were given on day 8, 10, 12, 14 and 16. The average tumor volume of control group on day 10, 12, 14, 16 and 18 were 78, 151, 372, 739 and 1257 mm$^3$, respectively.
[b]One mouse died of toxicity on day 22.
[c]Four mice died of toxicity on day 24.

TABLE 10

Extended Experiment of Desoxyepothilone B, Taxol, Cisplatin and Cyclophophamide in Nude Mice Bearing Human MX-1 Xenograft[a]

| Drug | Dose (mg/kg) | Average Body Weight Change (g) | | | | | | Tumor Disappearance | | | | | Average Tumor Disappearance Duration (Day) | # Died |
|---|---|---|---|---|---|---|---|---|---|---|---|---|---|---|
| | | Day 8 | 20 | 22 | 24 | 26 | 28 | Day 20 | 22 | 24 | 26 | 28 | | |
| Desoxyepo B | 40 | 23.0 | −1.7 | −2.4 | −2.4 | −1.4 | −1.2 | 2/10[b] | 2/10 | 3/10 | 5/10 | 5/10 | 44(5/10) | 0/10 |
| Taxol | 5 | 24.0 | −1.6 | −0.3 | +0.1 | −0.6 | −0.4 | 0/10 | 0/10 | 0/10 | 0/10 | 0/10 | | 2/10 |
| | 10 | No extended test | | | | | | 1/6 on day 16 | | | | | Reappear on day 38 | 2/6 |

[a]Extended experiment was carried out after 5 times injection (on day 8, 10, 12, 14 and 16). Every other day i.p. treatments were given continuously: Desoxyepothilone B and Taxol on day 18, 20, 22, 24 and 26; control group mice were sacrificed.
[b]One of the mice tumor reappeared on day 20.

TABLE 11

Toxicity of Epothilone B and Desoxyepothilone B in normal nude mice.

| Group | Dose and Schedule (mg/kg) | Number of mice | Died | Disappearance | Duration |
|---|---|---|---|---|---|
| Control | | 4 | 0 | | |
| Epothilone B[a] | 0.6 QD × 4 | 8 | 8 | | |
| Desoxyepothilone B | 25 QD × 4 | 6 | 0 | | |

[a]Mice died of toxicity on day 5, 6, 6, 7, 7, 7, 7, 7

TABLE 12

Therapeutic Effect of Epothilone B, Desoxyepothilone B and Taxol in B6D2F$_1$ Mice Bearing B16 Melanoma[a]

| Drug | Dose (mg/kg) | Average Weight Change (g) | | | | | | Average Tumor Volume (T/C) | | | | # Mice Died |
|---|---|---|---|---|---|---|---|---|---|---|---|---|
| | | Day 0 | 3 | 5 | 7 | 9 | 11 | Day 5 | 7 | 9 | 11 | |
| Control | 0 | 26.5 | −0.2 | 0 | −0.2 | 0 | +1.0 | 1.00 | 1.00 | 1.00 | 1.00 | 0/15 |
| Epothilone B | 0.4 QD × 6[b] | 27.1 | −0.2 | −0.6 | −1.1 | −3.4 | −3.9 | 1.08 | 1.07 | 1.27 | 1.07 | 1/8 |
| | 0.8 QD × 5[c] | 27.0 | 0 | −0.8 | −3.1 | −4.7 | −4.7 | 0.57 | 0.89 | 0.46 | 0.21 | 5/8 |
| Desoxyepothilone B | 10 QD × 8 | 27.0 | −0.7 | −0.9 | −1.1 | −1.5 | −0.3 | 0.23 | 0.22 | 0.51 | 0.28 | 0/6 |
| | 20 QD1-4,7-8 | 26.9 | −1.3 | −2.2 | −1.3 | −1.6 | −0.8 | 0.59 | 0.63 | 0.58 | 0.33 | 0/6 |
| Taxol | 4 QD × 8 | 26.7 | +0.1 | +0.2 | +0.3 | +0.4 | +0.8 | 0.62 | 0.39 | 0.56 | 0.51 | 0/8 |
| | 6.5 QD × 8 | 26.7 | +0.1 | +0.3 | +0.3 | +0.4 | +1.7 | 0.19 | 0.43 | 0.20 | 054 | 0/8 |

Figure 44A:
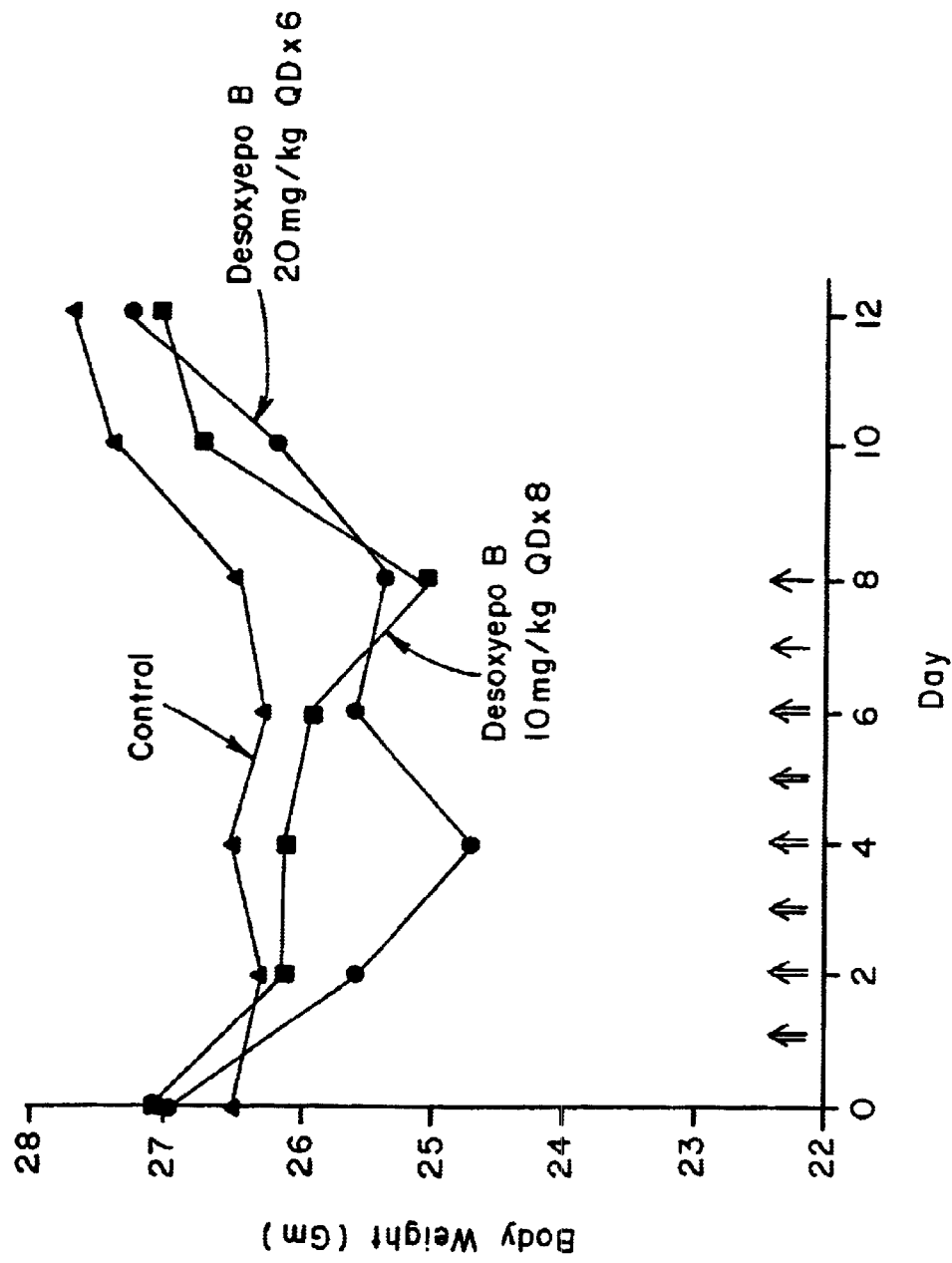
FIG. 44(A) shows toxicity of desoxyepothilone B in B6D2F, mice bearing B16 melanoma. Body weight was determined at 0, 2, 4, 6, 8, 10 and 12 days. Control (▲); desoxyepothilone B (○; 10 mg/kg QDx8; 0 of 8 died); desoxyepothilone B (●; 20 mg/kg QDx6; 0 of 8 died). Injections were started on day 1.
Figure 44B:
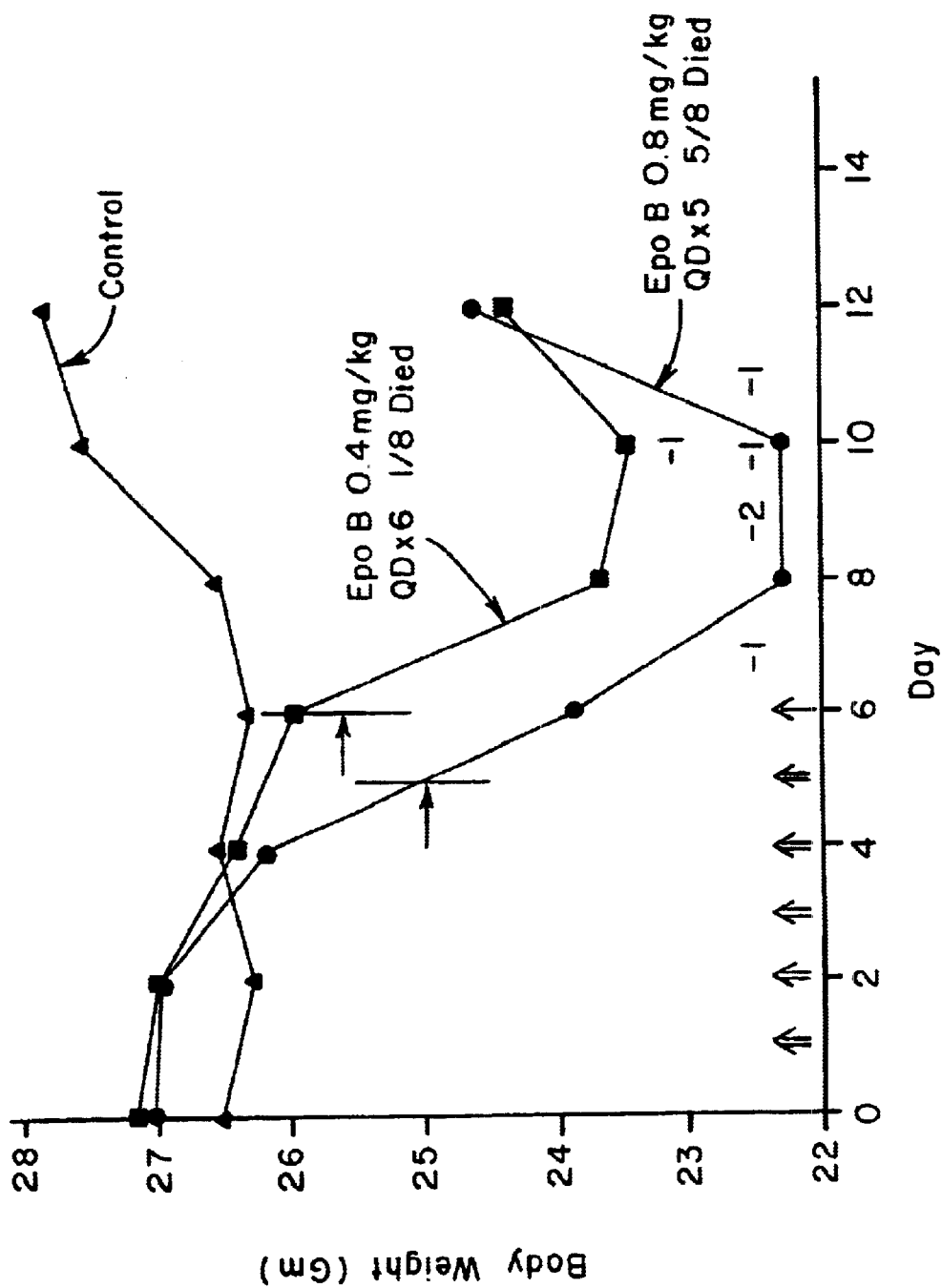
FIG. 44(B) shows toxicity of epothilone B in B6D2F, mice bearing B16 melanoma. Body weight was determined at 0, 2, 4, 6, 8, 10 and 12 days. Control (▲); epothilone B (○; 0.4 mg/kg QDx6; 1 of 8 died of toxicity); epothilone B (●; 0.8 mg/kg QDx5; 5 of 8 died). Injections were started on day 1.

[a]B16 melanoma cells 1.2 × 10$^6$/mouse was implanted S.C. on day 0. Daily treatments start on day 1 after inoculation. Number of mice in each group: Control, 15; Epothilone B, 8; Desoxythilone B, 5 and Taxol, 8. The average tumor volume of control group on day 5, 7, 9 and 11 were 16, 138, 436 and 1207 mm$^3$, respectively. See FIGS. 44(a) and (b).
[b]One mouse died of toxicity on day 10.
[c]Five mice died of toxicity on day 8, 10, 10, 11, 12. One moribund mouse was sacrificed for toxicological examinations on day 11.

TABLE 13

Therapeutic Effect of Desoxyepothilone B,
Epothilone B, Taxol and Vinblastine in Nude Mice Bearing Human MX-1 Xenograft[a]

| Drug | Dose (mg/kg) | Average Body Weight Change (g) | | | | | Average Tumor Volume (T/C) | | | | Note |
|---|---|---|---|---|---|---|---|---|---|---|---|
| | | Day 7 | 11 | 13 | 15 | 17 | Day 11 | 13 | 15 | 17 | |
| Control | | 27.9 | +0.8 | +1.1 | +1.9 | +0.6 | 1.00 | 1.00 | 1.00 | 1.00 | 0/8 died |
| Desoxyepothilone B | 15 | 27.1 | +0.8 | +1.1 | +1.6 | +1.5 | 0.65 | 0.46 | 0.49 | 0.41 | 0/6 died |
| | 25[b] | 27.0 | +0.4 | +0.7 | +1.0 | +0.7 | 0.38 | 0.11 | 0.05 | 0.04 | 0/6 died (1/6 cured on day 35) |
| Epothilone B | 0.3 | 26.9 | +0.5 | +0.4 | −0.3 | −1.2 | 1.00 | 0.71 | 0.71 | 0.84 | 0/7 died |
| | 0.6[c] | 27.4 | −0.3 | −1.3 | −2.1 | −2.1 | 1.08 | 0.73 | 0.81 | 0.74 | 3/7 died |
| Taxol | 5 | 26.9 | −0.1 | +0.4 | +1.1 | +1.2 | 0.54 | 0.46 | 0.40 | 0.45 | 0/7 died |
| | 10[d] | 27.6 | −2.7 | −1.1 | −0.3 | +2.2 | 0.43 | 0.37 | 0.12 | 0.11 | 4/7 died |
| Vinblastine | 0.2 | 25.7 | +0.6 | +1.4 | +2.3 | +2.9 | 0.65 | 0.54 | 0.56 | 0.88 | 0/7 died |
| | 0.4[e] | 26.4 | +0.8 | +0.5 | +1.9 | +2.1 | 0.80 | 0.56 | 0.83 | 0.88 | 1/7 died |

Figure 45A:
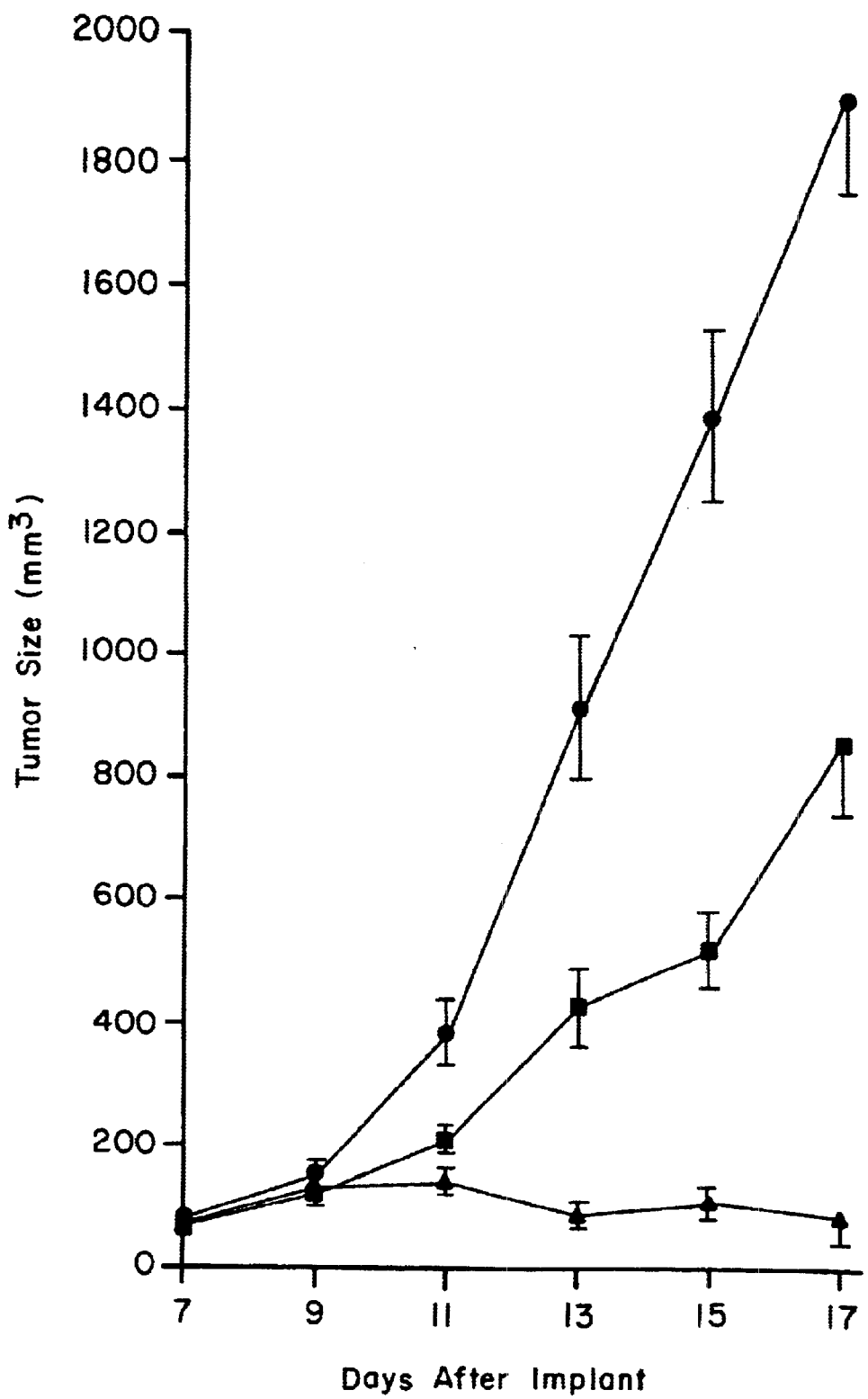
FIG. 45(A) shows comparative therapeutic effect of desoxyepothilone B and taxol on nude mice bearing MX-1 xenoplant. Tumor, s.c.; drug administered i.p., Q2Dx5, start on day 7. control (♦); Taxol (□; 5 mglkg, one half of LD$_{50}$); desoxyepothilone B (Δ; 25 mg/kg; nontoxic dose).

[a]MX-1 tissue 50 μl/mouse was implanted s.c. on day 0. Every other day i.p. treatments were given on day 7, 9, 11, 13 and 15. Number of mice in each group: Control, 8; Desoxyepothilone B, 6; Epothilone B, 7; Taxol, 7 and Vinblastine, 7. The average tumor volume of control group on day 11, 13, 15 and 17 were 386, 915, 1390 and 1903 mm³, respectively See FIG. 45.
[b]One out of six mice with no detectable tumor on day 35.
[c]Three mice died of drug toxicity on day 17. Every other day i.p. treatments were given except day 15.
[d]Four mice died of drug toxicity on day 13, 13, 13, 15.
[e]One mouse died of drug toxicity on day 15.

TABLE 14

Toxicity of Hematology and
Chemistry of Desoxyepothilone B, and Taxol in Nude Mice Bearing Human MX-1 Xenograft[a]

| Drug | Dose (mg/kg ip) | Hematology[b] | | | | | Chemistry[b] | |
|---|---|---|---|---|---|---|---|---|
| | | WBC | | | RBC (10³/mm³) | PLT (10⁶/mm³) | GOT (U/L) | GPT (U/L) |
| | | Total (10³/mm³) | Neutrophils (%) | Lymph (%) | | | | |
| Control | | 12.9 | 38 | 61 | 8.1 | 800 (n = 4) | 203 | 45 (n = 4) |
| Desoxyepo-thilone B | 25 and 35[c] | 11.8 | 48 | 48 | 8.4 | 700 (n = 6) | 296 | 55 (n = 3) |
| Taxol | 5 and 6[d] | 10.9 | 51 | 48 | 6.1 | 1083 (n = 5) | 438 | 79 (n = 5) |
| Normal range[e] | | 6.91~12.9 | 8.25~40.8 | 62~90 | 10.2~12.0 | 190~340 | 260 | 138.7 |

[a]Minced MX-1 tumor tissue 50 μl/mouse was implanted s.c. on day 0.
[b]All assays were determined on day 30; averaged values were given.
[c]Desoxyepothilone B 25 mg/kg was given i.p on day 7, 9, 11, 13, 15; 35 mg/kg on day 17, 19, 23, 24, 25.
[d]Taxol 5 mg/kg was given i.p. on day 7, 9, 11, 13, 15; 6 mg/kg on day 17, 19, 23, 24, 25.
[e]Normal ranges are for wild type deer mice and C₃/Hej mice (obtained from clinical, biochemical and hematological Reference values in Normal Experimental Animals, Brtjm Mitruka, ed., Masson Publishing USA, Inc., N.Y., 1977, and from Clinical Chemistry of Laboratory Animals, Weter F. Loeb, ed., Pergamon Press, 1989)

TABLE 15

Therapeutic Effect of Desoxyepothilone B, Taxol, Adriamycin, and Camptothecin in Nude Mice Bearing MDR Human MCF-7/Adr Tumor.

| Drug | Dose (mg/kg) | Average Body Weight Change (g) | | | | | Average Tumor Volume (T/C) | | | | Died |
|---|---|---|---|---|---|---|---|---|---|---|---|
| | | Day 8 | 11 | 13 | 15 | 17 | Day 11 | 13 | 15 | 17 | |
| Control | 0 | 25.0 | +2.0 | +2.6 | +3.1 | +3.7 | 1.00 | 1.00 | 1.00 | 1.00 | 0/8 |
| DesoxyEpoB | 35 | 25.0 | +0.3 | +0.7 | +0.6 | +0.8 | 0.31 | 0.27 | 0.30 | 0.34 | 0/8 |
| Taxol | 6 | 25.3 | +1.7 | +1.8 | +0.8 | +0.9 | 0.57 | 0.66 | 0.85 | 0.90 | 0/8 |
| | 12 | 24.5 | +0.7 | −1.3 | −2.4 | 0 | 0.50 | 0.51 | 0.32 | 0.40 | 3/6 |
| Adriamycin | 1.8 | 25.6 | +0.2 | −0.4 | −0.6 | −0.4 | 0.70 | 0.68 | 0.84 | 0.78 | 0/8 |
| | 3 | 24.6 | +0.5 | −1.5 | −3.2 | −1.6 | 0.66 | 0.83 | 0.57 | 0.53 | 3/6 |
| Camptothecin | 1.5 | 24.4 | +1.1 | +0.9 | +1.7 | +1.4 | 1.08 | 0.72 | 0.61 | 0.72 | 0/8 |
| | 3.0 | 24.5 | −0.6 | −0.4 | −0.8 | −0.9 | 0.95 | 0.76 | 0.61 | 0.43 | 0/6 |

MCF-7/Adr cell 3 × 10⁶/mouse was implanted s.c. on day 0. Every other day i.p. treatments were given on day 8, 10, 12, 14 and 16.
The average tumor volume of control group on day 11, 13, 15 and 17 were 392, 919, 1499 and 2372 mm³, respectively.

As evident from Table 15, desoxyepothilone B performs significantly better than taxol, vinblastine, adriamycin and camptothecin against MDR tumor xenografts (human mammary adeoncarcinoma MCF-7/Adr xenografts). This drug-resistant tumor grows very aggressively and is refractory to taxol and adriamycin at half their lethal doses. Taxol at 6 mg/kg i.p. Q2Dx5 reduced tumor size only 10% while adriamycin resulted in only a 22% reduction on day 17. Whereas, desoxyepothilone B at 35 mg/kg reduced tumor size by 66% on day 17 and yet showed no reduction in body weight or apparent toxicity. Even at the $LD_{50}$ dosage for taxol (12 mg/kg) or adriamycin (3 mg/kg), desoxyepothilone B still performed more effectively. By comparison, camptothecin at 1.5 and 3.0 mg/kg reduced tumor size by 28% and 57%, respectively. Overall, in comparison with the four important anticancer drugs in current use, i.e., taxol, adriamycin, vinblastine and camptothecin, desoxyepothilone B showed superior chemotherapeutic effect against MDR xenografts.

TABLE 16

Extended Experiment of Desoxyepothilone B, Taxol in Nude Mice Bearing Human MX-1 Xenograft[a]

| Drug | Dose (mg/kg) | Average Body Weight Change (g) | | | | | | Tumor Disappearance | | | | | Average Tumor Disappear Duration (Day) | Died |
|---|---|---|---|---|---|---|---|---|---|---|---|---|---|---|
| | | Day 8 | 20 | 22 | 24 | 26 | 28 | Day 20 | 22 | 24 | 26 | 28 | | |
| Desoxyepo B | 40 | 23.0 | −1.7 | −2.4 | −2.4 | −1.4 | −1.2 | 2.10[b] | 2/10 | 3/10 | 5/10 | 5/10 | 44$_{(5/10)}$ | 0/10 |
| Taxol | 5 | 24.0 | −1.6 | −0.3 | +0.1 | −0.6 | −0.4 | 0/10 | 0/10 | 0/10 | 0/10 | 0/10 | | 2/10 |
| | 10 | No Extended Test | | | | | | 1/6 on day 16, | | | | | Reappear on day 38 | 2/6$_{(0/6)}$ |

[a]Extended experiment was going on after 5 times injection (on day 8, 10, 12, 14 and 16). Every other day i.p. treatments were given continuously: Desoxyepothilone B and Taxol on day 18, 20, 22, 24 and 26; Control group mice were sacrificed.
[b]In one of the mice, a tumor reappeared on day 20.

As evident form Table 16, extended treatment of nude mice bearing human MX-1 xenographs were desoxyepothilone B results in complete tumor disappearance, with no mortality in any test animals. In conclusion, treatment with desoxyepothilone B shows remarkable specificity with respect to tumor toxicity, but very low normal cell toxicity.

TABLE 17

Therapeutic Effects of Desoxyepothilone B, Taxol in Nude Mice Bearing MX-1 Xenograft.

| | Treatment Schedule | | | | | | | | | | | | | | # Died of toxicity |
|---|---|---|---|---|---|---|---|---|---|---|---|---|---|---|---|---|
| CONTROL | | | | | | | | | | | | | | | | 0/10 |
| Day | 8 | 10 | 12 | 14 | 16 | 18 | 20 | | | | | | | | | |
| Tumor Size (mm³) | 19 ± 2 | 78 ± 8 | 151 ± 15 | 372 ± 55 | 739 ± 123 | 1257 ± 184 | 1991 ± 331 | Sacrificed (n = 10) | | | | | | | | |
| DESOXYEPOTHILONE B | | | | | | | | | | | | | | | | 0/10 |
| Dose Schedule | 35 mg/kg on day | | | | 40 mg/kg on day | | | | No Treatment | | | | | | |
| Day | 8 | 10 | 12 | 14 | 16 | 18 | 20 | 22 | 24 | 26 | 28 | 30 | 45 | 47 | 50 | 60 |
| Tumor Size | | | | | | | | | | | | | | | | |
| Mouse 1 | 15 | 15 | 40 | 40 | 15 | 32 | 30 | 30 | 30 | 30 | 0 | 0 | 0 | 24 | S* | — |
| Mouse 2 | 23 | 23 | 15 | 15 | 15 | 15 | 30 | 48 | 48 | 0 | 30 | 48 | 900 | 1200 | S | — |
| Mouse 3 | 15 | 60 | 90 | 105 | 105 | 126 | 96 | 150 | 180 | 0 | 48 | 64 | 600 | 600 | S | — |
| Mouse 4 | 21 | 38 | 38 | 0 | 0 | 10 | 8 | 8 | 8 | 8 | 0 | 0 | 0 | 0 | 0 | 0 |
| Mouse 5 | 12 | 23 | 50 | 12 | 0 | 4 | 0 | 0 | 0 | 0 | 0 | 0 | 0 | 0 | 0 | 0 |
| Mouse 6 | 15 | 40 | 32 | 8 | 8 | 8 | 8 | 12 | 12 | 12 | 12 | 30 | 120 | 120 | S | — |
| Mouse 7 | 21 | 30 | 15 | 15 | 8 | 8 | 8 | 8 | 8 | 8 | 8 | 8 | 180 | 280 | S | — |
| Mouse 8 | 20 | 48 | 70 | 15 | 15 | 8 | 8 | 0 | 0 | 0 | 0 | 0 | 0 | 8 | S | — |
| Mouse 9 | 25 | 50 | 40 | 15 | 8 | 0 | 0 | 0 | 0 | 0 | 0 | 0 | 0 | 0 | 4 | 4 |
| Mouse 10 | 20 | 38 | 38 | 38 | 38 | 25 | 25 | 25 | 0 | 0 | 15 | 15 | 100 | 100 | S | — |
| TAXOL | | | | | | | | | | | | | | | | 2/10 |
| Dose Schedule | 5 mg/kg on day | | | | | 5 mg/kg on day | | | | | | | | | | |
| Day | 8 | 10 | 12 | 14 | 16 | 18 | 20 | 22 | 24 | 26 | 28 | 30 | 45 | 47 | 50 | 60 |
| Tumor Size | 17 ± 2 | 45 ± 7 | 54 | 128 ± 13 | 311 ± 42 | 596 ± 115 | 1114 ± 151 | 1930 ± 346 | 2285 ± 569 | S ± 597 | (n = 10) | | | | | |
| | | | | | | Extended studies → | | | Extended observations → | | Experiment ended | | | | |

*S: Sacrificed due to tumor burden

TABLE 18

Toxicity of Epothilone B and Desoxyepothilone B in normal nude mice

| Group | Dose and Schedule (mg/kg) | Number of mice | Died |
|---|---|---|---|
| Control | | 4 | 0 |
| Epothilone B[a] | 0.6 QD × 4 | 8 | 8 |
| Desoxyepothilone B | 25 QD × 4 | 6 | 0 |

[a] Mice died of toxicity on day, 5, 7, 7, 7.

What is claimed is:

1. A purified compound having the structure:

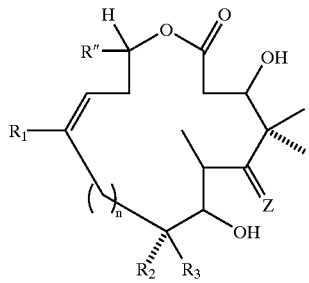

or a compound having the structure:

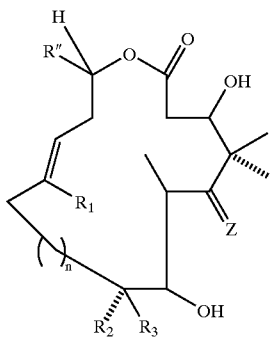

wherein $R_1$, $R_2$, and $R_3$ are each independently H, or linear or branched chain alkyl, which alkyl may be singly or multiply substituted by hydroxy, substituted or unsubstituted alkoxy, substituted or unsubstituted carboxy, carboxaldehyde, substituted or unsubstituted, linear or branched alkyl, substituted or unsubstituted cyclic acetal, fluorine, $NR_4R_5$, N-hydroximino, or N-alkoxyimino, wherein $R_4$ and $R_5$ are independently H, phenyl, benzyl, linear or branched chain alkyl;

R″ is —CY═CHX, or H, linear or branched chain alkyl, phenyl, or 2-methyl-1,3-thiazol-4-yl, wherein X is H, linear or branched chain alkyl, phenyl, or 2-methyl-1,3-thiazol-4-yl, and Y is H or linear or branched chain alkyl;

Z is O, $N(OR_6)$ or N—$NR_7R_8$, wherein $R_6$, $R_7$ and $R_8$ are independently H or a linear or branched chain alkyl or alkoxy; and n is 0, 1, 2, or 3.

2. The compound of claim 1, wherein $R_1$=hydrogen, methyl, ethyl, propyl, hexyl, 2-(1,3-dioxolanyl)methyl, hydroxymethyl or hydroxypropyl.

3. The compound of claim 1, wherein Z═O.

4. The compound of claim 1, wherein $R_2$ is hydrogen, and $R_3$ is methyl.

5. The compound of claim 1, wherein n=3.

6. The compound of claim 1, wherein R″ is —CY═CHX, and X is 2-methyl-1,3-thiazol-4-yl, and Y is H.

7. A purified compound having the structure:

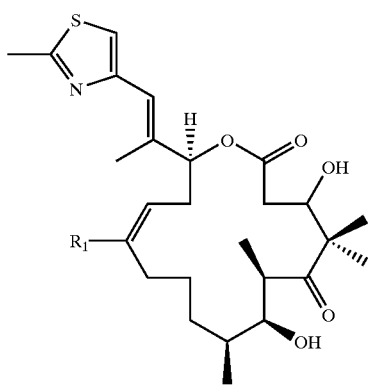

wherein $R_1$ is H, or linear or branched chain alkyl, which alkyl may be singly or multiply substituted by hydroxy, substituted or unsubstituted alkoxy, substituted or unsubstituted carboxy, carboxaldehyde, substituted or unsubstituted, linear or branched alkyl, substituted or unsubstituted cyclic acetal, fluorine, $NR_4R_5$, N-hydroximino, or N-alkoxyimino, wherein $R_4$ and $R_5$ are independently H, phenyl, benzyl, linear or branched chain alkyl.

8. The compound of claim 7, wherein $R_1$ is substituted or unsubstituted, linear or branched chain alkyl.

9. The compound of claim 7, wherein $R_1$ is linear or branched chain alkyl, optionally substituted by hydroxy, fluorine, cyclic acetal, or $NR_4R_5$, wherein $R_4$ and $R_5$ are independently H, phenyl, benzyl, or linear or branched chain alkyl.

10. The compound of claim 7, wherein $R_1$ is linear or branched chain alkyl substituted by fluorine.

11. The compound of claim 7, wherein $R_1$ is linear or branched chain alkyl substituted by hydroxy.

12. The compound of claim 7, wherein $R_1$ is linear or branched chain alkyl substituted by $NR_4R_5$, wherein $R_4$ and $R_5$ are independently H, phenyl, benzyl, or linear or branched chain alkyl.

13. The compound of claim 7, wherein $R_1$ is linear or branched chain alkyl substituted by cyclic acetal.

14. The compound of claim 7, wherein $R_1$ is linear or branched chain alkyl substituted by a substituted carboxy group.

15. The compound of claim 7, wherein $R_1$ is ethyl, and the compound has the structure:

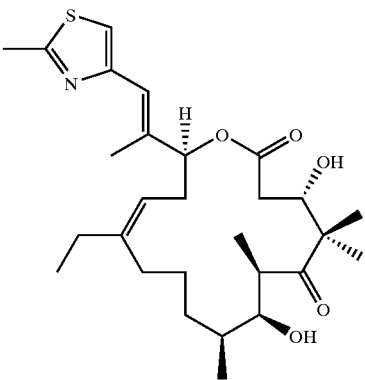

16. The compound of claim 7, wherein $R_1$ is propyl and the compound has the structure:

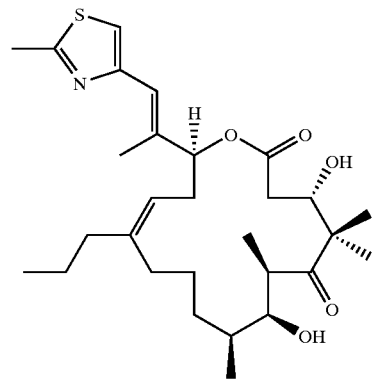

17. The compound of claim 7, wherein $R_1$ is hexyl and the compound has the structure:

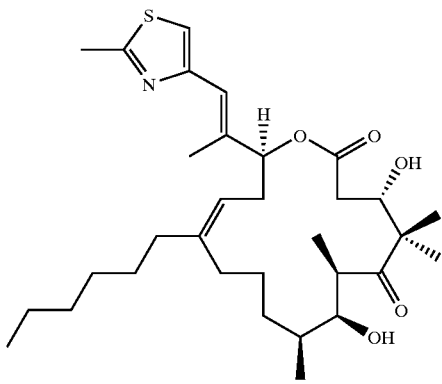

18. The compound of claim 7, wherein $R_1$ is 2-(1,3-dioxolanyl)methyl and the compound has the structure:

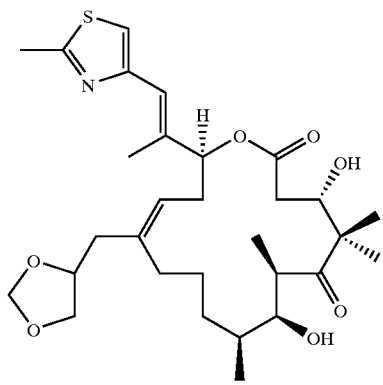

19. The compound of claim 7, wherein $R_1$ is hydroxymethyl and the compound has the structure:

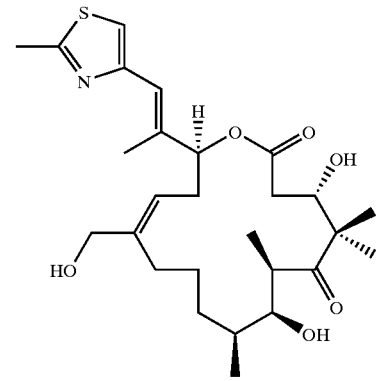

20. The compound of claim 7, wherein $R_1$ is hydroxypropyl and the compound has the structure:

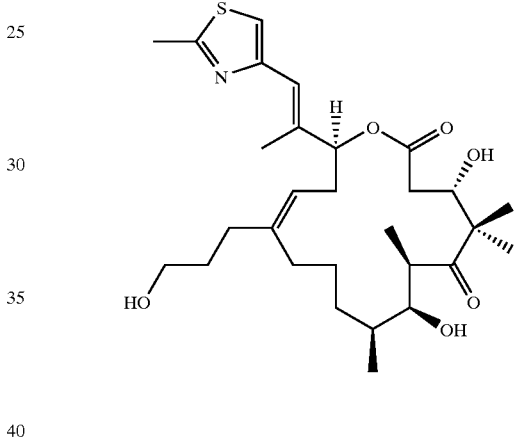

21. The compound of claim 7, wherein $R_1$ is a linear or branched chain alkyl substituted by aroyloxy.

22. The compound of claim 7, wherein $R_1$ is a linear or branched chain alkyl substituted by substituted or unsubstituted benzoyloxy.

23. The compound of claim 7, wherein $R_1$ is a propyl group substituted by benzoyloxy, and the compound has the structure:

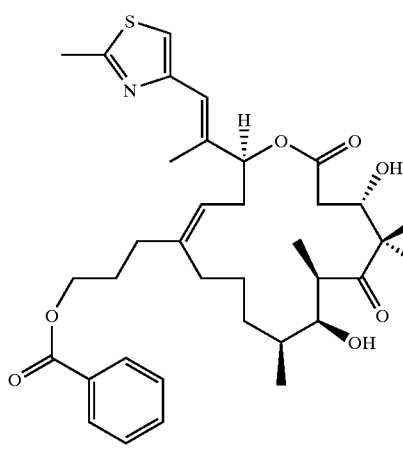

24. A pharmaceutical composition comprising:
a compound having a structure:

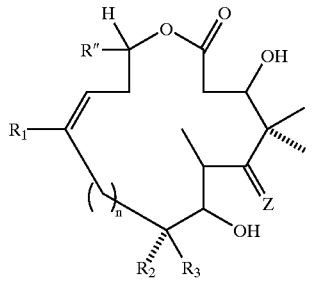

or a compound having a structure:

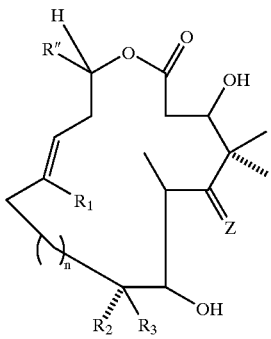

wherein $R_1$, $R_2$, and $R_3$ are each independantly H, or linear or branched chain alkyl, which alkyl may be singly or multiply substituted by hydroxy, substituted or unsubstituted alkoxy, substituted or unsubstituted carboxy, carboxaldehyde, substituted or unsubstituted, linear or branched alkyl, substituted or unsubstituted cyclic acetal, fluorine, $NR_4R_5$, N-hydroximino, or N-alkoxyimino, wherein $R_4$ and $R_5$ are independently H, phenyl, benzyl, linear or branched chain alkyl;

R" is —CY═CHX, or H, linear or branched chain alkyl, phenyl, or 2-methyl-1,3-thiazol-4-yl, wherein X is H, linear or branched chain alkyl, phenyl, or 2-methyl-1,3-thiazol-4-yl, and Y is H or linear or branched chain alkyl;

Z is O, $N(OR_6)$ or N—$NR_7R_8$, wherein $R_6$, $R_7$ and $R_8$ are independently H or a linear or branched chain alkyl or alkoxy; and n is 0, 1, 2, or 3; and a pharmaceutically acceptable carrier,
said composition optionally further comprising a cytotoxic agent.

25. The compound of claim 24, wherein $R_1$=hydrogen, methyl, ethyl, propyl, hexyl, 2-(1,3-dioxolanyl)methyl, hydroxymethyl or hydroxypropyl.

26. The pharmaceutical composition of claim 24, wherein in the compound Z═O.

27. The pharmaceutical composition of claim 24, wherein in the compound $R_2$ is hydrogen, and $R_3$ is methyl.

28. The pharmaceutical composition of claim 24, wherein in the compound n=3.

29. The pharmaceutical composition of claim 24, wherein in the compound R" is —CY═CHX, and X is 2-methyl-1,3-thiazol-4-yl, and Y is H.

30. A pharmaceutical composition comprising:
a compound having the structure:

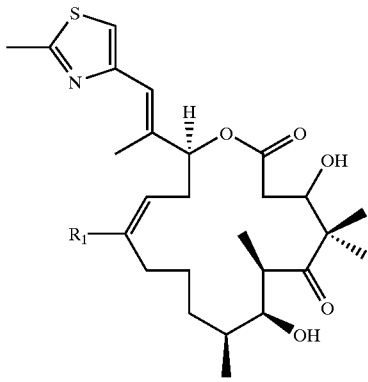

wherein $R_1$ is H, or linear or branched chain alkyl, which alkyl may be singly or multiply substituted by hydroxy, substituted or unsubstituted alkoxy, substituted or unsubstituted carboxy, carboxaldehyde, substituted or unsubstituted, linear or branched alkyl, substituted or unsubstituted cyclic acetal, fluorine, $NR_4R_5$, N-hydroximino, or N-alkoxyimino, wherein $R_4$ and $R_5$ are independently H, phenyl, benzyl, linear or branched chain alkyl; and
a pharmaceutically acceptable carrier,
said composition optionally further comprising a cytotoxic agent.

31. The pharmaceutical composition of claim 30, wherein in the compound $R_1$ is substituted or unsubstituted, linear or branched chain alkyl.

32. The pharmaceutical composition of claim 30, wherein in the compound $R_1$ is linear or branched chain alkyl, optionally substituted by hydroxy, fluorine, cyclic acetal, or $NR_4R_5$, wherein $R_4$ and $R_5$ are independently H, phenyl, benzyl, or linear or branched chain alkyl.

33. The pharmaceutical composition of claim 30, wherein in the compound $R_1$ is linear or branched chain alkyl substituted by fluorine.

34. The pharmaceutical composition of claim 30, wherein in the compound $R_1$ is linear or branched chain alkyl substituted by hydroxy.

35. The pharmaceutical composition of claim 30, wherein in the compound $R_1$ is linear or branched chain alkyl substituted by $NR_4R_5$, wherein $R_4$ and $R_5$ are independently H, phenyl, benzyl, or linear or branched chain alkyl.

36. The pharmaceutical composition of claim 30, wherein in the compound $R_1$ is linear or branched chain alkyl substituted by cyclic acetal.

37. The pharmaceutical composition of claim 30, wherein in the compound $R_1$ is linear or branched chain alkyl substituted by a substituted carboxy group.

38. The pharmaceutical composition of claim 30, wherein in the compound $R_1$ is hydrogen and the compound has the structure:

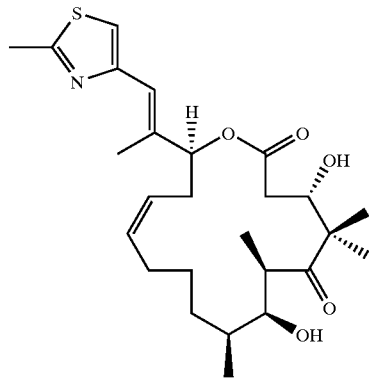

39. The pharmaceutical composition of claim 30, wherein in the compound $R_1$ is methyl and the compound has the structure:

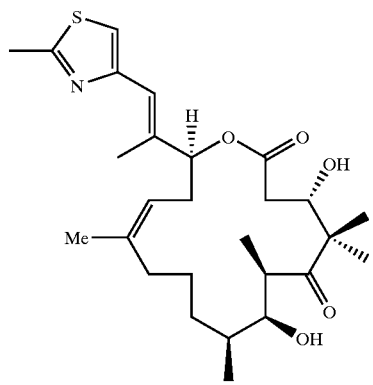

40. The pharmaceutical composition of claim 30, wherein in the compound $R_1$ is ethyl and the compound has the structure:

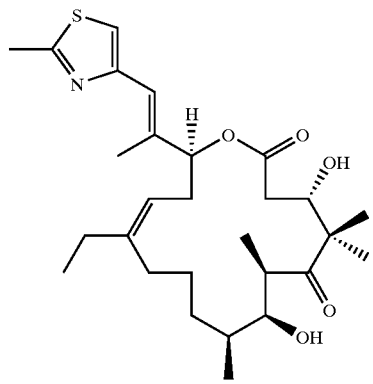

41. The pharmaceutical composition of claim 30, wherein the compound $R_1$ is propyl and the compound has the structure:

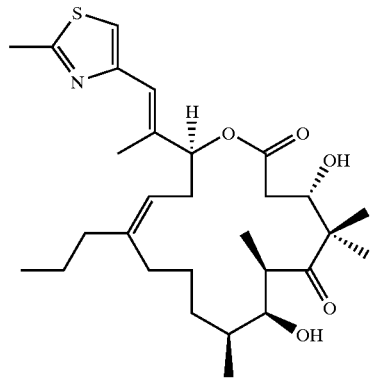

42. The pharmaceutical composition of claim 30, wherein in the compound $R_1$ is hexyl and the compound has the structure:

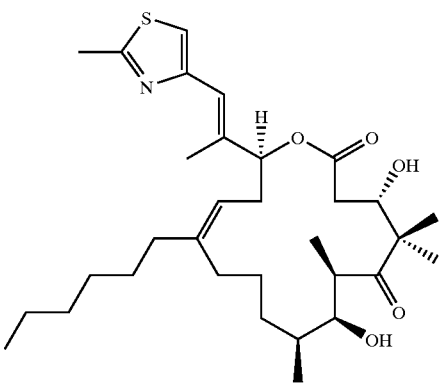

43. The pharmaceutical composition of claim 38, wherein in the compound $R_1$ is 2-(1,3-dioxolanyl)methyl and the compound has the structure:

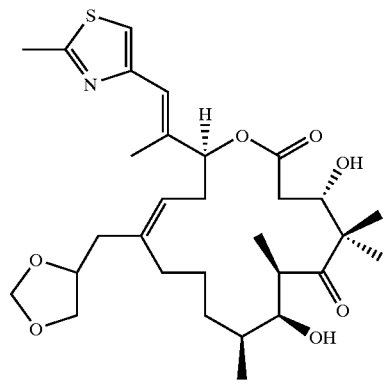

44. The pharmaceutical composition of claim 30, wherein in the compound $R_1$ is hydroxymethyl and the compound has the structure:

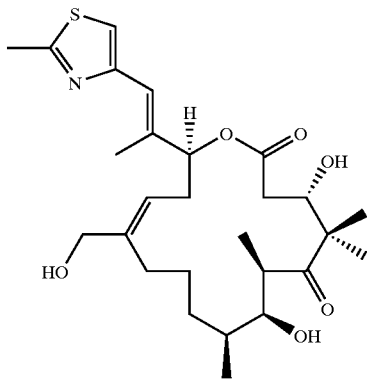

45. The pharmaceutical composition of claim 30, wherein in the compound $R_1$ is hydroxypropyl and the compound has the structure:

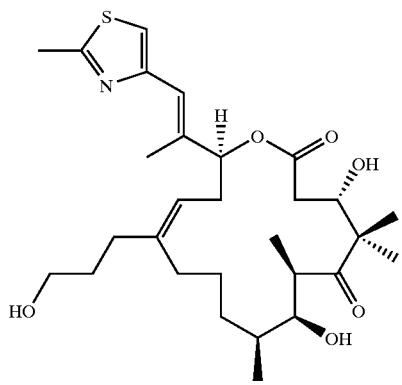

46. The pharmaceutical composition of claim 30, wherein in the compound $R_1$ is a linear or branched chain alkyl substituted by aroyloxy.

47. The pharmaceutical composition of claim 30, wherein in the compound $R_1$ is a linear or branched chain alkyl substituted by substituted or unsubstituted benzoyloxy.

48. The pharmaceutical composition of claim 30, wherein in the compound $R_1$ is a propyl group substituted by benzoyloxy, and the compound has the structure:

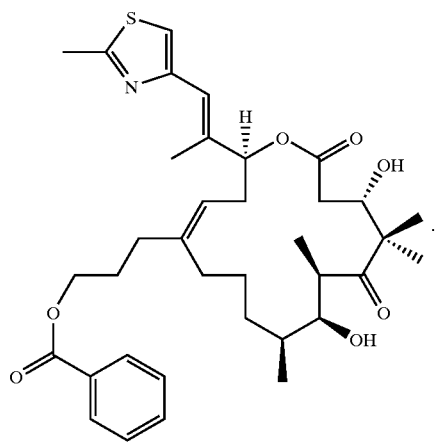

49. The pharmaceutical composition of claim 24 or 30, wherein the cytotoxic agent is an anticancer agent.

50. The pharmaceutical composition of claim 49, wherein the anticancer agent is adnamycin.

51. The pharmaceutical composition of claim 49, wherein the anticancer agent is vinblastin.

52. The pharmaceutical composition of claim 49, wherein the anticancer agent is paclitaxel.

53. A method of treating cancer in a subject comprising: administering to the subject a therapeutically effective amount of a compound having the structure:

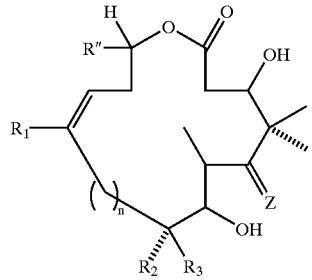

or a compound having the structure:

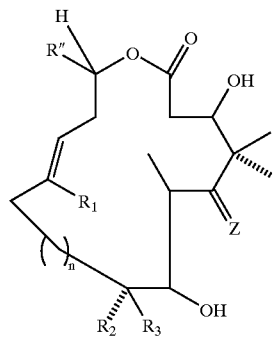

wherein $R_1$, $R_2$, and $R_3$ are each independently H, or linear or branched chain alkyl, which alkyl may be singly or multiply substituted by hydroxy, substituted or unsubstituted alkoxy, substituted or unsubstituted carboxy, carboxaldehyde, substituted or unsubstituted, linear or branched alkyl, substituted or unsubstituted cyclic acetal, fluorine, $NR_4R_5$, N-hydroximino, or N-alkoxyimino, wherein $R_4$ and $R_5$ are independently H, phenyl, benzyl, linear or branched chain alkyl;

R" is —CY=CHX, or H, linear or branched chain alkyl, phenyl, or 2-methyl-1,3-thiazol-4-yl, wherein X is H, linear or branched chain alkyl, phenyl, or 2-methyl-1,3-thiazol-4-yl, and Y is H or linear or branched chain alkyl;

Z is O, $N(OR_6)$ or $N-NR_7R_8$, wherein $R_6$, $R_7$ and $R_8$ are independently H or a linear or branched chain alkyl or alkoxy; and n is 0, 1, 2, or 3, said method optionally further comprising administering a cytotoxic agent.

54. The method of claim 53, wherein in the compound $R_1$=hydrogen, methyl, ethyl, propyl, hexyl, 2-(1,3-dioxolanyl)methyl, hydroxymethyl or hydroxypropyl.

55. The method of claim 53, wherein in the compound Z=O.

56. The method of claim 53, wherein in the compound $R_2$ is hydrogen, and $R_3$ is methyl.

57. The method of claim 53, wherein in the compound n=3.

58. The method of claim 53, wherein in the compound R" is —CY=CHX, and X is 2-methyl-1,3-thiazol-4-yl, and Y is H.

59. A method for treating cancer in a subject comprising: administering to a subject a therapeutically effective amount of a compound having the structure:

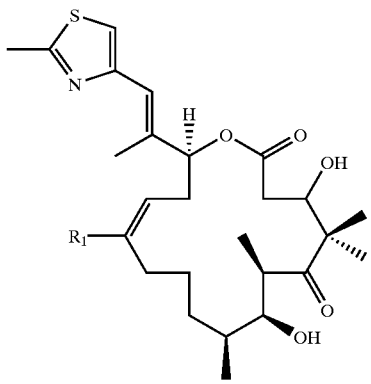

wherein R₁ is H, or linear or branched chain alkyl, which alkyl may be singly or multiply substituted by hydroxy, substituted or unsubstituted alkoxy, substituted or unsubstituted carboxy, carboxaldehyde, substituted or unsubstituted, linear or branched alkyl, substituted or unsubstituted cyclic acetal, fluorine, $NR_4R_5$, N-hydroximino, or N-alkoxyimino, wherein $R_4$ and $R_5$ are independently H, phenyl, benzyl, linear or branched chain alkyl, said method optionally further comprising administering a cytotoxic agent.

60. The method of claim 59, wherein in the compound $R_1$ is substituted or unsubstituted, linear or branched chain alkyl.

61. The method of claim 59, wherein in the compound $R_1$ is linear or branched chain alkyl, optionally substituted by hydroxy, fluorine, cyclic acetal, or $NR_4R_5$, wherein $R_4$ and $R_5$ are independently H, phenyl, benzyl, or linear or branched chain alkyl.

62. The method of claim 59, wherein in the compound $R_1$ is linear or branched chain alkyl substituted by fluorine.

63. The method of claim 59, wherein in the compound $R_1$ is linear or branched chain alkyl substituted by hydroxy.

64. The method of claim 59, wherein in the compound $R_1$ is linear or branched chain alkyl substituted by $NR_4R_5$, wherein $R_4$ and $R_5$ are independently H, phenyl, benzyl, or linear or branched chain alkyl.

65. The method of claim 59, wherein in the compound $R_1$ is linear or branched chain alkyl substituted by cyclic acetal.

66. The method of claim 59, wherein in the compound $R_1$ is linear or branched chain alkyl substituted by a substituted carboxy group.

67. The method of claim 59, wherein in the compound $R_1$ is hydrogen and the compound has the structure:

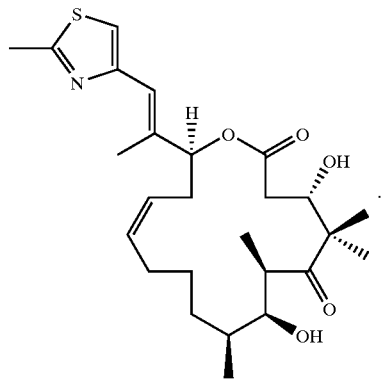

68. The method of claim 59, wherein in the compound $R_1$ is methyl and the compound has the structure:

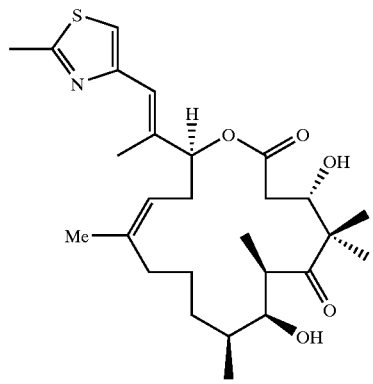

69. The method of claim 59, wherein in the compound $R_1$ is ethyl and the compound has the structure:

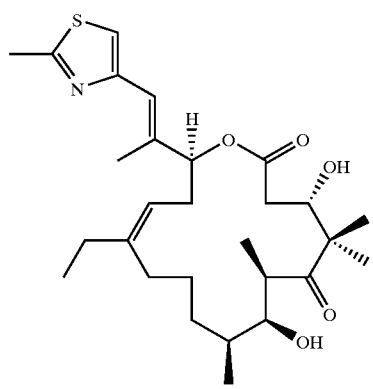

70. The method of claim 59, wherein in the compound $R_1$ is propyl and the compound has the structure:

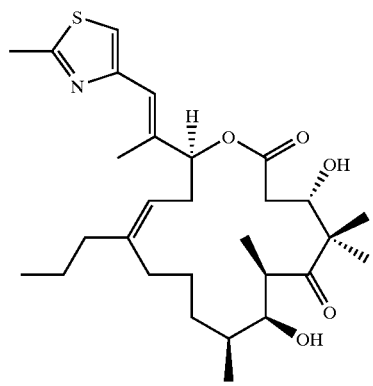

71. The method of claim 59, wherein in the compound $R_1$ is hexyl and the compound has the structure:

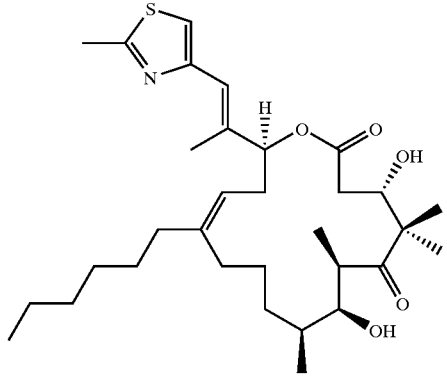

72. The method of claim 59, wherein in the compound $R_1$ is 2-(1,3-dioxolanyl)methyl and the compound has the structure:

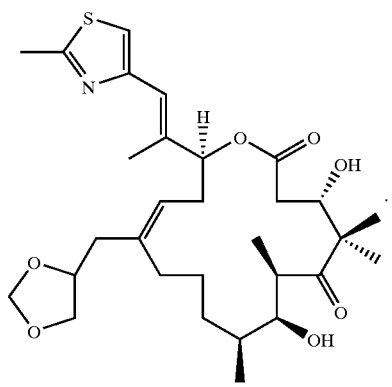

73. The method of claim 59, wherein in the compound $R_1$ is hydroxymethyl and the compound has the structure:

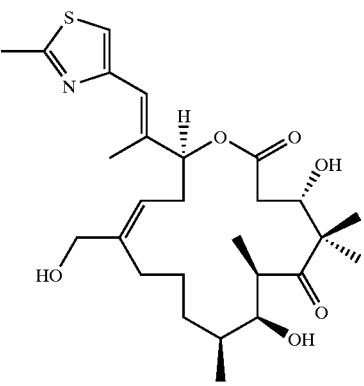

74. The method of claim 59, wherein in the compound $R_1$ is hydroxypropyl and the compound has the structure:

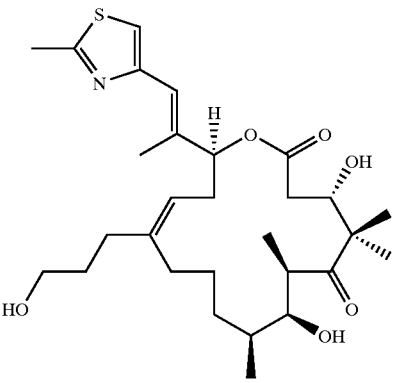

75. The method of claim 59, wherein in the compound $R_1$ is a linear or branched chain alkyl substituted by aroyloxy.

76. The method of claim 59, wherein in the compound $R_1$ is a linear or branched chain alkyl substituted by substituted or unsubstituted benzoyloxy.

77. The method of claim 59, wherein in the compound $R_1$ is a propyl group substituted by benzoyloxy, and the compound has the structure:

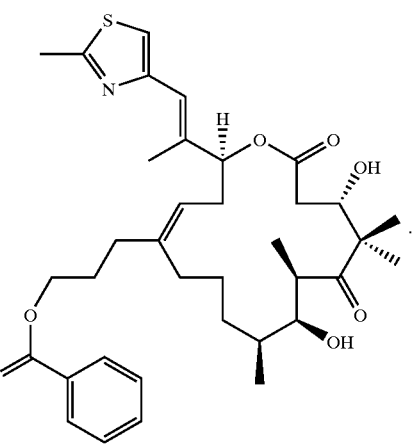

78. The method of claim 53 or 59, wherein the method further comprises administering a cytotoxic agent, wherein said cytotoxic agent is an anticancer agent.

79. The method of claim 78, wherein the anticancer agent administered is adriamycin.

80. The method of claim 78, wherein the anticancer agent administered is vinblastin.

81. The method of claim 78, wherein the anticancer agent administered is paclitaxel.

82. The method of claim 53 or 59, wherein the cancer is a solid tumor.

83. The method of claim 53 or 59, wherein the cancer is breast cancer, melanoma, leukemia or ovarian cancer.

84. The method of claim 53 or 59, wherein the therapeutically effective amount of the compound is between about 0.001 mg/kg to about 40 mg/kg of body weight.

85. The method of claim 53 or 59, wherein the therapeutically effective amount of the compound is between about 0.01 mg/kg to about 40 mg/kg of body weight.

86. The method of claim 53 or 59, wherein the therapeutically effective amount of the compound is between about 0.001 mg/kg to about 25 mg/kg of body weight.

87. The method of claim 53 or 59, wherein the therapeutically effective amount of the compound is between about 0.01 mg/kg to about 25 mg/kg of body weight.

88. The method of claim 53 or 59, wherein the therapeutically effective amount of the compound is between about 0.001 mg/kg to about 10 mg/kg of body weight.

89. The method of claim 53 or 59, wherein the therapeutically effective amount of the compound is between about 0.01 mg/kg to about 10 mg/kg of body weight.

90. The method of claim 53 or 59, wherein the therapeutically effective amount of the compound is between about 0.001 mg/kg to about 1.0 mg/kg of body weight.

91. The method of claim 53 or 59, wherein the therapeutically effective amount of the compound is between about 0.01 mg/kg to about 1.0 mg/kg of body weight.

92. The method of claim 53 or 59, wherein the therapeutically effective amount of the compound is 25 mg/kg or greater of body weight.

93. The method of claim 53 or 59, wherein the therapeutically effective amount of the compound is between about 25 mg/kg to about 40 mg/kg of body weight.

* * * * *

UNITED STATES PATENT AND TRADEMARK OFFICE
CERTIFICATE OF CORRECTION

PATENT NO. : 6,656,961 B2
DATED : December 2, 2003
INVENTOR(S) : Samuel J. Danishefsky et al.

It is certified that error appears in the above-identified patent and that said Letters Patent is hereby corrected as shown below:

Title page,
Item [75], Inventors, "Dang Fang Meng" should be -- Dongfang Meng --.
Item [22], PCT Filed, "Mar. 14, 2001" should be -- Mar. 13, 2001 --.
Item [56], References Cited, OTHER PUBLICATIONS, add the following reference:
-- Balog et al., "Stereoselective Syntheses and Evaluation of Compounds in the 8-Desmethylepothilone A Series: Some Surprising Observations." *Tetrahedron Letters* 38:26 4529-4532. --.

Signed and Sealed this

Eighteenth Day of April, 2006

JON W. DUDAS
*Director of the United States Patent and Trademark Office*

UNITED STATES PATENT AND TRADEMARK OFFICE
CERTIFICATE OF CORRECTION

Page 1 of 1

PATENT NO.        : 6,656,961 B2
APPLICATION NO.   : 09/808451
DATED             : December 2, 2003
INVENTOR(S)       : Samuel Danishefsky It is certified that error appears in the above-identified patent and that said Letters Patent is hereby corrected as shown below:

In the Specification

In column 1, beginning at line 14 and ending at line 21, please delete:

"This invention was made with government support under grants CA-28824, CA-39821, CA-GM 72231, CA-62948, and AI0-9355 from the National Institutes of Health, and grant CHE-9504805 from the National Science Foundation. Additionally, the present invention was supported in part by a fellowship from the United States Army to Dongfang Meng (DAMD 17-97-1-7146) and thus the government has certain rights in the invention."

and insert:

--This invention was made with government support under grant numbers: AI009355, CA028824, CA062948, CA081704, GM072231, GM199721 awarded by National Institutes of Health and DAMD 17-98-1-8155 awarded by the Army Medical Research and Materiel Command. The government has certain rights in the invention.--

Signed and Sealed this
Twenty-third Day of February, 2016

Michelle K. Lee
*Director of the United States Patent and Trademark Office*